(12) United States Patent
De Rossi et al.

(10) Patent No.: US 11,324,655 B2
(45) Date of Patent: May 10, 2022

(54) ASSISTIVE FLEXIBLE SUITS, FLEXIBLE SUIT SYSTEMS, AND METHODS FOR MAKING AND CONTROL THEREOF TO ASSIST HUMAN MOBILITY

(71) Applicants: Trustees of Boston University, Boston, MA (US); President and Fellows of Harvard College, Cambridge, MA (US)

(72) Inventors: Stefano Marco Maria De Rossi, Cambridge (GB); Kathleen Elizabeth O'Donnell, Cambridge, MA (US); Jaehyun Bae, Cambridge, MA (US); Alan Thomas Asbeck, Waltham, MA (US); Kenneth G. Holt, Shutesbury, MA (US); Conor J. Walsh, Cambridge, MA (US)

(73) Assignees: Trustees of Boston University, Boston, MA (US); President and Fellows of Harvard College, Cambridge, MA (US)

( * ) Notice: Subject to any disclaimer, the term of this patent is extended or adjusted under 35 U.S.C. 154(b) by 955 days.

(21) Appl. No.: 15/102,694

(22) PCT Filed: Dec. 3, 2014

(86) PCT No.: PCT/US2014/068462
§ 371 (c)(1),
(2) Date: Mar. 31, 2017

(87) PCT Pub. No.: WO2015/088863
PCT Pub. Date: Jun. 18, 2015

(65) Prior Publication Data
US 2017/0202724 A1    Jul. 20, 2017

Related U.S. Application Data

(63) Continuation-in-part of application No. PCT/US2014/040340, filed on May 30, 2014.
(Continued)

(51) Int. Cl.
*A61H 3/00* (2006.01)
*A61H 1/00* (2006.01)
(Continued)

(52) U.S. Cl.
CPC ............... *A61H 3/00* (2013.01); *A61B 5/112* (2013.01); *A61B 5/4851* (2013.01);
(Continued)

(58) Field of Classification Search
CPC .. A61H 3/00; A61H 2201/165; A61H 1/0266; A61H 1/0244; A61H 1/024;
(Continued)

(56) References Cited

U.S. PATENT DOCUMENTS 3,387,305 A    6/1968  Shafer
3,411,511 A    11/1968 Marino
(Continued)

FOREIGN PATENT DOCUMENTS

CN    1431084 A    7/2003
CN    1868434 B    11/2006
(Continued)

OTHER PUBLICATIONS

PCT International Search Report and Written Opinion, issued in International Application No. PCT/US2017/042286, dated Sep. 28, 2017.
(Continued)

*Primary Examiner* — Quang D Thanh
(74) *Attorney, Agent, or Firm* — Wolf, Greenfield & Sacks, P.C.

(57) ABSTRACT

In at least some aspects, the present concepts include a method for configuring an assistive flexible suit including the acts of outfitting a person with an assistive flexible suit, monitoring an output of at least one sensor of the assistive flexible suit as the person moves in a first controlled move-
(Continued)

ment environment, identifying at least one predefined gait event using the output of the at least one sensor, adjusting an actuation profile of the at least one actuator and continuing to perform the acts of monitoring, identifying and adjusting until an actuation profile of the at least one actuator generates a beneficial moment about the at least one joint to promote an improvement in gait. The at least one controller is then set to implement the actuation profile.

39 Claims, 52 Drawing Sheets

Related U.S. Application Data

(60) Provisional application No. 62/052,562, filed on Sep. 19, 2014, provisional application No. 62/048,076, filed on Sep. 9, 2014, provisional application No. 61/980,961, filed on Apr. 17, 2014, provisional application No. 61/977,880, filed on Apr. 10, 2014, provisional application No. 61/936,162, filed on Feb. 5, 2014, provisional application No. 61/928,281, filed on Jan. 16, 2014, provisional application No. 61/913,863, filed on Dec. 9, 2013.

(51) Int. Cl.
*A61F 5/00* (2006.01)
*A61B 5/11* (2006.01)
*A61F 5/01* (2006.01)
*A61H 1/02* (2006.01)
*A61B 5/00* (2006.01)
*A61F 13/08* (2006.01)
*A61F 2/72* (2006.01)

(52) U.S. Cl.
CPC .............. *A61B 5/6811* (2013.01); *A61F 2/72* (2013.01); *A61F 5/0102* (2013.01); *A61F 5/0127* (2013.01); *A61F 13/08* (2013.01); *A61H 1/024* (2013.01); *A61H 1/0244* (2013.01); *A61H 1/0266* (2013.01); *A61F 2005/0155* (2013.01); *A61F 2005/0158* (2013.01); *A61F 2005/0179* (2013.01); *A61F 2005/0188* (2013.01); *A61H 2201/1207* (2013.01); *A61H 2201/14* (2013.01); *A61H 2201/164* (2013.01); *A61H 2201/165* (2013.01); *A61H 2201/169* (2013.01); *A61H 2201/1623* (2013.01); *A61H 2201/1628* (2013.01); *A61H 2201/501* (2013.01); *A61H 2201/5028* (2013.01); *A61H 2201/5061* (2013.01); *A61H 2201/5064* (2013.01); *A61H 2201/5079* (2013.01); *A61H 2201/5084* (2013.01); *A61H 2230/60* (2013.01)

(58) Field of Classification Search
CPC ........ A61H 2230/60; A61H 2201/5084; A61H 2201/5079; A61H 2201/5064; A61H 2201/5061; A61H 2201/501; A61H 2201/169; A61H 2201/164; A61H 2201/1628; A61H 2201/1623; A61H 2201/1207; A61H 2201/5028; A61H 2201/14; A61F 5/0102; A61F 2005/0155; A61F 13/08; A61F 5/0127; A61F 2005/0188; A61F 2005/0179; A61F 2005/0158; A61B 5/112; A61B 5/04888; A61B 5/6811; A61B 5/4851
See application file for complete search history.

(56) References Cited

U.S. PATENT DOCUMENTS

| | | | |
|---|---|---|---|
| 3,831,467 | A | 8/1974 | Moore |
| 4,023,215 | A | 5/1977 | Moore |
| 4,252,112 | A | 2/1981 | Joyce |
| 4,370,977 | A | 2/1983 | Mauldin et al. |
| 4,682,776 | A | 7/1987 | Mitchell et al. |
| 4,697,808 | A | 10/1987 | Larson et al. |
| 4,724,827 | A | 2/1988 | Schenck |
| 4,760,850 | A | 8/1988 | Phillips et al. |
| 5,020,790 | A | 6/1991 | Beard et al. |
| 5,282,460 | A | 2/1994 | Boldt |
| 5,485,402 | A | 1/1996 | Smith et al. |
| 5,584,799 | A | 12/1996 | Gray |
| 5,599,283 | A | 2/1997 | Lindenmeyer et al. |
| 5,667,461 | A | 9/1997 | Hall |
| 5,826,578 | A | 10/1998 | Curchod |
| 5,865,714 | A | 2/1999 | Marlowe |
| 5,865,770 | A | 2/1999 | Schectman |
| 5,955,667 | A | 9/1999 | Fyfe |
| 6,123,649 | A | 9/2000 | Lee et al. |
| 6,129,691 | A | 10/2000 | Ruppert |
| 6,168,634 | B1 | 1/2001 | Schmitz |
| 6,213,922 | B1 | 4/2001 | Afanasenko et al. |
| 6,500,138 | B1 | 12/2002 | Irby et al. |
| 6,517,503 | B1 | 2/2003 | Naft et al. |
| 6,633,783 | B1 | 10/2003 | Dariush et al. |
| 6,635,024 | B2 | 10/2003 | Hatton et al. |
| 6,666,831 | B1 | 12/2003 | Edgerton et al. |
| 6,689,075 | B2 | 2/2004 | West |
| 6,741,911 | B2 | 5/2004 | Simmons |
| 6,783,555 | B2 | 8/2004 | Kuhn et al. |
| 6,790,165 | B2 | 9/2004 | Huang |
| 6,796,926 | B2 | 9/2004 | Reinkensmeyer et al. |
| 6,812,624 | B1 | 11/2004 | Pei et al. |
| 6,955,692 | B2 | 10/2005 | Grundei |
| 6,989,669 | B2 | 1/2006 | Low et al. |
| 7,034,432 | B1 | 4/2006 | Pelrine et al. |
| 7,034,527 | B2 | 4/2006 | Low et al. |
| 7,049,732 | B2 | 5/2006 | Pei et al. |
| 7,056,297 | B2 | 6/2006 | Dohnu et al. |
| 7,064,472 | B2 | 6/2006 | Pelrine et al. |
| 7,090,650 | B2 | 8/2006 | Ou et al. |
| 7,153,242 | B2 | 12/2006 | Goffer |
| 7,153,246 | B2 | 12/2006 | Koscielny et al. |
| 7,166,953 | B2 | 1/2007 | Heim et al. |
| 7,190,141 | B2 | 3/2007 | Ashrafiuon et al. |
| 7,199,501 | B2 | 4/2007 | Pei et al. |
| 7,211,937 | B2 | 5/2007 | Kornbluh et al. |
| 7,224,106 | B2 | 5/2007 | Pei et al. |
| 7,229,390 | B2 | 6/2007 | Fujii et al. |
| 7,233,097 | B2 | 6/2007 | Rosenthal et al. |
| 7,252,644 | B2 | 8/2007 | Dewald et al. |
| 7,259,503 | B2 | 8/2007 | Pei et al. |
| 7,259,553 | B2 | 8/2007 | Arns, Jr. et al. |
| 7,307,418 | B2 | 12/2007 | Low et al. |
| 7,331,906 | B2 | 2/2008 | He et al. |
| 7,341,295 | B1 | 3/2008 | Veatch et al. |
| 7,355,519 | B2 | 4/2008 | Grold et al. |
| 7,367,958 | B2 | 5/2008 | McBean et al. |
| 7,368,862 | B2 | 5/2008 | Pelrine et al. |
| 7,378,878 | B2 | 5/2008 | Pelrine et al. |
| 7,390,309 | B2 | 6/2008 | Dariush |
| 7,410,471 | B1 | 8/2008 | Campbell et al. |
| 7,411,332 | B2 | 8/2008 | Kornbluh et al. |
| 7,429,253 | B2 | 9/2008 | Shimada et al. |
| 7,436,099 | B2 | 10/2008 | Pei et al. |
| 7,445,606 | B2 | 11/2008 | Rastegar et al. |
| 7,456,549 | B2 | 11/2008 | Heim et al. |
| 7,476,185 | B2 | 1/2009 | Drennan |
| 7,494,450 | B2 | 2/2009 | Solomon |
| 7,521,840 | B2 | 4/2009 | Heim |
| 7,521,847 | B2 | 4/2009 | Heim |
| 7,537,573 | B2 | 5/2009 | Horst |
| 7,549,969 | B2 | 6/2009 | van den Bogert |
| 7,567,681 | B2 | 7/2009 | Pelrine et al. |
| 7,578,799 | B2 | 8/2009 | Thorsteinsson et al. |

(56) References Cited

U.S. PATENT DOCUMENTS

| | | |
|---|---|---|
| 7,595,580 B2 | 9/2009 | Heim |
| 7,598,651 B2 | 10/2009 | Kornbluh et al. |
| 7,598,652 B2 | 10/2009 | Kornbluh et al. |
| 7,626,319 B2 | 12/2009 | Heim |
| 7,650,204 B2 | 1/2010 | Dariush |
| 7,652,386 B2 | 1/2010 | Donelan et al. |
| 7,654,973 B2 | 2/2010 | Firsov |
| 7,679,267 B2 | 3/2010 | Heim |
| 7,684,896 B2 | 3/2010 | Dariush |
| 7,705,521 B2 | 4/2010 | Pelrine et al. |
| 7,737,685 B2 | 6/2010 | Low et al. |
| 7,750,532 B2 | 7/2010 | Heim |
| 7,758,481 B2 | 7/2010 | Drennan |
| 7,774,177 B2 | 8/2010 | Dariush |
| 7,775,999 B2 | 8/2010 | Brown |
| 7,785,279 B2 | 8/2010 | Sankai |
| 7,785,656 B2 | 8/2010 | Pei |
| 7,787,646 B2 | 8/2010 | Pelrine et al. |
| 7,804,227 B2 | 9/2010 | Pelrine et al. |
| 7,857,774 B2 | 12/2010 | Sankai |
| 7,860,562 B2 | 12/2010 | Endo et al. |
| 7,883,546 B2 | 2/2011 | Kazerooni et al. |
| 7,887,471 B2 | 2/2011 | McSorley |
| 7,897,168 B2 | 3/2011 | Chen et al. |
| 7,911,761 B2 | 3/2011 | Biggs et al. |
| 7,915,790 B2 | 3/2011 | Heim et al. |
| 7,918,808 B2 | 4/2011 | Simmons |
| 7,921,541 B2 | 4/2011 | Pei et al. |
| 7,923,064 B2 | 4/2011 | Pelrien et al. |
| 7,923,902 B2 | 4/2011 | Heim |
| 7,947,004 B2 | 5/2011 | Kazerooni et al. |
| 7,952,261 B2 | 5/2011 | Lipton et al. |
| 7,985,193 B2 | 6/2011 | Thorsteinsson et al. |
| 7,977,923 B2 | 7/2011 | Pelrine et al. |
| 7,981,508 B1 | 7/2011 | Shanna et al. |
| 7,990,022 B2 | 8/2011 | Heim |
| 7,998,040 B2 | 8/2011 | Kram et al. |
| 8,048,007 B2 | 11/2011 | Roy |
| 8,057,410 B2 | 11/2011 | Angold et al. |
| 8,058,861 B2 | 11/2011 | Pelrine et al. |
| 8,060,337 B2 | 11/2011 | Kulach et al. |
| 8,075,633 B2 | 12/2011 | Herr et al. |
| 8,083,644 B2 | 12/2011 | Purdy et al. |
| 8,096,965 B2 | 1/2012 | Goffer et al. |
| 8,114,034 B2 | 2/2012 | Ikeuchi et al. |
| 8,125,755 B2 | 2/2012 | Garcia et al. |
| 8,127,437 B2 | 3/2012 | Lipton et al. |
| 8,142,370 B2 | 3/2012 | Weinberg et al. |
| 8,147,436 B2 | 4/2012 | Agrawal et al. |
| 8,164,232 B2 | 4/2012 | Kornbluh et al. |
| 8,183,739 B2 | 5/2012 | Heim |
| 8,222,799 B2 | 7/2012 | Polyakov et al. |
| 8,231,687 B2 | 7/2012 | Bedard et al. |
| 8,235,869 B2 | 8/2012 | Rastegar et al. |
| 8,246,559 B2 | 8/2012 | Hoffman et al. |
| 8,248,750 B2 | 8/2012 | Biggs et al. |
| 8,274,244 B2 | 9/2012 | Bhugra et al. |
| 8,283,839 B2 | 10/2012 | Heim |
| 8,287,477 B1 | 10/2012 | Herr et al. |
| 8,292,836 B2 | 10/2012 | Matsuoka et al. |
| 8,299,634 B2 | 10/2012 | Donelan et al. |
| 8,311,623 B2 | 11/2012 | Sanger |
| 8,316,526 B2 | 11/2012 | Pei et al. |
| 8,316,719 B2 | 11/2012 | Majidi et al. |
| 8,323,355 B2 | 12/2012 | Latour |
| 8,325,458 B2 | 12/2012 | Prahlad et al. |
| 8,348,875 B2 | 1/2013 | Goffer et al. |
| 8,376,971 B1 | 2/2013 | Herr et al. |
| 8,409,117 B2 | 4/2013 | Cheng et al. |
| 8,436,508 B2 | 5/2013 | Kornbluh et al. |
| 8,438,757 B2 | 5/2013 | Roser |
| 8,460,001 B1 | 6/2013 | Chuang |
| 8,467,904 B2 | 6/2013 | Dariush |
| 8,488,295 B2 | 7/2013 | Garcia et al. |
| 8,508,109 B2 | 8/2013 | Pelrine et al. |
| 8,551,029 B1 | 10/2013 | Herr et al. |
| 8,551,184 B1 | 10/2013 | Herr |
| 8,562,691 B2 | 10/2013 | Endo et al. |
| 8,564,926 B2 | 10/2013 | Prahlad et al. |
| 8,573,982 B1 | 11/2013 | Chuang |
| 8,585,620 B2 | 11/2013 | McBean et al. |
| 8,597,369 B2 | 12/2013 | Hansen et al. |
| 8,608,479 B2 | 12/2013 | Liu |
| 8,608,674 B2 | 12/2013 | Krebs et al. |
| 8,622,938 B2 | 1/2014 | Sankai |
| 8,663,133 B2 | 3/2014 | Johnson et al. |
| 8,665,578 B2 | 3/2014 | Pelrine et al. |
| 8,679,575 B2 | 3/2014 | Biggs et al. |
| 8,715,208 B2 | 5/2014 | Hodgins et al. |
| 8,766,925 B2 | 6/2014 | Perlin et al. |
| 8,764,850 B2 | 7/2014 | Hansen et al. |
| 8,773,148 B2 | 7/2014 | Sankai et al. |
| 8,847,611 B2 | 9/2014 | Ulmen et al. |
| 8,905,955 B2 | 12/2014 | Goffer et al. |
| 8,920,517 B2 | 12/2014 | Smith et al. |
| 8,926,534 B2 | 1/2015 | McBean et al. |
| 8,938,289 B2 | 1/2015 | Einav et al. |
| 8,961,439 B2 | 2/2015 | Yang et al. |
| 8,975,888 B2 | 3/2015 | Pelrine et al. |
| 8,981,621 B2 | 3/2015 | Pelrine et al. |
| 8,986,233 B2 | 3/2015 | Aoki et al. |
| 9,044,346 B2 | 6/2015 | Langlois et al. |
| 9,072,941 B2 | 7/2015 | Duda et al. |
| 9,101,323 B2 | 8/2015 | Einarsson et al. |
| 9,144,528 B2 | 9/2015 | Agrawal et al. |
| 9,149,370 B2 | 10/2015 | Herr et al. |
| 9,195,794 B2 | 11/2015 | Dariush |
| 9,198,821 B2 | 12/2015 | Unluhisarcikli et al. |
| 9,221,177 B2 | 12/2015 | Herr et al. |
| 9,227,108 B1 | 1/2016 | Chuang |
| 9,228,822 B2 | 1/2016 | Majidi et al. |
| 9,231,186 B2 | 1/2016 | Busgen et al. |
| 9,266,233 B2 | 2/2016 | Kornbluh et al. |
| 9,333,097 B2 | 5/2016 | Herr et al. |
| 9,351,900 B2 | 5/2016 | Walsh et al. |
| 9,387,096 B2 | 6/2016 | Sverrisson et al. |
| 9,403,272 B2 | 8/2016 | Kornbluh et al. |
| 9,427,864 B2 | 8/2016 | Kornbluh et al. |
| 10,028,881 B2 | 7/2018 | Yamamoto et al. |
| 10,115,319 B2 | 10/2018 | Asbeck et al. |
| 10,278,883 B2 | 5/2019 | Walsh et al. |
| 10,427,293 B2 | 10/2019 | Asbeck et al. |
| 10,434,030 B2 | 10/2019 | Asbeck et al. |
| 2001/0007845 A1 | 7/2001 | Afanasenko et al. |
| 2003/0009120 A1 | 1/2003 | MacAllister |
| 2003/0030397 A1 | 2/2003 | Simmons |
| 2003/0064869 A1 | 4/2003 | Reinkensmeyer et al. |
| 2003/0092545 A1 | 5/2003 | Koscielny et al. |
| 2003/0096310 A1 | 5/2003 | Hansen et al. |
| 2003/0120183 A1 | 6/2003 | Simmons |
| 2003/0125781 A1 | 7/2003 | Dohno et al. |
| 2004/0043879 A1 | 3/2004 | Huang |
| 2004/0064195 A1 | 4/2004 | Herr |
| 2004/0087418 A1 | 5/2004 | Eldridge |
| 2004/0106881 A1 | 6/2004 | McBean et al. |
| 2004/0116260 A1 | 7/2004 | Drennan |
| 2004/0147378 A1 | 7/2004 | Conklin et al. |
| 2004/0191321 A1 | 9/2004 | Guan et al. |
| 2004/0204294 A2 | 10/2004 | Wilkinson et al. |
| 2005/0010150 A1 | 1/2005 | Firsov |
| 2005/0049865 A1 | 3/2005 | Yaxin et al. |
| 2005/0070834 A1 | 3/2005 | Herr et al. |
| 2005/0101448 A1 | 5/2005 | He et al. |
| 2005/0107725 A1 | 5/2005 | Wild |
| 2005/0157893 A1 | 7/2005 | Pelrine et al. |
| 2005/0184878 A1 | 8/2005 | Grold et al. |
| 2005/0288157 A1 | 12/2005 | Santos-Munne et al. |
| 2006/0079817 A1 | 4/2006 | Dewald et al. |
| 2006/0108755 A1 | 5/2006 | Smyler et al. |
| 2006/0136206 A1 | 6/2006 | Ariu et al. |
| 2006/0192465 A1 | 8/2006 | Kornbluh et al. |
| 2006/0249315 A1 | 11/2006 | Herr et al. |
| 2007/0004570 A1 | 1/2007 | Afanasenko et al. |
| 2007/0004571 A1 | 1/2007 | Gonzalez |

(56) References Cited

U.S. PATENT DOCUMENTS

| | | |
|---|---|---|
| 2007/0066918 A1 | 3/2007 | Dewald et al. |
| 2007/0111868 A1 | 5/2007 | Fujii et al. |
| 2007/0123997 A1* | 5/2007 | Herr .................. A61F 2/60 623/27 |
| 2007/0135279 A1 | 6/2007 | Purdy et al. |
| 2007/0276270 A1 | 11/2007 | Tran |
| 2008/0000317 A1 | 1/2008 | Patton et al. |
| 2008/0039756 A1 | 2/2008 | Thorsteinsson et al. |
| 2008/0062589 A1 | 3/2008 | Drabing |
| 2008/0071386 A1 | 3/2008 | McBean et al. |
| 2008/0075930 A1 | 3/2008 | Kornbluh et al. |
| 2008/0097269 A1 | 4/2008 | Weinberg et al. |
| 2008/0156363 A1 | 7/2008 | Ikeuchi et al. |
| 2008/0173365 A1 | 7/2008 | Unger et al. |
| 2008/0218132 A1 | 9/2008 | Pelrine et al. |
| 2008/0224564 A1 | 9/2008 | Pelrine et al. |
| 2008/0255488 A1* | 10/2008 | Agrawal .......... A63B 21/00181 602/23 |
| 2008/0289952 A1 | 11/2008 | Pelrine et al. |
| 2008/0294019 A1 | 11/2008 | Tran |
| 2008/0300118 A1 | 12/2008 | Wehrell |
| 2009/0042702 A1 | 2/2009 | Toronto et al. |
| 2009/0221928 A1 | 9/2009 | Einav et al. |
| 2009/0255531 A1 | 10/2009 | Johnson et al. |
| 2009/0256817 A1 | 10/2009 | Perlin et al. |
| 2009/0306548 A1 | 12/2009 | Bhugra et al. |
| 2009/0319054 A1 | 12/2009 | Sankai |
| 2010/0000547 A1 | 1/2010 | Johnson et al. |
| 2010/0007240 A1 | 1/2010 | Kornbluh et al. |
| 2010/0024180 A1 | 2/2010 | Pei et al. |
| 2010/0026143 A1 | 2/2010 | Pelrine et al. |
| 2010/0030343 A1 | 2/2010 | Hansen et al. |
| 2010/0038983 A1 | 2/2010 | Bhugra et al. |
| 2010/0056966 A1 | 3/2010 | Toth |
| 2010/0113980 A1* | 5/2010 | Herr .................. A61F 2/72 600/587 |
| 2010/0144490 A1 | 6/2010 | Purdy et al. |
| 2010/0152630 A1 | 6/2010 | Matsuoka et al. |
| 2010/0185259 A1 | 7/2010 | Shiba et al. |
| 2010/0185301 A1 | 7/2010 | Hansen et al. |
| 2010/0204804 A1 | 8/2010 | Garrec |
| 2010/0271051 A1 | 10/2010 | Sankai et al. |
| 2010/0274364 A1 | 10/2010 | Pacanowsky |
| 2010/0280628 A1 | 11/2010 | Sankai |
| 2010/0286796 A1 | 11/2010 | Clausen |
| 2010/0298834 A1 | 11/2010 | Hildebrandt |
| 2010/0319215 A1 | 12/2010 | Roser |
| 2010/0324698 A1 | 12/2010 | Sverrisson et al. |
| 2011/0004322 A1 | 1/2011 | Sankai |
| 2011/0009793 A1 | 1/2011 | Lucero |
| 2011/0022349 A1 | 1/2011 | Kulach et al. |
| 2011/0033835 A1 | 1/2011 | Endo et al. |
| 2011/0025170 A1 | 2/2011 | Rosenthal et al. |
| 2011/0040216 A1 | 2/2011 | Herr et al. |
| 2011/0062948 A1 | 3/2011 | Arns, Jr. et al. |
| 2011/0071647 A1 | 3/2011 | Mahon |
| 2011/0093089 A1 | 4/2011 | Martin |
| 2011/0105966 A1 | 5/2011 | Kazerooni et al. |
| 2011/0150966 A1 | 5/2011 | Kazerooni et al. |
| 2011/0152696 A1 | 6/2011 | Ryan |
| 2011/0154641 A1 | 6/2011 | Pelrine et al. |
| 2011/0155307 A1 | 6/2011 | Pelrine et al. |
| 2011/0174524 A1 | 7/2011 | Sharma et al. |
| 2011/0193362 A1 | 8/2011 | Prahlad et al. |
| 2011/0201978 A1 | 8/2011 | Jeon et al. |
| 2011/0209337 A1 | 9/2011 | Pei et al. |
| 2011/0245738 A1 | 10/2011 | Agrawal et al. |
| 2011/0282255 A1 | 11/2011 | Nace |
| 2011/0295384 A1 | 12/2011 | Herr et al. |
| 2011/0295385 A1 | 12/2011 | Herr et al. |
| 2011/0313331 A1 | 12/2011 | Dehez et al. |
| 2012/0019223 A1 | 1/2012 | Pelrine et al. |
| 2012/0023638 A1 | 2/2012 | Leicester |
| 2012/0056903 A1 | 3/2012 | Shinohara et al. |
| 2012/0071797 A1 | 3/2012 | Aoki et al. |
| 2012/0100286 A1 | 4/2012 | Sharma et al. |
| 2012/0109031 A1 | 5/2012 | Vollbrecht |
| 2012/0120544 A1 | 5/2012 | Pelrine et al. |
| 2012/0128960 A1 | 5/2012 | Busgen et al. |
| 2012/0165709 A1 | 6/2012 | Goffer et al. |
| 2012/0169184 A1 | 7/2012 | Pelrine et al. |
| 2012/0177934 A1 | 7/2012 | Vogel et al. |
| 2012/0179075 A1 | 7/2012 | Perry et al. |
| 2012/0181896 A1 | 7/2012 | Kronbluh et al. |
| 2012/0185052 A1 | 7/2012 | Lefeber |
| 2012/0209152 A1 | 8/2012 | Cordo |
| 2012/0238914 A1 | 9/2012 | Goldfield et al. |
| 2012/0248942 A1 | 10/2012 | Biggs et al. |
| 2012/0253234 A1 | 10/2012 | Yang et al. |
| 2012/0271207 A1 | 10/2012 | Schoen et al. |
| 2012/0279175 A1 | 11/2012 | Biggs et al. |
| 2012/0283844 A1* | 11/2012 | Langlois ................ A61F 2/60 623/24 |
| 2012/0289870 A1 | 11/2012 | Hsiao-Wecksler et al. |
| 2012/0330198 A1 | 12/2012 | Patoglu |
| 2013/0013085 A1 | 1/2013 | Smith et al. |
| 2013/0019749 A1 | 1/2013 | Hufton et al. |
| 2013/0040783 A1 | 2/2013 | Duda et al. |
| 2013/0041617 A1 | 2/2013 | Pease et al. |
| 2013/0045530 A1 | 2/2013 | Gracias et al. |
| 2013/0058001 A1 | 3/2013 | Prahlad et al. |
| 2013/0079686 A1 | 3/2013 | Sessions |
| 2013/0093439 A1 | 4/2013 | Ulmen et al. |
| 2013/0102935 A1 | 4/2013 | Kazerooni et al. |
| 2013/0123672 A1 | 5/2013 | Goffer et al. |
| 2013/0130866 A1 | 5/2013 | Wehrell |
| 2013/0131555 A1 | 5/2013 | Hook |
| 2013/0158444 A1 | 6/2013 | Herr et al. |
| 2013/0165817 A1 | 6/2013 | Horst et al. |
| 2013/0179154 A1 | 7/2013 | Okuno |
| 2013/0186699 A1 | 7/2013 | Prahald et al. |
| 2013/0199064 A1 | 8/2013 | O'Kell |
| 2013/0211295 A1 | 8/2013 | Johnson et al. |
| 2013/0225371 A1 | 8/2013 | Harrer et al. |
| 2013/0226048 A1* | 8/2013 | Unluhisarcikli ......... A61H 1/00 601/34 |
| 2013/0230667 A1 | 9/2013 | Sharma et al. |
| 2013/0237884 A1 | 9/2013 | Kazerooni et al. |
| 2013/0245512 A1 | 9/2013 | Goffer et al. |
| 2013/0253385 A1 | 9/2013 | Goffer et al. |
| 2013/0261513 A1 | 10/2013 | Goffer et al. |
| 2013/0261766 A1 | 10/2013 | Langlois et al. |
| 2013/0268256 A1 | 10/2013 | Dariush |
| 2013/0274640 A1 | 10/2013 | Butters et al. |
| 2013/0288863 A1 | 10/2013 | Yamamoto et al. |
| 2013/0289452 A1 | 10/2013 | Smith et al. |
| 2013/0296746 A1* | 11/2013 | Herr .................. A61H 3/00 601/34 |
| 2013/0307370 A1 | 11/2013 | Jenninger et al. |
| 2013/0310979 A1 | 11/2013 | Herr et al. |
| 2013/0312541 A1 | 11/2013 | Majidi et al. |
| 2013/0328440 A1 | 12/2013 | Kornbluh et al. |
| 2014/0046455 A1 | 2/2014 | Herr et al. |
| 2014/0194781 A1 | 7/2014 | Einarsson et al. |
| 2014/0213951 A1* | 7/2014 | Pietrusisnki ............ A61H 1/024 602/23 |
| 2014/0277739 A1 | 9/2014 | Kombluh et al. |
| 2014/0358040 A1 | 12/2014 | Kim et al. |
| 2015/0099945 A1 | 4/2015 | Hawkins, III et al. |
| 2015/0142130 A1* | 5/2015 | Goldfarb ................ A61H 1/024 623/25 |
| 2015/0173993 A1 | 6/2015 | Walsh et al. |
| 2015/0266180 A1 | 9/2015 | Kornbluh et al. |
| 2015/0266181 A1 | 9/2015 | Kornbluh et al. |
| 2015/0297934 A1 | 10/2015 | Agrawal et al. |
| 2015/0298765 A1 | 10/2015 | Golden, Jr. |
| 2015/0321339 A1 | 11/2015 | Asbeck et al. |
| 2015/0321399 A1 | 11/2015 | Hong et al. |
| 2016/0346156 A1 | 1/2016 | Walsh et al. |
| 2016/0101516 A1 | 4/2016 | Kornbluh et al. |
| 2016/0101517 A1 | 4/2016 | Kornbluh et al. |
| 2016/0107309 A1* | 4/2016 | Walsh .................. A61H 3/00 248/550 |
| 2016/0220438 A1 | 8/2016 | Walsh et al. |

(56) References Cited

U.S. PATENT DOCUMENTS

| | | | |
|---|---|---|---|
| 2016/0278948 A1 | 9/2016 | Piercy et al. | |
| 2016/0284231 A1 | 9/2016 | Walsh et al. | |
| 2017/0027735 A1 | 2/2017 | Walsh et al. | |
| 2017/0163435 A1 | 6/2017 | Ehsani et al. | |
| 2017/0176167 A1 | 6/2017 | Keller et al. | |
| 2018/0008502 A1* | 1/2018 | Asbeck ................... | A61F 5/01 |
| 2018/0056104 A1 | 3/2018 | Cromie et al. | |
| 2018/0370020 A1 | 12/2018 | Murakami et al. | |
| 2019/0008714 A1 | 1/2019 | Murakami et al. | |
| 2019/0021933 A1 | 1/2019 | Murakami et al. | |
| 2019/0029912 A1 | 1/2019 | Murakami et al. | |
| 2019/0060156 A1 | 2/2019 | Swift et al. | |
| 2019/0060157 A1 | 2/2019 | Lamb et al. | |
| 2019/0070062 A1 | 3/2019 | O'Donnell et al. | |

FOREIGN PATENT DOCUMENTS

| | | |
|---|---|---|
| CN | 202342034 | 7/2012 |
| CN | 101175456 | 3/2013 |
| CN | 102327173 | 5/2013 |
| DE | 19944139 | 4/2001 |
| DE | 20 2012 100 952 U1 | 4/2012 |
| EP | 0016268 | 10/1980 |
| EP | 0141640 | 10/1984 |
| EP | 0302148 | 2/1989 |
| EP | 0509723 A1 | 10/1992 |
| EP | 1306792 | 5/2003 |
| EP | 1324403 | 7/2003 |
| EP | 1260201 | 12/2008 |
| EP | 2226053 | 9/2010 |
| EP | 1842518 | 9/2011 |
| EP | 1589059 | 6/2012 |
| EP | 2497610 | 9/2012 |
| EP | 2548543 | 1/2013 |
| EP | 1550689 | 4/2013 |
| EP | 2649976 | 10/2013 |
| GB | 2 516 073 A | 1/2015 |
| JP | H07163607 A | 6/1995 |
| JP | 2002301124 A | 10/2002 |
| JP | 2005000500 A | 1/2005 |
| JP | 2007000391 A | 1/2007 |
| JP | 2008067762 | 3/2008 |
| JP | 4345025 | 10/2009 |
| JP | 2010042069 A | 2/2010 |
| JP | 2010-051416 | 3/2010 |
| JP | 4424269 | 3/2010 |
| JP | 2010075656 A | 4/2010 |
| JP | 4582523 | 11/2010 |
| JP | 2011/036375 | 2/2011 |
| JP | 4848260 | 12/2011 |
| JP | 2012/192013 | 10/2012 |
| JP | 2013146328 A | 8/2013 |
| JP | 2013-208397 A | 10/2013 |
| JP | 2014018536 A | 2/2014 |
| JP | 2014034145 A1 | 3/2014 |
| WO | WO 97/12646 A1 | 4/1997 |
| WO | WO 00/12041 A2 | 3/2000 |
| WO | WO2004/017890 | 3/2004 |
| WO | WO2004/039292 | 5/2004 |
| WO | WO2004/047928 | 6/2004 |
| WO | WO2005/102208 | 11/2005 |
| WO | WO2011/008934 | 1/2011 |
| WO | WO2011/026086 | 3/2011 |
| WO | WO2011/030641 | 3/2011 |
| WO | 2011126985 A2 | 10/2011 |
| WO | 2012014164 A2 | 2/2012 |
| WO | WO2012/050938 | 4/2012 |
| WO | WO2012/103073 | 8/2012 |
| WO | WO2012/124328 | 9/2012 |
| WO | WO2012/178171 | 12/2012 |
| WO | WO2013/019749 | 2/2013 |
| WO | 2013033669 A2 | 3/2013 |
| WO | WO2013/033669 | 3/2013 |
| WO | WO2013/044226 | 3/2013 |
| WO | 2013049658 A1 | 4/2013 |
| WO | WO 2013/146231 A1 | 10/2013 |
| WO | WO2014/109799 | 7/2014 |
| WO | WO2014/194257 | 12/2014 |
| WO | WO 2015/074070 A1 | 5/2015 |
| WO | WO2015/120186 | 8/2015 |
| WO | WO2015/157731 | 10/2015 |
| WO | WO2015/088863 | 12/2015 |
| WO | WO 2016/044251 A1 | 3/2016 |
| WO | WO2016/089466 | 6/2016 |
| WO | 2017040669 | 3/2017 |
| WO | 2017160751 A1 | 9/2017 |
| WO | 2018017436 A1 | 1/2018 |

OTHER PUBLICATIONS

Supplementary European Search Report issued in European Application No. 15 77 6544 dated Oct. 20, 2017.
USPTO Office Action in U.S. Appl. No. 14/660,704 dated Feb. 7, 2018.
Ghodsi et al. "De novo Likelihood-based measures for comparing genome assemblies" In: BMC Research Notes 2013, Aug. 22, 2013—online retrieved on Oct. 25, 16.
Malcolm, Philippe et al., "Fast Exoskeleton Optimization" Science, vol. 356, Issue 6344, pp. 1230-1231, Jun. 23, 2017.
Polonen et al. "Automatic Intensity Quantification of Fluorescence Targets from microscope Images with Maximum Likelihood Estimation" 17th European Signal Processing Conference, Aug. 24-28, 2009—retrieved online Oct. 25, 2016.
Zhang, Juanjuan et al., "Human-in-the-Loop Optimization of Exoskeleton Assistance During Walking", Science, vol. 356, pp. 1280-1284, Jun. 23, 2017.
PCT International Search Report and Written Opinion in International Application No. PCT/US2015/051107, dated Aug. 5, 2016.
PCT International Search Report and Written Opinion in International Application No. PCT/US2016/049706, dated Nov. 29, 2016.
Extended European Search Report issued in European Application No. 14803880.5 dated May 19, 2017.
PCT International Search Report and Written Opinion in International Application No. PCT/US2017/022150, dated Jun. 9, 2017.
Banala, S K et al., "Active leg exoskeleton (alex) for gait rehabilitation of motor-impaired patients," in. Proc. 2007 IEEE 10th Int. Conf. Rehabil Robotics, pp. 401-407, Jun. 2007.
Browning, R. C. et al., "The effects of adding mass to the legs on the energetics and biomechanics of walking," Medicine and science in sports and exercise, Col. 39, p. 515, 2007.
Chu, a. et al, on the biomimetric design of the Berkeley lower extremity exoskeleton (BLEEX), Proc 2005 in IEEE Int. Conf. Robotics and Automation (ICRA) (IEEE Press, Barcelona, Spain, Apr. 2006), pp. 4356-4363.
Clevertex,: Development of strategic Master Plan for the transformation of the traditional textile and clothing into a knowledge driven industrial sector by 2015, 160 pages, dated prior to Jul. 2014.
Collins, S., et al., Efficient Bipedal Robots Based on Passive-Dynamic Walkers. Science, 307(5712): p. 1082-1085, 2005.
Cool, J.C. Biomechanics of orthoses for the subluxed shoulder. Prosthetics & Orthotics International; 13:90- 6, 1989.
Da Silva, A. F. et al., "FBG Sensing Glove for Monitoring Hand Posture," IEEE Sensors Journal, . . . , vol. 11, No. 10, pp. 2442-2448, Oct 2011. [Online]. Available: http://ieeexplore.ieee.org/xpls/absall.jsp?arnumber=5742669.
De Rossi, D. et al., "Wearable technology for biomechanics: e-textile or micromechanical sensors?" IEEE engineering in medicine and biology magazine, vol. 29, No. 3, pp. 37-43, May/Jun. 2010. [Online]. Available: http://www.ncbi.nlm.nih.gov/pubmed/20659856.
Delp, S. L. et al., "OpenSim: open-source software to create and analyze dynamic simulations of movement." IEEE transactions on bio-medical engineering, vol. 54, No. 11, pp. 1940-50, Nov. 2007. [Online]. Available: http://www.ncbi.nlm.nih.gov/pubmed/18018689.
Dollar, A. M. et al., "Lower extremity exoskeletons and active orthoses: Challenges and state-of-the-art,", IEEE Transactions on Robotics, vol. 24, No. 1, pp. 144-158, Feb. 2008.

(56) References Cited

OTHER PUBLICATIONS

Erk, K. A. et al., "Strain stiffening in synthetic and biopolymer networks," Biomacromolecules, vol. 11, No. 5, pp. 1358-1363, May 2010.
Farris D.J., et al., Human medial gastrocnemius force-velocity behavior shifts with locomotion speed and gait. Proc Natl Acad Sci USA. Jan. 2012; 109:977-982.
Ferris, D. P. et al., "Robotic lower limb exoskeletons using proportional myoelectric control," in EMBC 2009, Annual International Conference of the IEEE Engineering in Medicine and Biology Society, 2009.
Ferris, D.P. et al., A Physiologist's Perspective on Robotic Exoskeletons for Human Locomotion. Int J HR, 4(3): p. 507-528, 2007.
Gibbs, P. et al.: Wearable Conductive Fiber Sensors for Multi-Axis Human Joint Angle Measurements. Journal of NeuroEngineering and Rehabilitation, Mar. 2, 2005.
Goodvin, C.I.: Development of a Real-time Spinal Motion Inertial Measurement System for Vestibular Disorder Application, University of Victoria, 155 pages, date 2003.
Gregorczyk, K. N., et al., The effects of a lower body exoskeleton load carriage assistive device on oxygen consumption and kinematics during walking with loads, in 25th Army Sci. Conf., Florida, USA, 2006.
Hallemans, A. et al.: 3D joint dynamics of walking in toddlers. A cross-sectional study spanning the first rapid development phase of walking Gait & Posture, 22:107-118, 2005.
Kadaba, M. P., et al., "Measurement of lower extremity kinematics during level walking." Journal of orthopaedic research: official publication of the Orthopaedic Research Society, vol. 8, No. 3, pp. 383-392, May 1990. [Online]. Available: http://www.ncbi.nlm.nih.gov/pubmed/2324857.
Kawamoto, H., et al., Power assist method for HAL-3 using EMG-based feedback controller. In Systems, Man and Cybernetics, 2003. IEEE International Conference on. 2003.
Kim, D.-H. et al., "Epidermal electronics." Science, vol. 333, No. 6044, pp. 838-843, Aug. 2011. [Online] Available: http://www.sciencemag.org/cgi/doi/10.1126/science.1206157.
Kramer, R. K. et al., "Soft curvature sensors for joint angle proprioception," in 2011 IEEE/RSJ International Conference on Intelligent Robots and Systems. IEEE, pp. 1919-1926, Sep 2011. [Online]. Available: http://ieeexplore.ieee.org/lpdocs/epic03/wrapper.htm?arnumber=6094701.
Kramer, R. K. et al., "Wearable tactile keypad with stretchable artificial skin," 2011 IEEE International Conference on Robotics and Automation, pp. 1103-1107, May 2011. [Online]. Available: http://ieeexplore.ieee.org/lpdocs/epic03/wrapper.htm?arnumber=5980082.
Kulyukin, V. A.: Advances in Human-Robot Interaction, 354 pages, Dec. 2009.
Lee, S. W. et al.: Biomimetic Approach Enables Functional Movements of Hand Post Stroke: A Pilot Study, 2 pages, dated 2012.
Lipomi, D. J. et al., "Skin-like pressure and strain sensors based on transparent elastic films of carbon nanotubes." Nature nanotechnology, vol. 6, No. 12, pp. 788-792, Jan. 2011. [Online]. Available: http://www.ncbi.nlm.nih.gov/pubmed/22020121.
Majidi, C. et al., "A non-differential elastomer curvature sensor for softer-than-skin electronics," Smart Materials and Structures, vol. 20, No. 10, p. 105017, Oct. 2011. [Online]. Available: http://stacks.iop.org/0964-1726/20/i=10/a=105017?key=crossref.0cca7e97d6ad7110bcdcaf45f30f3b60.
Mattila, H. R., Intelligent textiles and clothing, Woodhead Publishing Limited, 525 pages, © 2006.
McGeer, T., Passive Bipedal Running. Proceedings of the Royal Society of London. Series B, Biological Sciences, 240(1297): p. 107-134, May 1990.
Newman, D. J. et al., Astronaut Bio-Suit System to Enable Planetary Exploration. In International Astronautical Conference, Vancouver, Canada, Oct. 2004.
Park, Y. L. et al., Active Modular Elastomer Sleeve for Soft Wearable Assistance Robots, 2012 IEEE/RSJ International Con. on Intelligent Robots and Systems Vilamoura, Algarve, Portugal, 8 pages, Oct. 7-12, 2012.
Park, Y.-L., et al., "Design and Fabrication of Soft Artificial Skin Using Embedded Microchannels and Liquid Conductors," IEEE Sensors Journal, vol. 12, No. 8, pp. 2711-2718, Aug. 2012. [Online]. Available: http://ieeexplore.ieee.org/lpdocs/epic03/wrapper.htm?arnumber=6203551.
Park, Y.-L., "Hyperelastic pressure sensing with a liquid-embedded elastomer," Journal of Micromechanics and Microengineering, vol. 20, No. 12, p. 125029, Dec. 2010. [Online]. Available: http://stacks.iop.org/0960-1317/20/i=12/a=125029?key=crossref.84cffc44789ba7bde0bdfd169e25af91.
Park, Y.-L., et al.: Bio-inspired Active Soft Orthotic Device for Ankle Foot Pathologies, 2011 IEEE/RSJ International Conference on Intelligent Robots and Systems, San Francisco, CA, USA, 8 pages, Sep. 25-30, 2011.
Pereira da Fonseca, P. F.: Validation of two types of textile electrodes for electrocardiography and electromyography measurement applications, 126 pages, dated Jul. 2012.
Pratt, J. et al., The RoboKnee: An exoskeleton for enhancing strength and endurance during walking, in IEEE Int. Conf. Robotics and Automation (ICRA), New Orleans, USA (IEEE Press), pp. 2430-2435, Apr. 2004.
Quintero, H. A. et al., "Control and Implementation of a Powered Lower Limb Orthosis to Aid Walking in Paraplegic Individuals," in IEEE International Conference on Rehabilitation Robotics, Switzerland, pp. 1-6, Jun. 29-Jul. 1, 2011.
Ramuz, M. et al., "Transparent, Optical, Pressure-Sensitive Artificial Skin for Large-Area Stretchable Electronics," Advanced Materials, May 2012. [Online]. Available: http://doi.wiley.com/10.1002/adma.201200523.
Reid, S. A. et al., "Biomechanical assessment of rucksack shoulder strap attachment location: effect on load distribution to the torso," presented at the RTO HFM specialists' Meeting on "Soldier Mobility: Innovations in Load Carriage System Design and Evaluation," NATO-RTO Meeting Proceedings: MP-056 (Neuilly-sur-Seine: NATO). Jun. 1-6, 2000.
Royer, T.D. et al., (2005) Manipulations of Leg Mass and Moment of Inertia: Effects on Energy Cost of Walking, Medicine & Science in Sports & Exercise, vol. 37. No. 4: p. 649-656, 2005.
Salvendy, G.: Smart Clothing Technology and Applications, Human Factors and Ergonomics, by Taylor and Francis Group, LLC, 290 pages, © 2010.
Schiele, A. "Ergonomics of Exoskeletons: Objective Performance Metrics" in Euro Haptics conference and symposium on Haptic Interfaces for Virtual Environmental Teleoperator Systems, Salt Lake City, UT, USA, Mar. 2009.
Scilingo, E. P. et al., "Strain-sensing fabrics for wearable kinaesthetic-like systems," IEEE Sensors Journal, vol. 3, No. 4, pp. 460-467, Aug. 2003. [Online]. Available: http://ieeexplore.ieee.org/lpdocs/epic03/wrapper.htm?arnumber=1226639.
Silva, H. R., et al.: Wireless Hydrotherapy Smart-Suit Network for Posture Monitoring, 5 pages, dated 2007.
Strauser, K. A. et al., "The development and testing of a human machine interface for a mobile medical exoskeleton" in IEEE Int Conf, Intelligent Robots and Systems, San Francisco, CA. USA, Sep. 2011.
Tesconi, M., et al., "Wearable sensorized system for analyzing the lower limb movement during rowing activity," 2007 IEEE International Symposium on Industrial Electronics, pp. 2793-2796, Jun. 2007. [Online]. Available: http://ieeexplore.ieee.org/lpdocs/epic03/wrapper.htm?arnumber=4375052.
Tiwana, M. I., et al., "A review of tactile sensing technologies with applications in biomedical engineering," Sensors and Actuators A: Physical, vol. 179, pp. 17-31, Jun. 2012. [Online]. Available: http://linkinghub.elsevier.com/retrieve/pii/S0924424712001641.
Vogt, D. M., et al., Design and Characterization of a Soft Multi-Axis Force Sensor Using Embedded Microfludic Channels, IEEE Sensors Journal, vol. 13. No. 10, 9 pages, Oct. 2013.

(56) References Cited

OTHER PUBLICATIONS

Walsh, C. J., et al., A Quasi-Passive Leg Exoskeleton for Load Carrying Augmentation. International Journal of Humanoid Robotics, Special Issue: Active Exoskeletons, 4(3): 487-506, 2007.
Wehner, M., 2012 "Man to Machine, Applications in Electromyography," EMG Methods for Evaluation Muscle and Nerve Functions. Intech Publishing, Sep. 13, 2012 http://intechopen.com/articles/show/title/man-to-machine-applications-in-electromyography.
Wehner, M., et al., "Experimental characterization of components for active soft orthotics," in Proc. IEEE. Int. Conf. Biomed. Rob. Biomechatron., Roma, Italy, Jun. 2012.
Wehner, M., et al., "Lower Extremity Exoskeleton Reduces Back Forces in Lifting" ASME Dynamic Systems and Control Conference, Hollywood, California, USA pp. 49-56, Oct. 12-14, 2009.
Woodman, O.J. "An introduction to inertial navigation," Technical Report UCAM-CL-TR-696, Aug. 2007.
Yamada, T. et al., "A stretchable carbon nanotube strain sensor for human-motion detection." Nature Nanotechnology, vol. 6, No. 5 pp. 296-301, May 2011. [Online]. Available: http://ncbi.nlm.nih.gov/pubmed/21441912.
Zhang, R. et al., "Carbon nanotube polymer coatings for textile yarns with good strain sensing capability," Sensors and Actuators A: Physical, vol. 179, pp. 83-91, Jun. 2012. [Online]. Available: http://linkinghub.elsevier.com/retrieve/pii/S0924424712001938.
Zoss, A.B., et al., Biomechanical design of the Berkeley lower extremity exoskeleton (BLEEX), IEE/ASME Transactions on Mechatronics, 11(2): p. 128-138, Apr. 2006.
PCT International Search Report, issued in International Application No. PCT/EP2003/012123, dated Jun. 22, 2004.
PCT International Search Report, issued in International Application No. PCT/US2013/060225, dated May 27, 2014.
PCT International Written Opinion, in International Application No. PCT/US2013/060225, dated May 27, 2014.
PCT International Search Report, issued in International Application No. PCT/US2014/040340, dated Oct. 31, 2014.
PCT International Written Opinion, in International Application No. PCT/US2014/040340, dated Oct. 31, 2014.
PCT International Search Report, issued in International Application No. PCT/US2014/068462, dated May 22, 2015.
PCT International Written Opinion, in International Application No. PCT/US2014/068462, dated May 22, 2015.
PCT International Search Report, issued in International Application No. PCT/US2015/014672, dated Jul. 6, 2015.
PCT International Written Opinion, in International Application No. PCT/US2015/014672, dated Jul. 6, 2015.
PCT International Search Report, issued in International Application No. PCT/US2015/025472, dated Sep. 4, 2015.
PCT International Written Opinion, in International Application No. PCT/US2015/025472, dated Sep. 4, 2015.
PCT International Search Report and Written Opinion issued in International Application PCT/US2015/051107 dated Aug. 5, 2016.
Extended European Search Report issued in European Application No. 13871010.8 dated Sep. 2, 2016.
Extended European Search Report issued in European Application No. 15746146.8 dated Feb. 27, 2018.
USPTO Office Action in U.S. Appl. No. 14/660,704 dated Jun. 28, 2018.
USPTO Office Action in U.S. Appl. No. 15/117,034 dated Oct. 5, 2018.
USPTO Office Action in U.S. Appl. No. 14/660,704 dated Nov. 8, 2018.
International Search Report and Written Opinion for International Application No. PCT/US2019/033143, dated Oct. 9, 2019.
International Search Report and Written Opinion for International Application No. PCT/US2018/022494, dated Jun. 8, 2018.
Bae et al., A Soft Exosuit for Patients with Stroke: Feasibility study with a mobile off-board actuation unit. 2015 IEEE International Conference on Rehabilitation Robotics (ICORR). Aug. 11, 2015; 131-8.
Laughton et al., Effect of Strike Pattern and Orthotic Intervention on Tibial Shock During Running. Journal of Applied Biomechanics. May 1, 2003; 19(2): 153-68.
Lenhart et al., Increasing Running Step Rate Reduces Patellofemoral Joint Forces. Medicine & Science in Sports & Exercise. Mar. 2014; 46(3): 557-64.
Lieberman et al., Effects of stride frequency and foot position in landing on braking force, hip torque, impact peak force and the metabolic cost of running in humans. Journal of Experimental Biology. Nov. 1, 2015; 218(21):3406-14.
Sinclair et al., Determination of Gait Events Using an Externally Mounted Shank Accelerometer. Journal of Applied Biomechanics. Feb. 1, 2013; 29(1): 118-22.

\* cited by examiner

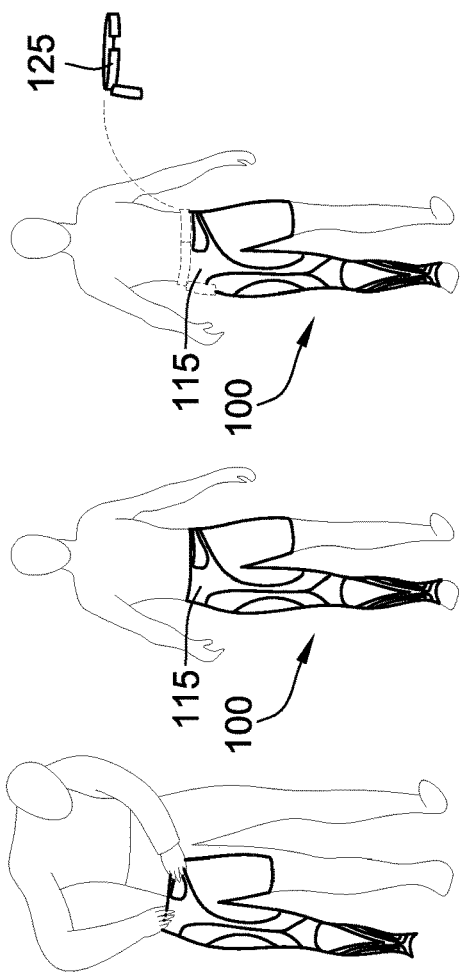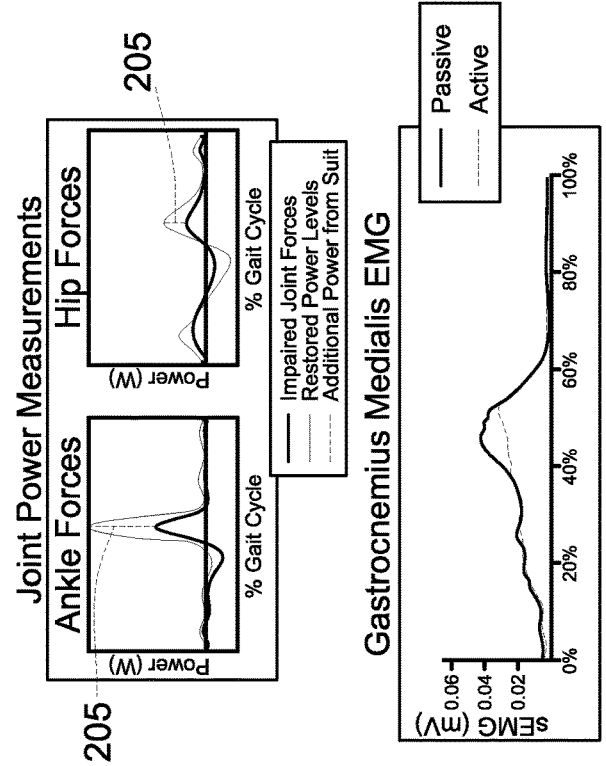
FIG. 1C
FIG. 1D
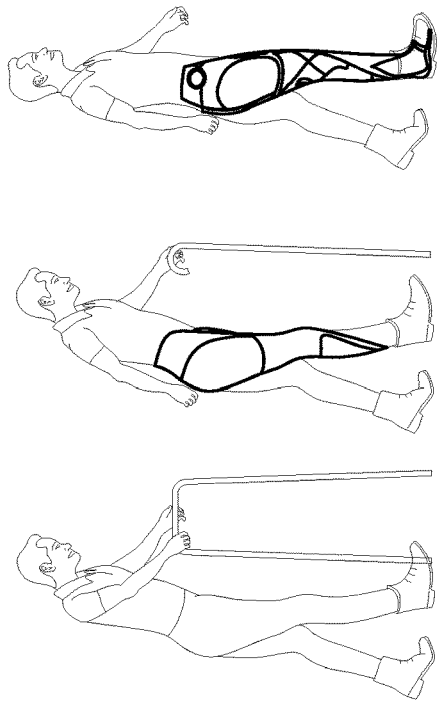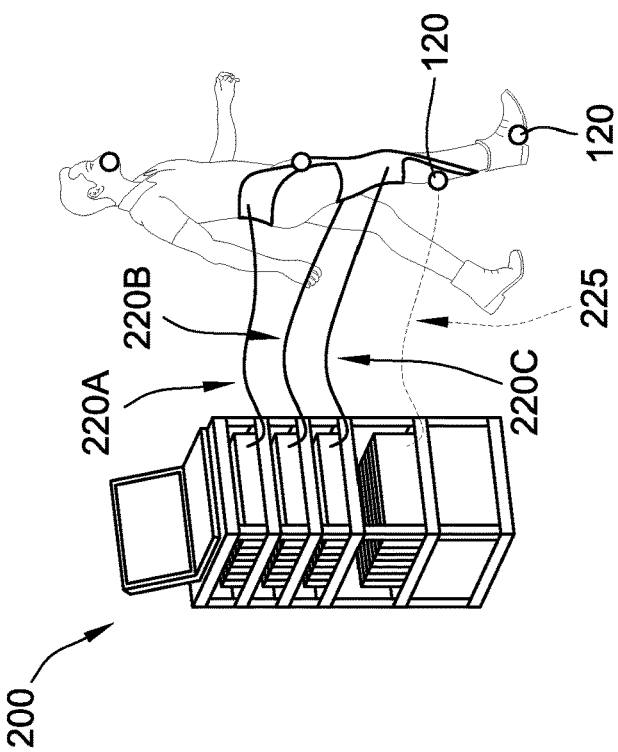

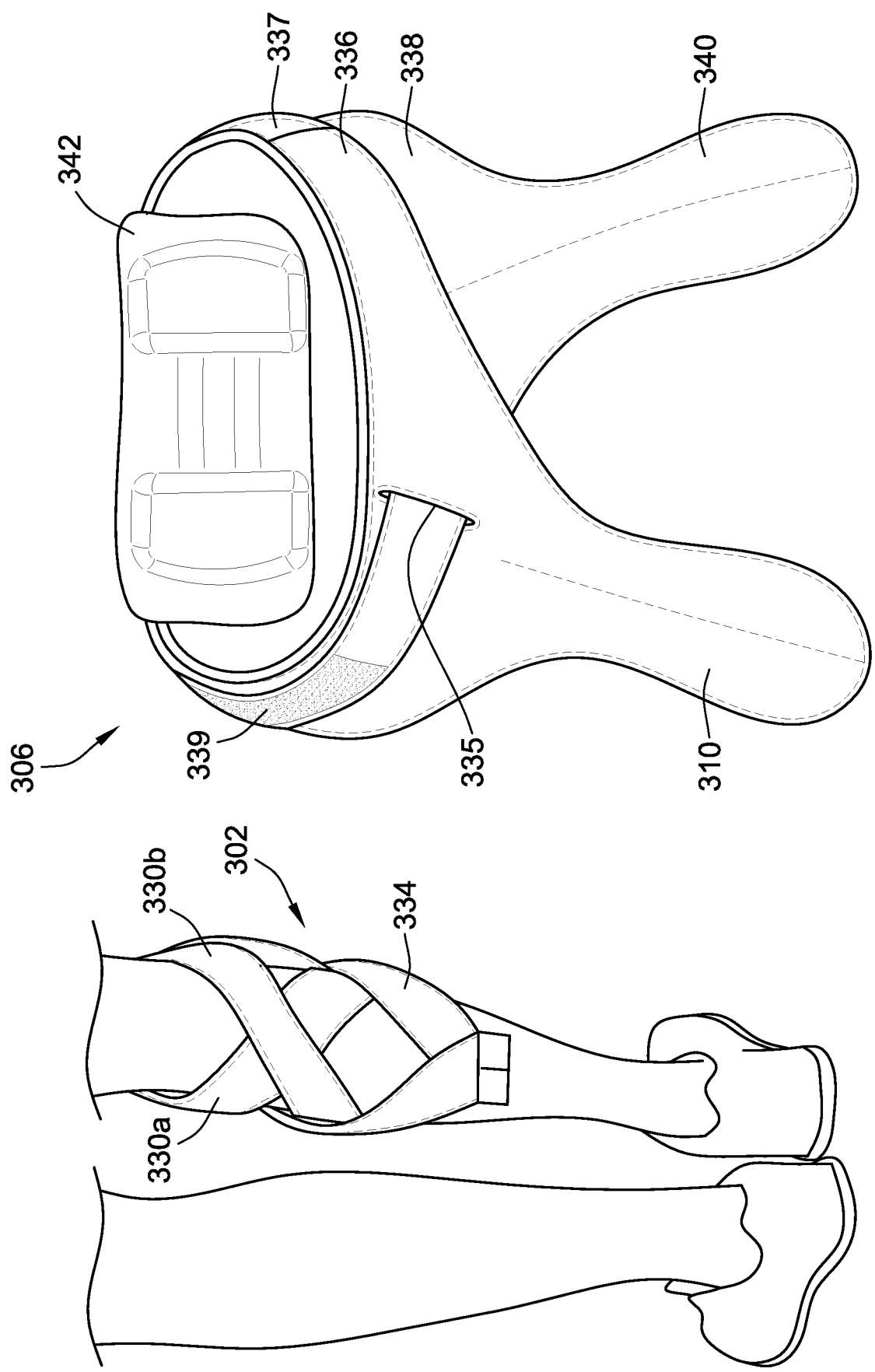

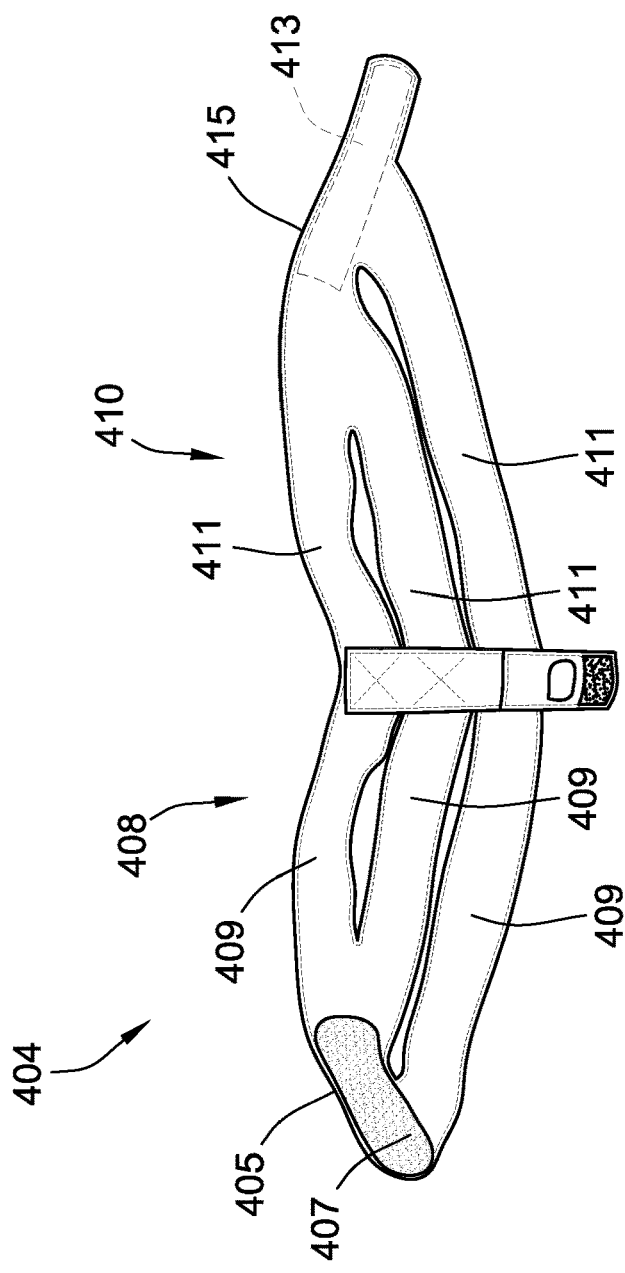
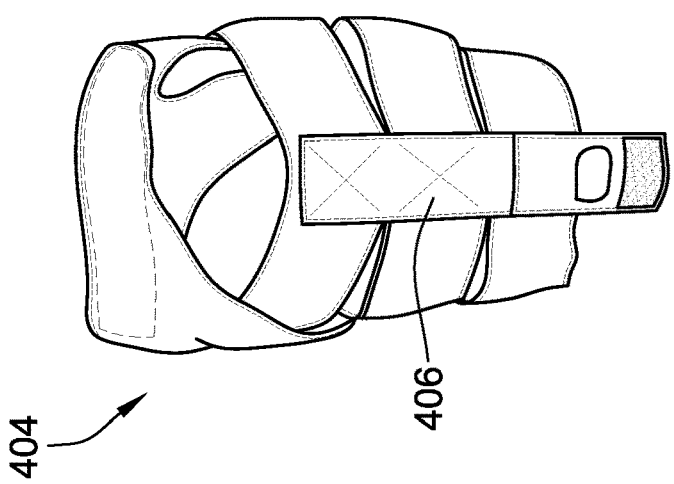
FIG. 4B
FIG. 4A

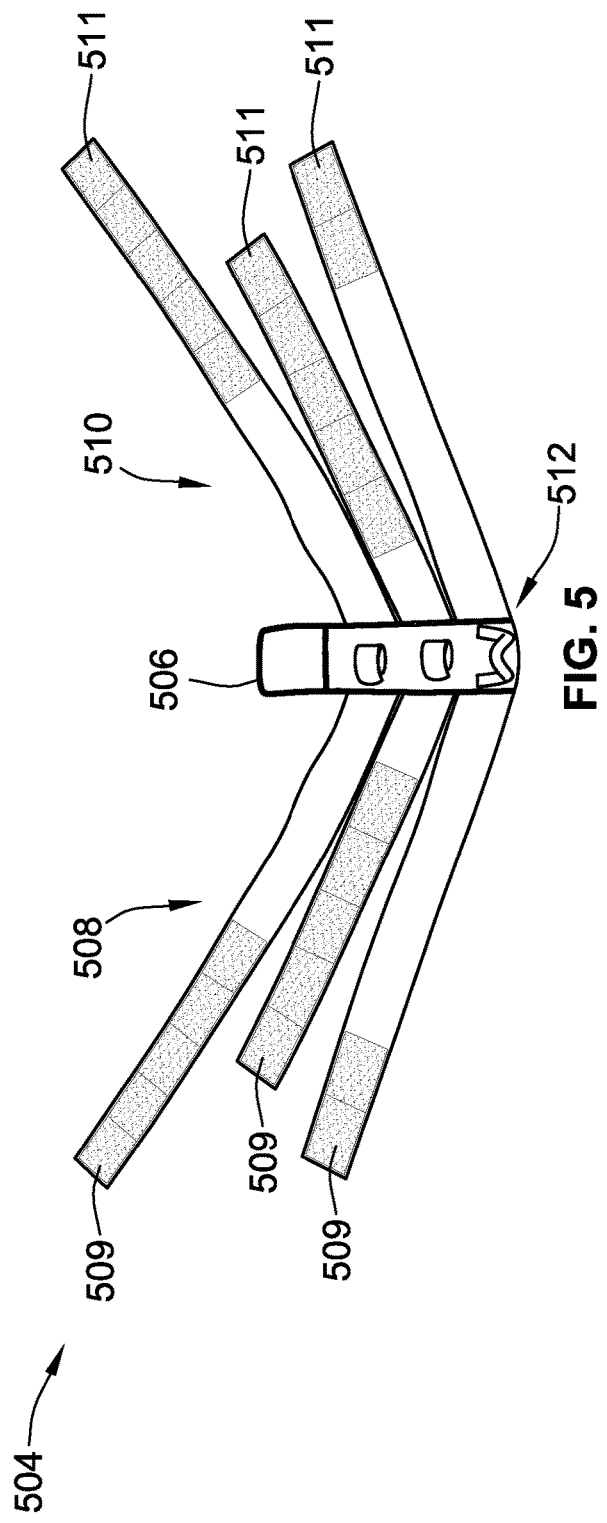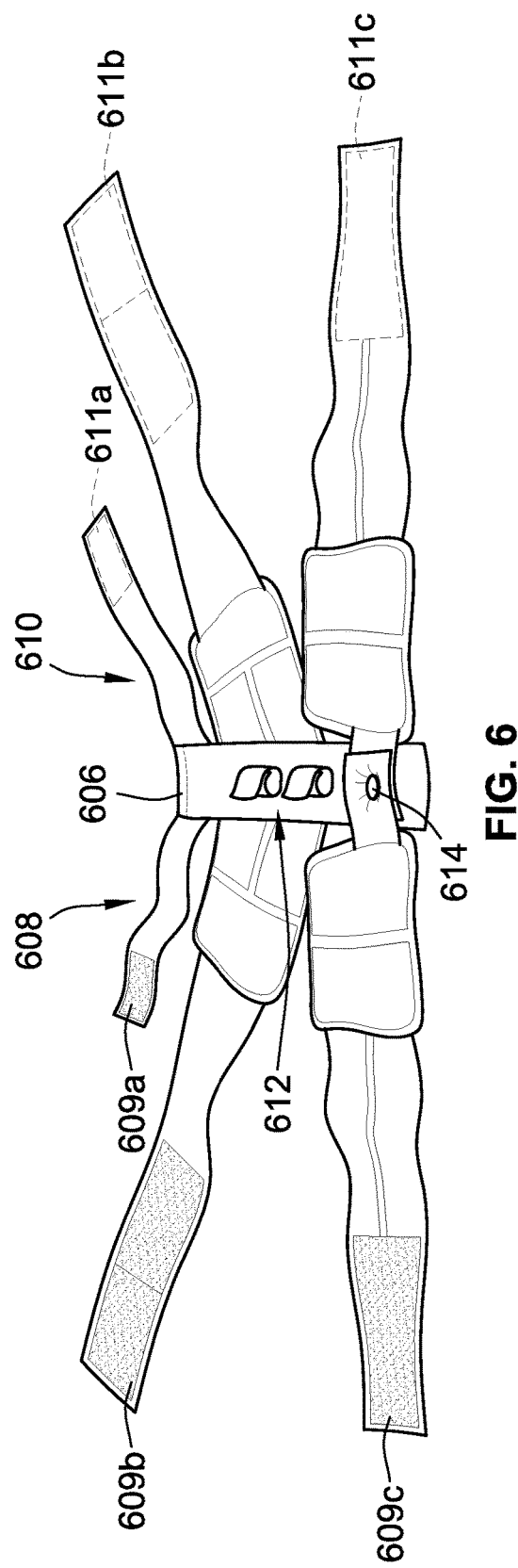
FIG. 5
FIG. 6

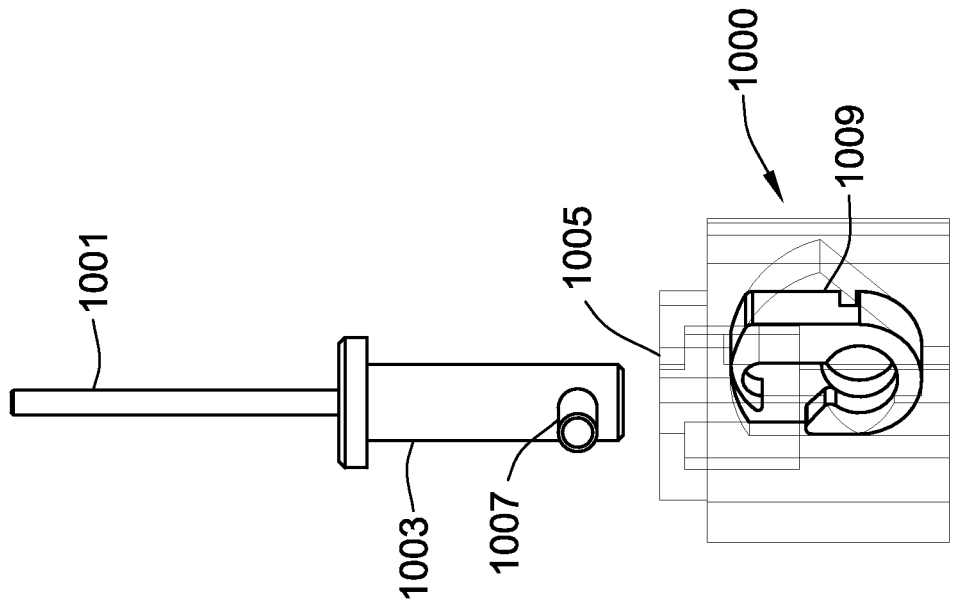
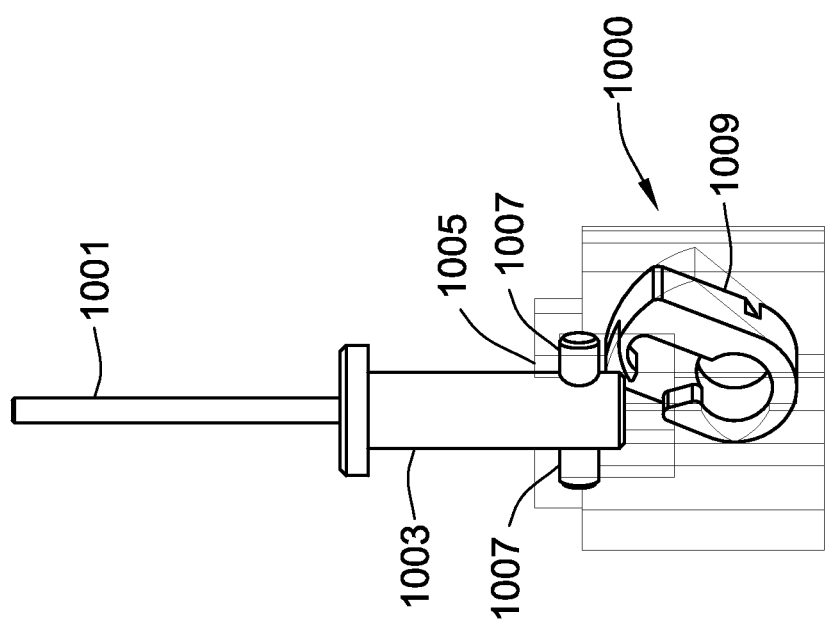

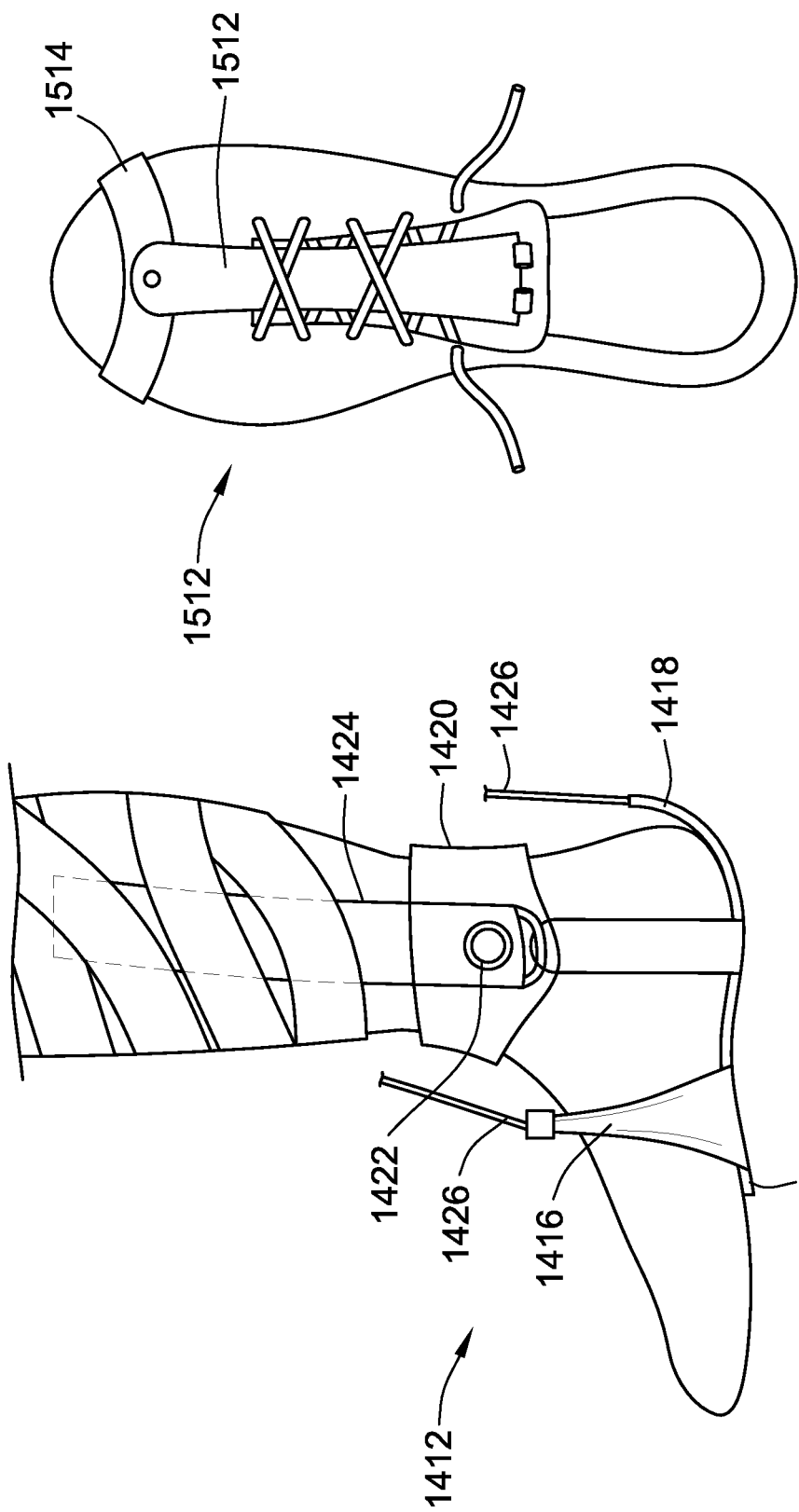

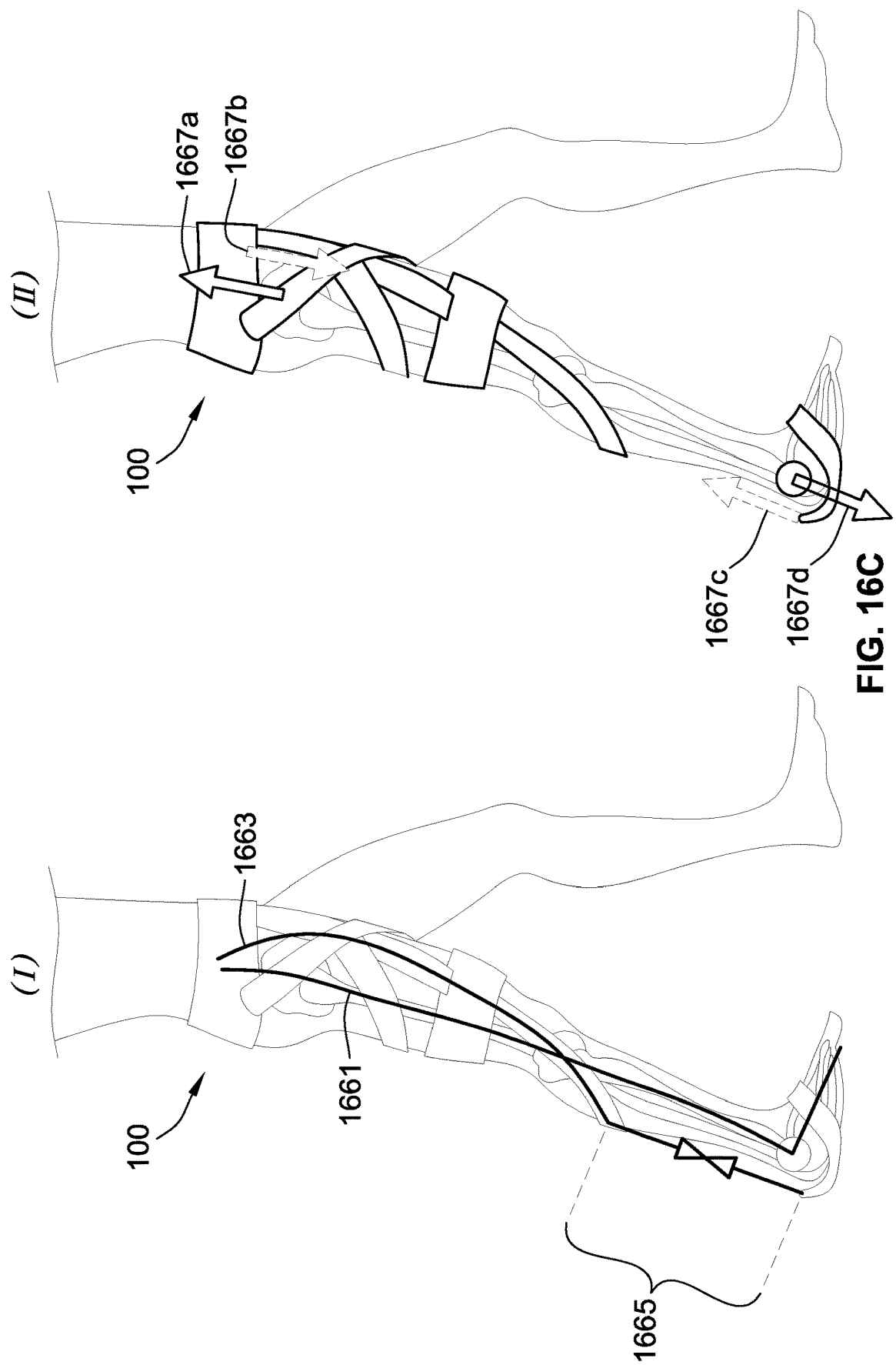

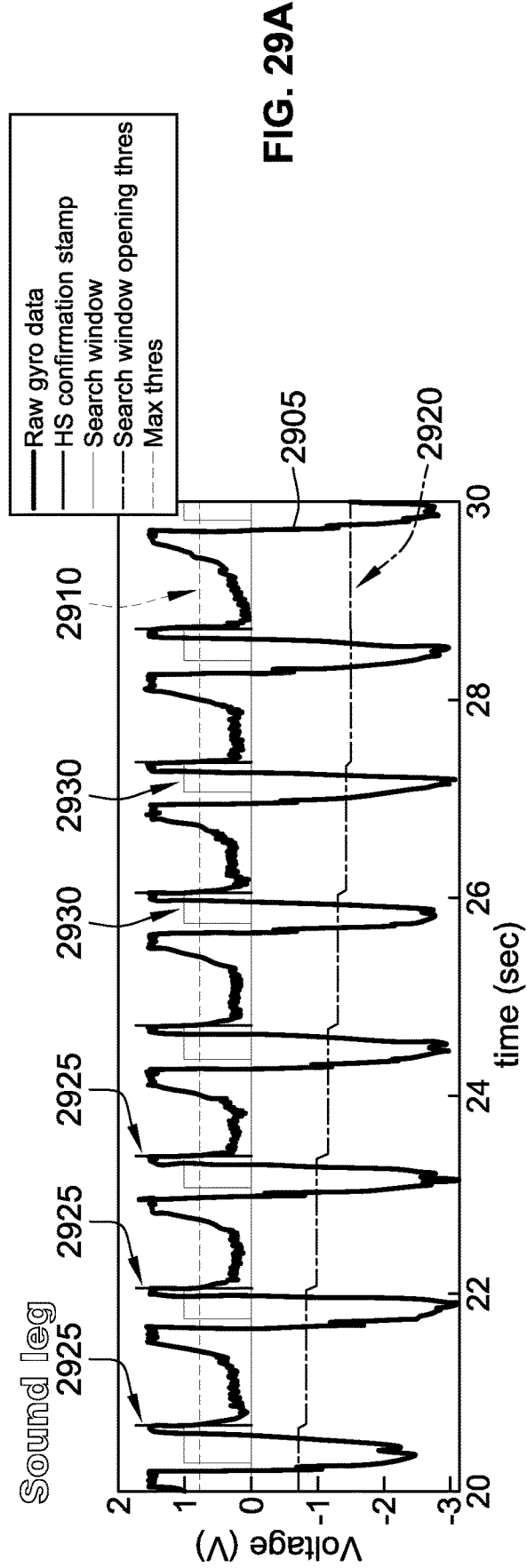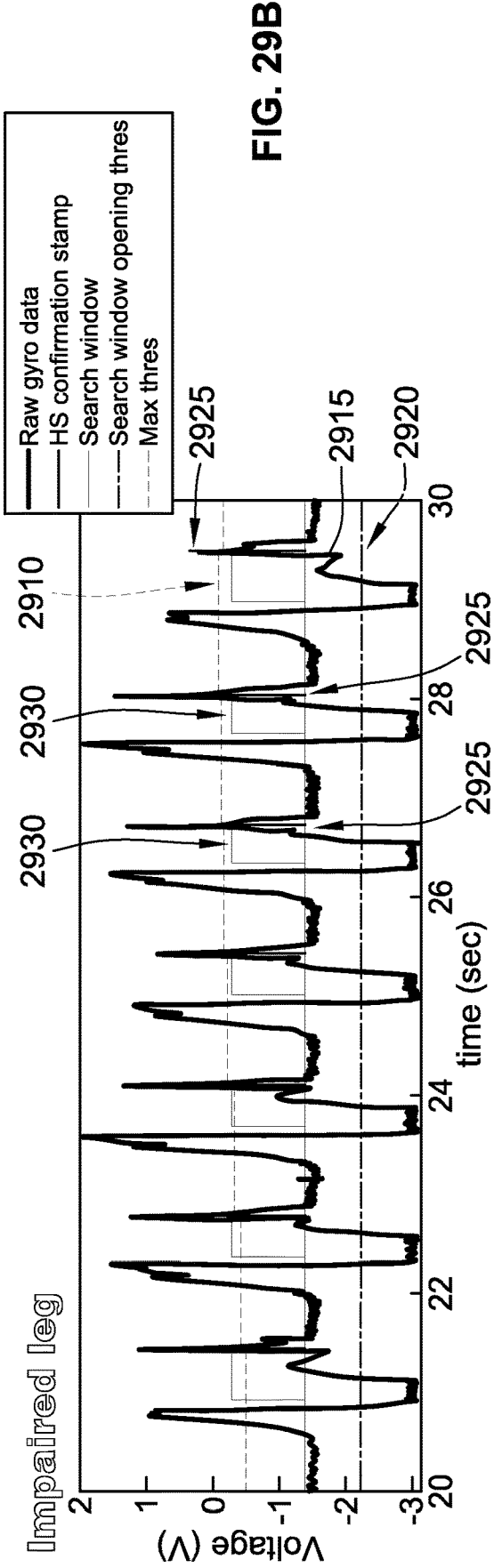

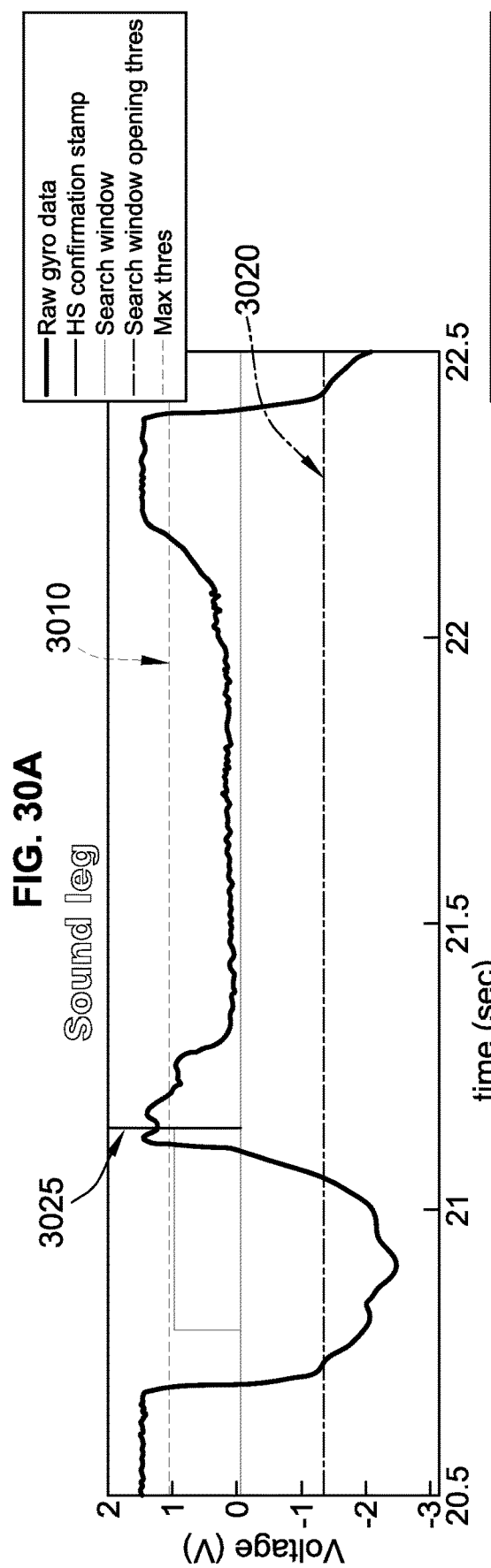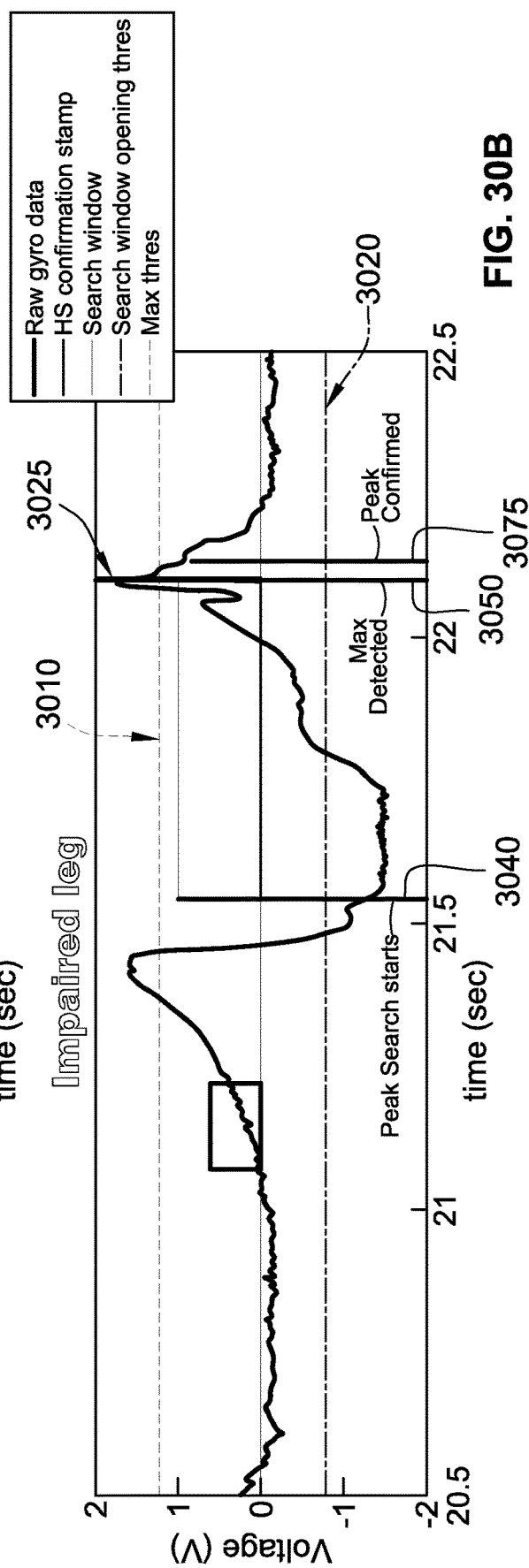

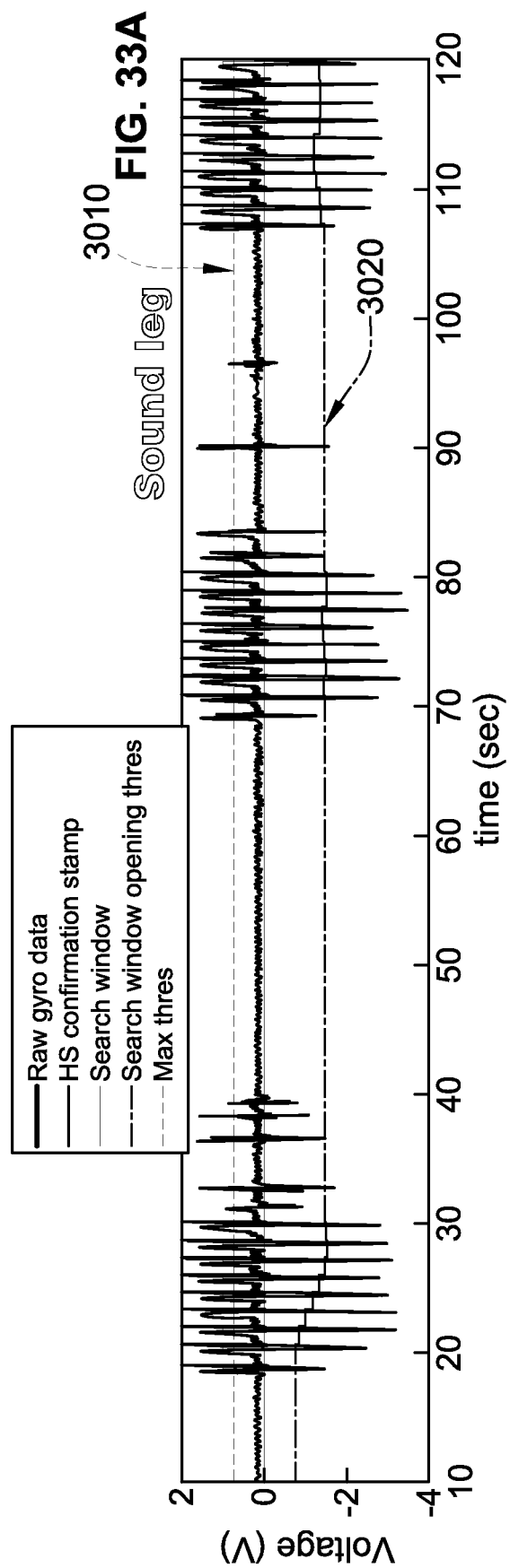
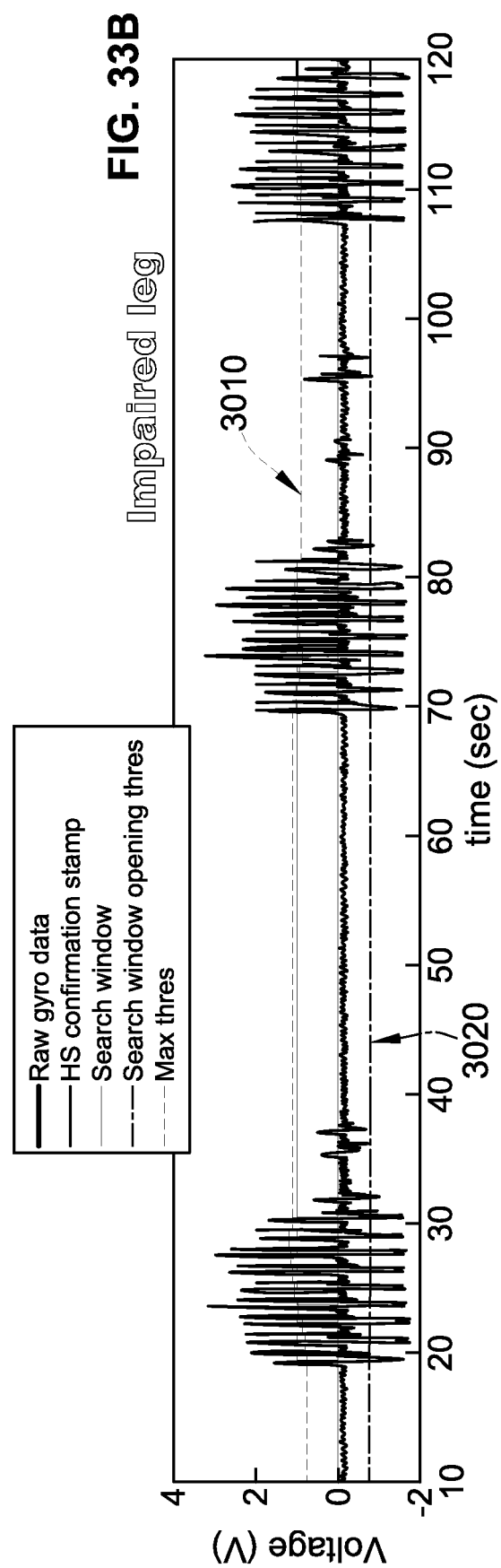

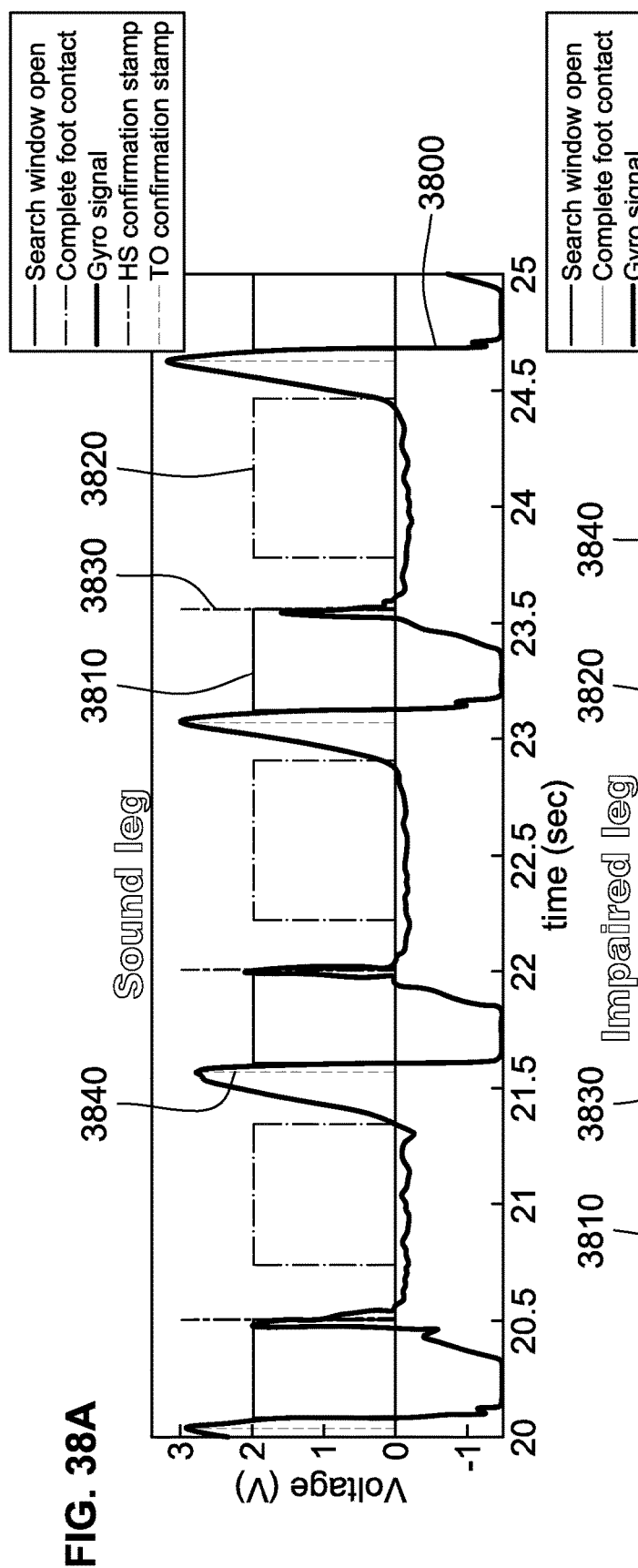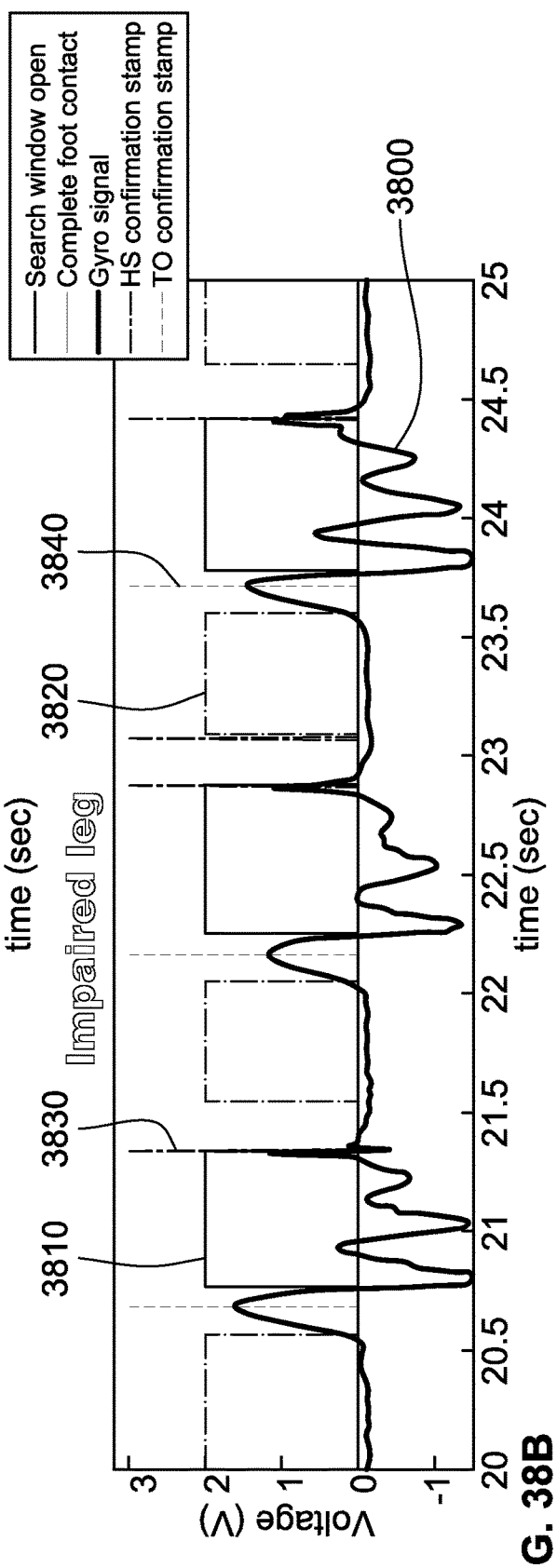
FIG. 38A
FIG. 38B

ASSISTIVE FLEXIBLE SUITS, FLEXIBLE SUIT SYSTEMS, AND METHODS FOR MAKING AND CONTROL THEREOF TO ASSIST HUMAN MOBILITY

CROSS-REFERENCE AND CLAIM OF PRIORITY TO RELATED APPLICATIONS

The present application is a U.S. national phase application of PCT International Patent Application No. PCT/US2014/068462, filed on Dec. 3, 2014, titled, "Assistive Flexible Suits, Flexible Suit Systems, and Methods for Making and Control Thereof to Assist Human Mobility", which claims priority to U.S. Provisional Patent Application No. 61/913,863, titled "Soft, Wearable Assistive flexible suits, Assistive Devices and Related Systems," filed Dec. 9, 2013; U.S. Provisional Patent Application No. 61/928,281, titled "Soft, Wearable Assistive flexible suits, Assistive Devices and Related Systems," filed Jan. 16, 2014; U.S. Provisional Patent Application No. 62/048,076, titled "Assistive flexible suit For Assisting People With Limited Mobility," filed Sep. 9, 2014; U.S. Provisional Patent Application No. 62/052,562, titled "Assistive flexible suit for Gait Assistance and Control Thereof," filed Sep. 19, 2014; U.S. Provisional Patent Application Ser. No. 61/936,162, titled "Multi-robot Cyberphysical System for Assisting Walking in Developmentally-Delayed Toddlers," filed Feb. 5, 2014; U.S. Provisional Patent Application Ser. No. 61/977,880, titled "Knee Exoskeleton and Downhill Walking Device," filed Apr. 10, 2014; U.S. Provisional Patent Application No. 61/980,961, titled "Assistive flexible suit for Assisting the Lower Body," filed on Apr. 17, 2014; and is a continuation-in-part of International Patent Application Serial No. PCT/US2014/040340, titled "Soft Exosuit for Assistance with Human Motion," filed May 30, 2014, each of the preceding applications being incorporated herein by reference in its entirety.

STATEMENT REGARDING FEDERALLY SPONSORED RESEARCH

Some aspects of the present disclosure were made with government support, under Grant No. W911NF-14-C-0051-P00003 awarded by the U.S. Army, and the government shares rights to such aspects of the present disclosure.

TECHNICAL FIELD

The present concepts are generally directed to systems, methods and devices for assisted motion in humans. More particularly, aspects of the present disclosure are directed to systems, methods and devices for providing assistance with motion (e.g., restoring more natural motion) and reducing the energy expending during motion (e.g., walking) by passively and/or actively adding assistive energy or resistive energy, as appropriate, to one or more movements.

BACKGROUND

According to the 2010 Americans with Disability report from the U.S. Census Bureau, roughly 30.6 million individuals aged 15 years and older (12.6% of the U.S. population) had limitations associated with ambulatory activities of the lower body including difficulty walking. About 23.9 million people (9.9% of the U.S. population) had difficulty walking a quarter of a mile, including 13.1 million who could not perform this activity. This represents a significant healthcare, societal and economic problem as these people are at significant risk of developing co-morbidities, rapidly declining health, and face significant challenges associated with integrating into the community and re-joining the workforce. Neurological disorders such as Parkinson Disease ("PD") and stroke are significant contributors to this large and growing segment of the population. An estimated 5 million people throughout the world have PD with about one million living in the United States and the number of individuals with PD is expected to double from 2005 to 2030. Every year, more than 795,000 people in the United States have a stroke, with approximately 87% of these strokes being ischemic (thrombotic and embolic). The 30 day mortality following an ischemic stroke is approximately 10%, meaning that the remaining 90% live with disabilities, resulting in upwards of 7 million stroke survivors living in the United States today. The costs of these two diseases to the United States are significant, with estimated annual costs of $38.6 billion for stroke and $23 billion for Parkinson Disease. Disorders, such as muscular dystrophy, polio, multiple sclerosis (MS), amyotrophic lateral sclerosis (ALS), spinal cord injury, cerebral palsy, or age-related deterioration also present varied degrees of mobility impairment. Some disorders, such as ALS, present issues of progressive mobility impairment that change and worsen over time.

As to stroke patients, many patients are capable of ambulation, but struggle with slow, fatigue-inducing gait patterns resulting from weakened ankle dorsiflexion and plantar flexion, as well as reduced movement during hip flexion and extension. Persons recovering from ischemic stroke in the middle cerebral artery (MCA) often suffer from diminished lower-extremity abilities, exhibiting hemiparesis and limited endurance.

Patients who have suffered severe lower extremity trauma (including polytrauma) will often undergo major reconstructive surgery to repair damaged skeletal and soft tissue (including peripheral nerves) in an effort to enable them to ambulate independently. Other mechanisms of injury that affect patient mobility are mild TBI (loss of coordination movement), severe TBI (loss of muscle force generation capacity), stroke and other neuromuscular disorders.

A pressing need exists for effective interventions for persons with mobility impairments, including impairments resulting from, but not limited to, Parkinson's disease, stroke, muscular dystrophy, polio, multiple sclerosis (MS), amyotrophic lateral sclerosis (ALS), spinal cord injury, cerebral palsy, and/or age-related deterioration. Taking impairments resulting from PD and stroke as illustrative examples, these diseases have different underlying causes and presentations, yet present similar co-morbidities and consequences on quality of life. Despite medical and surgical interventions for PD patients, they face deterioration in mobility over time resulting in a loss of independence and a decline in health related quality of life (HRQoL). Deterioration of walking is perhaps the most important single factor contributing to decline in HRQoL. In one study, a significant decrease (12%) in the number of steps (effect size=0.28) walked per day over the course of one year highlights the rapid decline in walking ability that occurs with disease progression. In stroke, an infarction in the middle cerebral artery (MCA) is the most common site of cerebral ischemia. Most persons regain some ability to ambulate following physical therapy; however, they often require rigid braces (ankle-foot orthoses) and various forms of assistive devices (i.e., walkers and canes), which limit walking efficiency.

Walking is slow, labor intensive and inefficient, with most persons post-stroke ambulating slower than about 0.8 meters/second.

Such limited walking speeds after stroke can restrict individuals to the household and limit reintegration into the community. It is therefore not surprising that the restoration of walking function is the ultimate goal of rehabilitation for the majority of stroke survivors and the focus of much rehabilitation research. However, current therapies are often unable to improve subjects' community ambulation status, regardless of the mode or sophistication of the training as walking deficits persist for most patients. Community-based rehabilitation programs have been proposed to address the limitations of the clinic-based model; however, an evaluation of community-based outcomes demonstrates mixed results with subjects remaining largely sedentary. A simple explanation for this is that many of these programs rely heavily on patient education and motivational feedback (e.g. daily step counts) to improve physical activity and do not address the specific motor impairments limiting mobility. Consequently, these programs tend to neglect the real impact that an impaired motor system has on an individual's walking ability and community engagement.

Beyond slowed walking speeds, post-stroke gait can also be characterized by altered kinematics and kinetics in both magnitude (e.g., joint angle range, peak moment, peak power) and pattern (e.g., shape and direction of curves). These deficits are more marked on the paretic side; however both limbs are often impaired. There are indications that impaired improvements in gait mechanics contribute to a higher reduced energy cost of walking and improved reduced long-distance walking ability after stroke, major factors limiting determinants of community engagement. Indeed, a hallmark of post-stroke walking is the use of inefficient compensatory strategies, such as stiff-legged and circumduction gait, to advance the body through space. Because a rapid achievement of walking independence—not necessarily the reduction of impairment—is the goal of current neuro-rehabilitation practice, the prevalence of such compensatory strategies following rehabilitation is not surprising as gains in walking function are achievable via compensatory mechanisms. Furthermore, current assistive devices such as canes and walkers, which are often provided during the early phases of stroke recovery to promote safe, independent ambulation, may also contribute to this reliance on compensation. Considering that compensatory strategies are known to increase the energy cost of walking, increase the risk of falls, reduce endurance, and reduce speed, gains in walking independence through such mechanisms may impose bounds on the degree of community reintegration possible after stroke. The impact on post-stroke physical activity of such walking deficits is evidenced in a markedly reduced total number of steps walked per day compared to even the most sedentary healthy adults. Given that reduced physical activity increases the risk of second stroke, heart disease, diabetes, hypertension and depression, and is further associated with a reduced health-related quality of life, a need exists for the development of interventions that directly modify walking ability in a manner that facilitates long term improved physical activity, ultimately building healthier lives for persons after stroke.

A chief limitation of the current rehabilitation model is that training and evaluation often occur in the confines of the clinic and are often divorced from the constraints and demands of a patient's home and daily environment. For example, recent intervention studies have demonstrated marked improvements in clinic-measured walking speed without concurrent translation of these improvements in community ambulation. Beyond poor ecological validity, current efforts are also limited by logistical and economic constraints. For example, current reimbursement models are such that after a stroke, patients only receive physical therapy in outpatient centers for 10-12 weeks, after which individuals typically do not participate in a rehabilitation program. During these 10-12 weeks, the frequency of therapy is often limited to only 3-5 sessions per week. Thus, subjects may amass between 30 to 60 total sessions during the course of their rehabilitation—with much, if not all, taking place in environmental contexts substantially different than what they encounter on a daily basis. Despite rehabilitation efforts, marked physical inactivity is emblematic of persons post-stroke and continues to worsen across the first year after occurrence. Thus, effective interventions focused on improving mobility (e.g., restoring more natural motion) for an affected patient having a gait impairment or disorder is a significant factor in reducing their disability, improving integration with the community and improving HRQoL.

Difficulty with walking is frequently followed by problems with gait-dependent activities such as housework, dressing, transferring in and out of bed. For patients with neurological disorders, limited gait velocity commonly results in walking that is predominantly restricted to the household with limited reintegration into the community.

The clinical hallmarks of Parkinson disease include resting tremor, rigidity (i.e., stiffness), bradykinesia (i.e., slowness of movement) and gait disturbance. Pathologically, PD is characterized by degeneration of dopaminergic neurons in the substantia nigra of the midbrain. As a result of this deficiency, there is a loss of the normal internal cueing mechanism resulting in lack of automaticity and synchronization of movement. This contributes to the characteristic gait of persons with PD—impaired regulation of stride length, reduced gait speed, altered cadence and stride time variability. This is in part due to a decreased rate of torque generation in the plantar flexors during terminal stance. Dopamine replacement therapy, the gold standard pharmacological treatment in PD, is ineffective in remediating step frequency and gait variability.

A stroke patient's gait is characterized by a decrease in self-selected speed and previous studies have reported altered kinematics and kinetics in both magnitude (e.g., joint angle range, peak moment, peak power) and pattern (i.e., shape and direction of curves). In addition, while there are reported reductions in both legs, there is typically a greater reduction on the paretic side. Compared to healthy adults, walking patterns post-stroke are also commonly associated with greater physiological effort during walking. One of the primary factors contributing to these abnormal walking patterns in persons post stroke in the MCA distribution is the impaired functions of the distal limb musculature (e.g., ankle joint plantarflexors or calf muscles) of the involved paretic leg.

For all these conditions, a challenge for care givers is to restore a patient's physical function in order to minimize the delay they face for returning to normal activities while they complete a rehabilitation program, which can typically be expected to take 3-6 months. The medical consequences of restricted mobility are staggering. Complications associated with immobility affect the musculoskeletal system (e.g., atrophy, osteoporosis, etc.), respiratory system (e.g., pulmonary embolism, decreased ventilation, etc.), vasculature (e.g., deep vein thrombosis, etc.), skin (e.g., pressure sores, tissue breakdown, infection, etc.) and the patient's mental state.

Conventional exoskeletons have been developed that amplify human strength by applying assistive torques to the joints and/or by supporting a payload. Prior art systems for assisted motion utilize exoskeletons, comprising rigid components (e.g., linkages) and joints (e.g., pin joint), attached to the wearer's body with the exoskeleton joint(s) being disposed to have an axis of rotation ideally collinear with a natural axis of rotation for adjacent joint(s). Exemplary prior art exoskeletons are shown in U.S. Published Patent Application Nos. 2007/0123997 and 2011/0040216, both to Herr et al. Such rigid exoskeletons provide the ability to replace human movements that have been lost or severely compromised and are accordingly designed to enhance the wearer's stability, balance and safety. However, these rigid exoskeletons rely on rigid frameworks of linkages, coupled to the body at select locations via pads, straps, or other interface techniques. As the wearer flexes or extends their limbs, these rigid links move in parallel with the limb, adding considerable inertia to movement which must be overcome by motors or by the wearer. Though great effort has been made to reduce the weight and profile of these devices, they still cause considerable restriction to the wearer's motion and, in particular, add considerable impedance to the natural dynamics and kinematics of gait. This change to the normal kinematics of walking is one reason why these exoskeleton systems do not reduce the metabolic power required for locomotion. Yet further, due to the high inertia of these rigid systems, they are not suitable for applying small levels of assistance to the large number of patients who have limited mobility. Thus, there is a need for fundamentally new approaches to wearable robotics that assist with mobility.

Wearable robotic devices or exoskeletons have recently demonstrated that it is possible to enable a paralyzed spinal cord injury patient to walk upright, holding promise to transform the lives of many patients with disabilities. Rehabilitation robots can generally be classified into two groups: treadmill-bound robots and over ground gait assistive exoskeletons. Treadmill robotic systems, such as the LokoMat and ReoAmbulator, are intended to substitute or complement labor-intensive traditional gait rehabilitation therapies in confined clinical settings. Wearable rigid exoskeletons (e.g., ReWalk, etc.), on the other hand, have the potential to provide gait assistance outside clinical settings.

However, while previously developed systems have demonstrated the capability of allowing fully immobile patients to "walk" again, the majority of attention has gone into designing systems for fully paralyzed patients (e.g. spinal cord injury) where the robot is designed as a powerful machine to help support a patient's body weight and provide high levels of assistance, if not entirely drive all lower limb movement. Such existing approaches share the general principle of attaching heavy rigid structures to the leg and using large, heavy and power intensive actuators with large battery packs to drive the combined weight of the system and the person. Due to the rigid linkages, large inertia and corresponding kinematic restrictions to natural movement (DOFs) (e.g., due to misalignment between the exoskeleton and biological joints, etc.), patients do not walk with a dynamic and fluid gait, but rather in a slow, unnatural and inefficient gait (e.g., a stiff robotic manner). These characteristics limit the usage of powered exoskeletons to restoring mobility in patients with severe impairments (e.g. spinal cord injury or severe stroke). These systems are typically not able to address the needs of patients with only mild to moderate ambulatory limitations, such as those in the latter stages of stroke recovery. As such, these existing approaches are not suitable for the rapidly growing and large number of patients with partial mobility, because they do not provide sufficient benefit over unaided walking. In addition, the long time to don and doff these systems, high weight, and limited battery life and range (e.g., running out of battery power could leave a patient stranded with a heavy device that they are unable to transport) present significant practical challenges or barriers to patients using these systems outside of a clinical environment. Thus, new approaches to providing assistance with robotic technology are needed for the large population of patients with limited mobility.

SUMMARY

The present concepts are directed to methods, systems, and devices configured to assist and/or resist movements of a wearer in a manner that is assistive to mobility.

In at least some aspects of the present concepts, an assistive flexible suit is worn as a lower-body undergarment for gait rehabilitation and for assistance of people with reduced mobility. The assistive flexible suit includes a soft undergarment, a foot attachment, an actuation system, and at least one user interface (e.g., a remote interface for a clinician to modify the actuation system, a patient interface, etc.). Desirably, the assistive flexible suit is worn under regular clothes, and is worn continuously for extended periods of time (e.g., 2 hours, 4 hours, 8 hours, all-day long, etc.) to facilitate rehabilitation or assistance during activities of daily living. The degree of assistance provided by the assistive flexible suit is variable over time, so that it can accommodate varied rehabilitative needs. For example, the assistive flexible suit can provide high force rehabilitation at an early-stage of rehabilitation where higher levels of force may be required, with a tapering level of force over time as the patient's muscles strengthen and muscle activation in task-based activities is retrained. As another example, the assistive flexible suit can provide small levels of force rehabilitation at an early-stage of rehabilitation, with an increasing level of force over time as the patient's rehabilitation progresses to help the patient achieve greater mobility.

Aspects of the present disclosure are directed towards systems, methods, and devices for assisting, automating and/or modifying movements of a wearer. More particularly, aspects of the present concepts are directed to systems, methods, and devices utilizing an assistive flexible suit with a variety of non-extensible, semi-extensible or semi-rigid connection elements (e.g., webbing, straps, cords, functional textile, wires, cables, composites or combinations thereof, etc.) disposed between suspension anchors, anchor straps or other anchor elements located at anchor points or anchor areas on the wearer's body (e.g., pelvis, iliac crest(s), shoulder(s), thigh(s), ankle(s), calf(s), etc.), and one or more actuators for selectively creating tension between selected members at times at which the transmitted forces to specific limbs or body parts would be beneficial (either in an assistive or resistive capacity) to movement of the specific limbs or body parts. An assistive flexible suit, as described herein, generally refers to and includes a wearable device (e.g., one or more pieces of garment) utilizing flexible connection elements to provide assistive forces and/or resistive forces to one or more limbs (e.g., a leg) or one or body segments or portions of a limb (e.g., a foot). In some aspects, the assistive flexible suit utilizes flexible connection elements to provide assistive forces and/or resistive forces to a plurality of limbs (e.g., two legs) and/or a plurality of body segments (e.g., two feet).

In at least some aspects, apart from actuating one or more joints in opposite legs or opposite arms to facilitate motions wherein the limbs move in different directions at different times (e.g., walking), the present concepts also include any movement-based assistance, which may include, for example, assistance with motion of any one or more body parts or body segments relative to other body parts or body segments. By way of example, the present concepts include any movement-based assistance (and/or resistance), which may include, for example, assistance with motion of only one limb (e.g., one arm relative to the torso, one leg relative to the hip, or one foot relative to the corresponding leg), a plurality of limbs (e.g., two arms relative to the torso, two legs relative to the hip, one arm relative to the torso and one leg relative to the hip, etc.), the head and/or the torso.

As compared to the prior art rigid exoskeletons, the assistive flexible suit is lighter, more comfortable to wear and permits a more complete, and more natural, range of joint(s) motion(s), while still being able to transfer forces or torques able to beneficially assist motion. In accord with the present concepts, the flexible connection elements can optionally be used in combination with rigid or semi-rigid connection elements and it is not necessary that all connection elements be flexible.

In at least some aspects of the present concepts, a method for configuring an assistive flexible suit, includes the act of outfitting a person with an assistive flexible suit, the assistive flexible suit comprising at least a first anchor element configured for positioning at or near a first body part, a second anchor element configured for positioning at or near a second body part, a plurality of connection elements extending between the first anchor element and the second anchor element, and at least one of the plurality of connection elements spanning at least one joint disposed between the first anchor element and the second anchor element, at least one sensor, at least one actuator, at least one force transmission element connecting an output of the at least one actuator to the second body part, and at least one controller configured to actuate the at least one actuator responsive to one or more predefined events occurring during movement to produce an actuation profile generating a moment about the at least one joint during movement of the at least one joint. The method further includes the acts of monitoring an output of the at least one sensor as the person moves in a first controlled movement environment, identifying at least one predefined event using the output of the at least one sensor, adjusting an actuation profile of the at least one actuator, continuing to perform the acts of monitoring, identifying and adjusting until an actuation profile of the at least one actuator generates a beneficial moment about the at least one joint to yield an improvement in gait and setting the at least one controller to implement the actuation profile.

In at least some other aspects of the present concepts, a method for configuring an assistive flexible suit, includes the act of outfitting a person with an assistive flexible suit, the assistive flexible suit comprising at least a first anchor element configured for positioning at or near a first body part, a second anchor element configured for positioning at or near a second body part, a plurality of connection elements extending between the first anchor element and the second anchor element, and at least one of the plurality of connection elements spanning at least one joint disposed between the first anchor element and the second anchor element, at least one sensor, at least one actuator, at least one force transmission element connecting an output of the at least one actuator to the second body part, and at least one controller configured, responsive to the at least one sensor, to actuate the at least one actuator attachment at a predetermined time during movement of the at least one joint to generate a beneficial moment about the at least one joint. The method also includes the acts of connecting the assistive flexible at least one force transmission element to at least one offboard actuator to connect an output of the at least one offboard actuator to the second body part, the at least one offboard actuator corresponding in operation to the at least one actuator, monitoring an output of the at least one sensor as the person moves in a first controlled movement environment, identifying at least one predetermined gait event using the output of the at least one sensor, controlling an actuation of the at least one offboard actuator, using an offboard controller, responsive to the output of the at least one sensor, adjusting an actuation profile of the at least one offboard actuator and continuing to perform the acts of monitoring, identifying, controlling and adjusting until an actuation profile yields the beneficial moment about the at least one joint to provide an improvement in gait.

In at least some other aspects of the present concepts, a method for dynamically adjusting control outputs of an assistive flexible suit to enhance mobility of a person exhibiting an off-normal gait pattern, the method including the acts of setting at least one assistive flexible suit actuator to output a first force profile to impart a first torque profile across a first joint over a first range of movement during a gait cycle, monitoring an output of at least a first sensor on a first body part during the gait cycle, the first sensor being configured to provide first information relating to a gait pattern to an assistive flexible suit controller, and monitoring an output of at least a second sensor on a second body part during the gait cycle, the second sensor being configured to provide second information relating to the gait pattern to the assistive flexible suit controller, the second body part being out of phase with the first body part over at least a portion of the gait cycle. The method also includes the acts of determining, using the assistive flexible suit controller, a variance in the gait pattern from a reference gait pattern using the first information and the second information and determining a second force profile necessary to impart a second torque profile across the first joint during the gait cycle to decrease the variance in the gait pattern from the reference gait pattern. The method also includes the act of setting the at least one assistive flexible suit actuator to output the second force profile to impart the second torque profile across the first joint during successive gait cycles. In yet other aspects of this exemplary method, and in other aspects of the present concepts disclosed herein, in addition to tuning one or more actuators to improve gait, a plurality of actuators may further advantageously be timed relative to each other to ensure that the resulting application of forces to the wearer are complementary (e.g. the ankle doesn't turn on until the hip starts or stops, as appropriate, etc.).

In at least some other aspects of the present concepts, a system for modifying gait of an individual wearing an assistive flexible suit is presented. Such a system includes one or more sensors that measure one or more gait parameters of the individual, and one or more actuators, in mechanical communication with the individual through the assistive flexible suit, that modify one or more gait moments of the individual. The system also includes a control unit that controls the one or more actuators based, at least in part, on the one or more gait parameters, and that accepts one or more inputs, from a medical provider external to the system (and/or optionally a patient or wearer) and monitoring the one or more gait parameters, to adjust the one or more actuators and improve the one or more gait moments.

In at least some other aspects of the present concepts, a method for modifying gait of an individual wearing an assistive flexible suit includes the act of determining one or more gait parameters of the individual based on one or more sensors connected to the individual through the assistive flexible suit. The method also includes the act of monitoring, by a medical provider (and/or optionally a patient or wearer) through a control unit or user interface, the one or more gait parameters. As to the presently described example, as well as all other aspects of the present concepts disclosed herein, this monitoring can occur in real-time or, alternatively, could occur at some later point in time after collection of the sensor data (e.g., after a walking trial, etc.). The method also includes the act of receiving, from the medical provider (and/or optionally a patient or wearer), one or more inputs based on the monitoring, and modifying the gait of the individual, through the assistive flexible suit, according to the one or more inputs.

In at least some other aspects of the present concepts, an actuator system of an assistive flexible suit is presented. The actuator system includes a mobile cart including one or more motors, and one or more drive shafts driven by the one or more motors. The actuator system further includes one or more anchor elements configured for positioning at or near one or more body parts of an individual on the assistive flexible suit. The actuator system further includes one or more force transmission elements connecting the one or more drive shafts to the one or more anchor elements. According to the actuator system of the present concepts, operation of the one or more motors, through the one or more force transmission elements, improves movement of the individual.

In at least some aspects, the assistive flexible suit adapted to assist the gait in patients with limited mobility and/or undergoing gait rehabilitation includes four modules: a suit for ankle plantar flexion and hip assistance, a shin attachment for dorsiflexion assistance and ankle stabilization, a modified shoe, and one or more actuator units. In general, the present concepts encompass a modular assistive flexible suit comprising a plurality of interchangeable modules that are configurable in any combination required to provide a required level and variety of assistance to a particular wearer. For example, one patient may only require one module (e.g., ankle plantar flexion), whereas another patient may require two modules (e.g., ankle plantar flexion and dorsiflexion), and still another patient may require three modules (ankle plantar flexion, dorsiflexion, and hip assistance). In addition to the movement-assistive modules, other modular functional units may be provided, including but not limited to, functional electric stimulation units, haptic feedback units, and vibro/electro tactile feedback units. In some aspects, a controller generating actuation profiles may also advantageously activate, in conjunction with actuation (e.g., prior to actuation, concurrent with actuation, etc.), one or more other functional units, such as vibrotactile feedback, eletrotactile feedback, or functional electrical stimulation.

In at least some aspects of the present concepts, a control system is configured to assist single muscle groups through a mix of any one or more of actively generated force/torque (e.g., through actively-controlled contractile elements, such as Bowden cables) and active stimuli (e.g., Functional Electrical Stimulation (FES), haptic cueing (electrotactile elements, vibrotactile elements). The control system can generate a mix of control signals to time each of these active units in order to assist with movement. Depending on the type of movement, the suit control can be altered to modify the mix between the different active units. For example, in some situations or for some subjects, the control could deliver assistance only through FES or only by generating active forces. The mix of outputs could be varied situationally, such as based on the specific condition of a patient (e.g., a degree of recovery) or the type of rehabilitation therapy (e.g., the mix could be altered to favor active force assistance, as opposed to functional electrical stimulation).

In at least some aspects of the present disclosure, a method of manufacturing an assistive flexible suit system for aiding one or more gait movements during walking of a wearer includes the acts of providing a suspension anchor configured to mount to the body of the wearer and transmit loads to one or more predetermined load-bearing segments of the body of the wearer and providing a body segment module configured to mount on or adjacent to a respective body segment. The method further includes the acts of attaching an actuator to the suspension anchor and to the body segment module, the actuator being selectively actuable to generate tension between the body segment module and the suspension anchor, providing at least one sensor to detect a gait characteristic of the wearer and to output a signal indicative thereof and communicatively connecting a controller to the sensor and the actuator, the controller being configured to analyze the gait characteristic signal output by the sensor and, based at least in part on the analyzed signal, selectively actuate the actuator to thereby assist movement of the body segment relative to at least one joint.

According to aspects of the present disclosure, assistive flexible suit systems for assisting or modifying motion of a wearer are presented. In one configuration, the assistive flexible suit system includes a suspension anchor (or "anchor element") that is configured to mount to the body of the wearer and transmit loads to one or more predetermined load-bearing segments of the wearer's body. In addition, a foot module (or "foot attachment element") is configured to mount on or adjacent to a foot of the wearer and transmit loads to a hindfoot segment and/or a forefoot segment of the wearer's foot. The suit system further includes an actuator (or "force generating element") that is attached, e.g., at one end, to the foot module and, e.g., at a second end, to the suspension anchor. The actuator is selectively actuable to generate tension between the foot module and the suspension anchor. A sensor (or "sensing element"), which is mounted on or proximate to the foot of the wearer, is operable to detect a gait characteristic of the wearer and output a signal indicative thereof. The flexible suit system also comprises a controller (or "control element") that is communicatively connected to the sensor and the actuator. The controller analyzes the gait characteristic signal that is output by the sensor and, based at least in part on this analyzed signal, selectively actuates the actuator to thereby assist plantar flexion or dorsiflexion, or both, of the foot of the wearer.

In accordance with other aspects of this disclosure, assistive flexible suit systems are disclosed for generating assistive forces for aiding or modifying one or more gait movements during walking of a wearer. For example, an assistive flexible suit system is disclosed which includes an assistive flexible suit. The assistive flexible suit utilizes at least one suspension anchor (or "anchor element") that is configured to mount to the body of the wearer and transmit loads to one or more predetermined load-bearing segments of the wearer's body, and at least one foot module (or "foot attachment element") that is configured to mount to at least one foot of the wearer and transmit loads to a hindfoot segment and/or a forefoot segment of the at least one foot of the wearer. The assistive flexible suit system also includes at least one actuator (or "force generating element") that is mounted on or proximate to the assistive flexible suit and is attached to the at least one foot module. The actuator(s) selectively actuate to generate a tensile force between the at least one foot module and the at least one suspension anchor. At least one sensor (or "sensing element"), which is mounted on or proximate to the at least one foot module, is operable to detect a gait characteristic of the wearer and output a signal indicative thereof. In addition, at least one controller (or "control element") is communicatively connected to the sensor(s) and the actuator(s). The at least one controller is configured to analyze one or more gait characteristic signals output by the sensor(s) and, based at least in part on the analyzed signal(s), selectively actuate at least one of the one or more actuators to thereby assist plantar flexion or dorsiflexion, or both, of the foot of the wearer Other aspects of the present disclosure are directed to methods of making and methods of using an assistive flexible suit. One embodiment is directed towards a method of manufacturing an assistive flexible suit system for aiding one or more gait movements during walking of a wearer. This method includes: providing a suspension anchor (or "anchor element") that is configured to mount to the body of the wearer and transmit loads to one or more predetermined load-bearing segments of the body of the wearer; providing a foot module (or "foot attachment element") that is configured to mount on or adjacent to a foot of the wearer and transmit loads to a hindfoot segment and/or a forefoot segment of the wearer's foot; attaching an actuator (or "force generating element") to the foot module and the suspension anchor, the actuator being selectively actuable to generate tension between the foot module and the suspension anchor; mounting a sensor (or "sensing element") on or proximate the wearer's foot, the sensor being operable to detect a gait characteristic of the wearer and output a signal indicative thereof; and, communicatively connecting a controller (or "control element") to the sensor and the actuator, wherein the controller is operable to analyze the gait characteristic signal output by the sensor and, based at least in part on the analyzed signal, selectively actuate the actuator to thereby assist plantar flexion or dorsiflexion, or both, of the foot of the wearer.

Any of the disclosed systems, methods and devices, including those described in the preceding and following paragraphs, may include any of the following options (singly or collectively or in any combination): the suspension anchor comprises a calf sleeve which couples to (e.g., extends around and attaches circumferentially to) the calf of the wearer adjacent the assisted foot; the calf sleeve includes an elastic wrap which wraps around the wearer's calf, and has one or more calf straps attached to the elastic wrap and configured to increase circumferential tension around at least a top portion of the calf of the wearer; optionally, the calf sleeve can include an elastic wrap that wraps around the calf of the wearer, and multiple pairs of hook-and-loop straps attached to the elastic wrap and configured to attach in overlapping relation to one another to thereby increase stability and attachment strength of the calf sleeve; the calf sleeve may comprise a central sternum with first and second rib sets projecting from opposing sides thereof, each rib set includes numerous vertically spaced ribs, wherein the central sternum lays over the wearer's tibia above the assisted foot, while the first and second rib sets wrap around the wearer's calf and attach together; the vertically spaced ribs of each rib set can be connected together at proximal ends thereof via the central sternum and connected together at distal ends thereof via a respective webbing; in addition to or as an alternative for the calf sleeve, the suspension anchor may comprise a thigh sleeve that couples to (e.g., wraps around and attaches circumferentially to) the wearer's thigh; the calf sleeve couples to the thigh sleeve via one or more straps (or "connection elements"); in addition to or as an alternative for the calf sleeve, the suspension anchor may comprise a waist belt that couples to (e.g., wraps around and attaches circumferentially to) the wearer's waist over the iliac crest(s); the calf sleeve is coupled to the waist belt via one or more straps (or "connection elements"); the actuator can be mounted on the waist belt and attached to the thigh sleeve such that the actuator is selectively actuable to generate tension between the thigh sleeve and the waist belt and thereby assist hip extension (or flexion).

Any of the above or below disclosed systems, methods and devices may include the following options, singly or collectively or in any combination: an adjustable ankle strap which attaches the calf sleeve to the foot module; the adjustable ankle strap has multiple attachment fingers each of which is configured to detachably couple to the calf sleeve in a distinct orientation and thereby selectively vary the tension between the foot module and the suspension anchor; the adjustable ankle strap can be configured to create passive ankle support and thereby prevent inadvertent ankle roll; the calf sleeve or foot module, or both, may comprise an interwoven webbing structure (e.g., comprising a biaxial helical braid) that is configured to circumscribe the calf/foot and automatically tighten when tension is generated between the calf sleeve/foot module and a suspension anchor; in configurations where the foot module is mounted to the foot of the wearer (e.g., on or in their footwear), the foot module may include numerous actuator attachment points on the hindfoot and/or forefoot segment to which the actuator can be detachably connected; each actuator attachment point can be configured to provide a distinct angle along which tensile forces generated by the actuator are applied to the foot of the wearer; the foot module may include an actuator attachment point on the hindfoot segment of the wearer's foot adjacent the underside of the heel bone.

Any of the disclosed systems, methods and devices, including those described in the preceding and following paragraphs, may include any of the following options (singly or collectively or in any combination): the foot module may optionally comprise a shoe into which is nested the wearer's foot; alternatively, the foot module fits inside the shoe of the wearer and mounts to the foot; the foot module may include an Achilles strap that extends out of the opening in the shoe upper, wherein the strap transmits tensile forces generated by the actuator to the hindfoot segment of the wearer; the foot module may include a tibia strap that extends out of the opening in the shoe upper, wherein the tibia strap transmits tensile forces generated by the actuator to the forefoot segment of the wearer; the sensor may take on various forms, including a foot switch, a gyroscope, an inertial transducer, or an accelerometer, or any combination thereof; the actuator may take on various forms, including a Bowden cable assembly, a McKibben actuator, or other mechanical, hydraulic or electrical actuators; the actuator may optionally be mounted on the suspension anchor; alternatively, the actuator is mounted on a movable cart or a platform positioned adjacent the assistive flexible suit system; the suspension anchor may take on various forms, including the aforementioned calf sleeve, as well as (or alternatively) a thigh sleeve and/or a waist belt.

Systems, methods and devices disclosed herein may optionally include any of the following options, be it individually, cooperatively or in various combinations: a second foot module (e.g., for a bilateral system) that mounts on or adjacent to the second foot of the wearer and transmit loads to the hindfoot segment or forefoot segment, or both, of the wearer's second foot; a second actuator that is attached to the second foot module and is selectively actuable to transmit tensile forces to the second foot module; a second sensor that is operable to detect a second gait characteristic of the wearer and output a second signal indicative thereof. For this configuration, the controller can be communicatively connected to the second sensor and the second actuator, wherein the controller analyzes the second gait characteristic signal output by the second sensor and, based at least in part on that second analyzed signal, selectively actuates the second actuator to thereby assist plantar flexion or dorsiflexion, or both, of the second foot of the wearer. Optionally, the suit further comprises a second suspension anchor that mounts to the wearer's body and transmits loads to a second predetermined load-bearing segment of the body, wherein the second actuator is selectively actuable to generate tension between the second foot module and the second suspension anchor.

In at least some aspects of the present concepts, a hybrid control system is provided to adjust operational characteristics of an assistive flexible suit comprising at least one actuator adapted to output a force trajectory across at least one axis of at least one joint during movement of the at least one joint to develop an assistive torque thereacross. The hybrid control system includes, in at least some aspects of the present concepts, a first control loop comprising the at least one actuator, a first communication device, at least one controller, a physical computer-readable storage device bearing an instruction set configured, upon execution by the at least one controller, to cause the at least one controller to output actuation signals to the at least one actuator, and at least one sensor configured to provide information relating to the movement of the at least one joint, the at least one controller receiving outputs from the at least one sensor and, responsive thereto, outputting actuation signals to the at least one actuator to, in turn, output the force trajectory across the at least one axis of the at least one joint during movement of the at least one joint to develop an assistive torque thereacross. The hybrid control system includes a second control loop comprising a clinician interface, the clinician interface comprising a display device, one or more processors, a user interface, a second communication device and a physical computer-readable storage device bearing an instruction set configured, upon execution by the one or more processors, to cause the one or more processors to receive, via the second communication device, an output of the at least one sensor or an output of another one or more sensors configured to provide information relating to movement of the at least one joint and display on the display device the information relating to movement of the at least one joint in relation to at least one gait event. The one or more processors are also configured to receive an input from a clinician, a patient or wearer and/or other supervising individual, via the user interface, comprising an instruction to modify one or more aspects of the force trajectory output by the at least one actuator to thereby modify the assistive torque developed across the at least one axis of the at least one joint during movement of the at least one joint and output to the first communication device, using the second communication device, the instruction to modify the one or more aspects of the force trajectory.

In at least some aspects of the present concepts, one or more processors (located locally and/or remotely to the assistive flexible suit), in accord with one or more instruction sets borne by physical memory devices (located locally and/or remotely to the assistive flexible suit), are configured to monitor a wearer's gait in an unassisted condition (e.g., via one or more sensors disposed on the assistive flexible suit or externally thereto) and then modify one or more aspects of a force trajectory output by the at least one actuator to thereby modify the assistive torque developed across the at least one axis of the at least one joint during movement of the at least one joint, the wearer's modified gait being used as a further input to the one or more processors and associated one or more instruction sets for further evaluation of the wearer's gait and further iterative modification of one or more aspects of a force trajectory output by the at least one actuator.

Although the present concepts are described in association with biological joints (e.g., an ankle, knee, hip, etc.) at least some aspects of the present concepts may alternatively find application in control on one or more non-biological joints (e.g., an exoskeleton joint, a robotic joint, a joint in a prosthesis, etc.) to enable a more natural and fluid motion.

The assistive flexible suit is, moreover, well-suited for motion assessment, rehabilitation or gait assistance activities, and movement training, such as by providing resistance instead of assistance (e.g., to strengthen muscles, to provide negative feedback for improper movement, etc.) or by providing corrective assistance where needed.

In response to needs that remain unmet by conventional, rigid exosuits, the assistive flexible suits disclosed herein can be worn like a garment (e.g., under clothing, over clothing, or integrated with clothing) and uniquely provide an opportunity for continuous, targeted rehabilitation in a free-living community setting through two distinct, yet synergistic mechanisms: (1) orthotic effects that provide an immediate increase in walking capacity (i.e., improved walking quality and reduced energy cost of walking) and (2) an individualized, progressive rehabilitation program based on regular assessment of the walking activity and spatiotemporal gait data generated by the exosuit's embedded sensors. In at least some aspects of the present concepts, as an active orthotic, the assistive flexible suit applies restorative forces in parallel with the impaired musculature, and through one or more sensors, doubles as a rehabilitation system capable of measuring key parameters of walking (i.e., spatiotemporal variables and step activity) useful for the implementation of patient-specific walking activity programs that target both walking strategy and quantity. The assistive flexible suit provides a suit comprising soft materials (e.g. textiles, elastomers, etc.) that provide, relative to existing technology, a more conformal, unobtrusive and compliant interface to the human body.

The above summary is not intended to represent each embodiment or every aspect of the present disclosure. Rather, the foregoing summary merely provides an exemplification of some of the novel aspects and features presented herein. The above features and advantages, and other features and advantages of the present disclosure, will be readily apparent from the following detailed description of exemplary embodiments and modes for carrying out the present invention when taken in connection with the accompanying drawings and the appended claims.

BRIEF DESCRIPTION OF THE FIGURES

FIGS. 1A-1D show representations of assistive flexible suits (FIGS. 1A-1C) and a method for configuring an assistive flexible suit (FIG. 1D) in accord with at least some aspects of the present concepts.

FIG. 3C is a rear perspective-view illustration of the calf sleeve module of the assistive flexible suit of FIGS. 3A and 3B.

FIG. 3D is a front perspective-view illustration of the waist belt module of the assistive flexible suit of FIGS. 3A and 3B.

FIGS. 4A and 4B are front perspective-view illustrations of a representative unitary "fishbone" calf sleeve module (close-ended rib configuration) for an assistive flexible suit shown in closed and open states, respectively, in accord with aspects of the present disclosure.

FIG. 5 is a front perspective-view illustration of a representative unitary "fishbone" calf sleeve module (open-ended rib configuration) for an assistive flexible suit in accord with aspects of the present disclosure.

FIG. 6 is a front perspective-view illustration of a representative unitary "fishbone" calf sleeve module (open-ended pivoting rib configuration) for an assistive flexible suit in accord with aspects of the present disclosure.

FIGS. 10A-10E show a quick-connect/quick-release actuator attachment anchor element according to at least some aspects of the present concepts.

FIG. 14 is a side perspective-view illustration of another representative in-shoe foot module for an assistive flexible suit in accord with aspects of the present disclosure.

FIG. 15 is a plan-view illustration of a representative over-the-shoe foot module for an assistive flexible suit in accord with aspects of the present disclosure.

FIG. 16C shows distribution of forces with respect to an assistive flexible suit according to at least some aspects of the present concepts.

FIGS. 29A-29B show examples of adaptive thresholds according to at least some aspects of the present concepts.

FIGS. 30A-30B show an example of detection of heel strike according to at least some aspects of the present concepts.

FIGS. 33A-33B show gait patterns for initiation and termination of walking (non-continuous walking) of a stroke patient, including gait pattern analysis according to at least some aspects of the present concepts.

FIG. 38 shows a representation of detection of full ground contact and toe-off according to at least some aspects of the present concepts.

Figure 1B:
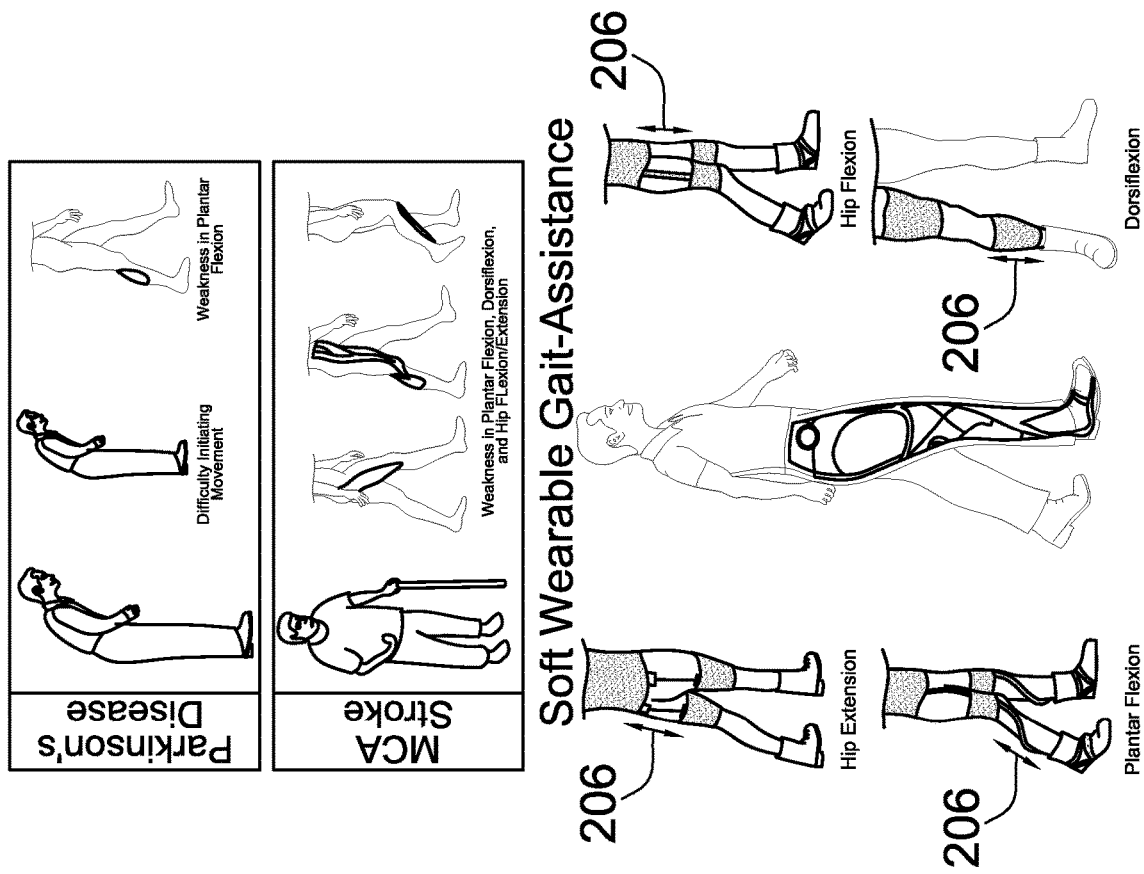

While the inventive aspects are susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the disclosure and the appended claims, without limitation.

DETAILED DESCRIPTION OF REPRESENTATIVE EMBODIMENTS

Concepts disclosed herein are directed assistive flexible suits adapted to augment human performance and/or reduce the metabolic cost of locomotion (e.g., walking over ground). Some configurations help to improve the quality of life for persons desiring to improve their mobility (whether laden or unladen), inclusive of able-bodied persons and persons with mobility issues. For example, stroke survivors or persons with lower-extremity impairments (e.g., persons undergoing rehabilitation due to lower-extremity injury, elderly with age-related limitations to lower-extremity movement, etc.) can experience improved mobility and, thus, an improved quality of life through utilization of an assistive flexible suit in accord with one or more of the disclosed concepts.

Stroke is the leading cause of long-term disability worldwide; rehabilitation is the cornerstone for recovery from stroke. However, despite various rehabilitation efforts, marked physical inactivity is emblematic of persons post-stroke and continues to worsen across the first year after occurrence. To address this issue, there is growing interest to develop means for improving activity in the community as part of future neurorehabilitative strategies. While a number of community-based programs have been developed, their effects are limited and patients remain sedentary, largely because many of these programs rely heavily on patient education and motivational feedback (e.g. daily step counts) and do not address the specific motor impairments that limit mobility. Moreover, while there have been significant advances in rigid exoskeletons that apply 100% assistance to patients, these technologies are not suitable for patients with partial impairments.

In response to this need, there is disclosed the concept of soft wearable robotics in the form of an assistive suit that can be worn like garments (under or over clothing) that afford the opportunity for continuous targeted rehabilitation in a free-living community setting. This if afforded, for example, through two distinct, yet synergistic mechanisms: (1) orthotic effects that provide an immediate increase in walking capacity (e.g., improved walking quality and reduced energy cost of walking) and (2) individualized, progressive rehabilitation programs designed to increase walking activity and monitor patient progress through the provision of both assistance and assessment. As an active orthotic, the assistive suit applies restorative forces in parallel with the impaired musculature. Through advanced sensing abilities, the suit can double as a "rehabilitation robot" capable of measuring key parameters of walking (e.g., spatiotemporal variables and step activity) useful for the implementation of patient-specific walking activity programs that target both walking strategy and quantity. Disclosed are wearable robots made of soft materials (e.g. textiles and elastomers) that provide a more conformal, unobtrusive and compliant interface to the human body, and improve mobility through clinical evaluations of patients.

In at least some aspects of the present concepts, an assistive flexible suit is adapted to improve the mobility of patients, such as those with Parkinson's disease, stroke, MS, ALS or other disabling condition whatever the cause, enabling them to more fully integrate into their communities. While the nature of these gait impairments stem from different underlying neuropathologies, patients with both conditions present with gait limitations which can be markedly improved with the assistance that the assistive flexible suits disclosed herein are able to provide. Unlike traditional exoskeletons, which employ rigid external skeletal supports and linkage elements, exclusively or in large part, the presently disclosed assistive flexible suits predominantly use soft or flexible or otherwise non-rigid materials (e.g., textiles, fabrics, elastomers etc.) to provide a more conformal, unobtrusive and compliant means to interface to the human body and may be comfortably worn under regular clothing. As discussed herein, the present inventors have demonstrated the efficacy of this approach, which represents a fundamental change to the wearable robotics paradigm that has persisted for half a century. With the disclosed assistive flexible suit, the assistive flexible suit can be extremely light and, further, the wearer's joints are not constrained by external rigid structures that would interfere with the body's natural biomechanics.

In accord with at least some aspects of the present concepts, an assistive flexible lower-extremity suit is configured to be worn over the feet, leg and/or pelvic regions (similar to pants and shoes). Some configurations provide a controlled level of assistance to a patient's leg joints (e.g., applying torques to the patient's joints at the appropriate time in a gait cycle) during locomotion (e.g., walking). This can help to reduce metabolic cost to the wearer (the amount of energy expended on a task) and to improve key gait markers, such as step length, gait velocity, and cadence. It is oftentimes desired to permit the wearer (e.g., patient) to be able to easily don and doff the assistive flexible suit. Likewise, it is often desirable to control at least certain aspects of operation of the assistive flexible suit, possibly within parameters externally set for the particular wearer, to not only promote movement, but to promote normal walking patterns. As therapy progresses over time, levels of assistance to one or more joints can be tailored to correspond to (e.g., decreasing levels of assistance, altered timing of assistance, etc.) to changes in the patient's condition improves. For example, as the force generating capacity and neuromuscular control aspects of the biological muscles improves, levels of assistance may be decreased.

Various aspects of the lower-extremity assistive flexible suits disclosed herein provide solutions to particularly address the populations (e.g., stroke survivors, etc.) facing such diminished lower-extremity abilities. The assistive flexible suit incorporates, in at least some aspects, passive elements for energy storage (e.g. artificial exotendons, etc.) and actuators (e.g. cable drive, pneumatic, etc.) powered via on-board or off-board power supplies and interfacing with the wearer via compliant materials and a soft wearable fabric. In some aspects, the exotendons are resilient and behave biomimetically as tendons (e.g., as an elastic band), storing energy supplied from natural biomechanical movement or from actuators configured in series within the exotendons themselves, and releasing such stored energy during complementary movement. The actuators may comprise, by way of example, one or more air-powered pneumatic actuators, one or more DC motors, one or more electro-active materials (e.g. polymer), or combinations thereof. The actuator(s) is (are) configured to apply torque to the wearer's joints at controlled levels at or below levels normally experienced during human walking.

The actuator(s) and exotendon(s) are adapted to assist the wearer by providing assistive force or acting as antagonists, mimicking the normal human muscle-tendon construction found in human anatomy/physiology. By way of non-limiting example, in mimicking the natural motions and forces present during human walking, the assistive flexible suit system is inherently safe and operates in synergy with the wearer's needs (e.g., restoring the wearer to more normal levels of movement), which may or may not necessarily be in synergy with a pathological muscle activity. It at least some aspects, the assistive flexible suit system is able to be worn under clothing and provides assistance to restore physical function and mobility to therapeutically engage injured patients to enable them to more quickly reintegrate back into the services and their community.

In at least some aspects, the assistive flexible suit system comprises one or more sensors to measure, monitor or otherwise detect one or more joint angles and/or to detect events (e.g., heel strike, toe off, etc.) which characterize a particular state of the wearer, such as a state corresponding to a predefined phase of the gait cycle. One or more sensors are advantageously used, in conjunction with one or more controllers and/or processors, to command the actuator(s) and/or other suit components or systems. By way of example, sensor readings are used by the assistive flexible suit control system or controller to determine a walking speed of the wearer. The control system or controller then commands an appropriate actuation (e.g., amount of movement, profile of movement, etc.) from the actuator(s) to thereby provide (e.g., via exotendons) a desired degree of assistance (e.g., toque) to one or more joints.

In at least some aspects of the present concepts, external forces are provided at least substantially in parallel with the underlying biological musculature. The external forces provide, at smaller levels of assistance, mechanical cues that can assist with the initiation of movement and reestablishing of normal neuromuscular control and, at larger levels of assistance, restoration of a normal power-generating capability of the biological joints and restoration of normal gait mechanics. Such assistive cues to aid gait initiation may be used to minimize or prevent episodes of "freezing" or assist with the initiation of movement, symptoms that can be typical in Parkinson's disease.

In contrast, existing approaches to wearable robotics impose kinematic restrictions on the wearer and use heavy structures, having significant inertia, for which it is difficult to apply small levels of assistance. The rigid and heavy nature of these systems is not suitable for these patients because they do not provide sufficient benefit over unaided walking. In addition, the long time to don and doff the conventional systems and their limited range (running out of battery power could leave a patient stranded with a heavy device that they are unable to transport) present significant practical challenges to patients using these systems outside of a clinical environment. It has been shown that a higher class of ambulation such as a transition from household to community ambulation results in better function and quality of life.

In various aspects, the disclosed assistive flexible suit system is used in combination with an actuation system to provide active assistance to natural motions and/or corrective assistance (e.g., assistance or resistance) to motions that are not biologically optimal, with the goal of enhancing mobility and/or restoring more normal movement, preferably both enhancing mobility and restoring more normal movement.

The assistive flexible suit greatly reduces the mechanical impedance and kinematic restrictions compared to traditional exoskeletons with rigid components and does not significantly constrain or restrict the wearer's degrees of freedom. With such a system, it is possible to add controlled impulses of energy (e.g., small or moderate levels of assistance during key portions of the gait cycle), rather than direct control of limb position(s), to provide assistance to locomotion and reduce the metabolic cost of movement (e.g., walking/load carrying) without significantly constraint of movement. As noted above, conventional rigid exosuits are not able to provide small or moderate levels of assistance.

Figure 1A:
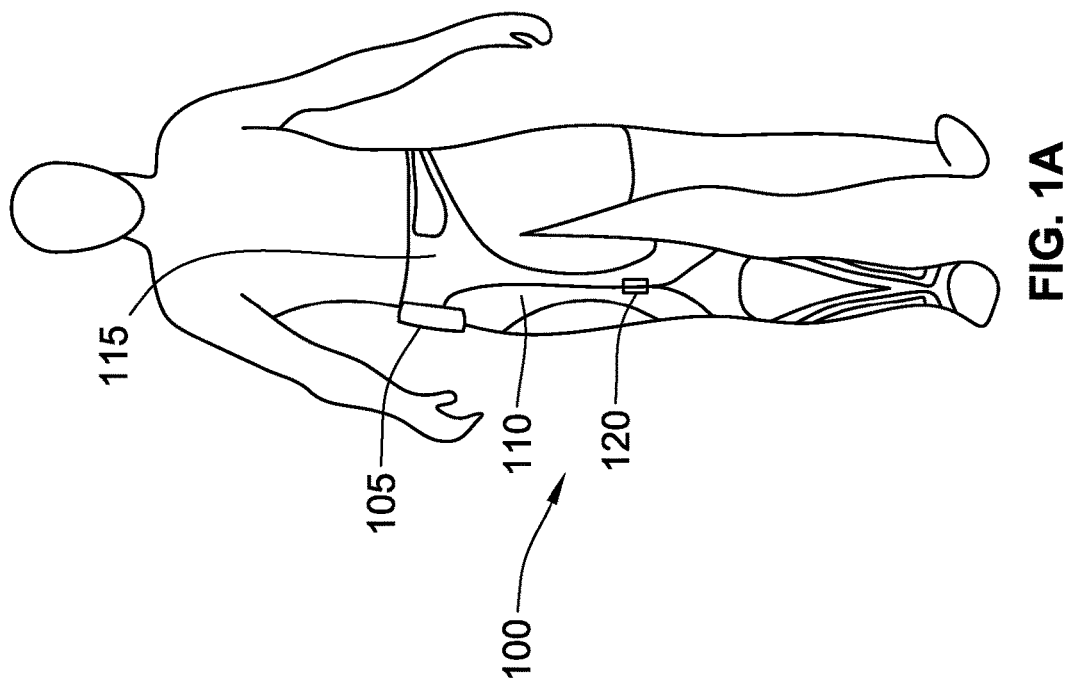

FIG. 1A generally shows an embodiment of an assistive flexible suit 100 in accord with at least some aspects of the present concepts. The assistive flexible suit 100 is configured to apply a moment, via forces generated by one or more actuators 105, to one or more joints (e.g., a hip joint and ankle joint) using one or more tensioned connection elements 110. In at least some aspects of the present concepts, it is desired to minimize the distal mass that is added to the legs. In such aspects, power is transmitted from one or more proximally-mounted actuators 105 to distally located body parts through a flexible transmission, such as is represented in FIG. 1A, wherein an actuator 105 is disposed on a waist belt 115 to deliver torques across an ankle joint. In other aspects, the actuator may be disposed elsewhere (e.g., distally closer to an actuated joint(s)) or a plurality of actuators may be distributed about the assistive flexible suit 100 or the body of the wearer.

The assistive flexible suit 100 described here, in at least some aspects, utilizes functional textiles and/or other conformal materials that enable forces to be comfortably and effectively applied to the lower extremity joints through a biologically-inspired architecture. In so doing, force transmission paths can be provided through a wearable garment to generate force couples at the biological joints in a manner that does not impede movement or gait. As described herein, one or more sensors 120 are provided to monitor the wearer kinematics, such as to detect gait transitions or events. In at least some aspects, sensors 120 are embedded in or on the assistive flexible suit 100 (e.g., in or on a connection element 110, in or on a fabric, etc.) and/or at a variety of attachment points (e.g., at the hip, knee, ankle, foot, etc.) to monitor the interaction forces between the wearer and the device.

In at least some aspects of the present concepts, the assistive flexible suit 100 performs complementary functions of: (1) providing small mechanical cues to assist with the initiation of movement and restore normal neuromuscular control, and (2) restoring normal force-generating capability of the biological joints (see FIG. 1B). It is to be noted that this solution, as well as other solutions disclosed herein, have broad impact and can find application to multiple potential patient populations (e.g., to children with Cerebral Palsy, to elderly individuals with muscle weakness, persons with MD, ALS, or PD, stroke survivors, etc.).

FIG. 1B shows, on the left, some biomechanical reasons for mobility impairments of patients with Parkinson's disease (top) and MCA stroke (bottom). Whereas Parkinson's disease causes difficulty initiating movement and weakness in plantar flexion, MCA stroke presents multiple different challenges of weakness in plantar flexion, dorsiflexion, and hip flexion/extension. In the case of stroke patients, they suffer from limitations in the power available from various joints (including ankle and hip), which play a critical role in accelerating the body forward. This reduction in power contributes to diminished progression of the hemiparetic limb contributing to an asymmetrical gait pattern and slow walking velocities. For both of these patient populations, at least some of the assistive flexible suit 100 configurations disclosed herein provide external forces in parallel with the underlying biological musculature, which are believed to beneficially provide external cues to patients, which separately are believed to improve gait outcomes. The concepts herein, which apply small or moderate levels of forces to a patient in an automated, synchronous manner, facilitate development of larger step lengths and greater gait speeds, thereby improving physical function and HRQoL. FIG. 1B shows, on the right, aspects of assistive flexible suits 100, adapted to provide, clockwise from the top left, hip extension, hip flexion, dorsiflexion and planar flexion, with arrows 206 showing how forces can be applied to assist the respective motions.

FIG. 1C shows, in the left three images, use of the assistive flexible suit 100 to transition a stroke patient from a walker or brace, to assisted motion with the assistive flexible suit 100 and a cane, to unassisted movement using the assistive flexible suit 100. Many stroke survivors are capable of ambulation, but struggle with slow, fatigue-inducing gait patterns resulting from weakened ankle dorsiflexion and plantar flexion, as well as reduced movement during hip flexion and extension. As the patient progresses through the rehabilitation, the assistive power on the suit can gradually be decreased, functionally retraining muscle activation in task-based activities. Alternatively, as noted above, in at least some aspects of the present concepts, the assistive power to the patient from the assistive flexible suit can start at a lower level initially and can then be gradually increased over time as the patient progresses through the rehabilitation. The assistive flexible suit is conformable not only to the particular wearer, but is also advantageously conformable to the type(s) of assistance required by the wearer. FIG. 1C shows conceptually, in the fourth image from the left, that the assistive flexible suit 100 is easy to don/doff (upper left), being donned and doffed similar to a pair of slacks. The rightmost two images of FIG. 1C show a non-limiting example of a modularity of the assistive flexible suit, with the first image showing a passive or actuator-less version of assistive flexible suit 100, and the second image at the right showing additional of optional power belt 125 being attached to provide the capability for delivering active assistance. In at least some aspects, the power belt 125 comprises all actuators (e.g., motors, pulleys, etc.), electronics and power sources (e.g., batteries, etc.) necessary to power the assistive flexible suit 100. It is to be emphasized that the present concepts include a passive version of the assistive flexible suit 100, which does not include any actuator and which may or may not include sensor(s) 120, and is adapted to provide small degrees of energy and assistance to a user via resilient elements (e.g., stretchable fabric, textile, a visco-elastic material, a viscous material, etc.) of the assistive flexible suit.

The assistive flexible suit 100 facilitates generation of baseline kinematics, kinetics, electromyography and/or other physiological (e.g. metabolic and heart rate) data to help quantify the particular biomechanical and physiological abnormalities of each patient. By way of example, and without limitation, biomechanical and physiological data may be collected using a motion capture system (e.g., a plurality of Vicon cameras, recording at 120 Hz, used in combination with passive reflective markers disposed at key body landmarks), ground reaction forces (GRF) for each leg may be measured using a Bertec instrumented treadmill or embedded AMTI force plates at 1200 Hz, steady-state oxygen consumption may be measured using a Cosmed K4b2 system, and/or electromyography (EMG) signals collected by a Delsys® Trigno system. The baseline data provides a starting point from which a clinician can then tailor the specific assistance applied to that patient, with characteristics of the assistance being selectively varied as to location, magnitude and timing of the forces applied to the patient's lower extremities (see FIG. 1D).

FIG. 1D shows a representation of a clinical usage of the assistive flexible suit 100, utilizing an offboard control system 200, to apply a specified level of assistance (e.g., small, moderate, or large levels of assistance) to a patient wearing the assistive flexible suit 100 via force transmission elements 220A-220C. Information from sensors 120, shown by way of example to be provided in the footwear and in the vicinity of a patient's calf, is transmitted to the offboard control system 200 (e.g., via a wireless communication pathway 225 or a hardwired connection). The top plots on the right of FIG. 1D ("Joint Power Measurements") show force measurements demonstrating a restoring of power of the ankle and hip joints and the lower plot on the right of FIG. 1D ("Gastrocnemius Medialis EMG") shows a reduction in muscle activity (reduction in sEMG mV) of the gastrocnemius. Whereas for a healthy person, the assistive flexible suit can be used to advantageously decrease some muscle activity, this may not be universally desired and, in some patients, it may be desirable instead from a rehabilitative point of view to increase muscle activity.

It is to be noted that, although the level of force provided by the assistive flexible suit is described herein in relation to particular examples in which a small or a moderate level of force is provided, the assistive flexible suit is not limited to generation of small or moderate forces. By way of example, in at least some aspects of the present concepts, an assistive flexible suit is configured to supply between 10-30% assistance, while minimally burdening the wearer while and minimally restricting the wearer. Instead, the assistive flexible suit is capable of generating, and applying to the wearer, large forces and higher levels of assistance than that described in the examples herein. The disclosed assistive flexible suits, whether adapted to apply assistance within a prescribed range (e.g., a small level of assistance, a moderate level of assistance, a large level of assistance, a moderate to large level of assistance, etc.) or with an open range (i.e., a suit configured to any level of assistance between 0%-100% assistance), provide a key advantage over the existing rigid exoskeletons in that the majority of the assistance goes to assist the person rather than to move a heavy rigid exoskeleton, thus providing more efficient use of and application of the suit's limited power source(s) no matter what level of assistance is required by the wearer.

With exceptions, the gait of patients (e.g., stroke patients) is often repeatable with clearly identifiable pathologies, which lends to application of a cyclic actuation force applied by the assistive flexible suit 100 to the wearer. By personally tuning the actuation timing, amplitude and profile, a medical provider is able to provide to the patient an optimal assistance strategy for that patient. One favorable initial step in the process of adjusting actuation parameters may comprise tuning of dorsiflexion assistance to ensure that the patient will adequately clear the ground and not trip or fall as they walk or as the walking speed is increased. This could then be followed, for example, by tuning of plantar flexion assistance at push off to assist with forward propulsion. Then, if needed, hip actuation assistance (flexion and extension) could be tuned after the effectiveness of ankle actuation is verified.

Figure 2A:
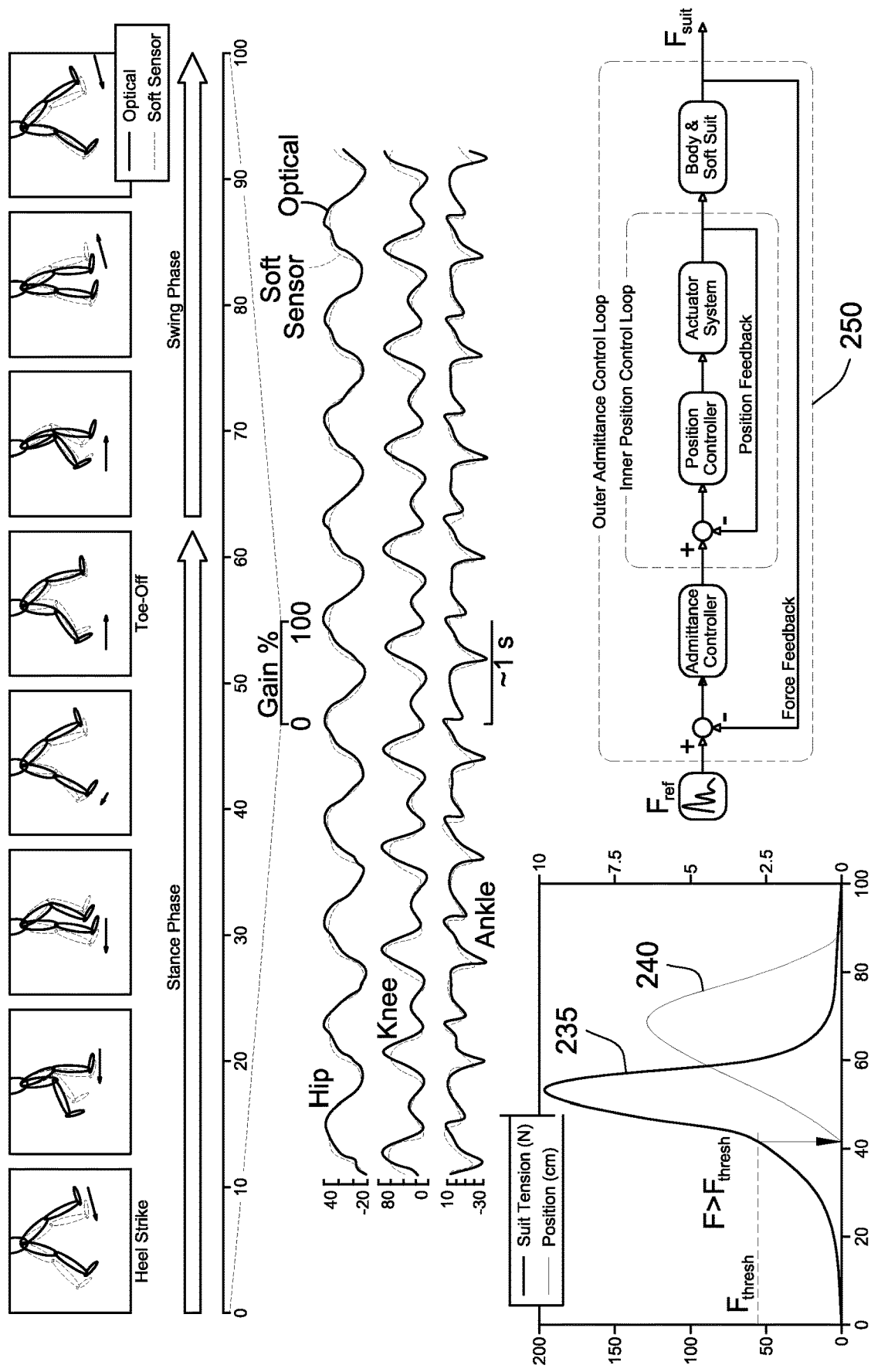
FIGS. 2A-2C are diagrams showing some aspects of controls for assistive flexible suits according to at least some aspects of the present concepts.

FIG. 2A shows validation of the sensor 120 fidelity via a comparison of movements of a person wearing an assistive flexible suit 100 measured, in real-time, by sensors 120 (dashed lines) and an external Vicon optical motion capture system (solid lines) for each of hip, knee and ankle joint angle sensors (e.g., hyper-elastic strain sensors disposed to monitor hip, knee and ankle sagittal plane joint angles). While walking, RMS errors in one embodiment of an assistive flexible suit were less than 5°. Accordingly, the assistive flexible suit 100 demonstrated the ability to accurately measure kinematic data for state-machine control and utilization of control algorithms enabling safe and intuitive interaction between the wearer and the device. This is achieved by obtaining and analyzing, in real-time, sensor 120 data providing information on kinematics (e.g., foot-switch, soft joint sensors, etc.) and human-system interaction forces (e.g., suit tension, etc.). As is shown in aspects of the present concepts illustrated at the bottom left of FIG. 2A, the suit tension (F) 235 is measured by one or more sensors 120 (e.g., hyperelastic strain sensors, load cells, etc.) and is used to trigger actuation of one or more actuators 105 (not shown) once a threshold force ($F_{thresh}$) is exceeded ($F>F_{thresh}$). FIG. 2A shows that, responsive to the trigger, the actuator actuates (in this instance, represented by a position change measured in cm) to deliver the forces represented. This control system provides a robust method of determining the correct times to actuate the system based on the human-suit interaction forces (e.g., monitoring passive tensioning in the assistive flexible suit 100) to produce a force-pattern that can be used to segment the wearer's gait. The threshold ($F_{Thresh}$) is set to actuate the one or more actuators 105 at the correct time in the gait in accord with a predetermined actuation profile. This method is very reliable and has minimal complexity. In still another control strategy, the correct times to actuate the system based on the human-suit interaction forces reliant on user kinematics or motion (e.g., joint angles, measured and/or inferred) to produce a force-pattern that can be used to segment the wearer's gait. This control system monitors one or more joint angles, or infers the position of one or more joint angles (e.g., from positions of other body segments), via one or more sensors 120 (e.g., hyperelastic strain sensors, etc.) and compares the one or more joint angles to a predetermined threshold to determine the correct time in the gait to begin actuation of one or more actuators 105. Namely, when the joint angle (Ø) exceeds a set threshold ($Ø_{Thresh}$), the actuator 105 is actuated in accord with a predetermined profile.

The assistive flexible suit 100 is, at least is some aspects, configured to operate responsive to an intent-based control system. The intent-based control system is informed by suit tensioning status and gait kinematics and/or other data (e.g., EMG, velocity, acceleration, discrete events, etc.). Owing to the assistive flexible suit's 100 passive, kinematic-based tension generation, tension patterns measured, for example, at the ankle and hip permit the detection of the intent of the wearer. The information from these sensors is advantageously, but optionally, integrated with data from other redundant sensors 120 (e.g., inertial measurement units, insole pressure switch(es), etc.) to ensure robust control. A multi joint low-level control strategy provide a reduced parameter set that can be controlled without having to do precise control locally at each joint. Rather, control is optimized across all joints together at least in part to ensure that the level of assistance to each muscle group is robust to gait cadence, step length, joint angle offset (due to inclined walking), and other joint-level variables. This control strategy also ensures a timely delivery of assistance during only the energy-relevant phases of gait for each muscle group (e.g. forward propulsion for the ankle joint during level walking, early stance for hip extension during uphill walking, etc.). Significantly, this approach provides an appropriate level of energy injection for a patient or wearer based on the severity of their impairment (or need for assistance) and desired movement, without the need to monitor the activity of the underlying biological muscle.

FIG. 2A (bottom right) shows, by way of example, sensor 120 data (e.g., $F_{ref}$) input into a multi joint low-level controller 250 configured to adapt the assistance given to each muscle group to gait cadence, step length, and other joint-level variables. Thus, energy injection is provided at an appropriate time and level for the desired movement. Controller 250 thus is able to advantageously utilize tension in the assistive flexible suit 100, passively generated by the motion of the wearer, as a trigger to begin the addition of energy via one or more actuators 105. The data from the sensors 120 (e.g., strain sensors, soft joint angle sensors, footswitches, IMUS, gyros, etc.) can be used to accurately segment the gait cycle, providing assistance based on timing in the gait cycle to provide assistance not only in sync with the wearer, but also responsive to an intent of the wearer (i.e., intent-based control strategies). The use of tension measurements to dynamically characterize the gait provides a simple, reliable control strategy that robustly adapts to changes in movement.

Figure 2B:
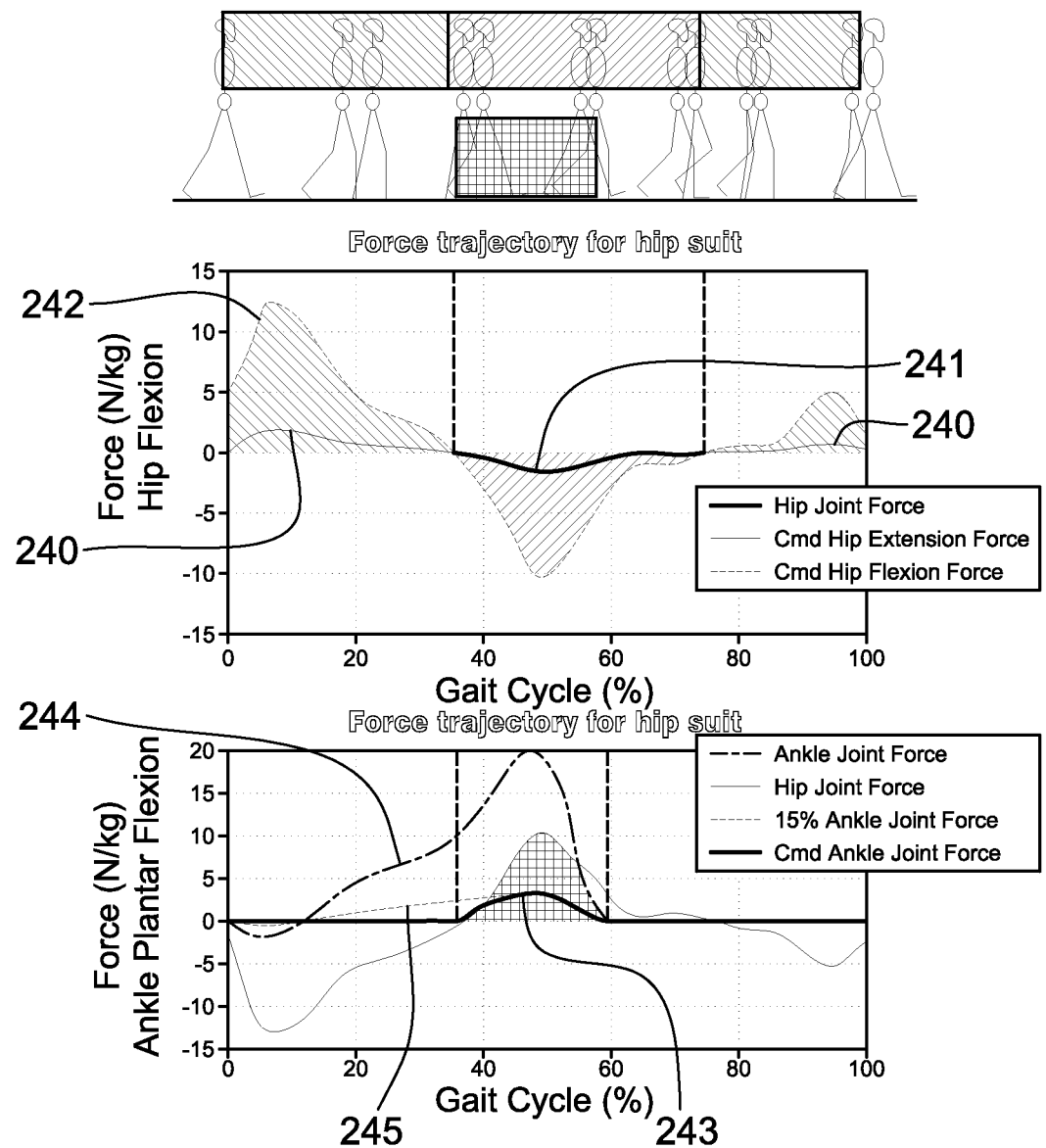

FIG. 2B shows a representation of a force trajectory for an assistive flexible suit 100 configured to provide hip actuation ("hip suit"), particularly hip flexion command forces for one gait cycle. FIG. 2B shows a standardized torque profile for the hip in flexion, with active engagement from about 35%-75% of the gait cycle, with a peak force of about 130N. In at least some aspects of the present concepts, the normalized reference force trajectories for each joint are predetermined, saved in a physical computer-readable medium, and adapted, in real-time, by control algorithm scaling responsive to the step frequency (e.g., obtained by foot switches).

While the assistive flexible suit 100 actuation platform is capable of delivering 100% of the torque required to match that of the biological joints for a wearer, without providing body weight unloading, the level of assistance provided by the assistive flexible suit is advantageously tailored to the needs of a particular wearer. For example, in at least one aspect, an assistive flexible suit is limited to provide only about 15% of the total torque required by the joint to be delivered (e.g., a small to moderate level of assistance). FIG. 2B shows the required torque for the ankle and hip joints during walking for a gait cycle, starting with heel strike of one leg to the next heel strike of the same leg. The hip joint force is shown in FIG. 2B plot 242, with the commanded hip extension force being shown as plot 240 (left and right portions of gait) and the commanded hip flexion force being shown as plot 241 (center portion of gait). In the middle of FIG. 2B, the commanded ankle joint force is shown by plot 243, with the ankle joint force being shown by plot 244 and the 15% ankle joint force being shown by plot 245. The force profiles are standardized joint torque profiles, divided by the moment arms of a particular version of an ankle and hip assistive flexible suit 100, and scaled to 15% of their amplitude. By way of example, for an 80 kg wearer, this would results in peak forces of 240N and 130N for ankle plantar flexion and hip flexion, respectively. These force values are for illustrative purposes and are not limiting values for the assistive flexible suit. The force profile for the ankle plantar flexion/hip flexion in FIG. 2B shows, in the bottom plot, that the hip and ankle force profiles are combined because the suit is affecting both joints simultaneously. In the presently described example, in order to avoid hindering the hip joint while actuating the ankle, the commanded force profile for the ankle begins at the point when the applied force benefits both joints (around 35% of the gait cycle), as shown at the bottom part of FIG. 2B.

The force control of the assistive flexible suit 100 is implemented, in at least some aspects of the present concepts, using a position-based admittance controller with force as an input. In addition to providing controlled force pulses, the system is flexible enough to also make the assistive flexible suit 100 transparent to the wearer by tracking the wearer's motions, an advanced technique beyond merely deactivating the actuator (e.g., making a Bowden cable slack in a configuration utilizing a Bowden cable transmission system). This approach is not possible to implement with traditional rigid exoskeletons since the wearer would need to take off the system in order to be able to walk freely again in the event of degraded voltage or power loss. Yet further, in this case of a zero-force mode, the cable travel of the Bowden cable(s) can be used to estimate joint angle(s), providing valuable data for use by the system, the wearer and/or a medical provider.

Figure 2C:
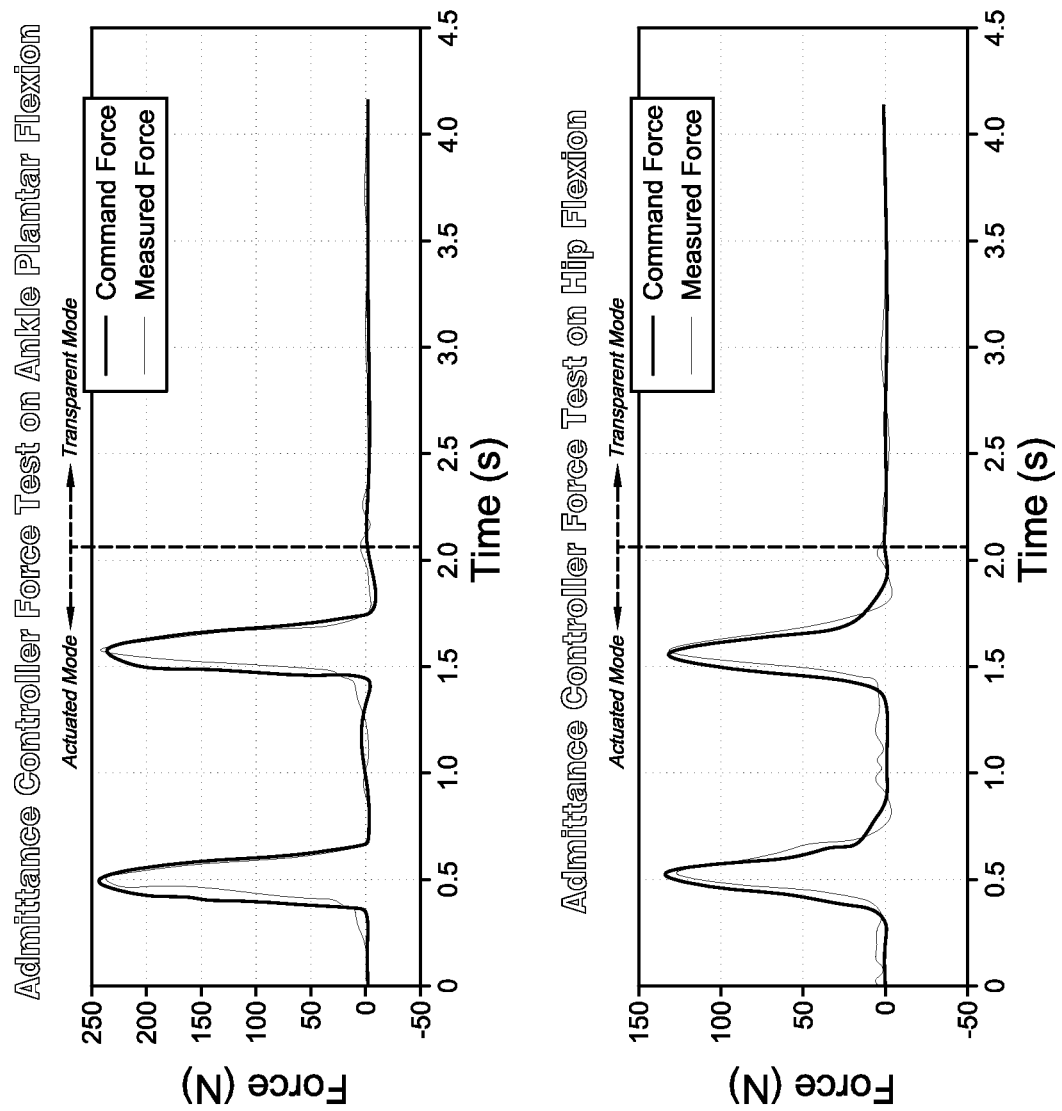

FIG. 2C shows admittance controller force tests on ankle plantar flexion (top) and hip flexion (bottom) during four gait cycles of walking by a subject at 1.25 m/s, as the suit transitions from an active or actuated mode (prior to about 2 seconds) to a deactivated or transparent mode shortly after the 2 second mark in the plots of FIG. 2C wherein the controller operates on (i.e., the command force) the ankle plantar flexion and hip flexion. In each plot of FIG. 2C, the controller provides assistance for two gait cycles, and then switches to a "transparent" mode in which the system tracks the wearer and ensures that no forces are applied to them (e.g., the measured force is close to about 0 N). A transparent mode, such as is shown, is not possible with traditional rigid exoskeletons because of their significant inertia.

Figure 2D:
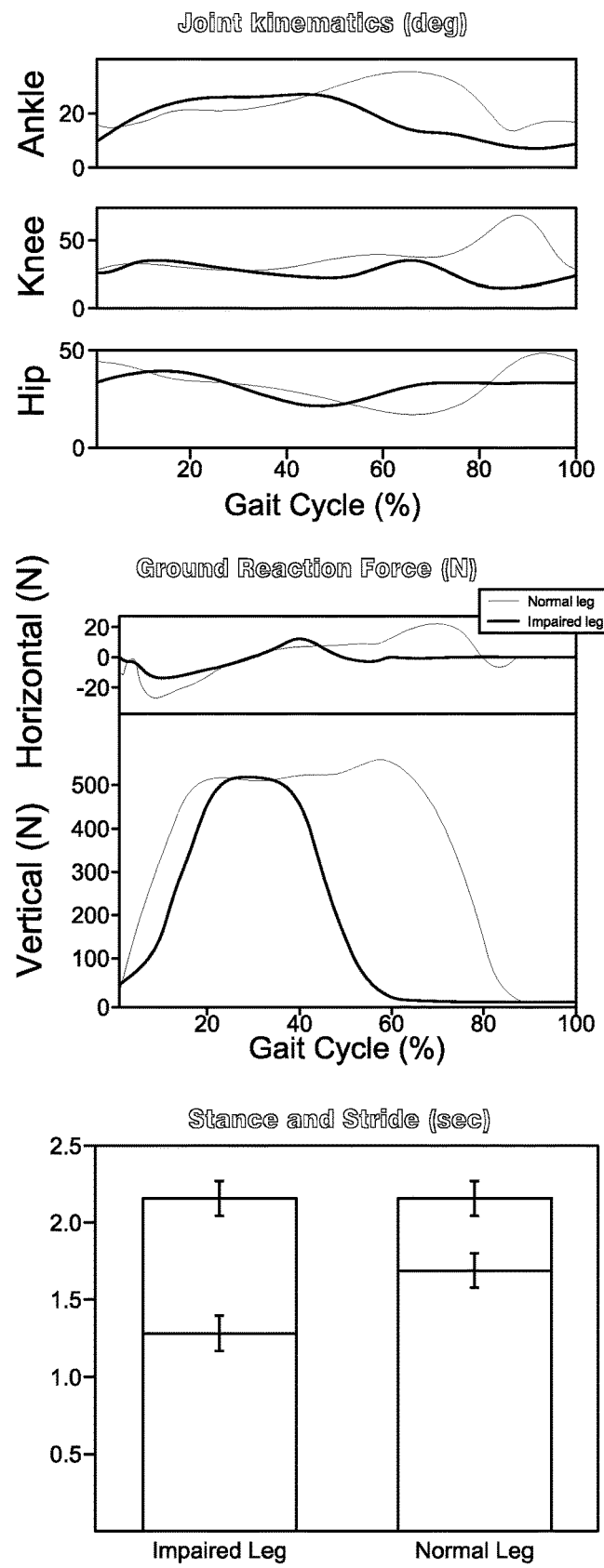
FIG. 2D shows gait information for a hemiparetic stroke patient.

FIG. 2D illustrates an example of gait asymmetry, particularly that of a hemiparetic stroke patient showing a foot-drop gait with weak planar flexion and ankle rolling. Kinematics for the hip, knee and ankle show reduced range of motion of the paretic leg. In the middle plots, the ground reaction forces (GRF) show reduced push off and reduced time on the paretic leg. On the right of FIG. 2D, a clear asymmetry is shown in stance duration and stride duration, as between the impaired leg (left) and sound leg (right), a lack of push-off of the impaired leg from GRF, and reduced ranges of motion of the hip, knee and ankle joints, the latter also clearly showing signs of foot-drop during the swing phase.

Figure 2E:
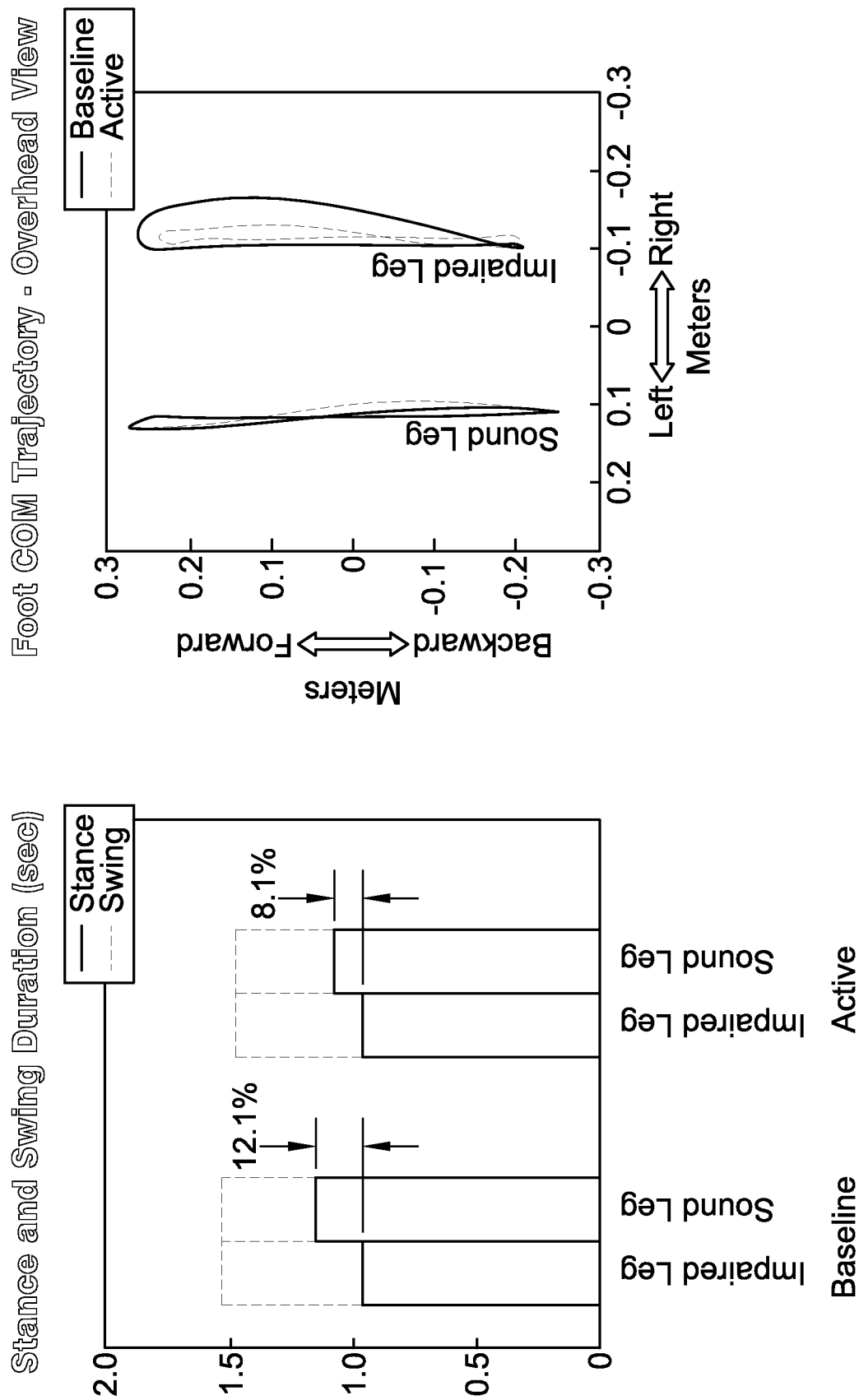
FIG. 2E shows and an example of data obtained from a pilot session of a stroke patient wearing an assistive flexible suit while walking on a treadmill according to at least some aspects of the present concepts.

FIG. 2E shows an example of data obtained from a pilot session of a stroke patient wearing an assistive flexible suit while walking on a treadmill and while using an off board actuation system (see, e.g., reference numeral 200, FIG. 1D) to apply forces. FIG. 2E represents an embodiment of an assistive flexible suit 100 configured to provide assistance for ankle dorsiflexion and plantar flexion. The left image of FIG. 2E shows improvements in gait symmetry between the impaired leg and the sound leg, as well as reduced stance duration (increased stride length). The baseline difference between the sound leg and the impaired leg is shown to be 12.1%, whereas the difference between the sound leg and the impaired leg when the assistive flexible suit is active is shown to be only 8.1%, an improvement of 4%. The right image of FIG. 2E shows a significant reduction in compensatory gait (hip circumduction), which is demonstrated by less lateral motion of foot center of mass (COM) on impaired leg.

In view of the above, and more detailed descriptions below, the present concepts include assistive flexible suit 100 that can be particularly suited to individuals to enhance their mobility. The assistive flexible suit 100 is selected for use (e.g., assembled from modules as a modular construct, designed as a custom suit specific to the patient, an "off-the-shelf" suit generally adapted to a particular malady or required assistance, etc.) and optimized for a specific individual utilizing components and systems, active and/or passive, appropriate for that individual's needs (e.g., single limb, multiple limbs, single joint, multiple joint, etc.) at a particular time (i.e., the needs may change over time).

Figure 3A:
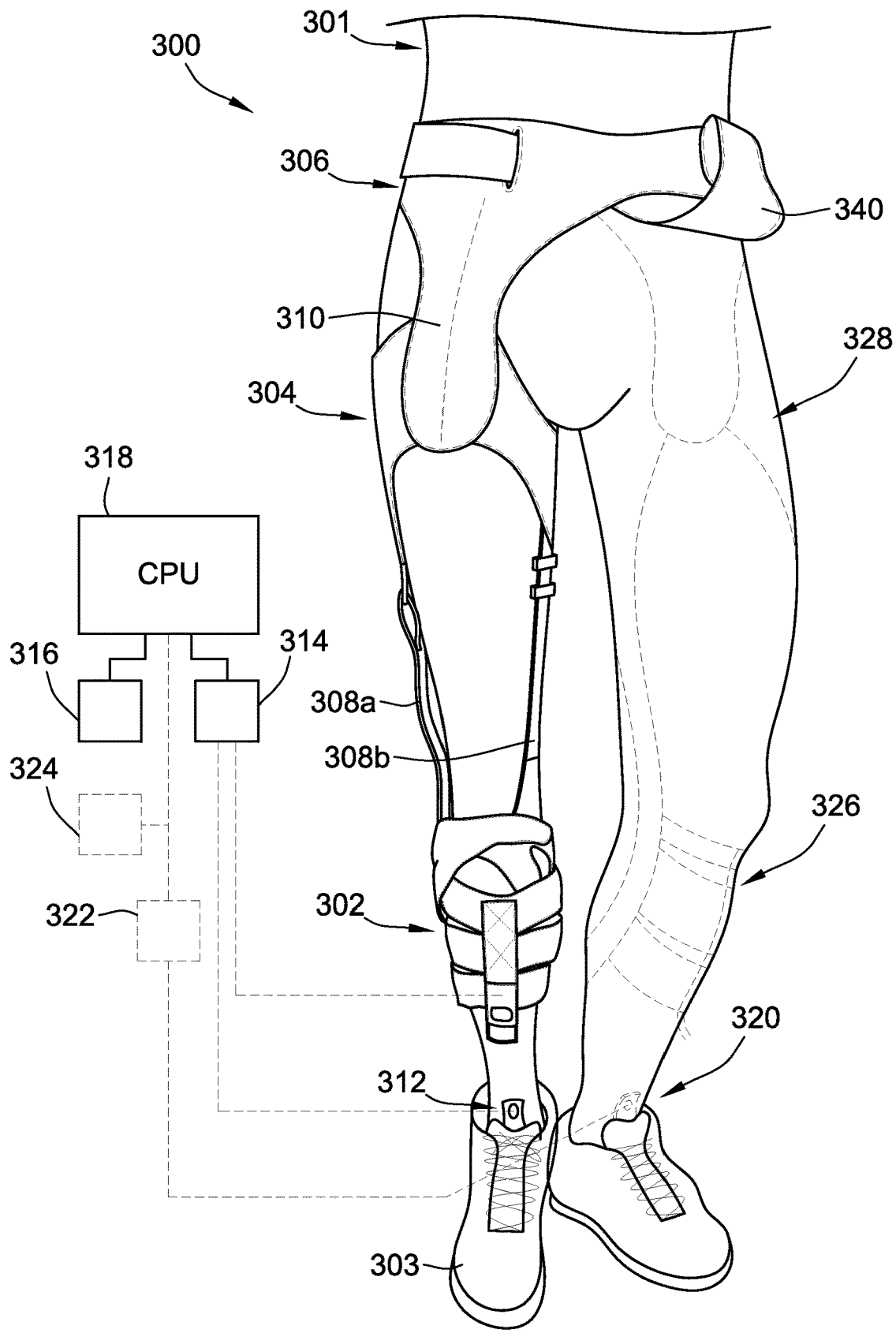
FIGS. 3A and 3B are front and side perspective-view illustrations, respectively, of a representative assistive flexible suit for aiding motion of a wearer in accord with aspects of the present disclosure.
Figure 3B:
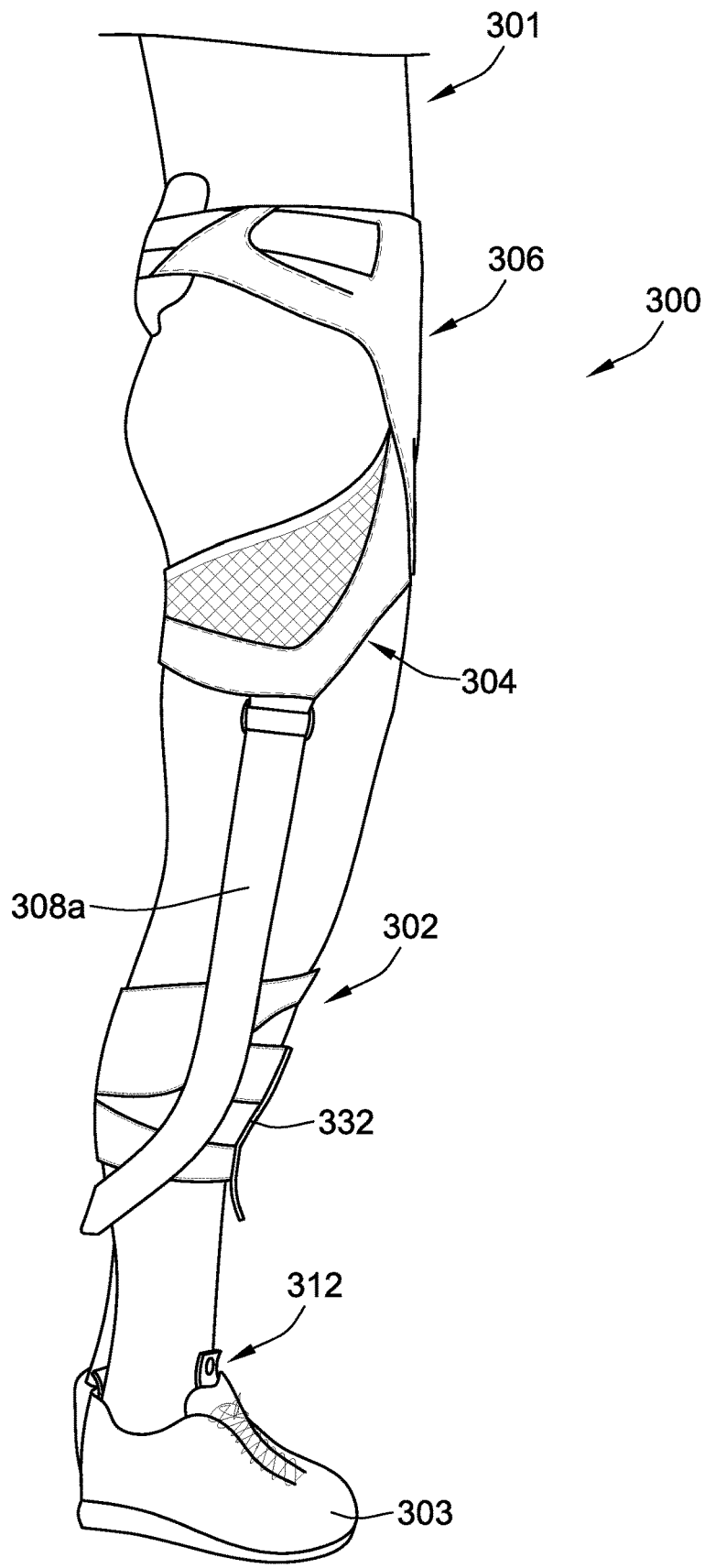

Turning next to FIGS. 3A and 3B, there is shown a representative assistive flexible suit, designated generally at 300, for aiding motion of a wearer. In general, the assistive flexible suit 300 can be implemented as an orthotic device that is used in combination with an actuator-and-control system to provide active assistance with mammalian locomotion, such as walking, running, jumping, stepping up (e.g., going up steps or stairs), stepping down (e.g., going down steps or stairs), sitting down (e.g., sitting in a chair), standing up (e.g., rising from a chair), etcetera. By way of contrast with contemporary exoskeleton systems, which utilize rigid external skeletal supports and rigid linkage elements, the mechanized assistive flexible suit 300 of FIGS. 3A and 3B utilizes conformable materials and stretchable fabrics in combination with light-weight actuators and sensor devices to mitigate, for example, limitations associated with rigid exoskeleton devices. Assistive flexible suit 300, as shown, does not have a load bearing exoskeleton, but rather relies on the wearer's biological skeleton to assist with the application of forces and transfer of load. It may be desirable, however, to combine the flexible suit 300 with a lightweight, rigid or semi-rigid skeletal system to create a hybrid system, e.g., for cases requiring the application of large levels of force or for cases where the wearer's biological skeleton cannot or should not bear the entire load. While differing in appearance from some of the other illustrated examples, the assistive flexible suit 300 can take on any of the features, options, and alternatives disclosed with respect to the other assistive flexible suits disclosed herein, singly and in any combination, unless explicitly disclaimed or otherwise logically prohibited.

With continuing reference to the representative embodiment portrayed in the drawings, assistive flexible suit 300 includes one or more suspension anchors (also referred to herein as "anchor elements") that are configured to mount to the body 301 of the wearer and transmit loads to one or more predetermined load-bearing segments of the wearer's body 301. Each illustrated suspension anchor redirects reaction forces generated by an actuator for dissipation at one or more "anchor points" on the wearer's body. These designated anchor points, such as, but not limited to, the shoulders and/or the iliac crests of the hips, have been determined to more readily support the systematic application of actuator-generated loads. Generally speaking, an anchor point can be characterized by a large bony landmark at or near the surface of the skin that is able to withstand large applied normal or nearly normal reaction forces (e.g., at the hips, downwardly directed loads borne on the top of the iliac crest region are preferable to forces in shear borne along the side of the hip). By way of non-limiting example, a first suspension anchor in the form of a calf sleeve 302 couples (e.g., extends around and attaches circumferentially via one or more hook-and-loop straps) to portions of the calf (gastrocnemius) and tibia (anterior tibialis) of the wearer's lower leg above the assisted foot. The calf sleeve 302 engages, among other portions of the lower leg, the crest of the gastroc as a load-bearing anchor point for supporting reaction forces. In addition, a second suspension anchor in the form of a thigh sleeve 304 couples (e.g., wraps around and attaches circumferentially via one or more hook-and-loop straps) to portions of the thigh (quadriceps and hamstrings) of the wearer's upper leg above the assisted foot. Thigh sleeve 304 provides a support point on the thigh to guide and align actuation forces from the hip down along the thigh to the calf and/or foot. Owing to the tapered shape of the thigh, the thigh can be used as a support point that prevents or otherwise minimizes upward movement of the thigh sleeve 304 response to tension applied to the sleeve 304. A third suspension anchor in the form of a waist belt 306 couples (e.g., wraps around and attaches circumferentially via one or more hook-and-loop straps) to the waist (pelvis) of the wearer. The waist belt 306 extends over the superolateral iliac crests of the pelvic girdle as load-bearing support members or anchor points for supporting reaction forces. By allowing the waist belt 306 to tightly conform to the wearer's body 301 at a narrow portion of the waist, the natural features of the body 301 at that junction help to maintain the belt in position.

It is also contemplated that the assistive flexible suit 300 include greater or fewer or alternative suspension anchors than the three illustrated in the drawings. For example, the assistive flexible suit 300 could eliminate the second and/or third suspension anchors 304, 306 while still providing plantar flexion and dorsiflexion assistance to the wearer by way of the first suspension anchor 302. Alternatively, the first suspension anchor 302 could be eliminated for embodiments which are designed to provide, for example, assisted hip flexion and/or extension by way of the second and third suspension anchors 304, 306. As yet another option, the third suspension anchor 306 could be eliminated for embodiments which are designed to provide, for example, assisted knee flexion and/or knee extension. Optionally, the assistive flexible suit 300 could employ shoulder straps to provide additional anchor points for reactionary load distribution.

Reaction forces from a desired actuator can be redirected to one or more of the anchor points along lines of non-flexion and lines of non-extension. This can be accomplished, for example, via a matrix of unstretchable or substantially unstretchable connectors (also referred to herein as "connection elements") from a desired actuation point, which maintains stability during normal range of motion, while redirecting the forces to terminate at one or more anchor points. According to the illustrated example, the calf sleeve 302 is coupled to the thigh sleeve 304 via a first (lateral) strap 308A and a second (medial) strap 308B. As shown, the lateral and medial straps 308A, 308B are generally parallel to one another and both extend rectilinearly along the length of the wearer's leg without obstructing flexion/extension of the associated knee joint. In this regard, first (anterior) flap 310, which extends downwardly along the rectus femoris muscle of the wearer's upper leg, couples the waist belt 306 to the thigh sleeve 304, which in turn connects the waist belt 306 to the calf sleeve 302 via straps 308A, 308B. It is envisioned that the assistive flexible suit 300 include greater or fewer or alternative means for coupling together the various suspension anchors. For example, cabling and/or webbing structures could be employed to connect the calf sleeve 302 to the thigh sleeve 304 or the waist belt 306 to the thigh sleeve 304.

If so desired, one or more connection elements can be pre-tensioned across a joint such that the biasing pre-tension imposes an assistive moment on the joint. Optionally, the wearer or a clinician can selectively increase or decrease the level of pre-tension at select location(s) on the assistive flexible suit 300. This feature of selective pre-tensioning modification can comprise one or more independent channels (e.g., whole suit and/or independent controls for left/right and/or front/back), controlled by a mechanical or an electro-mechanical tensioning device configured to adjust tension along the channel (e.g., by adjusting a functional length of one or more connection elements). For passive systems, the flexible suit system can omit actuators for actively generating assistive forces.

With continuing reference to FIGS. 3A and 3B, the flexible assistive suit 300 also includes a connection element that engages the wearer's foot such that a selectively generated moment force can be applied about the ankle joint to thereby assist with one or more segments of the wearer's gait. According to the illustrated example, a foot module 312 (also referred to herein as "foot attachment element") is configured to mount adjacent or around or, as shown, on the assisted foot of the wearer such that tensile forces can be transmitted to the hindfoot segment (e.g., at or adjacent the calcaneus region) and/or the forefoot segment (e.g., at or adjacent the metatarsal region) of the wearer's foot. As shown, the foot module 312 fits inside the wearer's shoe 303 and conforms to one or more portions of the wearer's foot. Alternative configurations, some of which are shown and described in detail above and below, utilize foot modules that attach to or are fabricated as an integral part of the wearer's shoe 303. With this module, the assistive flexible suit 300 can be tensioned or pre-tensioned between the hip (via waist belt 306), upper leg (via thigh sleeve 304), or lower leg (via calf sleeve 302) and the foot module 312 to create a beneficial plantar flexion moment or dorsiflexion moment at the ankle at a designated time during the gait cycle, as described more fully below.

To assist bipedal locomotion in the gait cycle of a human subject, one or more active components can be added to the assistive flexible suit to actively pull (or push) on one or more selected locations of the foot at pre-designated times to increase locomotive power at or during push-off phase and/or swing phase. An actuator 314 attached (e.g., at a distal end thereof) to the foot module 312 and attached (e.g., at a proximal end thereof) to at least one of the suspension anchors 302, 304, 306 is selectively actuable to generate tension between the foot module and the suspension anchor(s). For some embodiments, the driving end of the actuator 312 (e.g., the housing) is mounted to the waist belt 306 or the calf sleeve 302 for redistribution of reaction forces, while the driven end of the actuator 312 (e.g., the end of an attachment cable, strap, or piston rod) is attached to the foot module 312. The actuator may take on any of various known forms, such as a motor-driven Bowden cable, a Pneumatic Artificial Muscle (PAM), a dual-arm twisted string actuator, a spooled string actuator, a piezoelectric actuator, electro-active material (e.g. shape memory alloys and polymers), etc. In some embodiments, a clutch is employed to engage and/or disengage components (e.g. elastic member, actuator, damper, etc.). Optionally, the calf sleeve 302 can be connected by an inelastic member (e.g., a cable, a strap, a piston, a draw string, etc.) or an elastic member (e.g., braided nylon, shock cord, etc.) to the heel connection element of the foot module 312 such that (e.g., during normal walking) tensile forces applied to the foot module 312 create beneficial moments about the ankle joint to supplement natural muscle-driven motion. In alternative configurations, the actuator is mounted on a movable cart, an adjacent support platform, or otherwise positioned proximal to the assistive flexible suit 300, as will be developed in additional detail below.

Sensing devices are advantageously used to modulate and synchronize actuator activation with the gait cycle of the wearer. Continuing with the above example, one or more sensors (also referred to herein as "sensing elements"), illustrated schematically at 316 in FIG. 3A, are mounted on or proximate the wearer's assisted foot. Each said sensor 316 is operable to detect at least one gait characteristic of the wearer and output a signal indicative thereof. A gait characteristic may comprise a variable or parameter associated with the pattern of movement of one or both legs and/or one or both feet during bipedal locomotion. A characteristic can be partitioned from somewhere within or between a stance phase, where the foot is in contact with the ground, and a swing phase, where the foot is lifted and moved forward. This may include duration, length, symmetry, and/or frequency measurements associated with heel strike, flatfoot, toe off, and/or swing. Each said sensor 316 may comprise, singly or in any combination, a foot switch, a gyroscope, an inertial transducer, an accelerometer, a foot strike sensor, a joint angle sensor, etc. Monitored variable(s), once transformed into electronic data signals by a sensor, can be output to a central processing unit (CPU) or controller 318 for processing. By way of non-limiting example, tensile forces are sensed by a force sensor mounted on or adjacent the foot module 312 proximal to a connector element of the actuator 314, and these forces are monitored and evaluated by a controller 318 (e.g., for several cycles of movement) to estimate the gait cycle. The controller 318 progressively engages/disengages the actuator(s) 314 over a few or more cycles of movement or after instruction by the wearer to enable actuation. Alternatively, the CPU 318 may infer a gait pattern based on other feedback, such as a predetermined default pattern for wearers of a specific type (e.g., all 70th percentile males), manual inputs from the wearer, manual inputs from a clinician, or a combination thereof. The CPU 318 can learn how a particular person walks without assistance, thereafter start to apply assistance to see how gait changes, and then adjust appropriately.

The various active components of the flexible assistive flexible suit system are controlled by one or more processors (e.g., CPU, distributed processors, etc.), also referred to herein generally as a controller (e.g., microcontroller(s), microprocessor(s), etc.). A controller, microcontroller or central processing unit (CPU) 318 is communicatively connected to the sensor 316 and the actuator 314. CPU 318, as used herein, can comprise any combination of hardware, software, and/or firmware resident to the suit 300 (onboard) and/or distributed externally of the suit 300 (offboard). The CPU 318 can include any suitable processor or processors. By way of example, the CPU 318 includes a plurality of microprocessors including a master processor, a slave processor, and a secondary or parallel processor. The CPU 318 is generally operable to execute any or all of the various computer program products, software, applications, algorithms, methods and/or other processes disclosed herein. The CPU 318 can include a memory device or can be coupled to a memory device, which can comprise a volatile memory (e.g., a random-access memory (RAM) or multiple RAM) and a non-volatile memory (e.g., an EEPROM). The controller 318 analyzes the gait characteristic signal output by the sensor(s) 316 and, based at least in part on the analyzed signal, selectively actuates the actuator 314 to apply a tensile force to the foot module 312 and thereby generate a moment about the wearer's ankle and assist plantar flexion or dorsiflexion, or both, of the assisted foot of the wearer. With this configuration, the assistive flexible suit 300 actuates in parallel to the calf muscles during gait cycle to provide assistance at the ankle joint. Focused assistance at the ankle joint is provided, for example, because distal muscles are typically the most severely impaired in a stroke victim, and because addressing weakness at the ankle has been determined to have a positive cascading effect upon the knee and hip joints. Methods for using and methods for controlling the assistive flexible suit 300, which can be implemented in whole or in part via the CPU 318, are developed in further detail below.

Optionally, for configurations in which an actuator 314 is mounted on or otherwise coupled (e.g., at a driving end thereof, etc.), to the waist belt 306 and attached to the thigh sleeve 304, the controller 318 is operable to selectively actuate the actuator 314 to generate tension between the thigh sleeve 304 and waist belt 306 and thereby assist hip extension/flexion of the wearer during gait. Tensile forces created by the actuator(s) 314 in the flexible assistive flexible suit 300 can be routed from waist belt 306 down the posterior thigh region, generally parallel to the connection straps 308A, 308B, across the knee joint to the calf sleeve 302, and down to a heel strap of the foot module 312. This tensile force can create an assistive moment force in the hip joint to aid with hip extension. This tensile force can also create a beneficial moment in the ankle joint where it assists with dorsiflexion and, if desired, subsequently assists with plantar flexion, causing the foot to push off in a forward direction.

While the assistive motion discussed above is disclosed as being predominantly within (i.e., generally parallel to) the sagittal plane for ankle and hip motion, assistive motion generated by the flexible suit can be provided in other planes. In accord with at least some aspects, the assistive suit is configured to deliver torques or other assistive forces on the body in the sagittal plane and/or in one or more other planes (at the same time or independently). For example, the assistive suit can be provided with medial and lateral actuator attachment loops at the front and/or back of a foot attachment element (e.g., foot module 812 of FIG. 8) or more medial and more lateral actuator attachment elements on other attachment points (e.g., thigh, shank, etc.) to apply tensile forces along planes parallel or oblique to the sagittal plane. Such attachments allow the suit to deliver assistance (e.g., in the sagittal plane) coupled with stabilization (e.g., in a non-sagittal plane) on the frontal plane (medial lateral torque). In general, the assistive suit can be configured to use tensile forces to deliver joint torques that are not co-planar to the sagittal or frontal human joint plane, but that are purposefully aligned on another plane that combines two components.

While initially disclosed as a unilateral orthotic device for assisting motion in a single leg, the assistive flexible suit 300 may be constructed as a bilateral orthotic device for assisting both of the wearer's legs during locomotion. For such a configuration, the assistive flexible suit 300 comprises a second foot module 320 that mounts on or adjacent to the wearer's second foot, and transmit tensile loads to the hindfoot segment and/or forefoot segment of the second foot. While a single bilateral actuating device can be employed to drive both foot modules 312, 320, an optional second actuator 322 can be attached to at least one of the suit's suspension anchors, such as the waist belt 306, and the additional foot module 320. This additional actuator 322 is selectively actuable to transmit tensile forces to the second foot module 320. If so desired, the suit 300 may be provided with additional suspension anchors to which the second actuator 322 can be operatively mounted. By way of non-limiting example, a suspension anchor in the form of a second calf sleeve 326 extends around and attaches (e.g., circumferentially, etc.) via one or more hook-and-loop straps, to portions of the wearer's lower leg above the corresponding assisted foot. Another optional suspension anchor in the form of a second thigh sleeve 328 wraps around and attaches (e.g., circumferentially via one or more hook-and-loop straps) to portions of the wearer's upper leg above the corresponding assisted foot. As should be readily apparent, the second calf sleeve 326 and thigh sleeve 328 can be identical or substantially identical in structure, operation, and connectivity to the calf sleeve 302 and thigh sleeve 304, respectively, described above.

Sensing devices can be used to modulate and synchronize activation of the second actuator 322 with the gait cycle of the wearer. Depending on configuration, sensor 316 can provide this functionality or, optionally, a second sensor 324 can be provided to detect one or more gait characteristics of the wearer related to the second foot and/or leg and output a signal indicative thereof. The foregoing sensor may take on any of the various forms of sensing devices disclosed herein or otherwise known. In this implementation, the system controller or CPU 318 is communicatively connected to the second actuator 322 and sensor 324. The CPU 318 is programmed to analyze the gait characteristic signal(s) output by the second sensor 324 and, based at least in part on this analysis, selectively actuate the second actuator 322 to thereby assist plantar flexion or dorsiflexion, or both, of the second wearer's foot. Optionally, the controller 318 is operable to selectively actuate the actuator 3322 to generate tension between the thigh sleeve 328 and waist belt 306 and thereby assist hip extension/flexion of the wearer in the second leg during gait.

FIG. 3C provides a rear-view illustration of the calf sleeve 302 of FIGS. 3A and 3B. A crisscross arrangement of hook-and-loop fastening straps—namely first and second draw straps 330A and 330B—project from opposing sides of an elongated and vertically oriented central (shin) member, designated 332 in FIG. 3B. Shin member 332 is designed to lie against the wearer's lower length, extending lengthwise along the length of the leg such that member 332 is generally parallel to the wearer's tibia. The first and second draw straps 330A and 330B are drawn around and circumscribe the wearer's calf such that, when, tightened, the straps circumferentially attach the calf sleeve 302 to the wearer's lower leg above the assisted foot. Calf sleeve 302 is connected at the back of the leg via a V-connector strap 334 to a heel attachment or anchor element that directly (e.g., inside the wearer's footwear, between the sock or liner and inner surfaces of the footwear) or indirectly (e.g., through the footwear) engages the foot. Optional configurations may include an elongated generally cylindrical elastic wrap, similar in nature to a calf compression sleeve, that is configured to wrap around the tibia and calf and provide a more conformal and comfortable fit. For such configurations, multiple pairs of hook-and-loop fastening straps can be attached to the elastic wrap and configured to attach (e.g., in partial overlapping relation to one another, etc.), to thereby increase stability and attachment strength of the calf sleeve. An adjustable strap can be provided which circumscribes the lower leg and increases circumferential tension around at least a top portion of the calf of the wearer.

Turning next to FIG. 3D, there is shown a perspective view illustration of the waist belt 306 that was initially presented in FIGS. 3A and 3B. In accord with some embodiments of the present disclosure, the waist belt 306 includes a first (topside) chap 336 integral with a first (anterior) flap 310 and first connection belt strap 337. Also part of the waist belt 306 is a second (bottom-side) chap 338 with an integral second (anterior) flap 340 and second connection belt strap 339. Proximal ends of the first and second chaps 336, 338 are attached to the backside of a lumbar pad 342. To don the waist belt 306 exemplified in FIG. 3D, the lumbar pad 342 is placed against the lower spine region of the wearer's back, the second connection belt strap 339 is passed around the pelvis (over the right ilium) and through a belt slot 335 in the topside chap 336, and then fastened in place via a hook-and-look patch (not shown) on an underside of the strap 339 that mates with a complementary hook-and-look patch (not shown) on a topside of the chap 336. Prior to, contemporaneous with, or after securing the second belt strap 339 in place, the first belt strap 337 is passed around the pelvis (over the left ilium) and then fastened in place via a hook-and-look patch (not shown) on an underside of the strap 337 that mates with a complementary hook-and-look patch (not shown) on a topside of the chap 338. For alternative configurations, belt straps 337, 339 can be joined at distal ends via a buckle or other connection means that enables the waist belt to be fastened around the waist of the wearer over the superolateral iliac crests. The waist belt 306 keeps the various constituent parts of the assistive flexible suit 300 from being inadvertently pulled down under vertical loading and/or slipping over the pelvis region due to horizontal loading that is the result, for example, of the angle of the connection elements that attach the thigh sleeves to the waist belt. When implemented for a unilateral application, an unused anterior thigh flap (e.g., flap 340) can be rolled up and tucked in or otherwise attached to the waist belt band (as seen in FIG. 3A).

Figure 3E:
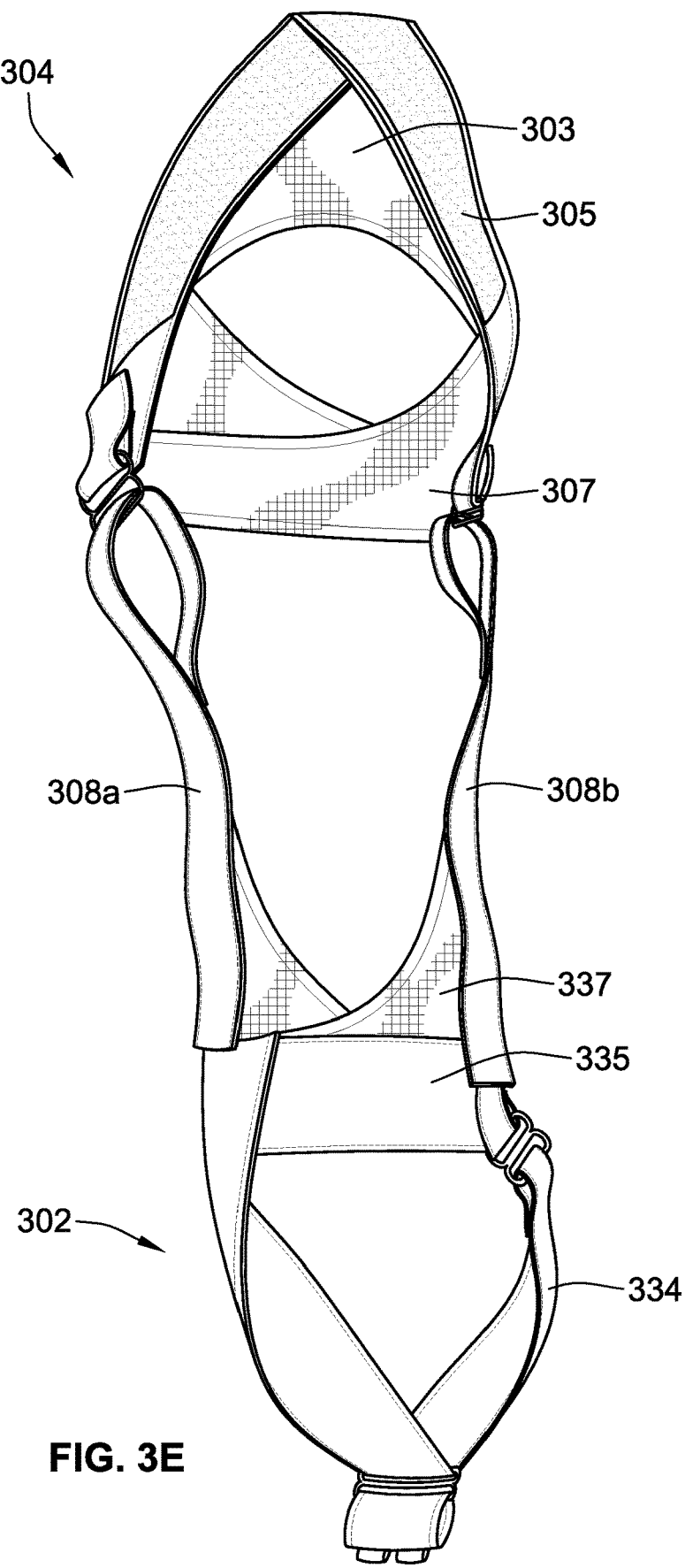
FIG. 3E is a rear perspective-view illustration of the thigh sleeve module, attachment straps and portions of the calf sleeve module of the assistive flexible suit of FIGS. 3A and 3B.

Shown in FIG. 3E are the thigh sleeve 304, first and second straps 308A, 308B, and the V-connector strap 334 of the calf sleeve 302. Thigh sleeve 304 has a frustoconical geometry defined by a power mesh insert 303 that is buttressed between an inverted-V connector segment 305 that is connected to a posterior cuff 307. The power mesh insert 303, which lies over a portion of the wearer's quadriceps (as seen in FIGS. 3A and 3B), helps to prevent slipping during operation of the assistive flexible suit 304 and absorbs small amounts of force on the back of the sleeve. The connector segment 305 operates to attach the thigh sleeve 304 (e.g., via intermeshing hook-and-loop fastening patches) to the waist belt 306 by way of the anterior flap 310. Posterior cuff 307, on the other hand, wraps around the back of the wearer's upper leg (e.g., over the hamstring muscle cluster) without interfering with gluteal movement. V-connector strap 334 includes a circumferentially adjustable calf cuff 335 that can be tightened immediately above the crest of the gastrocnemius to provide additional support. Optional power mesh inserts 337 on the adjustable calf cuff 335 help to prevent slipping and absorb force.

Figure 3F:
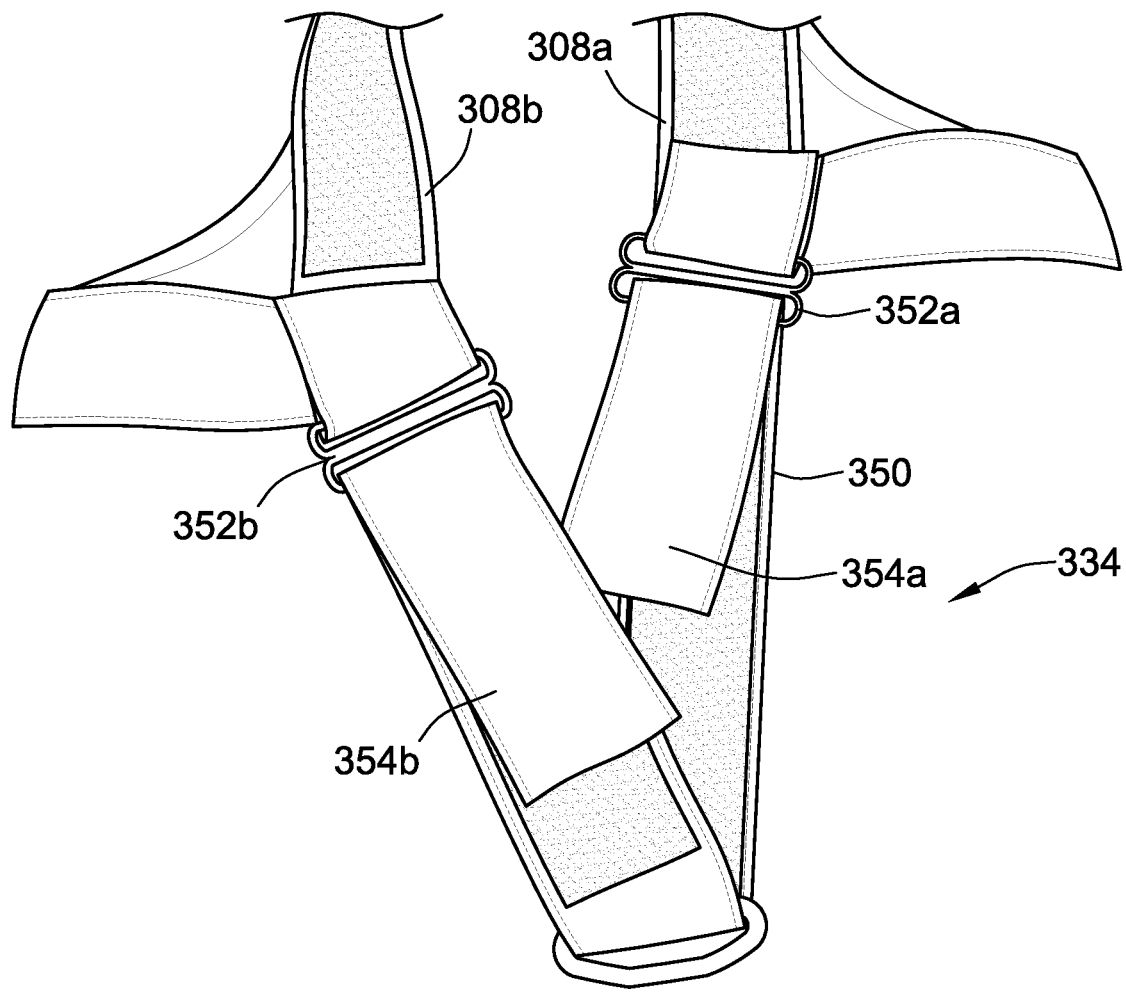
FIG. 3F is a perspective-view illustration of an optional adjustable V-connector attachment strap for the calf sleeve module of the assistive flexible suit of FIGS. 3A and 3B.

With reference now to FIG. 3F, there is shown an adjustable configuration of the V-connector strap 334A that is located at the bottom of the calf sleeve 302 (or "plantar flexion module"). V-connector strap 334 comprises a two-way adjustable strap 350 which is adjustably connected at opposing ends to the straps 308A, 308B via a pair of buckles 352A and 352B, respectively. Adjustable tabs 354A and 342B sewn into the opposing ends of the two-way adjustable strap 350 allow for adjustment of length and control over medial-lateral positioning of the attachment point for the calf sleeve 302. At the base of two-way adjustable strap 350 is a metal buckle configured to connect, for example, to a load cell and a Bowden cable sheath. If it is desired to provide plantar flexion support more medially, two-way adjustable strap 350 can be adjusted to move the buckle to the medial side of the calf; and, for lateral assistance, the opposite can be performed.

Presented in FIGS. 4A and 4B of the drawings is an alternative calf sleeve architecture, designated generally at 404, for the assistive flexible suit 300. As indicated above, while differing in appearance, calf sleeve 404 can take on any of the features, options and alternatives described herein with respect to the other calf sleeve configurations, and vice versa. The calf sleeve 404 (also referred to as "dorsiflexion module" or "fishbone module") comprises a central sternum 406 with first and second rib sets 408 and 410, respectively, that each projects from an opposing side of the sternum 406. Within each of the rib sets 408, 410 are two or more (e.g., three in the illustrated example) horizontally oriented, vertically spaced ribs 409 and 411, respectively. In this particular design, the vertically spaced ribs 409 of the first rib set 408 are connected together at proximal ends of the ribs 409 via the central sternum 406 and connected together at distal ends of the ribs 409 via a first webbing 405. In the same vein, the vertically spaced ribs 411 of the second rib set 410 are connected together at proximal ends of the ribs 411 via the central sternum 406 and connected together at distal ends of the ribs 411 via a second webbing 415. Reinforced attachment loops 412 at the base of the sternum 406 are provided for connecting the calf sleeve 404 to an actuator (e.g., to a Bowden cable sheath connector) and, optionally, a sensor (e.g., to the housing of a force transducer). The tighter connection points provided by the attachment loops 412 help to optimize cable travel distance, e.g., especially on subjects that are shorter in stature. Central sternum 406 of the calf sleeve 404 is configured to lay over and against the wearer's tibia above the assisted foot (similar to the configuration illustrated in FIGS. 3A and 3B). Once the sternum 406 of the calf sleeve 404 is properly positioned, the first and second rib sets 408 and 410 are sized and shaped to wrap around to the back of the wearer's calf and attach together, e.g., via mating hook-and-loop fastening patches 407 and 413. FIG. 4A illustrates the one-piece fishbone calf sleeve module 404 in a closed state, while FIG. 4B illustrates the calf sleeve module 404 in an open state. This particular configuration provides increased comfort and improved donnability and doffability.

Illustrated in FIG. 5 is another optional calf sleeve architecture, designated generally at 504, for the assistive flexible suit 300 of FIGS. 3A and 3B. Calf sleeve 504 of FIG. 5, which is considered an open-ended-rib type dorsiflexion module, has a central sternum 506 with first and second rib sets 508 and 510, respectively, that each projects from an opposing side of the sternum 506. Similar to the configuration presented in FIGS. 4A and 4B, each rib set 508, 510 of FIG. 5 includes at least two (e.g., three in the illustrated example) horizontally oriented, vertically spaced ribs 509 and 511, respectively. Unlike the calf sleeve 404 shown in FIG. 4B, the vertically spaced ribs 509, 511 in each rib set 508, 510 are not connected together at distal ends thereof by a respective webbing. The central sternum 506 is provided with reinforced attachment loops 512, which are similar to the reinforced attachment loops 412 of FIGS. 4A and 4B, for connecting the calf sleeve 504 to an actuator and, optionally, a sensor. Central sternum 506 of the calf sleeve 504 is designed to lay over and against the wearer's tibia above the assisted foot. Once the sternum 506 portion of the sleeve 504 is properly positioned over the wearer's tibia, each rib 509, 511 is configured to independently wrap around to the back of the wearer's calf and attach to complementary rib in the other rib set, e.g., via mating hook-and-loop fastening patches. Independent adjustability of the straps 509, 511 allows for more conformable fits on a wider variety of calf musculatures.

Designated generally at 604 in FIG. 6 is yet another calf sleeve architecture that may be integrated into the exosuit 300 of FIGS. 3A and 3B. Calf sleeve 604 of FIG. 6, like sleeves 404 and 504, is a modular unitary structure; however, unlike the other two embodiments, the calf sleeve 604 is considered an open-ended pivoting-rib type dorsiflexion module. According to the illustrated example, the calf sleeve 604 has a central sternum 606 with first and second rib sets 608 and 610, respectively, that each projects from an opposing side of the sternum 606. Similar to the configuration discussed above, each rib set 608, 610 comprises multiple horizontally oriented, vertically spaced ribs 609A-C and 611A-C, respectively. Similar to the ribs 409, 411 of FIGS. 4A and 4B and the ribs 509, 511 of FIG. 5, ribs 609A-B and 611A-B of FIG. 6 are rigidly attached (e.g., sewn in place) to the central sternum 606. Unlike the other calf sleeve configurations, however, the two bottom-most ribs 609C and 611C are pivotably attached, e.g., via a central pivot pin 614 to the central sternum 606. Optional configurations can be configured such that ribs 609B, 611B and/or ribs 609A, 611A are also pivotably attached to the central sternum 606. Central sternum 606 is also provided with centrally located reinforced attachment loops 612 for connecting the calf sleeve 604 to an actuator and, optionally, a sensor. Central sternum 606 of the calf sleeve 604 is designed to lay over and against the wearer's tibia above the assisted foot. When the sternum 606 segment of the calf sleeve 604 is properly positioned over the wearer's tibia, each rib 609, 611 is configured to independently wrap around to the back of the wearer's calf and attach to complementary rib in the other rib set, e.g., via mating hook-and-loop fastening patches. Pivoting straps 609C, 611C allow for adjustable angles to provide better conformability for wider and/or smaller calf shapes. An elastic band may be provided to hold the module 604 in place while donning/doffing. Overlapping velcro pads on the front of the module 604 provide more stability and create a landing pad for a lateral support module.

Figure 7:
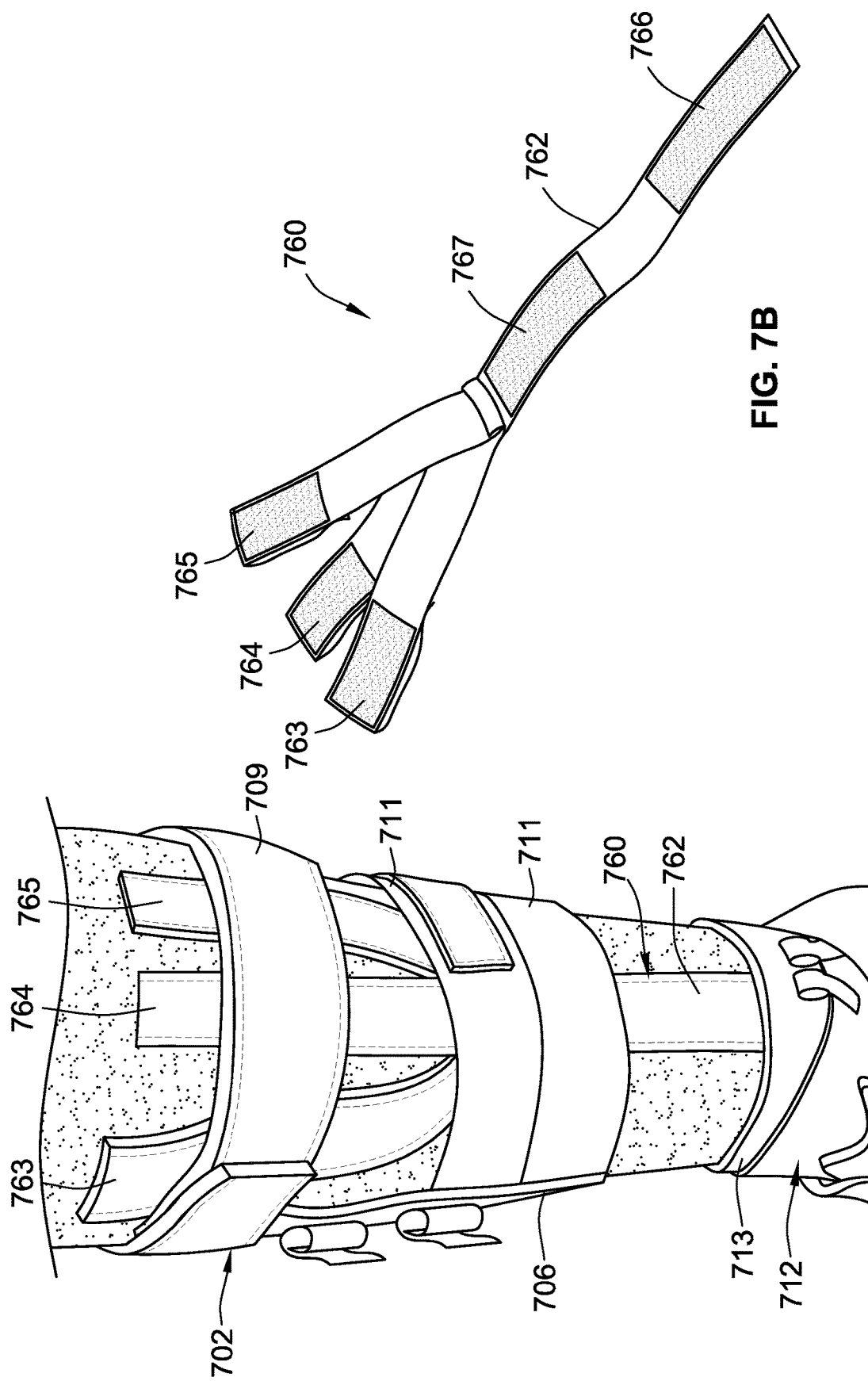
FIG. 7A is a side perspective-view illustration of a calf sleeve module and a foot module connected by an adjustable passive lateral support strap for an assistive flexible suit in accord with aspects of the present disclosure.
FIG. 7B is a perspective-view illustration of the lateral support strap of FIG. 7A.

Shown in FIGS. 7A and 7B is an optional ankle strap 760 that is designed for attachment between a calf sleeve 702 and a foot module 712 to provide passive lateral support for the wearer's ankle during use of the flexible assistive suit 300 of FIGS. 3A and 3B. As should be readily apparent, the calf sleeve 702 and foot module 712 of FIGS. 7A and 7B can take on any of the corresponding forms disclosed herein with respect to calf-type anchor attachments and foot-type attachments, respectively. Ankle strap 760 has a "chicken foot" geometry defined by an elongated primary (leg) attachment strap 762 and three integral secondary (toe) attachment straps 763-765 that project from a proximal (top) end of strap 762. The distal (bottom) end of the primary attachment strap 762 can be passed under and around an upper cuff 713 of the foot module 702, and then folded in half to mate complementary hook-and-loop fastening patches 766 and 767 on the strap 762 and thereby detachably couple the ankle strap 760 to the foot module 712. Concomitantly, one or more or all of the toe attachment straps 763-765 are then detachably coupled (e.g., via mating hook-and-loop fastening patches) in one of various available combinations to one or more of numerous available attachment sites on the ribs 709, 711 projecting from the central sternum 706 of the calf sleeve 702. The magnitude and angle of tension between the calf sleeve 702 and foot module 712 depends, for example, on the selected combination, orientation and attachment site(s) of the toe attachment straps 763-765. This helps to create passive ankle support and thereby prevent inadvertent ankle roll during operation of the suit 300. The multiple attachment points can also help to better distribute forces on the dorsiflexion module 702 and thereby reduce inadvertent pull-down. Hook-and-loop patches on the dorsiflexion straps/ribs 709, 711 help to attach the calf sleeve 702 directly to the exterior of the toes 763-765 of the ankle strap 760.

Figure 8:
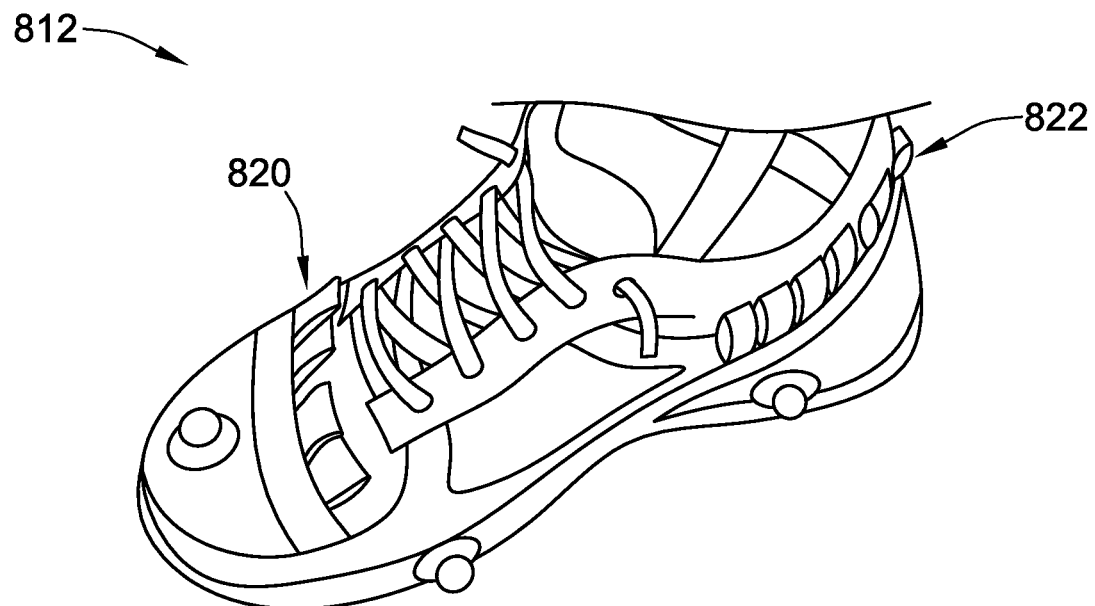
FIG. 8 is a side perspective-view illustration of a representative shoe-type foot module with multiple actuator attachment points for an assistive flexible suit in accord with aspects of the present disclosure.

As indicated above in the discussion of the foot module 312 of FIGS. 3A and 3B, each disclosed foot module is configured to mount to, around or adjacent the assisted foot of the wearer such that assistive forces can be distributed to the foot during gait to assist with bipedal movement. Like the other modules illustrated in FIGS. 3A and 3B, the foot module may take on various optional features and alternative forms. FIG. 8 of the drawings, for example, is a side-view illustration of a representative shoe-type foot module 812 for use with the assistive flexible suit 300. In contrast to the foot module 312, which is an insert-type foot module designed to fit inside the wearer's footwear, the foot module 812 of FIG. 8 is fabricated as or otherwise integrated into footwear configured to nest therein the wearer's assisted foot. According to this particular configuration, the foot module 812 comprises multiple actuator attachment points/loops to which an actuator can be detachably connected (e.g., the loops hold boa ratchets connected to the end of a Bowden cable). By way of non-limiting example, foot module 812 includes a first plurality of actuator attachment loops 820 proximate the forefoot segment of the foot, on the toe vamp portion of the shoe between the toe cap and base of the shoe's tongue. Moreover, a second plurality of actuator attachment loops 822 is located proximate the hindfoot segment of the wearer's foot, on the heel counter portion of the shoe, between the collar and the shoe's outer sole. Multiple attachment loops 820, 822 at the forefoot and hindfoot allow selectability of numerous medial/lateral attachment positions. In so doing, each of these actuator attachment points provide a distinct angle along which tensile forces generated by the actuator are applied to the foot of the wearer. Sewn in brackets inside the shoe-type foot module 812 transfer lateral support to the foot.

Figure 9:
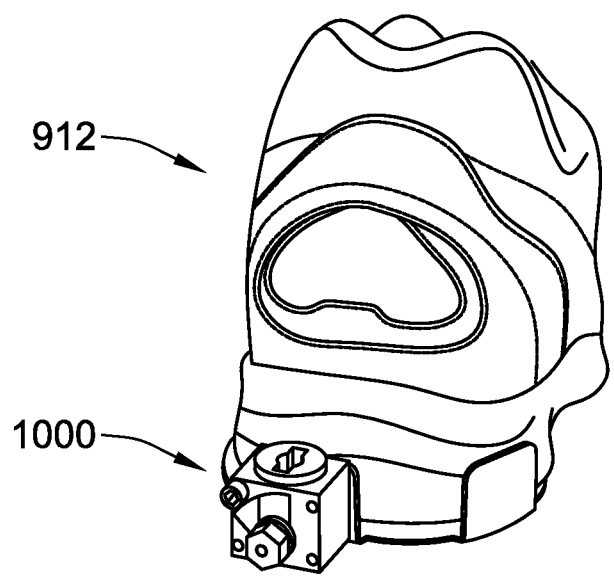
FIG. 9 is a rear perspective-view illustration of a representative shoe-type foot module with a quick-connect/quick-release actuator attachment module for an assistive flexible suit in accord with aspects of the present disclosure.

FIG. 9 is a rear perspective-view illustration of another representative shoe-type foot module, designated generally at 912, which includes a quick-connect/quick-release actuator attachment module 1000, which is developed in further detail in the discussion of FIGS. 10A-10E. The quick-connect/quick-release actuator attachment module 1000 acts as an actuator attachment point on the hindfoot segment adjacent the underside of a heel bone of the wearer's assisted foot. As described above, force transmission elements, such as force transmission elements 220A-220C, may connect to the assistive flexible suit 100 at one or more anchor elements. FIGS. 10A-10E illustrate one embodiment of an anchor element in the form of a quick-connect/quick-release anchor element 1000, according to at least some aspects of the present concepts. The quick-connect/quick-release anchor element 1000 may, for example, be positioned on the heel of a shoe of an individual to attach a force transmission element to the back of the shoe of the individual.

The end of a force transmission element 1001 (e.g., a Bowden cable) may have a connector that connects to the quick release anchor element 1000. As shown in FIG. 10A, the connector may be in the form of a T-connector 1003; however, the connector may be various other shapes and configurations for insertion and engagement with the quick release anchor element 1000. The T-connector 103 is configured or shaped such that it fits into an opening 1005 of the quick release anchor element 1000. Specifically, the T-connector 103 is configured or shaped so that the T-connector 1003 fits into the opening 105 according to a specific orientation with respect to the opening 1005. Once inserted into the quick release anchor element 1000, the T-connector 1003 may rotate (e.g., clockwise and/or counter-clockwise) such that ribs 1007 of the T-connector 1003 engage with the quick release anchor element 1000 at the opening 1005 and prevent the T-connector 1003 from being withdrawn from the opening.

Adverting to FIG. 10B, rotation of the T-connector 103 engaged within the quick release anchor element 1000 to the insertion orientation of the T-connector 1003 with respect to the opening 1005 releases the T-connector 1003 and corresponding force transmission element 1001 from the quick release anchor element 1000. That is, the ribs 1007 of the T-connector 1003 align with the opening 1005 such that the T-connector 1003 can be withdrawn from the quick release anchor element 1000.

Figure 10C:
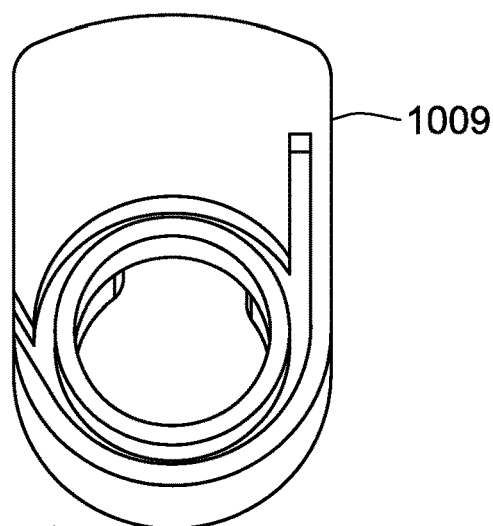
Figure 10D:
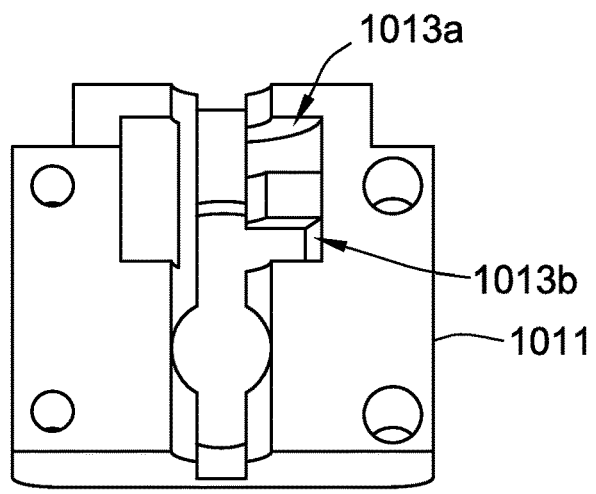
Figure 10E:
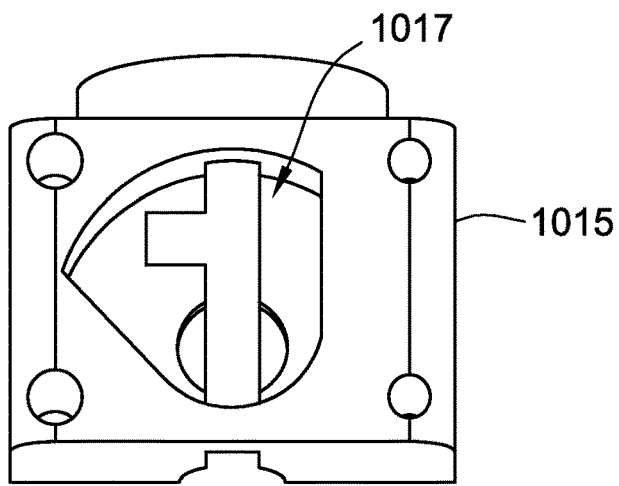

FIGS. 10C through 10E illustrate sub-elements of the quick release anchor element 1000, according to at least some aspects of the present concepts. Adverting to FIG. 10C, the quick release anchor element 1000 may include a lock back 1009. The lock back 1009 prevents objects from entering the quick release anchor element 1000 when the T-connector 1003 is not engaged within the quick release anchor element 1000. FIG. 10D illustrates an interior view of the quick release anchor element 1000. The interior view includes recesses 1011a and 1011b that permit the T-connector 1003 to rotate within and engage with the quick release anchor element 1000. FIG. 10E illustrates an exterior view of the quick release anchor element 1000. The exterior view includes a recess 1013 that accepts the lock back 1009 within the quick release anchor element 1000 and allows the lock back 1009 to actuate between a closed position (FIG. 10B) and an open position (FIG. 10A).

Figure 11B:
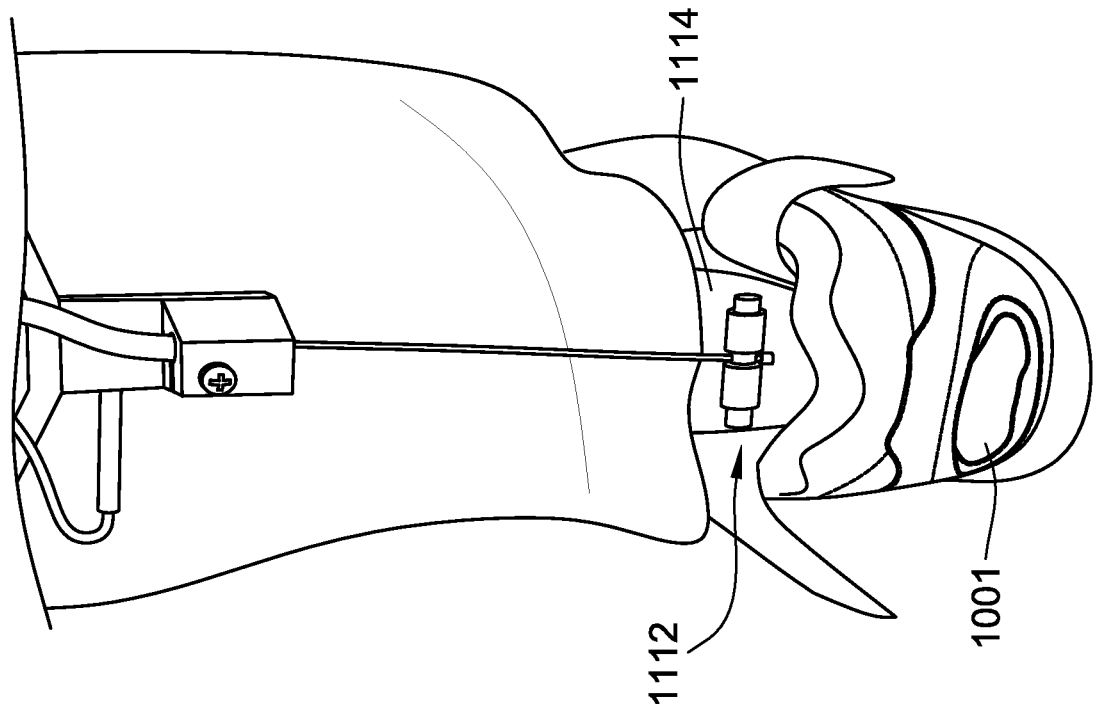
FIGS. 11A and 11B are front and rear perspective-view illustrations, respectively, of a representative insert-type foot module with Achilles and tibia straps for an assistive flexible suit in accord with aspects of the present disclosure.
Figure 11A:
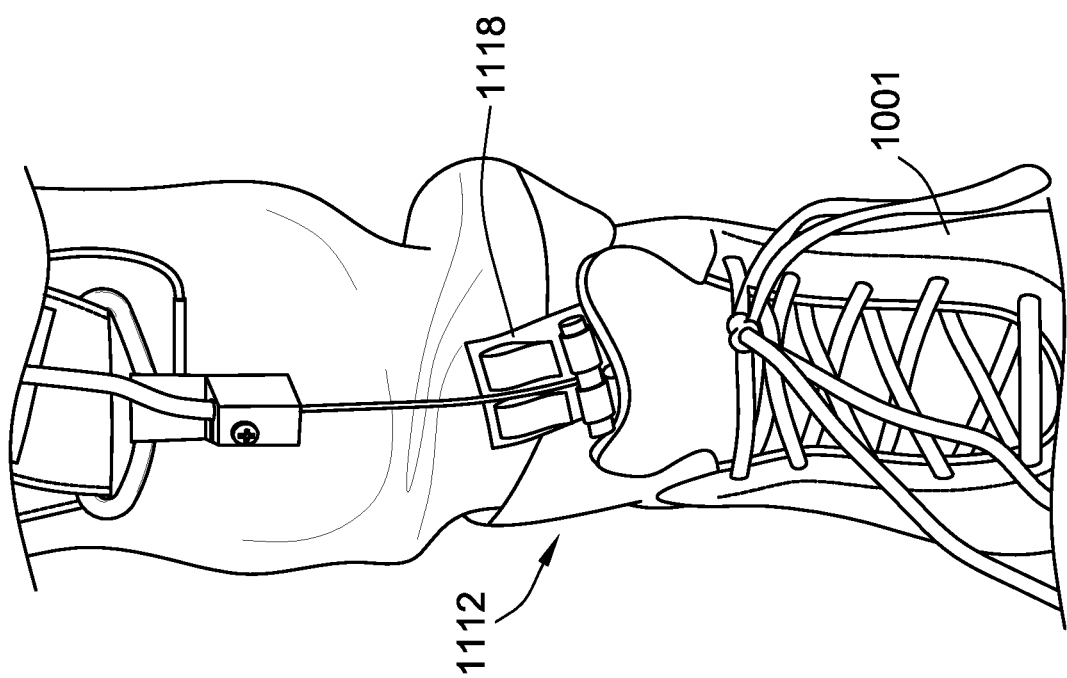

Foot modules 812 and 912 of FIGS. 8 and 9 are described above as shoe-type foot modules fabricated as footwear for nesting therein, covering, and securely attaching to the wearer's assisted foot. Alternative configurations are designed to conform directly to the wearer's foot and, in some designs, fit inside the wearer's footwear to anchor an actuator proximate the wearer's heel/toes. For example, FIGS. 11A and 11B illustrate segments of an insert-type foot module, designated generally at 1112, with an insole (not visible in the view provided) that fits inside a shoe or other footwear and situates comfortably underneath the palm and heel of the wearer's foot. This insole is either securely attached, e.g., via sewing, or removably attached, e.g., via hook-and-loop fasteners, to an Achilles strap 1114 and a tibia strap 1116. The Achilles strap 1114 extends from the insole on the underside of the wearer's heel, up along the length of the Achilles tendon, and out through a rearward portion of the opening in the upper of the shoe 1101. The Achilles strap 1114 is designed to transmit tensile forces generated by an actuator to the hindfoot segment of the wearer's foot. Such a force can be applied to generate/aid plantar flexion and, thus, assist with push off at the ankle, and can optionally be utilized to assist with flexion at the hip. Tibia strap 1116, on the other hand, extends from the insole on the underside of the wearer's forefoot, up along the metatarsal region, talus and tibia, then out through a forward portion of the opening in the upper of the shoe 1101. The Tibia strap 1116 transmits tensile forces generated by an actuator to the forefoot segment of the wearer. Such a force can be applied to generate/aid dorsiflexion and, thus, assist with heel strike, and can optionally be utilized to assist with extension at the hip. Optional ankle support straps can be employed to provide passive lateral support for the foot module 1112. For at least some embodiments, the ankle support strap is pivotably attached with a pivot axis that is aligned with the malleoli.

Figure 12:
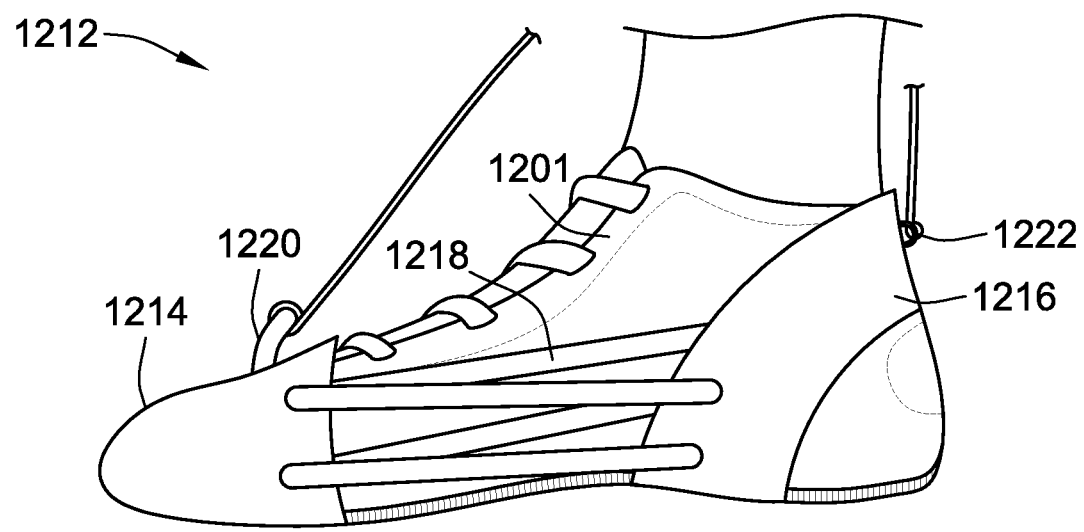
FIG. 12 is a side perspective-view illustration of a representative universal "over-the-shoe" foot module for an assistive flexible suit in accord with aspects of the present disclosure.
Figure 13:
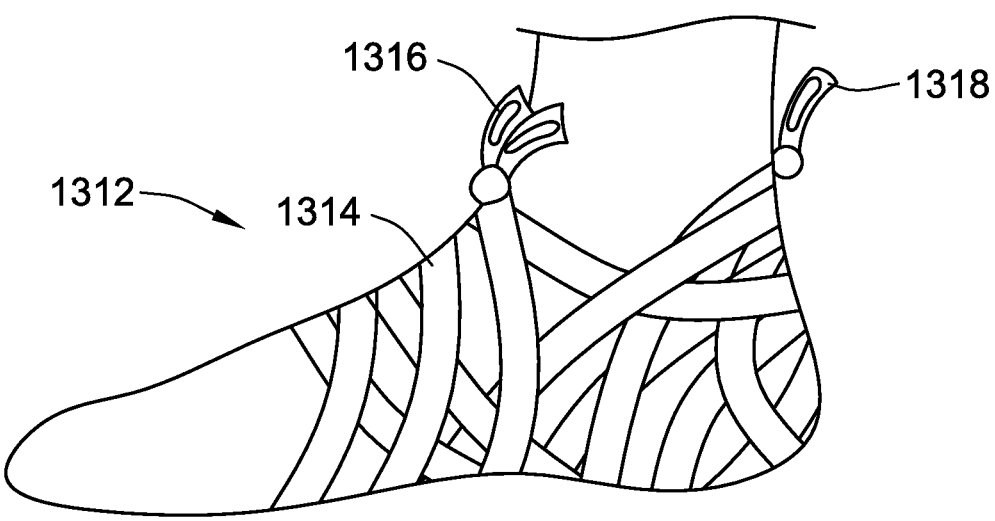
FIG. 13 is a side perspective-view illustration of a representative auto-tightening in-shoe foot module for an assistive flexible suit in accord with aspects of the present disclosure.

FIGS. 12-15 provide various other optional configurations for foot modules for an assistive flexible suit. FIG. 12, for example, is a side-view illustration of a representative universal over-the-shoe foot module 1212. This design is considered to be one of many potential "non-permanent, on-shoe" attachment solutions. Foot module 1212 includes a toe cup 1214 and a heel cup 1216 which are configured to seat therein and attach around the exterior toe and heel portions, respectively, of a person's shoe 1201. The toe and heel cup 1212, 1214 then lace (e.g., via laces 1218 on opposing sides of the shoe 1201), ratchet, or otherwise bias together to secure the universal foot module 1212 to the shoe 1201. Tensile forces are transmitted to the forefoot and/or hindfoot segments of the wearer's foot through foot module 1212 via forward and/or rearward anchors 1220 and 1222, respectively FIG. 13 is a side-view illustration of a representative auto-tightening in-shoe foot module 1312 in accord with other aspects of the present concepts. Foot module 3112 comprises an interwoven webbing structure 1314 that is configured to circumscribe the forefoot and hindfoot segments of the wearer's foot and automatically tighten when tension is generated between the foot module and a suspension anchor via an actuator. This concept utilizes a biaxial helically wound braid which is wrapped around either the wearer's foot or the wearer's shoe, and automatically constricts around the shoe/foot as one or both cable tabs 1316, 1318 are put in tension.

FIG. 14 is a side-view illustration of another representative in-shoe foot module 1412. This embodiment employs an insole 1414 that is seated underneath the wearer's foot and coupled to forefoot and hindfoot anchor swings 1416 and 1418 for coupling the foot module 1412 to one or more actuators via cables 1426. An ankle cuff 1420 is provided with an attachment tab 1422 for connecting to a lateral ankle support strap 1424. FIG. 15, by way of contrast, is a plan-view illustration of a modular in-shoe or over-the-shoe dorsiflexion foot module 1512. This embodiment utilizes a toe loop 1514 that is placed around the wearer's toes (inside or outside of the wearer's shoes). A tibia strap 1516 is detachably coupled to the toe loop 1514 then extends up along the tongue of the shoe, either on the inside or outside of the shoe. For at least this embodiment, an ankle support strap is pivotably attached with a pivot axis that is aligned with the lateral malleolus. This ankle support strap supports the ankle, preventing oversupinating (rolling) or reducing the risk of oversupinating. In other embodiments, an ankle support strap is pivotably attached with a pivot axis that is aligned with the medial malleolus. This ankle support strap supports the ankle and prevents it from overpronating or reduces the risk of overpronating. In yet other embodiments, two ankle support straps are provided and aligned with the medial and lateral malleoli.

The insole 1414 of FIG. 14 can be a full insole (going from heel to toes) or a partial insole teminating before, at or after the tarsal-metatarsal joint. In at least some aspects, the insole 1414 can have a variable stiffness value for different parts of the foot, to distribute the assistance differently to different parts of the underfoot (e.g. higher stiffness on the hind foot, less on the forefoot).

A method of manufacturing an assistive flexible suit system for aiding one or more gait movements during walking of a wearer, the method comprising: providing a suspension anchor configured to mount to the body of the wearer and transmit loads to one or more predetermined load-bearing segments of the body of the wearer; providing a foot module configured to mount on or adjacent to a foot of the wearer and transmit loads to a hindfoot segment or a forefoot segment, or both, of the foot of the wearer; attaching an actuator to the foot module and the suspension anchor, the actuator being selectively actuable to generate tension between the foot module and the suspension anchor; mounting a sensor on or proximate the foot of the wearer, the sensor being operable to detect a gait characteristic of the wearer and output a signal indicative thereof; communicatively connecting a controller to the sensor and the actuator, the controller being configured to analyze the gait characteristic signal output by the sensor and, based at least in part on the analyzed signal, selectively actuate the actuator to thereby assist plantar flexion or dorsiflexion, or both, of the foot of the wearer.

Figure 16A:
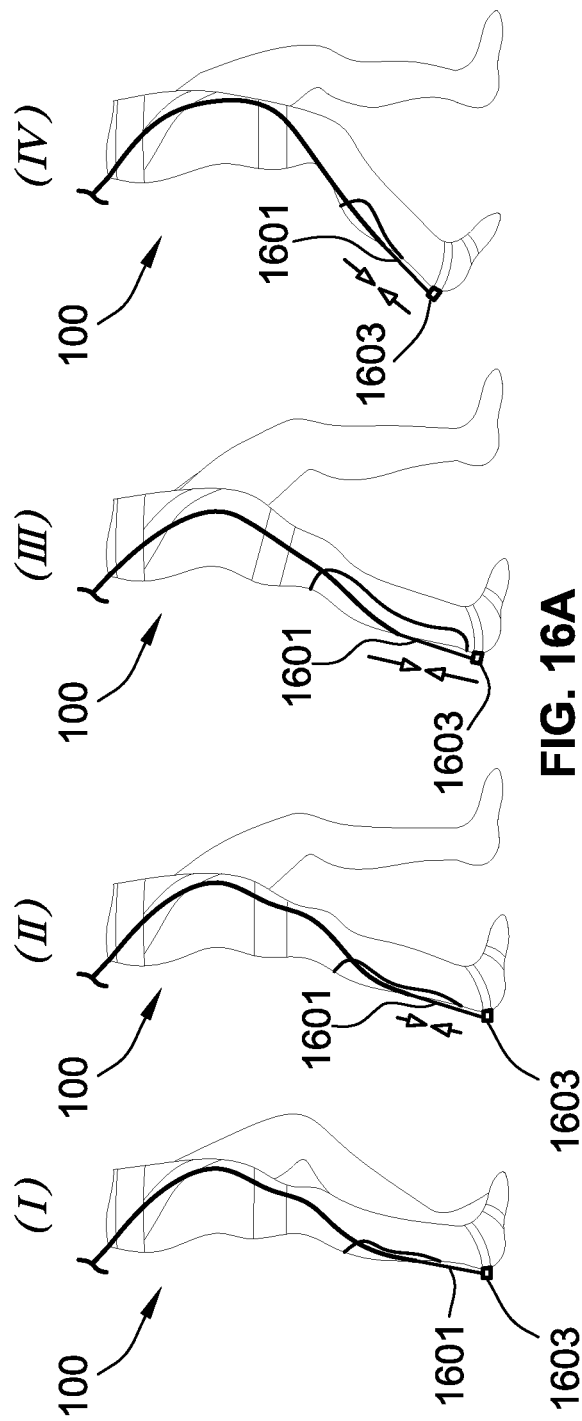
FIG. 16A shows modification of a plantar flexion actuation within a gait period of an individual according to at least some aspects of the present concepts.

FIG. 16A illustrates modification of a plantar flexion actuation within a gait period of an individual wearing the assistive flexible suit 100, according to at least some aspects of the present concepts. Plantar flexion occurs about the ankle of the individual based, at least in part, on actuation of a force transmission element 1601 that connects to the foot of the individual at a plantar flexion anchor element 1603 (such as quick release anchor element 1000). The force transmission element 1601 may be routed from the offboard control system 200 (not shown), as an example, to the plantar flexion anchor element 1603 through the assistive flexible suit 100. In the illustrated embodiment, routing of the force transmission element 1601 may occur through a portion of the assistive flexible suit 100 connected to the hip to provide hip flexion assistance, in addition to plantar flexion assistance. to the individual.

Starting from the left, FIG. 16A(I) illustrates a first position of the individual's right foot when the individual's right foot begins to push off of the ground. By way of example, the first position may be at 30 percent of a gait period during walking. At the first position, the calf muscles and hip muscles are in a state of eccentric contraction, and the assistive flexible suit 100 is in a corresponding state of extension. At or slightly after the first position of the gait period, the individual's right foot begins to push off of the ground as a result of force caused by a plantar flexion moment. Before and up to FIG. 16A(I), the force transmission element 1601 is slack.

FIG. 16A(II) shows a second position of the individual's right foot. At the second position, the offboard control system 200, as an example, actuates the force transmission element 1601 in parallel to the calf muscle of the individual to modify a plantar flexion moment and modify the torque applied to the ankle joint to provide plantar flexion. By way of example, the second position may be at 40 percent of the gait period. At the second position, the calf muscles and hip muscles are in a state of eccentric contraction, and the assistive flexible suit 100 is in a corresponding state of extension.

Actuation ramps up to a third position of the individual's right foot to provide maximum assistance to the plantar flexion moment generated by the individual, as illustrated in FIG. 16A(III). By way of example, the third position of the individual's right foot may be at 50 percent of the gait period. At the third position, the calf muscles are in a state of isometric contraction, the thigh muscles (e.g., quadriceps) are in a state of concentric contraction, and the assistive flexible suit 100 is in a corresponding state of contraction. Thus, at FIG. 16A(III), the force transmission element 1601 applies tension to the plantar flexion anchor element 1603. In one embodiment, based on the routing of the force transmission element 1601 across the hip of the individual through the assistive flexible suit 100, actuation of the force transmission element 1601 assists movement of the individual at the hip in addition to at the ankle. That is, the actuation may aid the wearer to swing the hip forward (e.g., hip flexion) during plantar flexion modification by the force transmission element 1601 actuating across the front of the hip. Such a configuration is multi-articular in that a single actuation across multiple body parts of the individual may assist movement of the multiple body parts. The multi-articular arrangement may improve the efficiency, transparency, and/or performance of the assistive flexible suit 100 by more closely mimicking the movement and activation of the individual's muscle and skeletal structure.

Assistance continues to a fourth position of the individual's right foot (e.g., at 60 percent of the gait period), as illustrated in FIG. 16A(IV). At the fourth position, the calf muscles and thigh muscles are in a state of concentric contraction, and the assistive flexible suit 100 is in a corresponding state of contraction. After this point, actuation by the offboard control system 200 ramps down to release the tension in the force transmission element 1601 after toe off of the individual's right foot. After toe off, actuation of the force transmission element 1601 no longer provides assistance. Therefore, actuation of the force transmission element 1601 stops to render the force transmission element 1601 slack and in a transparent state because plantar flexion modification is no longer beneficial.

Although the first through fourth positions are described above with respect to specific exemplary percentages of a gait period, the specific percentages may vary with respect to different gait periods of the same individual, and may vary with respect to different individuals. Thus, the specific percentages described above are merely exemplary and may be different for specific gait periods depending on the characteristics of the individual wearing the assistive flexible suit 100.

According to the above, the force transmission element 1601 increases tension between, for example, about 30 to 60 percent of the gait period, which is the time the leg is pushing off from the ground. This applies moments to the ankle and hip, which aids the ankle in pushing off of the ground and the hip in swinging the leg. Specifically, as illustrated in FIG. 16C, the skeletal structure of the individual supports the compressive loads generated by the assistive flexible suit 100, while the assistive flexible suit 100 acts in parallel with the musculature of the individual.

FIG. 16C(I) illustrates force paths generated by the plantar flexion assistance by the force transmission element 1601, according to at least some aspects of the present concepts. A force path 1661 is generated through the right leg skeletal structure of the individual, terminating at the right foot, in response to the individual generating a plantar flexion moment. A corresponding force path 1663 is generated through the force transmission element 1601 of FIG. 16A through the assistive flexible suit 100, particularly with respect to the actuation point 1665 of the force transmission element 1601 at the ankle. The force transmission element 1601 of FIG. 16A and, therefore, the corresponding force path 1663 of FIG. 16C(I) may be routed approximately 10 cm, less than 1 cm, and 8 cm from the joint centers of rotation of the hip, knee, and ankle, respectively, to generate the desired flexion and/or extension moments. As described above, because the force path 1663 travels across the front of the hip, the force path 1663 can provide a multi-articular benefit by benefitting plantar flexion at the ankle and hip flexion at the hip. The resulting force paths 1661 and 1663 alternatively may be represented by force vectors at the joints of the individual and where the assistive flexible suit 100 transmits the load of the force transmission element (e.g., 1601) to the individual through the assistive flexible suit 100. As illustrated in FIG. 16C(II), a force vector 1667*a* represents the force from the bone structure of the individual on the assistive flexible suit 100 at the hip. Force vector 1667*b* represents the force from the assistive flexible suit 100 on the bone structure of the individual at the hip. Similarly, a force vector 1667*d* represents the force from the bone structure of the individual on the assistive flexible suit 100 at the ankle. Force vector 1667*c* represents the force from the assistive flexible suit 100 on the bone structure of the individual at the ankle.

Figure 16B:
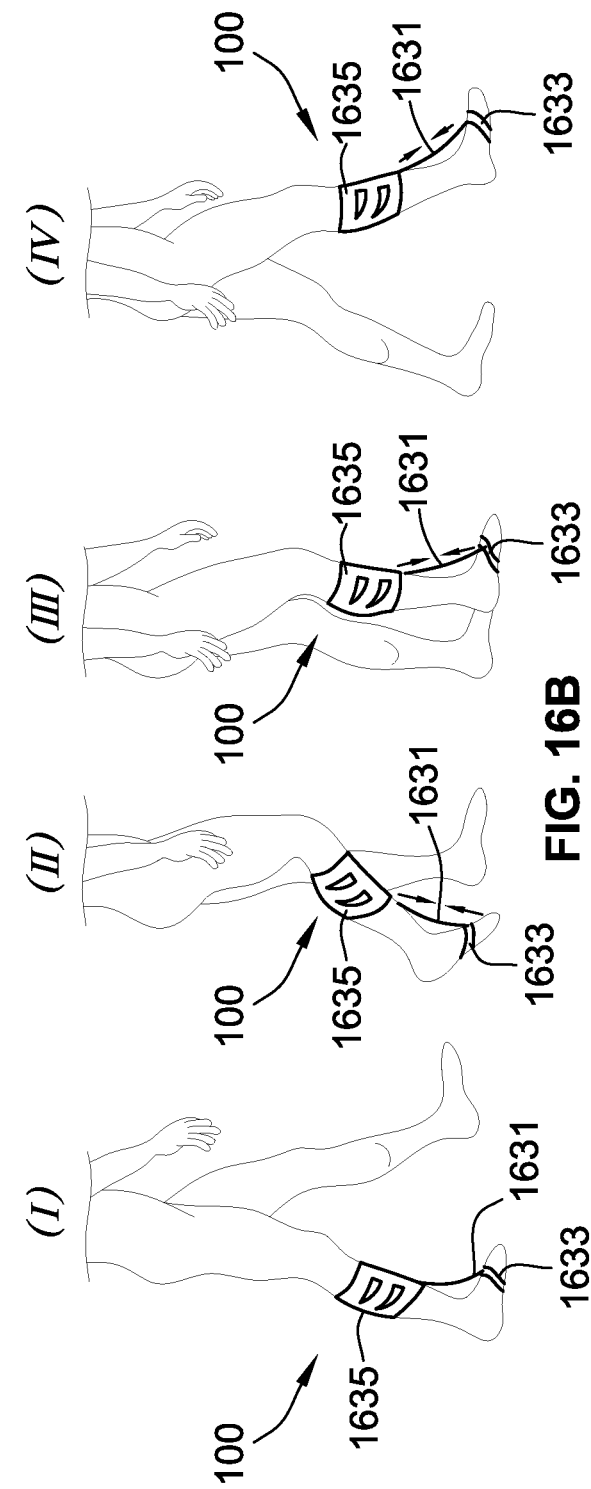
FIG. 16B shows modification of a dorsiflexion actuation within a gait period of an individual according to at least some aspects of the present concepts.
Figure 16E:
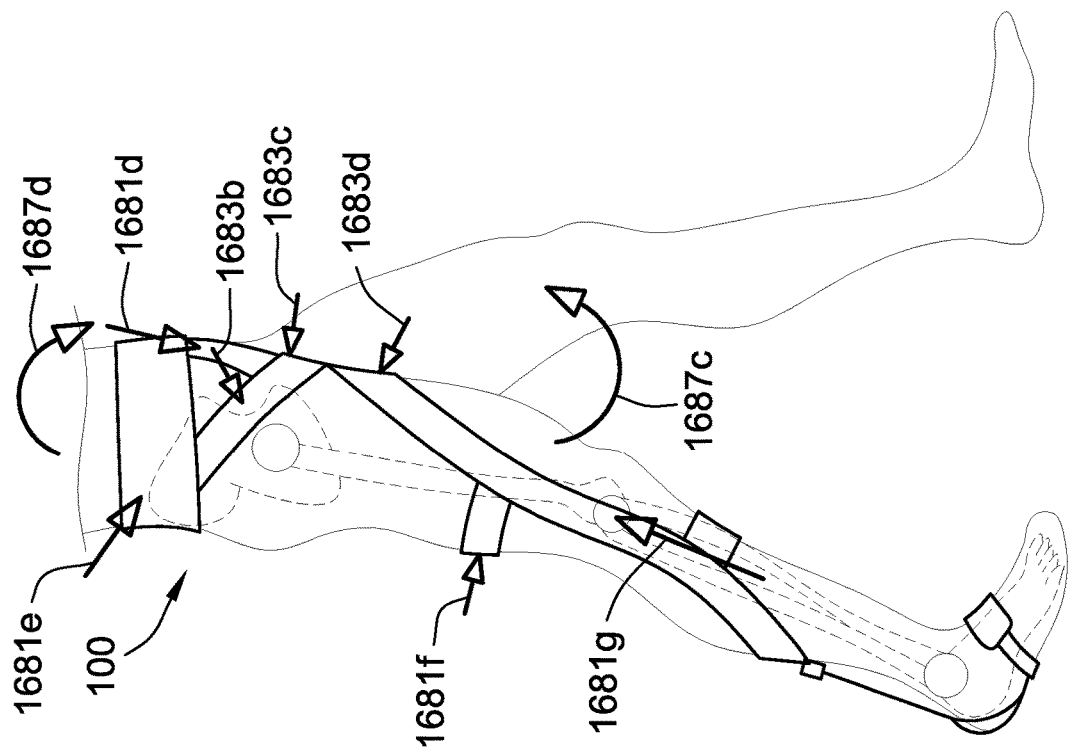
FIGS. 16D and 16E illustrate forces from an assistive flexible suit on an individual, according to at least some aspects of the present concepts.
Figure 16D:
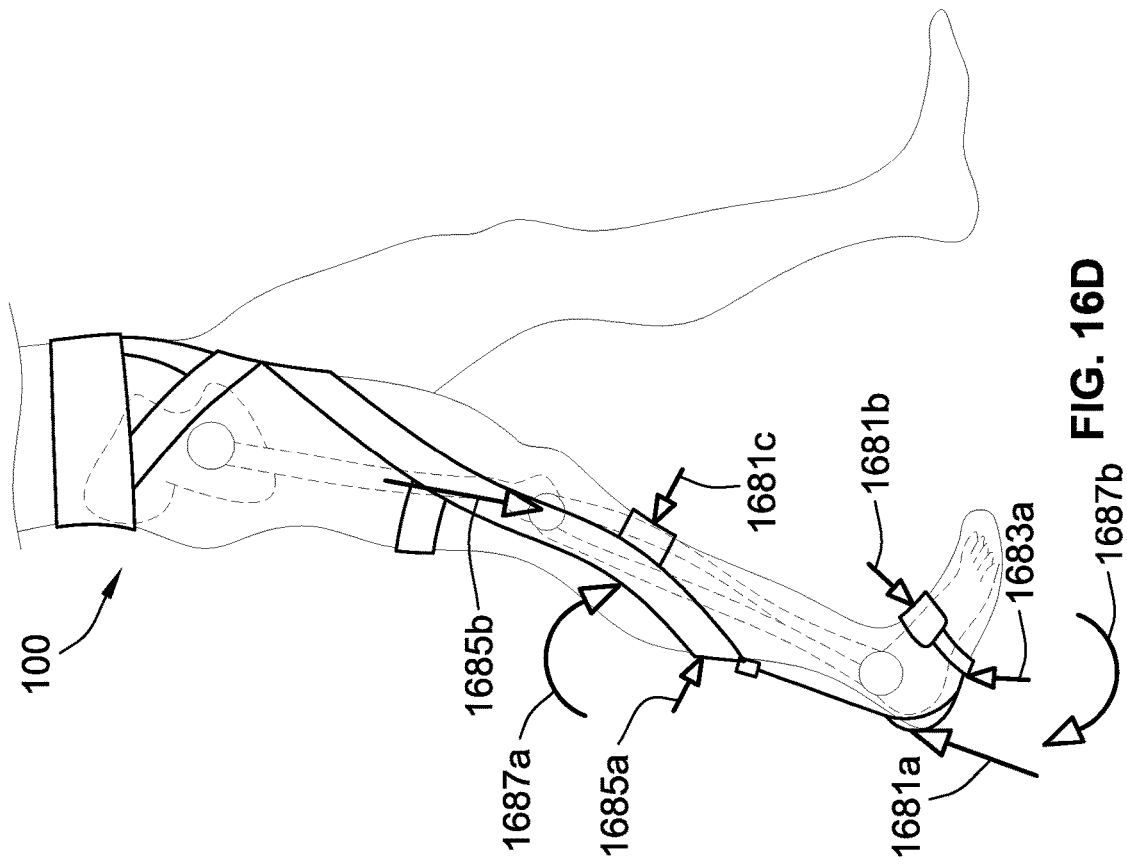

FIG. 16D illustrates forces from an assistive flexible suit 100 on an individual, according to at least some aspects of the present concepts. Specifically, FIG. 16D pertains to torques about the ankle and illustrates the various forces on the individual's right leg, as an example, in response to actuation of a force transmission element (e.g., force transmission element 1661). Arrows 1681*a*-1681*c* indicate forces that create beneficial moments about the individual's ankle. Arrow 1683*a* passes through the ankle joint's center of rotation and, thus, creates no moment. Arrows 1685*a* and 1685*b* create antagonistic moments. Based on arrows 1681*a*-1685*b*, arrows 1687*a* and 1687*b* represent the total forces above or below the ankle that benefit movement of the individual and that are generated by the assistive flexible suit 100.

FIG. 16E illustrates forces from an assistive flexible suit 100 on an individual, according to at least some aspects of the present concepts. Specifically, FIG. 16E pertains to torques about the hip and illustrates the various forces on the individual's right leg, as an example, in response to actuation of a force transmission element (e.g., force transmission element 1661). Arrows 1681d-1681g indicate forces creating beneficial moments about the individual's hip. Arrows 1683b-1683d pass through the hip joint's center of rotation and, thus, create no moment. Arrows 1687c and 1687d represent the total resulting forces above or below the hip that benefit movement of the individual and that are generated by the assistive flexible suit 100.

FIG. 16B illustrates modification of a dorsiflexion actuation within a gait period of an individual wearing the assistive flexible suit 100, according to at least some aspects of the present concepts. Dorsiflexion occurs about the ankle of the individual based, at least in part, on actuation of a force transmission element 1631 that connects to the foot of the individual at a dorsiflexion anchor element 1633, and may be routed from the offboard control system 200 (not shown), for example, to the dorsiflexion anchor element 1633 through a calf attachment 1635. Routing of the force transmission element 1631 between the offboard control system 200 and the dorsiflexion anchor element 1633 may be accomplished according to the same routing as described above with respect to FIG. 16A, but for the variation with respect to the calf attachment 1635 to route the force transmission element 1631 forward to engage with the dorsiflexion anchor element 1633.

Starting from the left, FIG. 16B(I) illustrates a first position of the individual's right foot, as an example, when the individual's right foot pushes off of the ground as a result of plantar flexion. By way of example, the first position may be between 40 to 60 percent of a gait period during walking. The force transmission element 1631 during the first position is in a transparent, slack state because modification with respect to dorsiflexion is not required at this point in the gait.

FIG. 16B(II) shows a second position of the individual's right foot, which is after plantar flexion at the ankle to push off of the ground. At the second position, the force transmission element 1631 actuates to modify the gait moment with respect to the tibialis anterior muscle. Actuation of the force transmission element 1631 shortens the distance between the dorsiflexion anchor element 1633 and the calf attachment 1635 relative to the individual's gait without assistance provided by the assistive flexible suit 100. By actuating the force transmission element 1631 at this point within the gait period, the individual may more easily swing his or her foot according to a proper gait movement because the reduced distance between the dorsiflexion anchor element 1633 and the calf attachment 1635 provides greater toe clearance with the ground than the individual may otherwise experience with assistance from the force transmission element 1631. By way of example, the second position may be at 70 percent of the gait period.

FIG. 16B(III) shows a third position of the right foot. At the third position, tension within the force transmission element 1631 may decrease after the foot has swung forward and prior to ankle impact. Reduction of the tension in the force transmission element 1631 may continue through the remainder of the gait period and into the next gait period after heel impact at the fourth position, as shown at FIG. 16B(IV). After heel strike of the next gait period, the force transmission element 1631 is slack and in a transparent state so as not to otherwise modify the gait of the individual during periods in which dorsiflexion modification is not needed. By way of example, the third position may be at 90 percent of the gait period, and the fourth position may be at 10 of the next gait period.

Although the first through fourth positions are described above with respect to specific exemplary percentages of a gait period, the specific percentages may vary with respect to different gait periods of the same individual, and may vary with respect to different individuals. Thus, the specific percentages described above are merely exemplary and may be different for specific gait periods depending on the characteristics of the individual wearing the assistive flexible suit 100.

The magnitude of the forces that can be applied to the individual wearing the assistive flexible suit 100 is a function of the effective stiffness $k_{eff}$ of the suit-individual system as seen at the point of application of the applied force. This can be determined by summing the body stiffness determined by the textile interface to the individual's soft tissues (e.g., skin, muscle, fat) and the suit stiffness determined by the textile elastic properties. The effective stiffness permits calculations for the actuator speeds/power as time/energy is required to displace the tissue/suit before the force is transmitted to the individual and can be determined according to Equation 1.

$$1/k_{eff} = (1/k_{body} + 1/k_{suit}) \tag{1}$$

The effective stiffness may be measured by having individuals stand in a pose similar to that in which the suit is actuated during a desired movement (e.g., walking). A force transmission element is then actuated in a trapezoidal profile while recording the induced force in the assistive flexible suit 100. Previous results have indicated potentially significant nonlinearity and hysteresis in the loading-unloading.

Figure 16F:
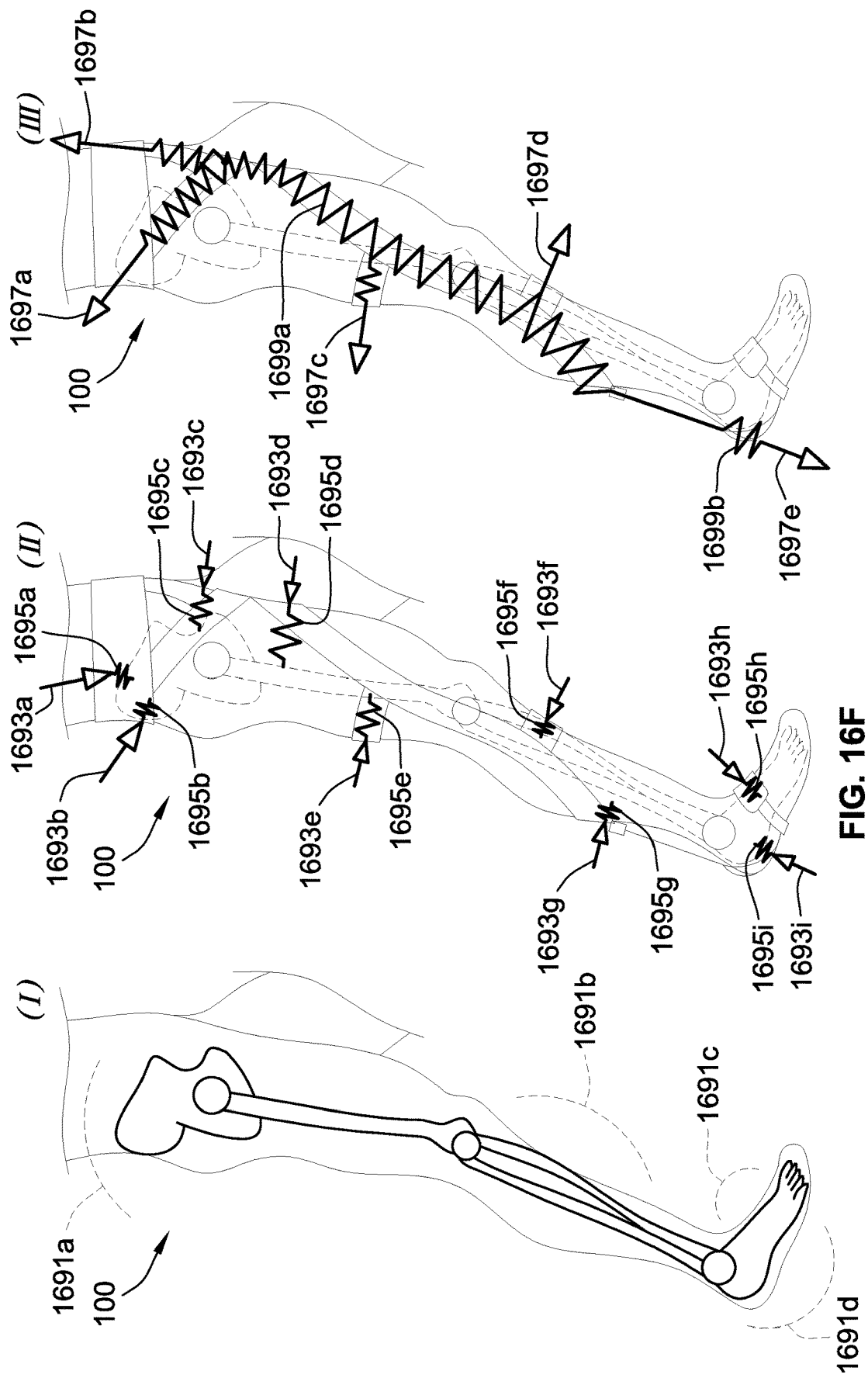
FIG. 16F illustrates forces created by the assistive flexible suit 100 distributing through the individual, according to at least some aspects of the present concepts.

FIG. 16F illustrates forces created by the assistive flexible suit 100 distributing through the individual, according to at least some aspects of the present concepts. As specifically shown in FIG. 16F(I), portions 1691a-1691d are areas of the leg with bone close to the skin, which provide suitable areas for distributing forces from the assistive flexible suit 100 to the individual. FIG. 16F(II) shows normal forces 1693a-1693i on the tissue of the individual between the assistive flexible suit 100 and the body that cause compression at areas 1695a-1695i of the individual's body based on the force distributing from the assistive flexible suit 100 to the individual. Further, FIG. 16F(III) shows reactive forces 1697a-1697e from the assistive flexible suit 100 causing the assistive flexible suit 100 to stretch from distributing the forces to the individual. Further, springs 1699a and 1699b show the expansion of the assistive flexible suit 100 under a load causing the reactive forces 1697a-1697e.

Because the assistive flexible suit 100 is fully-textile, the assistive flexible suit 100 does not restrict the individual's kinematics and has little mass. As a result, the assistive flexible suit 100 is transparent to the wearer if tension in the suit is relaxed; for example, wearing the assistive flexible suit 100 feels like wearing a pair of pants. Moreover, a majority of the assistance provided by the assistive flexible suit 100 is applied to the individual, rather than to accelerating and moving an otherwise heavy, rigid mass attached to the individual. Further, in one embodiment, the assistive flexible suit 100 is beneficial to the individual even if the assistive flexible suit 100 is not actively actuated, but instead just tensioned slightly and held at that tension.

As an example, the assistive flexible suit 100 may be constructed to pass over the front of a thigh and the back of an ankle. The leg moving into the position at which the leg pushes off from the ground causes the distances over the front of the thigh and around the back of the ankle to increase. This passively creates tension in the assistive flexible suit 100, with the assistive flexible suit 100 held at a fixed length. This passive tension functions like when the suit is actuated, but with lower force magnitudes. This works because the biological ankle and hip joints absorb power during certain parts of the gait cycle. When the assistive flexible suit 100 stretches passively, the assistive flexible suit 100 absorbs this power instead, and releases it during later parts of the gait cycle when the body is producing positive power.

For example, the tension force in the assistive flexible suit 100 may rise from 25 to 40 percent of the gait cycle with a force transmission element, such as a Bowden cable, held at a constant length, passively absorbing power. From 40 to 60 percent of the gait cycle, this energy is returned to the individual wearing the assistive flexible suit 100, but the active peak is much higher than the passive peak because of the force transmitting through the force transmission element as a result of actuation. At 60 percent of the gait cycle, both forces fall as the individual changes his or her body configuration during the normal course of walking, which releases the tension in the assistive flexible suit 100. This pattern of forces duplicates the natural biological pattern of gait moments and powers during walking.

Figure 17A:
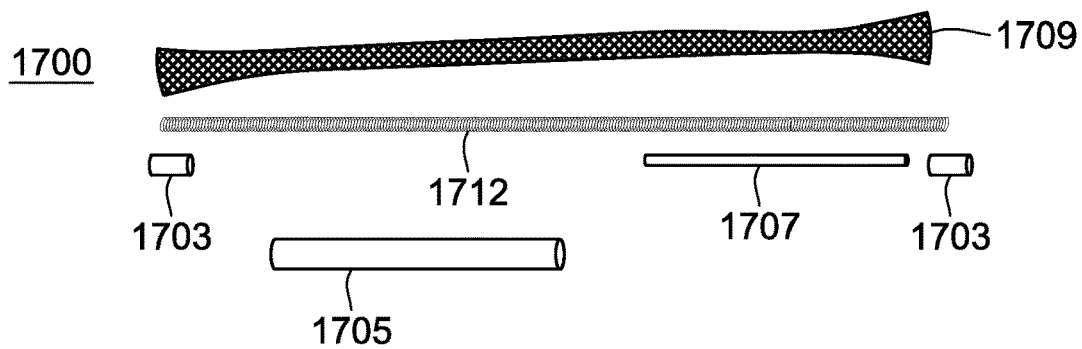
FIGS. 17A-17D show tensioning systems for force transmission elements according to at least some aspects of the present concepts.

FIG. 17A illustrates elements of a tensioning system 1700, according to at least some aspects of the present concepts. The tensioning system 1700 may include a spring 1701, end caps 1703, spring retention tube 1705, wear prevention tube 1707, and expandable sleeve 1709. The spring 1701, end caps 1703, spring retention tube 1705, wear prevention tube 1707, and expandable sleeve 1709 are hollow to allow at least part of a force transmission element, such as from a Bowden cable, to pass through when assembled.

The spring 1701 may be any type of spring, such as by forming metal into a spiral shape. The end caps 1703 fit into either end of the spring 1701 to cap the ends of the spring 1701. The wear prevention tube 1707 fits within the spring 1701 and prevents wear of the spring 1701 during actuation and tensioning, such as from the cable repeatedly rubbing against the spring 1701. The spring retention tube 1705 fits over the spring 1701. The length of the spring retention tube 1705 may be adjusted to limit the extent that the spring 1701 can be compressed. The expandable sleeve 1709 goes over the spring 1701 and the retention tube 1705. The expandable sleeve 1709 prevents objects from being pinched by the spring 1701 between periods of tensioning. The expandable sleeve 1709 further prevents environmental debris from being entrapped within the tensioning system 1700.

The tensioning system 1700 allows a force transmission element (not shown), such as a Bowden cable, to run down and through the length of the tensioning system 1700, such as through one end cap 1703, the spring 1701, the wear prevention tube 1707, and the other end cap 1703. When the force transmission element (e.g., Bowden cable) is actuated, motion of the force transmission element causes the spring 1701 to expand or compress. As the spring 1701 compresses, the expandable sleeve 1709 also compresses. In one embodiment, the spring 1701 causes a restoring force on the expandable sleeve 1709 to pull the force transmission element out of expandable sleeve 1709 when the force transmission element is actuated. Tension can be applied to force transmission element, independent from actuation, by controlling the properties of the spring 1701, such as the material of the spring, the length, the number of revolutions per unit of length, etc.

Figure 17B:
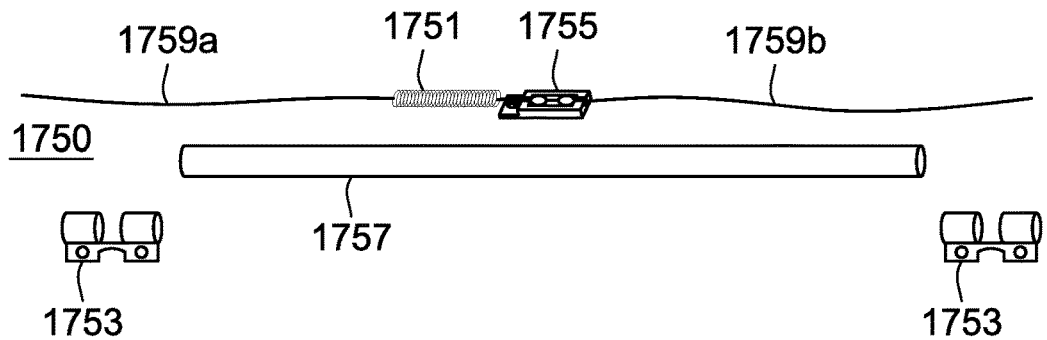
Figure 17C:
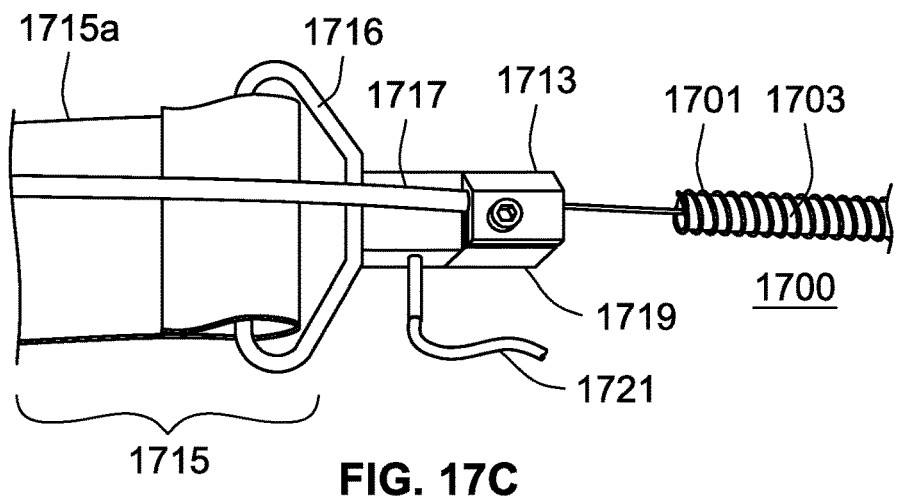

FIG. 17C illustrates the tensioning system 1700 applied to the assistive flexible suit 100, according to at least some aspects of the present concepts. As shown, a force transmission element 1717, such as a wire of a Bowden cable, passes through an end cap 1703 and the spring 1701. In the case of a Bowden cable, the wire further passes through force transmission element attachment 1713 that engages the sheath of the Bowden cable but allows the wire to freely pass through. The force transmission element attachment 1713 connected to an assistive flexible suit connector 1715. Thus, the force transmission element attachment 1713 connects the actuation system, such as an offboard control system 200, to the assistive flexible suit 100 by way of the assistive flexible suit connector 1715 in tandem with the force transmission element attachment 1713.

As described above, the assistive flexible suit connector 1715 may be of various different styles and configurations without departing from the spirit and scope of the disclosure. As illustrated, the assistive flexible suit connector 1715 may include a fabric loop 1715a made of the fabric material of the assistive flexible suit 100. The fabric loop 1715a may go through a metal loop 1715b, as illustrated. The metal loop 1715b connects to the force transmission element attachment 1713. The metal loop 1715b may attach to the force transmission element attachment 1713 by any suitable mechanical connection, such as a screw, latch, etc. In one embodiment, the metal loop 1715b and the force transmission element attachment 1713 may be a single, integral piece.

Optionally, a load cell 1719 may be located between the force transmission element attachment 1713 and the metal loop 1715b. Attachment of the load cell 1719 allows for the measurement of the forces transmitted through the force transmission element 1717. In one embodiment, there may be a pivot (not shown) between the load cell 1719 and the force transmission element attachment 1713. The pivot minimizes the off-axis moments transmitted through the load cell 1719, which could otherwise decrease the life of the load cell 1719. Attached to the load cell 1719 is a load cell output 1721 that can connect to, for example, the offboard control system 200 or other control device, to provide measurements of the forces transmitted through the force transmission element 1717. According to the foregoing, the load cell 1719 may be an additional, separate component, or may be integrated into the attachment methods, such as integrated into the attachment between a force transmission element and the assistive flexible suit 100 at the force transmission element attachment 1713.

FIG. 17B illustrates elements of another tensioning system 1750, according to at least some aspects of the present concepts. Tensioning system 1750 may include a spring 1751, end caps 1753, cable carriage mating point 1755, and spring retention tube 1757. The end caps 1753 and spring retention tube 1757 are hollow to allow at least part of a force transmission element, such as from a Bowden cable, to pass through. A force transmission element 1759a passes through the spring 1751 and connects to the cable carriage mating point 1755. Another force transmission element 1759b connects to the other end of the cable carriage mating point 1755.

Figure 17D:
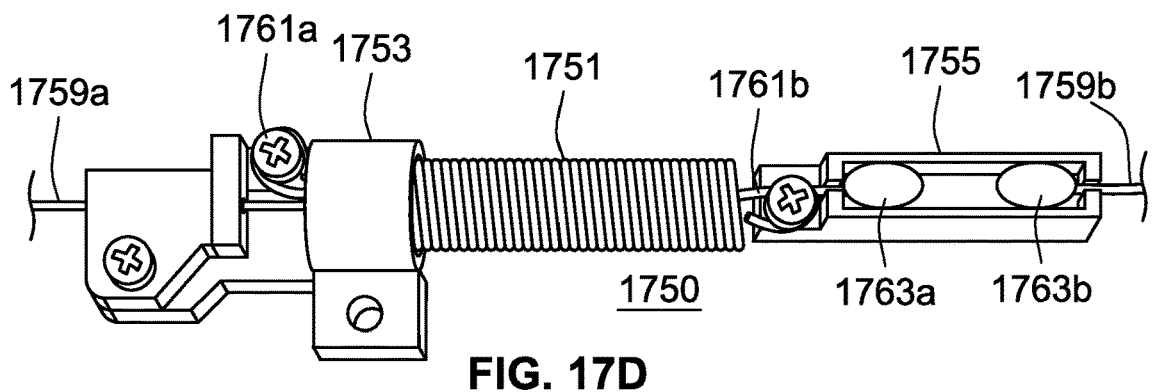

Adverting to FIG. 17D, in a connected state, one end of the spring 1751 connects to a spring attachment point 1761a on the end cap 1753. The other end of the spring 1751 connects to a spring attachment point 1761*b* on the cable carriage mating point 1755. Further, the force transmission element 1759*a* connects to one end 1763*a* of the cable carriage mating point 1755. The force transmission element 1759*b* connects to the other end 1763*b* of the cable carriage mating point.

When the force transmission elements 1769*a* and 1769*b* actuate, the spring 1751 expands or compresses. As the spring 1751 expands or compresses, tension is generated or released within the tensioning system 1750. The spring 1751 causes a restoring force acting on one end cap and the cable carriage mating point 1755 when the force transmission elements 1759*a* and 1759*b* are actuated. Tension can be applied to force transmission elements 1759*a* and 1759*b*, independent from actuation, by controlling the properties of the spring 1751, such as the material of the spring, the length, the number of revolutions per unit of length, etc.

Although two tensioning systems are described above, the assistive flexible suit 100 may include alternate tensioning systems, alone or in combination with the two tensioning systems 1700 and 1750. In one embodiment, the force transmission elements within the assistive flexible suit 100 may act like one or more springs. An alternate tensioning system may utilize the assistive flexible suit 100 acting like a spring, with a locking mechanism maintaining and/or controlling such tension provided by the force transmission elements. By way of example, connection points between force transmission elements of the assistive flexible suit 100 and anchor elements may include ratchets. Such ratchets may allow a medical provider-in-the-loop and/or the individual to control the tension within the assistive flexible suit 100 by tightening or loosening the force transmission elements. As a ratchet is tightened, the tension provided by the force transmission elements within the assistive flexible suit 100 increases. Conversely, as a ratchet is loosened or opened, the tension provided by the force transmission elements within the assistive flexible suit 100 decreases or becomes completely slack. Alternately or in addition, one or more ratchets may be positioned along the length of the force transmission elements, rather than at the above-described connection points, to control the natural tension of the assistive flexible suit 100.

In one embodiment, control of the ratchet may be manual such that, for example, a medical provider-in-the-loop or the individual can manually operate the ratchet to control the tension in the assistive flexible suit 100. Alternately, control of the ratchet may be active or dynamic, such as being based on the movement of the individual. As described above with respect to actuation of the force transmission elements (e.g., such as with respect to FIGS. 16A-16C), a ratchet may be controlled (e.g., electrically or mechanically) to ratchet during a specific movement or portion of a gait period to maintain tension within the assistive flexible suit 100. During a subsequent movement or portion of a gait period, the ratchet may be controlled (e.g., electrically or mechanically) to reduce or completely remove tension within the assistive flexible suit 100. Under such control, the ratchet can act like a locking mechanism, which locks or unlocks tension within the assistive flexible suit 100 to provide beneficial forces for the individual's movement.

Tensioning allows for the performance of the assistive flexible suit 100 to change independent of control of the actuators and/or the off-board control unit 200. In one embodiment, modification of the tension within the assistive flexible suit 100 by a medical provider in-the-loop and/or the individual wearing the assistive flexible 100 suit may be permitted. Such modification may change the baseline assistance provided by the assistive flexible suit 100 and can achieve the same force at a given gait percentage when desired, lower or higher forces to help the individual more or less (e.g., heavier load, longer steps, etc.), and/or render the assistive flexible suit 100 completely transparent during all motions. As described above, the tensioning may be active, such as dynamically changing during portions of a gait period, passive, or a combination thereof.

In one embodiment, the tension provided by the tensioning system 1700 or 1750 within the assistive flexible suit 100 can be adjusted during different movements, depending on if the wearer wants assistance or not, such as during steady-state walking. Such adjustment (e.g., by a medical provider-in-the-loop or the individual) may further be achieved by sliding elements along webbing of the assistive flexible suit 100 to equalize tension at connecting parts of webbing. Alternatively, devices, as discussed with respect to FIG. 19, may be inserted within the force transmission elements that allow a medical provider-in-the-loop or the individual to modify the length of the force transmission elements.

The force transmission element may be tensioned when not actuated by an actuation system such that in a passive state, such as when the force transmission element is not modifying movement and/or a moment of an individual, the force transmission element is under tension. A tensioning system, according to the above, may apply tension to a force transmission element that, at one end, is fixed to an object, such as a body part of the individual.

Figure 18:
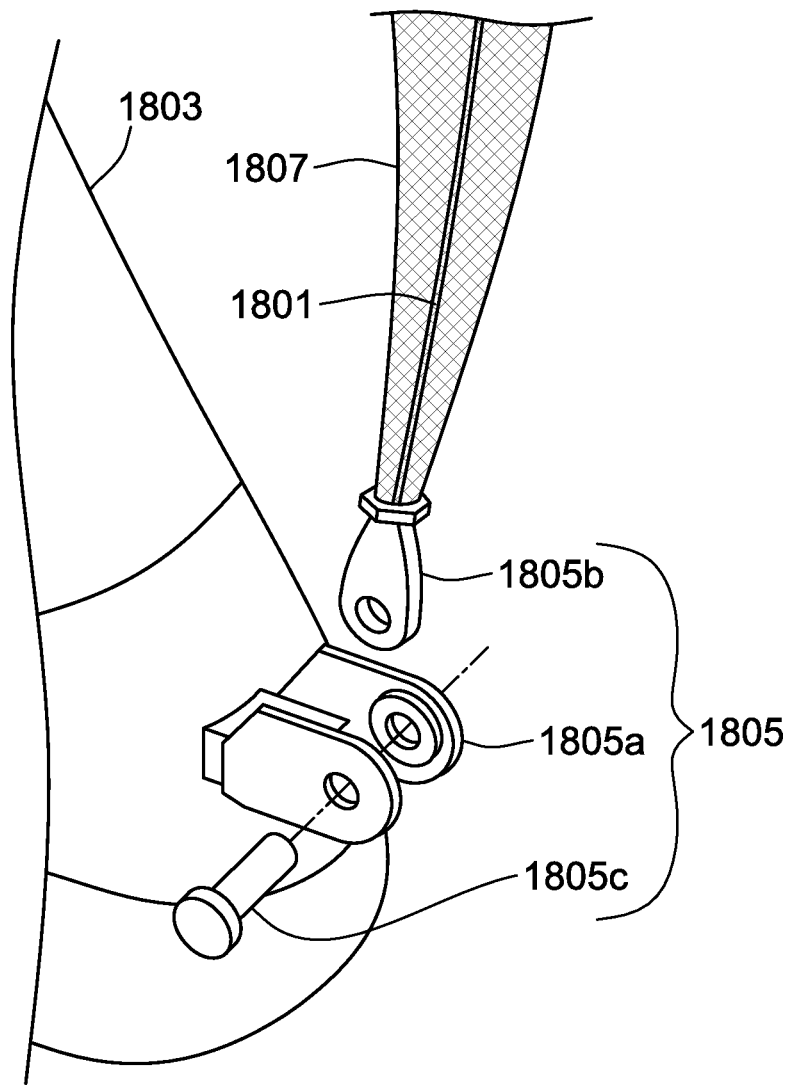
FIG. 18 shows an anchor element according to at least some aspects of the present concepts.

FIG. 18 illustrates an anchor element 1805 of the assistive flexible suit 100 with respect to the foot, according to at least some aspects of the present concepts. A force transmission element 1801, which may be within an expandable sleeve 1807 (such as expandable sleeve 1709), attaches to, for example, a boot 1803 through the anchor element 1805. Although illustrated with respect to the boot 1803, the anchor element 1805 may be located on other articles covering the foot and/or other portions of the individual, and is not limited to only the boot 1803. The anchor element 1805 may be a single revolute joint. A pivot at the single revolute joint allows the force transmission element 1801 to freely rotate in the sagittal plane so that force applied through the force transmission element 1801 does not kink or bend the force transmission element 1801. The anchor element 1805 includes a bearing interface 1805*a*, a force transmission element attachment interface 1805*b*, and a pivot pin 1805*c*.

Figure 19:
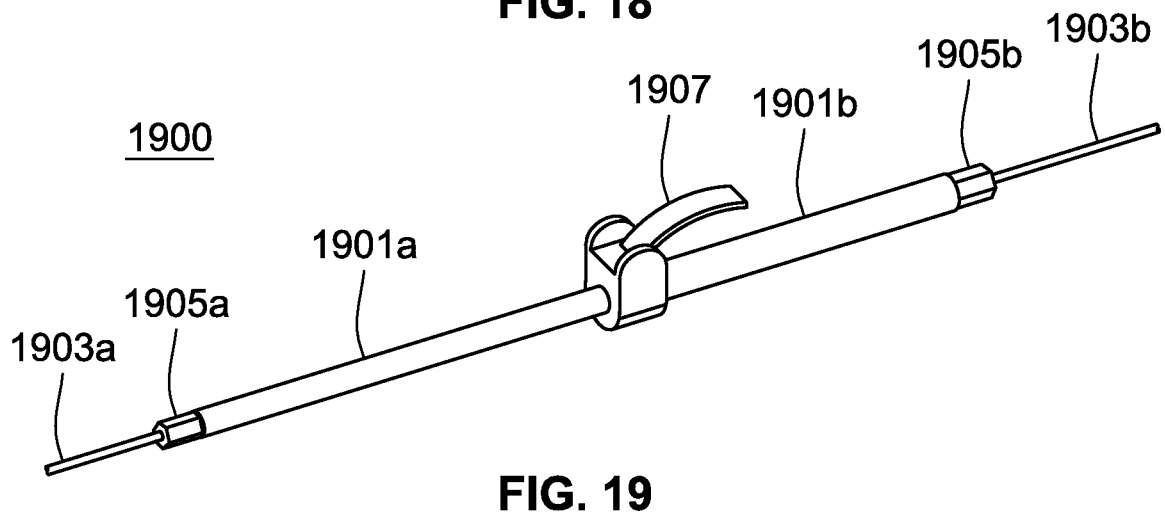
FIG. 19 shows a force transmission element length adjustment device according to at least some aspects of the present concepts.

FIG. 19 illustrates an example of a length adjustment device 1900 that allows a wearer to modify the length and passive tension within a force transmission element, according to at least some aspects of the present concepts. The length adjustment device 1900 may include cylinders 1901*a* and 1901*b* that allow a wire, such as from a Bowden cable, to pass through, while connecting to the sheaths 1903*a* and 1903*b* of the Bowden cable. The sheaths 1903*a* and 1903*b* connect to the cylinders 1901*a* and 1901*b* at connection points 1905*a* and 1905*b*, respectively. In one embodiment, one or both of the cylinders 1901*a* and 1901*b* may be flexible to provide sufficient flexibility to the wearer. The cylinders 1901*a* and 1901*b* may engage with each other at a clamping mechanism 1907. Adjustment of the clamping mechanism 1907 from a locked position to an unlocked position allows, for example, cylinder 1901*a* and sheath 1903*a* to move with respect to cylinder 1901*b* and sheath 1903*b* to adjust the effective length of the force transmission element within the sheaths 1903*a* and 1903*b*. That is, changing the length of a Bowden cable sleeve while keeping the Bowden cable wire length within the sleeve constant allows for adjustments to the maximum Bowden cable travel.

In one embodiment, the clamping mechanism 1907 may include a spring loaded clutch mechanism, such as an electric clutch, which can only be activated if the system is not currently actuated. In one embodiment, springs may be within the cylinders 1901*a* and 1901*b* that either retract or push the tubes in or out depending on the clutch position of the clamping mechanism 1907. Alternatively, the clamping mechanism 1907 may be manual to allow a medical provider-in-the-loop and/or an individual to manually adjust the cable travel length.

Sensors (e.g., sensor 120) of the assistive flexible suit 100 allow for the detection of one or more events during the gait of an individual, such as a patient suffering from limited mobility, based on, for example, one or more of suit tensioning status and gait kinematics. The assistive flexible suit 100 incorporates a body-wide sensor network (e.g., nervous system) of biomechanical, physical-interaction, and physiological sensors that feed into a controller (e.g., off-board control system 200) that provides control over the individual wearing the assistive flexible suit, monitor the individual's task and/or physical state (e.g., walking and/or fatigue status) and applies assistance. For example, during walking, the off-board control system 200 will continuously, periodically, or on-demand adjust the level of applied force based on terrain (e.g., uneven surfaces) and speed. The measurements of the sensors can detect other modes of movement, such as running, where assistance levels and timing are adjusted, or being stationary, where the assistive flexible suit 100 will enter a hyper-alert state so that the assistive flexible suit 100 can quickly react and synchronize with the individual once the individual initiates movement. In situations when the individual does not desire any assistance, the assistive flexible suit 100 can enter a fully transparent mode where zero force is applied based on measurements from the network of sensors.

One or more specific sensors can track gait, determine joint angles, and track the movement of specific body segments. The sensor type may vary depending on the environment of the sensor with respect to the individual and the specific measurement desired for the sensor. Exemplary sensor types may include biomechanical, physical-interaction, and physiological sensors. Specific sensors may include inertial measurement units (IMUs), gyroscopes, accelerometers, foot switches, foot pressure sensors, foot contact sensors, suit force sensors, and suit tension sensors. Kinematic sensors, as an example, may monitor joint angles in real-time so control systems (e.g., offboard controller 200) can analyze and determine an individual's body's motion.

With respect to communication within the assistive flexible suit 100, the sensors may be integrated using an open-network approach ensuring a common communication protocol, full robustness to single-sensor failures, and the possibility of changing, removing, or adding sensors within the assistive flexible suit 100 without requiring a change to the underlying architecture.

Sensors may be located at or on key areas of the individual, such as on the front of the individual (e.g., hip, across the front of the knee, pelvis, torso, etc.), on the side of the individual (e.g., on the side of the knee, on the side of the waist, pelvis, torso, etc.), and on the back of the individual (e.g., at the back of the thigh, behind the ankle, etc.). More specifically, as an example, sensors can be placed posteriorly, anteriorly, and laterally on the hip or on various position across the individual's chest, such as on a chest band.

One type of sensor is a force sensor that measures the tension in the individual side of a force transmission element (e.g., force transmission elements 220*a*-220*d*). The force sensors may be built into a structural joint of the assistive flexible suit. By way of example, and as described below, the sensor may be positioned on the assistive flexible suit at the junction of the force transmission element and the assistive flexible suit 100, such as at the cable sheath of a Bowden cable and the assistive flexible suit.

Consideration of where to place sensors throughout the body can take into account the operation of the sensors and the operation of the individual's body during movement. A principle of joint angle sensing and, therefore, operation may be based on the change in the distance between two points on the surface of an individual's body segments connected across a joint. The change in length between these points can be related to the change in the joint angle and scaled by the radius of the joint. A sensor place in such a position may provide a reading based on the extent the sensor is stretched, which relates to the distance across the joint. With respect to operation of the individual's body, sensor placement may consider avoiding bony landmarks on the individual to reduce sensitivity to pressure or impacts on the body. Locations on the body that avoid these issues are at, for example, the knees and ankles by attaching the sensors to inextensible attachments, such as nylon straps, that are routed over joints while the sensors remain on the thighs and calves, respectively.

One or more of the sensors may be integrated into the assistive flexible suit 100, such as being integrated within the fabric itself, which may be referred to as soft sensors. The sensors can be integrated into the fabric by embedded fabrics, such as conductive fabrics and threads. Sensors integrated into the assistive flexible suit 100 can be directly in line with the suit's pre-existing webbing and elastic elements. Further sensors integrated into the assistive flexible suit 100 may allow for the combining of sensing layers, such that multiple modes of sensing within the assistive flexible suit 100 are achieved. For example, biocompatible conductive fluidics may be used, alone or in combination with integrated embedded fabrics, that rely on how forces and motions deform the embedded microchannels, thus altering the electrical resistance path along the conductive liquid wires. Design of the elastomeric mechanisms and microchannel paths yields the desired sensing modes.

Integration of the sensors into the assistive flexible suit 100 allows the sensors to measure pressure levels at the physical interface between the suit and the individual in some areas of the body that support forces. Such areas may include bony areas, such as the iliac crest. Integrated sensors based on soft materials are conformal, lightweight, and non-restrictive. Such integrated sensors may provide information at such areas in real-time for adjusting the peak force or position profile to keep pressure at these areas within the desired comfort limits. The pressure transmitted by the assistive flexible suit 100 to the individual depends on the anatomy of the wearer, the assistive flexible suit 100, and the interface between the assistive flexible suit 100 and the wearer.

Further specific points of integration of sensors into the assistive flexible suit 100 may be at the chest for breathing rate monitoring and at locations to register blood flow, such as for blood pressure monitoring. The measurements from the sensors integrated into the assistive flexible suit can be combined with information from other sensors, such load cells at intersection between force transmission elements and assistive flexible suit attachment points. Information from the soft sensors could be used to detect different human motions, and to provide information about gait events.

With respect to the chest, one specific sensor may be a chest belt that can monitor the individual's heart rate, respiratory rate, body temperature, and galvanic skin response. The chest belt may alternatively, or additionally, measure electrocardiogram (EKG), electromyography (EMG), skin conductivity, and blood oxygen content. The chest belt may optionally include a small microcontroller (with embedded battery) for collecting synchronized data from sensors throughout the assistive flexible suit 100. The collected, synchronized data can be analyzed to determine a concise fatigue and physical condition of the individual.

In one embodiment, and for exemplary purposes only, sensors used with the assistive flexible suit 100 are compliant (e.g., joint torque resistances <0.17%), sensitive (e.g., gauge factors >2.2), electrically and mechanically stable for 1500 cycles (e.g., <2% change), and extensible (e.g., stretch to 396% at failure in an extreme case).

With the overall nervous system of sensors attached to and/or located about the assistive flexible suit 100, the information from the sensors may be analyzed to estimate the pose and/or velocity of the individual wearing the assistive flexible suit 100, or the power of the assistive flexible suit 100. For example, from sensors measuring motor position, position in gait cycle, kinematic model, and a suit-human interaction force-displacement model, the information can be analyzed to determine power/energy to-from the human, suit sliding, on how the assistive flexible suit 100 is pushing on individual, and impact on gait.

Monitoring the forces delivered to the individual and the individual/assistive flexible suit interaction forces at different parts of the assistive flexible suit 100 can provide for safe, adequate assistance under different conditions, while also enabling the monitoring of the system's performance. Such monitoring will also enable adaptive advanced control methods that monitor these interactions. Several different sensor types may be used to monitor these interactions, such as monitoring tension in the force transmission elements, and monitoring the individual/assistive flexible suit interaction forces in the webbing and/or fabric of the assistive flexible suit webbing, respectively.

Further, noise in any form (e.g., audio and/or visual) is thought to interfere with perception. However, presence of certain kinds of noise within certain systems can enhance information transmission. Human tactile and proprioceptive sensory networks are examples of such systems. The SHR sensors may provide below-sensory threshold haptic stimulations that increase proprioception and/or provide injury-mitigation. Such sensors can increase human proprioception during walking, which allows improvements to ligaments that are commonly injured and tendons that contribute to stabilizing joints related to movement, such as the ankle joint with respect to plantar flexion and dorsiflexion.

For example, the assistive flexible suit 100 may include piezo-ceramic elements embedded in the fabric and located in proximity to the knee and ankle joints. These elements can deliver both sub- and supra-threshold mechanical vibrations. Sub-threshold stimuli increase joint-level awareness, which can compensate for the loss of balance/proprioception when the offboard control system 200 (e.g., such as through an awareness engine) detects the onset of fatigue. The piezo-ceramic elements are also capable of above-threshold feedback to alert the medical provider and/or the individual of a breakdown in gait or extreme physical stress, or hardware failure, so that the medical provider and/or individual can adapt appropriately.

The haptic feedback unit may be outfitted within a knee and/or ankle brace, which can be connected to and integrated with the offboard control system. Braces outfitted with stoichastic haptic resonance (SHR) sensors to apply stimulation to the joints can improve underlying abnormalities within the tendons and ligaments in the joints. Knee and ankle injuries, such as ligament tears and sprains, have caused significant decreases in proprioception. Functional ankle instability (FAI) is characterized by weakness and repetitive sprains. These represent the common injuries during physical activity and are strong indicators of future ankle injuries.

By way of example, SHR sensors may be positioned at one or both of the following locations about the assistive flexible suit 100. Position one is located on the lateral dorsum of the foot, superficial to the lateral ligaments. This position is also superficial to the peroneus longus, peroneus brevis, extensor digitorum longus, and the peroneus tetius. The peroneus longus and brevis aid in plantar flexion, while the extensor digitorum longus and peroneus tetius aid in dorsiflexion. Position two is located on the medial side of the Achilles tendon over the soleus and gastroc tendons. This position aids in promoting plantar flexion within the ankle. With these stimulation positions, the assistive flexible suit 100, through the SHR sensors may influence ligaments that are commonly injured as well as tendons that contribute to stabilizing ankle plantar flexion and dorsiflexion. Such stochastic resonance simulation, either mechanical, electrical, or both, can improve rehabilitation. Neuroplasticity describes the capability of the nervous system to repair or remodel itself by creating new neural control pathways to bypass damaged control pathways or to learn new skills. This effect is frequently seen in stroke patients that learn to reuse paralyzed limbs through repetitive learning techniques. However, this is not limited to stroke. Mechanoreceptor sensory feedback is critical to this neuroplasticity process, and stochastic resonance is known to improve the sensitivity of mechanoreceptors; therefore, the application of stochastic resonance can improve the rehabilitation of patients with nervous system damage. This effect was demonstrated in an unpublished study using a rat model of stroke rehabilitation in which electrical SR stimulation was found to have a lasting positive impact on the neuroplasticity of rats. The functional gains following the stimulation regime were maintained after the stimulation was removed.

The force transmission element may be any component capable of transmitting a force. Although generally described as a cable, such as a Bowden cable, a force transmission element may alternatively include a fluidic muscle actuator, a webbing strap, an electroactive material actuator (e.g. polymer or shape memory alloy), an active or passive clutch, and non-Newtonian fluids within microchannels. With respect to a Bowden cable, such a force transmission element includes a metal cable surrounded by a sheath.

Further, a force transmission element may be any element capable of generating a force. Examples of force transmission elements that generate a force include springs, dampers, and other materials and/or shapes that behave as spring-damper systems in addition to active or passive clutches that can selectively engage and disengage such elements.

The force transmission elements modify one or more gait moments about the body of an individual wearing the assistive flexible suit 100. The force transmission elements may apply forces to the gastrocnemius and soleus muscles, such as for ankle plantar flexion, the quadriceps femoris, such as for hip flexion, and the gluteus and hamstrings, such as for hip extension and knee flexion.

With respect to hip extension, a webbing strap may connect an actuator to a thigh attachment, although any other force transmission element may be used, such as a Bowden cable. In one embodiment and as discussed above, force sensors may be embedded into the webbing strap or in series with the webbing strap. The force sensors may measure the force in the webbing strap and relay the measured force to, for example, an off-board control unit 200 for monitoring by a medical provider-in-the-loop. Such an arrangement allows the system to, for example, be operated without footswitches by instead closing a force-control loop that tracks the individual's hip motion. Assistive torques may be applied to the hip at the appropriate time in the gait cycle.

Specifically, the off-board control unit 200 may control the hip extension through a thigh attachment to assist a hip moment beginning slightly before heelstrike, to decelerate the leg. The assistance continues just after the heel strikes the ground to absorb the shock of the landing and help the body rebound. The off-board control unit creates an assistive force peaking at about 20% in the gait cycle, and the off-board control unit can apply about 25% of the nominal hip moment. Assisting the hip in extension is not only useful for level-ground walking, but also useful for uphill and downhill walking, ascending and descending stairs, and standing up from a seated position, because, for example, these movements have increased hip extension torques.

With respect to hip flexion, the assistive flexible suit 100 may include a waist belt, two thigh braces, and two stretchable webbing straps on each side of the legs for keeping the thigh braces from dropping. A force transmission element may extend between an anchor point on the waist belt and an anchor on the thigh brace, creating a flexion torque about the hip when the force transmission element is actuated, such as when a Bowden cable is retracted. This arrangement may alternatively be reversed on the individual and used to generate hip extension torques. Actuation of the force transmission element is achieved by an off-board actuation system 200, for example, based on the configuration described below.

With respect to plantar flexion and hip flexion, the assistive flexible suit 100 transfers force between the back of the calf and the waist through a series of webbing straps and fabric. To actuate this flexion, a force transmission element, such as a Bowden cable, extends from, for example, the offboard control system 200 to an ankle of the individual. The assistive flexible suit 100 attaches to the force transmission element at the back of the calf. By way of example with respect to a Bowden cable, the assistive flexible suit 100 may attach to a sheath of the Bowden cable. The cable inside the sheath extends downward from this point to the back of the heel, where the cable attaches to a foot attachment, such as, for example, a boot or shoe of the individual, through an anchor element. When the force transmission element is actuated, the back of the ankle is pulled upward and the bottom of the assistive flexible suit is pulled downward. The assistive flexible suit 100 then transfers the force up to the individual's waist, so the pelvis bone is pulled downward. The skeletal structure of the wearer then transfers this downward force back to the ankle joint and to the ground through the foot.

According to the above-described manner, the assistive flexible suit applies forces to the body in parallel with the underlying musculature, reducing the work required by the individual's muscles. At the same time, the actuation modifies the movement of the muscles by modifying gait moments.

Figure 20A:
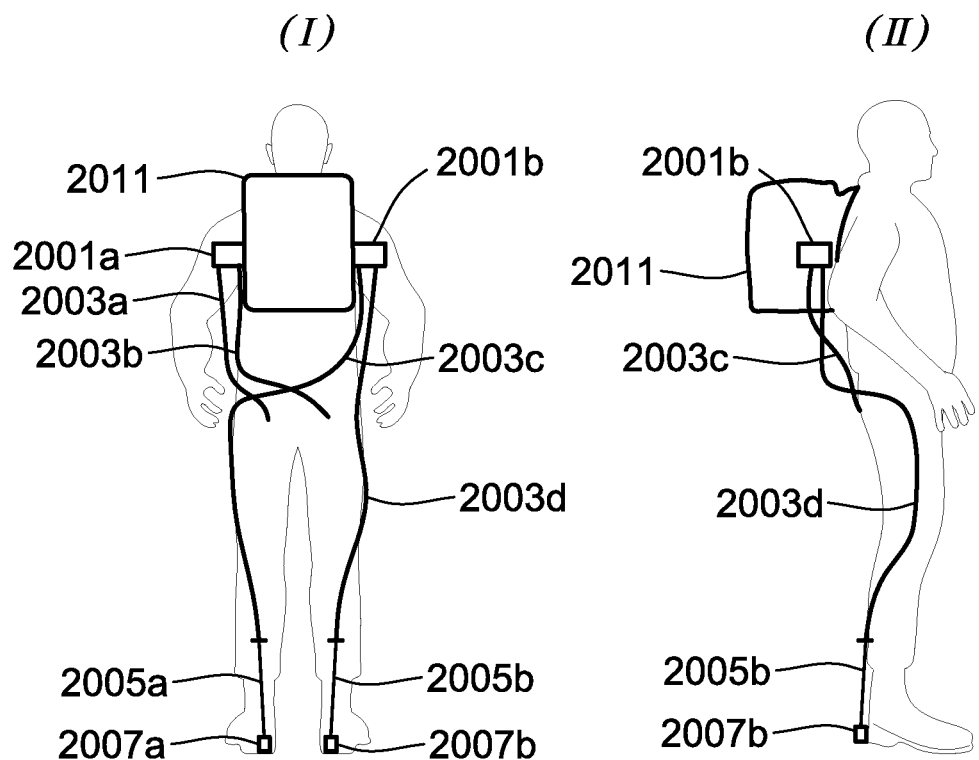
FIGS. 20A-20C show various configurations of actuators about an assistive flexible suit according to at least some aspects of the present concepts.

In one embodiment, one or more actuators may be located at or on the individual connected through the assistive flexible suit 100. FIG. 20A illustrates a rear view (FIG. 20A(I)) and a side view (FIG. 20A(II)) of an individual wearing an assistive flexible suit, according to at least some aspects of the present concepts. Actuators 2001a and 2001b may be attached to the assistive flexible suit on either side of, for example, a backpack 2011. Actuator 2001a may connect to the hips of the individual through force transmission elements 2003a and 2003b. Actuator 2001b may connect to the ankles of the individual through force transmission elements 2003c and 2003d. In a non-limiting example, the force transmission elements 2003a through 2003d may be Bowden cables. With Bowden cables constituting the force transmission elements 2003c and 2003d, wires 2005a and 2005b of the Bowden cables 2003c and 2003d may be exposed at the point of actuation of the ankles of the individual, where the wires 2005a and 2005b connect to anchor elements 2007a and 2007b connected to the shoes of the individual.

Although the actuators 2001a and 2001b are illustrated as connecting to the assistive flexible suit through a backpack 2011 on both sides of the individual, the actuators 2001a and 2001b may connect to the assistive flexible suit according to other configurations, such as both actuators 2001a and 2001b being on the same side of the individual, above and/or below the backpack 2011, on the hips and/or above the ankles of the individual, on the leg (e.g., thigh or calf) of the individual, etc., without departing from the spirit and scope of the disclosure. Further, the routes of the force transmission elements 2003a-2003d may vary depending on the locations of the actuators 2001a and 2001b.

Figure 20B:
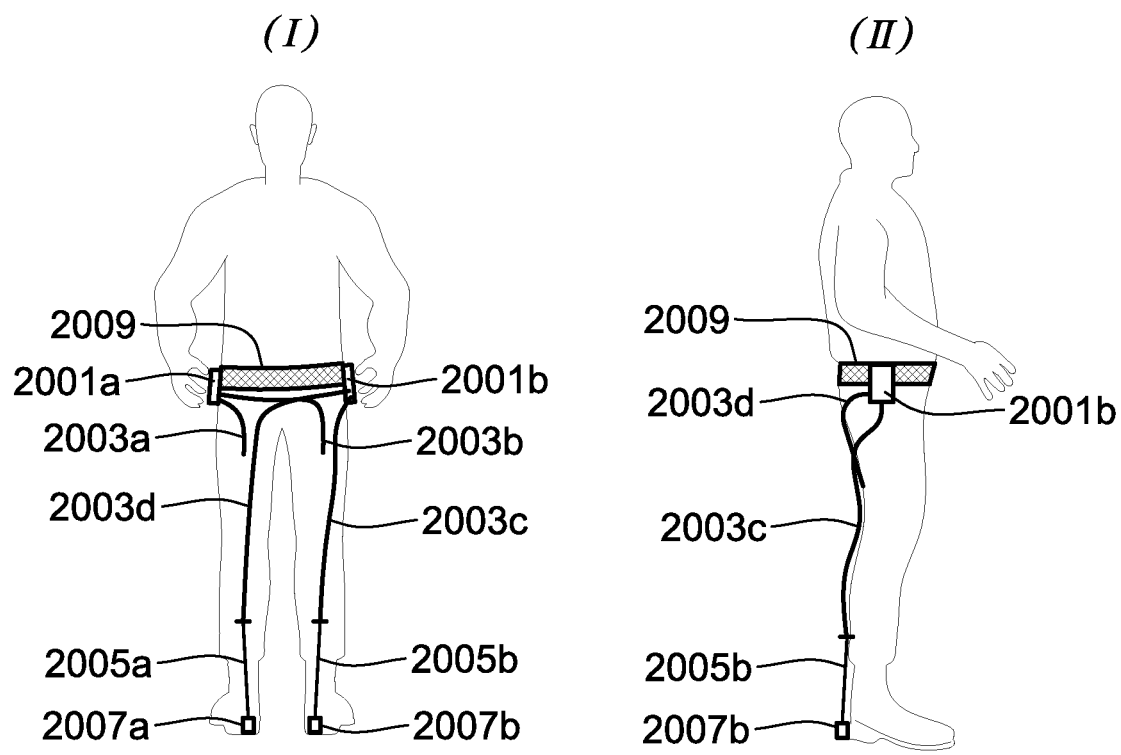

For example, FIG. 20B illustrates a rear view (FIG. 20B(I)) and a side view (FIG. 20B(II)) view of an individual wearing an assistive flexible suit, according to at least some aspects of the present concepts. Rather than being connected to the backpack 2011, actuators 2001a and 2001b may be attached to the assistive flexible suit 100 on either side of, for example, a power belt 2009. The power belt 2009 may optionally include one or more additional power sources for the actuators 2001a and 2001b, such as one or more additional batteries, or the power belt 2009 may include one or more batteries entirely (e.g., the actuators 2001a and 2001b do not have an integral power source). Like before, actuator 2001a may connect to the hips of the individual through force transmission elements 2003a and 2003b. Actuator 2001b may connect to the ankles of the individual through force transmission elements 2003c and 2003d. Again, as an example, the force transmission elements 2003a through 2003d may be Bowden cables. With respect to force transmission elements 2003c and 2003d being Bowden cables, the wires 2005a and 2005b of the Bowden cables 2003c and 2003d may be exposed at the point of actuation of the ankles of the individual, where the wires 2005a and 2005b connect to anchor elements 2007a and 2007b connected to the shoes of the individual.

Figure 20C:
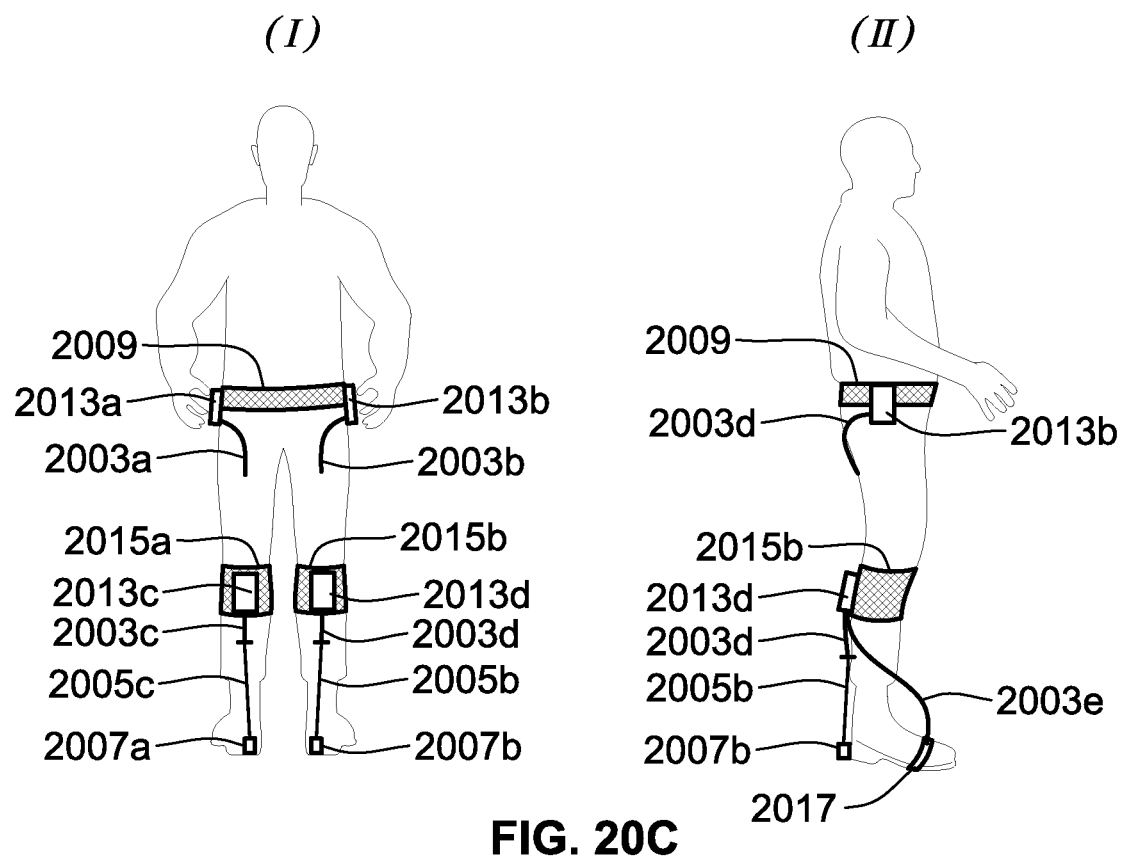

FIG. 20C illustrates a distributed arrangement of actuators, according to at least some aspects of the present concepts. Specifically, FIG. 20C illustrates a rear view (FIG. 20C(I)) and a side view (FIG. 20C(II)) of an individual wearing an assistive flexible suit 100. The distributed arrangement includes four actuators 2013a through 2013d, with actuators 2013a and 2013b connected to the power belt 2009, and actuators 2013c and 2013d connected to calf attachments 2015a and 2015b located on the calves of the individual. Each of the actuators 2013a and 2013b may actuate a different hip, such as for hip flexion and/or hip extension. Each of the actuators 2013c and 2013d may actuate a different ankle, such as for plantar flexion and/or dorsiflexion. According to the distributed arrangement of the actuators illustrated in FIG. 20C, the efficiency of force transmission can be improved by placing actuators configured for a specific purpose in close proximity to the body part tied to the specific purpose.

In one embodiment with respect to, for example, the individual's right foot and the actuator 2013d, a semi-rigid foot attachment (not shown) may be in mechanical cooperation with the actuator 2013d and the individual's right foot. The semi-rigid foot attachment may include a combination of rigid and flexible members below the right foot, such as inside and/or outside a shoe, and supports extending upward from the rigid member. The supports may connect to the semi-rigid member at joints that correspond to the motion about the ankle. The semi-rigid foot attachment may be mechanically coupled to the actuator 2013d. As described above, actuation of the actuator 2013d and the force transmission element 2003d connected to the anchor element 2007d generates a plantar flexion force. By including the semi-rigid foot attachment coupled to the actuator 2013d, a reactionary force opposite and corresponding to the plantar flexion force may be distributed, at least in part, to the semi-rigid foot element. Thus, the additional plantar flexion force generated at the ankle by the actuator 2013d may be distributed to the semi-rigid foot attachment, rather than the individual's skeletal structure bearing the entire corresponding force of the plantar flexion force through the assistive flexible suit 100. The semi-rigid foot attachment could be used as a standalone device or in combination with the textile components of the assistive flexible suit 100.

Further, according to the distributed arrangement of actuators 2013a through 2013d, each one of the actuators 2013a through 2013d may be configured for a single degree of freedom about a single joint, such as plantar flexion, dorsiflexion, hip extension, hip flexion, etc. However, as illustrated with respect to actuator 2013d, for example, actuator 2013d may be configured to apply both a plantar flexion force and a dorsiflexion force about the right ankle. Indeed, a single actuator can couple two other degrees of freedom or joints such that the coupling is not limited to plantar flexion and dorsiflexion. Further, a single actuator can couple degrees of freedom within different planes of movement, such as coupling degrees of freedom in two or more of the sagittal plane, the coronal plane, and the transverse plane. As described above, the plantar flexion force may be applied by the actuator 2013d through the force transmission element 2003d to the anchor element 2007b. Further, the dorsiflexion force may be applied by the actuator 2013d through the force transmission element 2003e connected to a dorsiflexion attachment 2017 on the right foot. As an example, plantar flexion and dorsiflexion may be applied to the same foot by the same actuator based on the forces being out of phase with respect to each other. The specifics of such an arrangement of the actuator 2013d are described in detail below with respect to FIG. 21 and FIGS. 22A through 22C.

Figure 21:
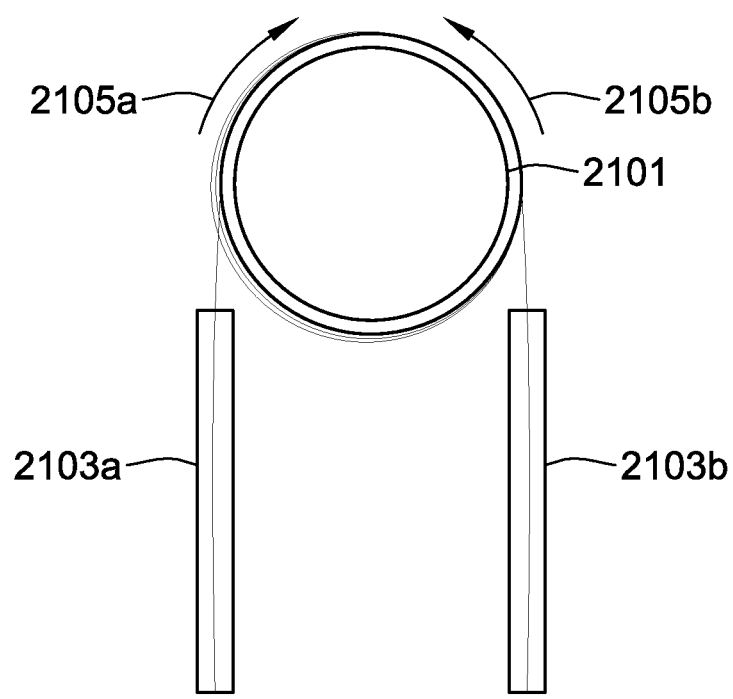
FIG. 21 shows a multi-wrap pulley system according to at least some aspects of the present concepts.

Specifically, FIG. 21 illustrates a multi-wrap pulley system 2100 that can be employed to control two actuations with a single motor, as the illustrations of FIGS. 20A-20C describe, according to at least some aspects of the present concepts. The multi-wrap pulley system 2100 includes a multi-wrap pulley 2101 with two force transmission elements 2103a and 2103b wrapped around the pulley 2101. Although illustrated with a single radius, the pulley 2101 may have two or more radii to modify two or more gait moments with different speeds and/or torques. The force transmission elements 2103a and 2103b may be Bowden cables; however, other force transmission elements may be employed within the same configuration. One force transmission element (e.g., 2103a) may be wrapped around the pulley 2101 in direction 2105a (e.g., clockwise), and the other force transmission element (e.g., 2103b) may be wrapped around the pulley 2101 in an opposite direction 2105b (e.g., counter-clockwise). By way of example, the multi-wrap pulley 2101 configured with the force transmission elements 2103a and 2103b can provide cable travel up to 15 inches, which ensures a sufficient amount of travel in order to assist, for example, an individual's hip and ankle.

In a state in which actuation is not applied to the system, the force transmission elements 2103a and 2103b through the multi-wrap pulley system 2100 may be slack. Alternatively, in the state in which actuation is not applied to the system, both force transmission elements 2103a and 2103b may be under tension. That is, the arrangement of the multi-wrap pulley 2101 and the force transmission elements 2103a and 2103b may be such that they system is engaged under tension. Such tension may be applied and/or modified as described above with respect to FIGS. 17A-17D. Further, depending on the needs of the individual wearing the assistive flexible suit 100, different tension may be applied to force transmission elements 2103a and 2103b, such as greater tension being supplied to a right ankle of an individual through force transmission elements 2103b as compared to the left ankle through force transmission element 2103a.

In a first operation of the multi-wrap pulley system 2100, such as rotating the pulley 2101 in the direction 2105a (e.g., clockwise), tension may be applied to the force transmission element 2103a and slack may be applied to the force transmission element 2103b. In a second operation of the multi-wrap pulley system 2100, such as rotating the multi-wrap pulley 2101 in the direction 2105b (e.g., counter-clockwise), tension may be applied to the force transmission element 2103b and slack may be applied to the force transmission element 2103a. According to the above operation of the multi-wrap pulley 2101, actuation may be applied to two joints, for example, using a single motor attached to the pulley 2101.

Force example, the multi-wrap pulley system 2100 may be applied to the actuator 2001b of FIG. 20A. The first operation of the multi-wrap pulley system 2100 may actuate the left ankle of the individual wearing the assistive flexible suit 100 by tensioning the force transmission element 2103a (constituting force transmission element 2003c of FIG. 20A). Conversely, the first operation of the multi-wrap pulley system 2100 may apply slack to the right ankle of the individual wearing the assistive flexible suit 100 by applying slack to the force transmission element 2103b (constituting force transmission element 2003d of FIG. 20A).

The second operation of the multi-wrap pulley system 2100 may actuate the right ankle of the individual wearing the assistive flexible suit 100 by tensioning the force transmission element 2103b (constituting force transmission element 2003d of FIG. 20A). Conversely, the second operation of the multi-wrap pulley system 2100 may apply slack to the left ankle of the individual wearing the assistive flexible suit 100 by applying slack to the force transmission element 2103a (constituting force transmission element 2003d of FIG. 20A).

In a specific embodiment with respect to modifying gait moments of an individual wearing the assistive flexible suit 100 while walking, each leg of an individual wearing the assistive flexible suit 100 may have its own characteristics as to when tension is applied. With respect to the right leg, for example, the multi-wrap pulley 2101 may be rotated to the tension position at a first position (e.g., about 28 percent in the gait cycle). At this first position, the force in the right leg begins increasing passively due to the kinematics of the wearer. At a second position (e.g., about 46 percent in the gait cycle), the multi-wrap pulley 2101 may further rotate, causing additional force at the right leg through the assistive flexible suit 100. The additional force may actively modify the gait moment about the right ankle of the individual. The force begins to decrease at a third position (e.g., about 56 percent in the gait cycle) due to the ankle of the right leg lifting up and beginning to swing. At a fourth position (e.g., 67 percent in the gait cycle), with the force less than 20 Newtons (N), for example, the multi-wrap pulley 2101 begins to rotate in an opposite direction to the first direction and moves immediately to the position that will enable the left leg to tension passively. This above-described scheme then repeats for the left leg. However, then tensioning points of the left leg may vary. For example, tension may be applied to the left leg beginning at less than 28 percent of the gait cycle, depending on the needs and characteristics of the individual's gate. Although described with respect to the right and left legs of an individual, other body parts described above can be actuated in a similar fashion to the foregoing.

As described above, the positions during gait, such as the first through fourth positions, can be detected by sensors within the assistive flexible suit 100. Based on the sensory information acquired, the off-board control unit 200 is able to estimate the correct timing when to operate a predefined motor trajectory. Hence, the sensor signals are used to sync the motor trajectory to the individual's gait. By following a predetermined position profile, the motor will start, for example, at the first state, and proceed to the first operation and the second operation, with the foregoing procedure repeating for subsequent gait cycles.

In accord with the foregoing, when the retracted force transmission element actuates to modify a gait moment of one joint, the force transmission element attached to another joint has a specific amount of slack ensuring that joint motion is not hindered. As such, an actuator within a single motor is able to provide multi joint actuation. Using one motor to operate two joints requires the pull times for each joint to be out of phase with each other, so that the motor will be able to apply torques to each joint alternately. In one embodiment, there may be a small period in between when the torque was applied to one joint and then the other joint, so that, for example, the motor can reel in slack in the force transmission elements (e.g., in the case of Bowden cables). If the joints to be actuated are on the same leg, and would normally act simultaneously or with overlapping actuation periods (e.g. ankle plantar flexion and hip flexion), then the two joints to be actuated may be on separate limbs, such as an ankle on the right leg and the hip on the left leg. This allows for the timings to be out of phase.

The two force transmission elements may be connected to two body parts on a single limb, such as modifying gait moments with respect to an individual's ankle and hip on a single leg. Alternatively, the two force transmission elements may be connected to two body parts of the same body part type on different limbs. For example, each of the two force transmission elements may be connected to a separate ankle on each leg of the individual. However, other arrangements are possible as long as the modification of the gait moments applied by the actuation of the two force transmission elements is out of phase giving that one force transmission element is tensioned when the other force transmission element is relaxed. Depending on the characteristics of the force transmission elements, such as length in the case of Bowden cables, although only a single one motor is used, it is still possible to exploit the passive spring characteristics of the assistive flexible suit by pre-tensioning it. The motor may be held in a middle position so that both body parts connected to the two force transmission elements are kept in tension.

In one embodiment, the same motor may actuator two different joints based on the motor being connected to a pulley that is connected to two force transmission elements. The same pulley radius can be used preferentially if the joints controlled require the same speed and torque; for example, in the case of ankles. Examples of combinations of joints that can be controlled in this way with equal pulley radii include: right ankle plantar flexion and left ankle plantar flexion, right ankle plantar flexion and right ankle dorsiflexion, right hip extension and left hip extension, and right hip flexion and left hip flexion. Because these combinations are the same joint on opposite legs or both directions of a joint on the same leg, they will naturally be out of phase with each other. However, having the same joint actuated on both legs (e.g., right ankle plantar flexion and left ankle plantar flexion) prohibits the device from being used in situations in which both ankles plantarflex simultaneously, such as jumping. However, for motions such as walking or running, the two legs will naturally be out of phase.

If the joints require different speeds and/or torques, a single pulley with different-sized radii may be used to apply the different speeds and/or torques. Examples of combinations of joints that can be controlled in this way, but with different pulley radii include: right ankle plantar flexion and right hip extension, and right ankle plantar flexion and left hip flexion (opposite leg is needed so they are out of phase).

Figure 22A:
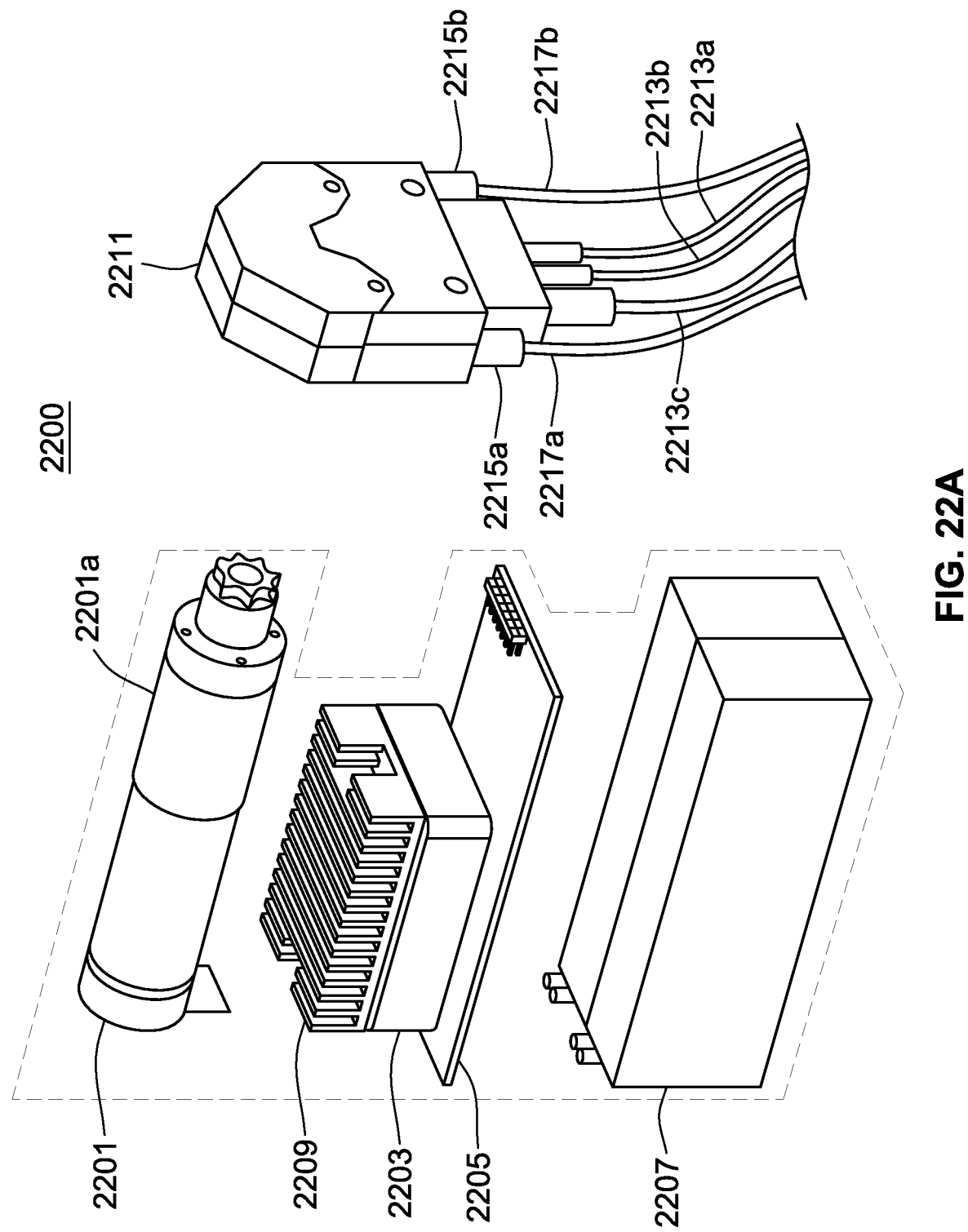
FIGS. 22A-22E show actuator systems for controlling the assistive flexible suit according to at least some aspects of the present concepts.

FIG. 22A illustrates an actuator system 2200 employing the multi-wrap pulley of FIG. 21, according to at least some aspects of the present concepts. The actuator system 2200 includes a motor 2201, a motor controller 2203, a logic controller board 2205, and one or more batteries 2207. The motor 2201 connects to a cassette 2211, which houses the multi-wrap pulley 2101 of FIG. 21, to drive at least two force transmission elements 2217a and 2217b (corresponding to force transmission elements 2103a and 2103b of FIG. 21) with the single motor 2201, as described above. The motor 2201 may connect to the multi-wrap pulley 2101 through a gearbox 2201a, such as a planetary gearbox, to modify the rotation of the motor 2201 with respect to the pulley 2101. The motor 2201 may be fastened to the motor controller 2203 and the logic controller board 2205 with a heat sink 2209 there between to regulate the temperature of one or more of the motor 2201 and the motor controller 2203. The one or more batteries 2207 attach to the bottom of the logic controller board 2205. The one or more batteries 2207 may be secured using one or more latches (not shown), which allow quick battery changes.

The motor controller 2203 commutates the motor 2201 and uses the sensors throughout the assistive flexible suit 100, such as load cells, footswitches, gyroscopes, and soft sensors to run the control algorithms that direct the motion of the motor 2201 based on the sensors and other inputs (e.g., medical provider-in-the-loop and/or wearer inputs). The motor controller 2203 can communicate with the motor 2201 and/or the logic controller board 2205 using open protocols, such as the CANOpen protocol, which can be implemented on high speed connections, such as a high speed CAN bus connection, between the various devices. The logic controller board 2205 may also communicate with a terminal, such as at the offboard control system 100, over a USB serial connection for data logging, synchronization, and programming. Alternatively, or in addition, the logic controller board 2205 may communicate with the terminal over a wireless connection, such as Wi-Fi, Bluetooth, a near field connection (NFC), etc. Further, the logic controller board 2205 may include storage space (e.g., 512 kb) to store one or more programs to execute the one or more control algorithms. The actuator system 2200 may include additional internal sensors to measure conditions of the actuator system 2200, such as temperature of the motor 2201 and voltage of the batteries 2207, and check for faults.

As illustrated, the motor 2201, the motor controller 2203, the logic controller board 2205, and the one or more batteries 2207 may be stacked-up lengthwise defining the main dimensions of the actuator system 2200 to reduce the space required.

As described above, the cassette 2211 incorporates the multi-wrap pulley 2101 of FIG. 21. The cassette 2211 may include one or more latches (not shown) so that the cassette 2211 can easily be attached to and detached from a housing (not shown) enclosing the motor 2201. The latches may be shaped in a way that, for example, pushes them down to disengage and eject the cassette 2211 from the motor 2201 immediately. Thus, the cassette/latches configuration allows for the cassette 2211 to be quickly and easily removed from the motor 2201.

The cassette 2211 further includes one or more inputs, such as inputs 2213a, 2213b, and 2213c, for connecting to and receiving measurements from one or more sensors. For example, the inputs 2213a and 2213b may be for inputs from gyroscopes located at the individual's ankles. Input 2213c may be for an input from a force sensor located at the connection point between a force transmission element and the assistive flexible suit.

The cassette 2211 may further include sleeve attachments 2215a and 2215b that guide force transmission elements 2217a and 2217b into the grooves of the multi-wrap pulley. The sleeve attachments 2215a and 2215b allow for the force transmission elements 2217a and 2217b to be changed quickly and easily. In the case of Bowden cables as the force transmission elements 2217a and 2217b, both the wires and the sheaths can be changed quickly. Thus, the sleeve attachments 2215a and 2215b allow for replacement of the force transmission elements 2217a and 2217b without disassembling the cassette 2211.

Although illustrated and described as a single cassette 2211 with a multi-wrap pulley 2101, in one embodiment, a cassette may include a single pulley with a single force transmission element. The single cassette may engage with the motor 2201 of the actuator system 2200 with an engagement member on one side of the cassette. The opposite side of the cassette may include an additional engagement member. This additional engagement member may engage with an engagement member of a similarly configured cassette.

According to this configuration, two or more cassettes may be connected to the motor 2201 in series to be able to control two or more degrees of freedom with a single motor (e.g., motor 2201). Further, each separate cassette may have a separate pulley that has the same or different radius of another cassette connected in series. As discussed herein, different pulleys with different radii may be used in combination to control multiple different body parts (e.g., hip and ankle) of an individual with a single motor. By including different pulleys with different radii in different cassettes, the system allows for a greater and more dynamic flexibility in the joints and/or body parts in which the actuator system 2200 provides assistance.

By way of example, the motor 2201 may be a Maxon Motor EC-4pole brushless DC motor. The motor controller 2203 may be a Copley Controls Accelnet Plus 1-Axis Module motor controller. The logic controller board 2205 may be an Atmel AT91SAM3X8E microcontroller. The batteries 2207 may be one or more rechargeable Li-Po batteries. Although not shown (for illustrative convenience), the actuator system 2200 may include an interface, such as an RS-232 serial connection and/or a RJ-45 jack, to connect to the offboard control system 200. Such a connection may allow, for example, a medical provider-in-the-loop to adjust one or more control profiles of the actuator system 2200 to modify assistance provided by the assistive flexible suit 100. According to the listed exemplary components, an exemplary actuator system can provide high power actuation (e.g., 300 watts (W)) and low power control/processing electronics (e.g., less than 1 W) for high performance with a long battery life.

In one embodiment, the electrical subsystems within the actuator system 2200 are isolated from each other. For example, the subsystems within the actuator system 2200 are galvanically isolated to prevent ground loops, which can waste energy, produce electrical interference, and damage components. By way of example, the logic controller board 2205 is isolated from the motor 2201, the motor controller 2203, and the one or more batteries 2207. Further, all connections between multiple actuator systems 2200 within the same assistive flexible suit 100 may also be isolated. The isolation between multiple actuator systems 2200, and between subsystems within a single actuator system 2200, helps reduce noise in the fine signals from the sensors (such as load cells) and protects the logic portions from high currents being drawn from the batteries and pushed back into the batteries as the motor 2201 accelerates and decelerates.

Figure 22B:
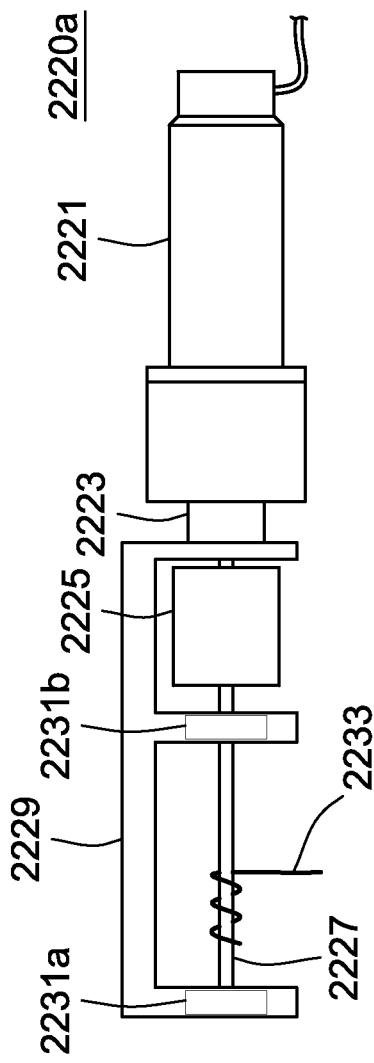
Figure 22C:
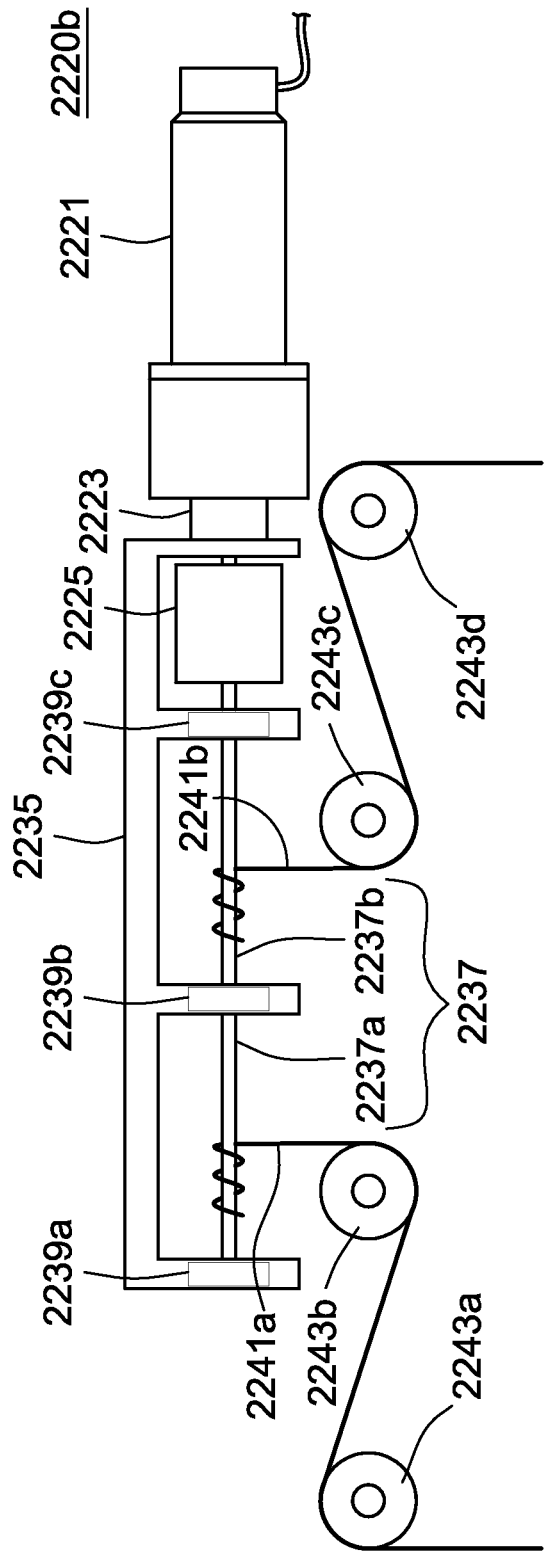

FIGS. 22B and 22C illustrate alternatives actuator systems to the actuator system 2200 of FIG. 22A, according to at least some aspects of the present concepts. Adverting to FIG. 22B, an alternative actuator system may be a spooled string actuator 2220a. The spooled string actuator 2220a includes a motor 2221. The motor employed within the spooled string actuator 2220a may be the same motor discussed above with respect to the actuator system 2200 and multi-wrap pulley 2101. The motor 2221 connects to a gearbox 2223, which connects to a shaft 2227 through a shaft coupler 2225. The shaft 2227 is supported by a frame 2229, with bearings 2231a and 2231b within the frame 2229, to allow the shaft 2227 to rotate freely while engaged to the frame 2239. A force transmission element 2233 may be wrapped around the shaft 2227 at one end, and connected to an anchor element (not shown) at the other end. In one embodiment, the force transmission element 2233 element may be a string or cable, such as Spectra® filament line, that can wrap around the shaft 2227. The diameter of the shaft 2227 may be, for example, 4 to 5 millimeters (mm) such that the flexibility of the force transmission element 2233 should be sufficient to wrap around the shaft 2227. The above-described spooled string actuator 2220a may be used as alternative or addition to (such as in a distributed configuration) the actuator system 2200 described above. In one embodiment with respect to the spooled string actuator 2220*a*, the current of the motor of the spooled string actuator 2220*a* may be monitored to estimate the force that the spooled string actuator 2220*a* delivers to the individual.

FIG. 22C illustrates a modified alternative actuator system from the actuator system 2200, according to at least some aspects of the present concepts. Similar to the spooled string actuator 2220*a*, the modified alternative actuator system 2220*b* may be a spooled string actuator, but with an extended shaft. That is, the extended spooled string actuator 2220*b* includes a motor 2221 connected to a gearbox 2223, which is connects to a shaft 2237 through a shaft coupler 2225. The motor 2221, the gearbox 2223, and the shaft coupler 2225 may be the same as those described above with respect to FIG. 22C.

The shaft 2237 is supported by a frame 2235, with bearings 2239*a*, 2239*b*, and 2239*c* within the frame 2235, to allow the shaft 2237 to rotate freely while engaged to the frame 2235 The shaft 2237 may include section 2237*a* and 2237*b*, with bearing 2239*b* separating the two sections 2237*a* and 2237*b*. The two sections 2237*a* and 2237*b* allow for two separate force transmission elements 2241*a* and 2241*b* to connect to the shaft 2237 without interfering with each other. Like the force transmission element 2233 described above, the force transmission elements 2237*a* and 2237*b* may wrap around the shaft 2237 at one end, and connect to anchor elements (not shown) at the other end. Further, the force transmission elements 2241*a* and 2241*b* may be a string or cable, such as Spectra® filament line, that can wrap around the shaft 2237. The diameter of the shaft 2237 may be, for example, 4 to 5 mm such that the flexibility of the force transmission elements 2241*a* and 2241*b* should be sufficient to wrap around the shaft 2237.

Similar to the multi-wrap pulley 2101 described above, the two sections of the shaft 2237 allow for a single motor and, therefore, single actuator system to actuate two different joints and/or body parts. Further, the two sections 2237*a* and 2237*b* may have the same or different diameters. Having the same diameter allows the two sections 2237*a* and 2237*b* to actuate the same body part type on different limbs, such as the right and left ankle. Having different diameters allows the two sections 2237*a* and 2237*b* to actuate different body part types that may require different speeds and/or torques, such as a hip and an ankle on the same leg.

According to one embodiment, the modified alternative actuator system 2220*b* may include the force transmission elements 2241*a* and 2241*b* routed through one or more pulleys 22431*a*-2243*d*. The one or more pulleys 2243*a*-2243*d* may be used to alter the ratios within the system to apply more or less force and/or torque over greater or less ranges of motion. Although the same number of pulleys is illustrated with respect to each force transmission element 2241*a* and 2241*b* and section 2237*a* and 2237*d* of the shaft 2237, the number of pulleys for each section/force transmission element may differ.

Figure 22D:
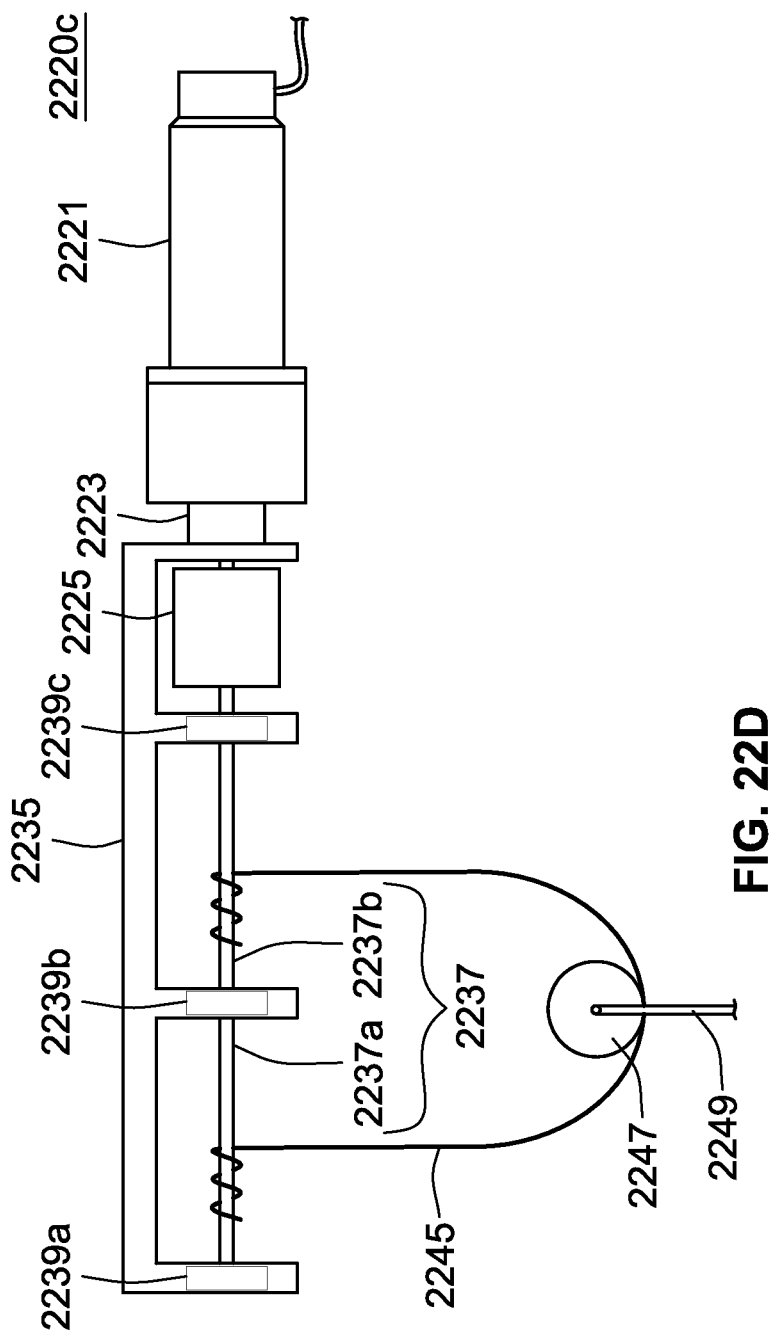

FIG. 22D illustrates another modified alternative actuator system according to a windlass actuator, according to at least some aspects of the present concepts. The windlass actuator 2220*c* includes the same arrangement of the motor 2221, gearbox 2223, shaft coupler 2225, frame 2235, shaft 2237 (with shaft sections 2237*a* and 2237*b*), and bearings 2239*a*, 2239*b*, and 2239*c* as FIG. 22C. However, the windlass actuator 2220*c* includes single force transmission element 2245. One end of the force transmission element 2245 wraps around, for example, section 2237*a* of the shaft 2237, and the other end of the force transmission element 2245 wraps around section 2237*b* of the shaft 2237. The force transmission element 2245 is routed through a pulley 2247, which is connected to a force transmission element 2259. Although the single pulley 2247 is shown, the force transmission element may be wrapped around more than one pulley. The force transmission element 2245 may connect to an anchor element of the assistive flexible suit (not shown). The force transmission element 2245 connects to the shaft 2237 such that rotation of the shaft 2237 in one direction retracts the force transmission element 2245 from one section 2237*a* or 2237*b* and extends the force transmission element 2245 from the other section 2237*b* or 2237*a*. As above, the two sections 2237*a* and 2237*b* may have the same or different diameters. Having different diameters allows for possibilities of the gear ratios resulting from the two sections 2237*a* and 2237*b* to be effectively limitless. Further, rotation of the shaft 2237 with two sections 2237*a* and 2237*b* of different diameters raises and lowers the pulley 2247, which transmits a force through the force transmission element 2249.

The actuator systems illustrated and described with respect to FIGS. 22A-22D (in addition to the multi joint actuation platform 2260 described below) may include a quick-release mechanism by which the individual wearing the assistive flexible suit 100 or the medical provider-in-the-loop can detach the powered-assistance from one or more actuators from the suit. Further, the actuator systems illustrated and described with respect to FIGS. 22A-22D (in addition to the multi joint actuation platform 2260 described below) may include safety features (e.g., mechanical, electrical, etc.) that limit the maximum travel of the actuators to prevent the actuators from applying forces that cause joints and/or body parts of the individual to exceed safe ranges of motion, positions, and/or forces.

In one embodiment, the assistive flexible suit 100 may include one or more switching mechanisms. A switching mechanism allows for the connection of a single motor, particularly a single force transmission element from a single motor, to connect to two or more force transmission elements extending from the switching mechanism. By way of example, an actuator connects to the switching mechanism through a single force transmission element. Such a force transmission element may be short in that it only bridges a short distance between the actuator and the switching mechanism. Three force transmission elements depart from the switching mechanism to assist, for example, the ankle (such as both plantar flexion and dorsiflexion) and the hip muscle groups (such as hip flexion and hip extension).

The switching mechanism exploits joint synergies, such as hip flexion and ankle plantar flexion, which are active simultaneously, and anti-phase joint synergies, which are active asynchronously, such as hip flexion and hip extension, to allow the use of a single motor to drive multiple actuations. The switching mechanism includes an actuator input that accepts a force transmission element from an actuator. The switching mechanism includes two more or more outputs that accept two or more force transmission elements connected to two or more anchor elements located about the individual wearing the assistive flexible suit 100. Within the switching mechanism is a device, such as a clutch, that selectively engages one or more of the two or more output force transmission elements to connect the selected output force transmission elements to the input force transmission element.

Switching by the switching mechanism can be automatic, such as based on one or more signals from a motor controller and/or the offboard control system 200, or may be manual based on a manual selection by the individual wearing the assistive flexible suit 100 or a medical provider-in-the-loop monitoring the individual. In one embodiment, the switching mechanism can include a quick-release mechanism by which the individual wearing the assistive flexible suit 100 or the medical provider can easily detach the powered-assistance from one or more actuators from the suit and continue walking with purely passive assistance. Further, in one embodiment, the switching mechanism, or an actuator, directly, can include one or more elements for quickly disengaging force transmission elements from the assistive flexible suit 100 and/or the actuators. Such an element may be a blade that cuts and/or destroys the force transmission elements to stop forces from being transmitted, such as in the case of an emergency.

The actuation systems illustrated in FIGS. 22A-22D may be used in combination with the assistive flexible suit 100 when, for example, an individual wearing the assistive flexible suit is outside of a controlled environment, such as outside of a medical provider environment. The actuation systems illustrated in FIGS. 22A-22D allow an individual to wear the assistive flexible suit 100 to further improve their movements. The actuation systems include the capability to connect to a control terminal, such as in the offboard control system 200, by a wired and/or wireless connection. Thus, a medical provider can modify the actuation systems of FIGS. 22A-22D when an individual wearing the assistive flexible suit 100 is local or remote to the medical provider. In certain situations, actuation may be provided by a system within the offboard control system 200 directly. Such situations may occur when the individual wearing the assistive flexible suit 100 is local to the medical provider.

Figure 22E:
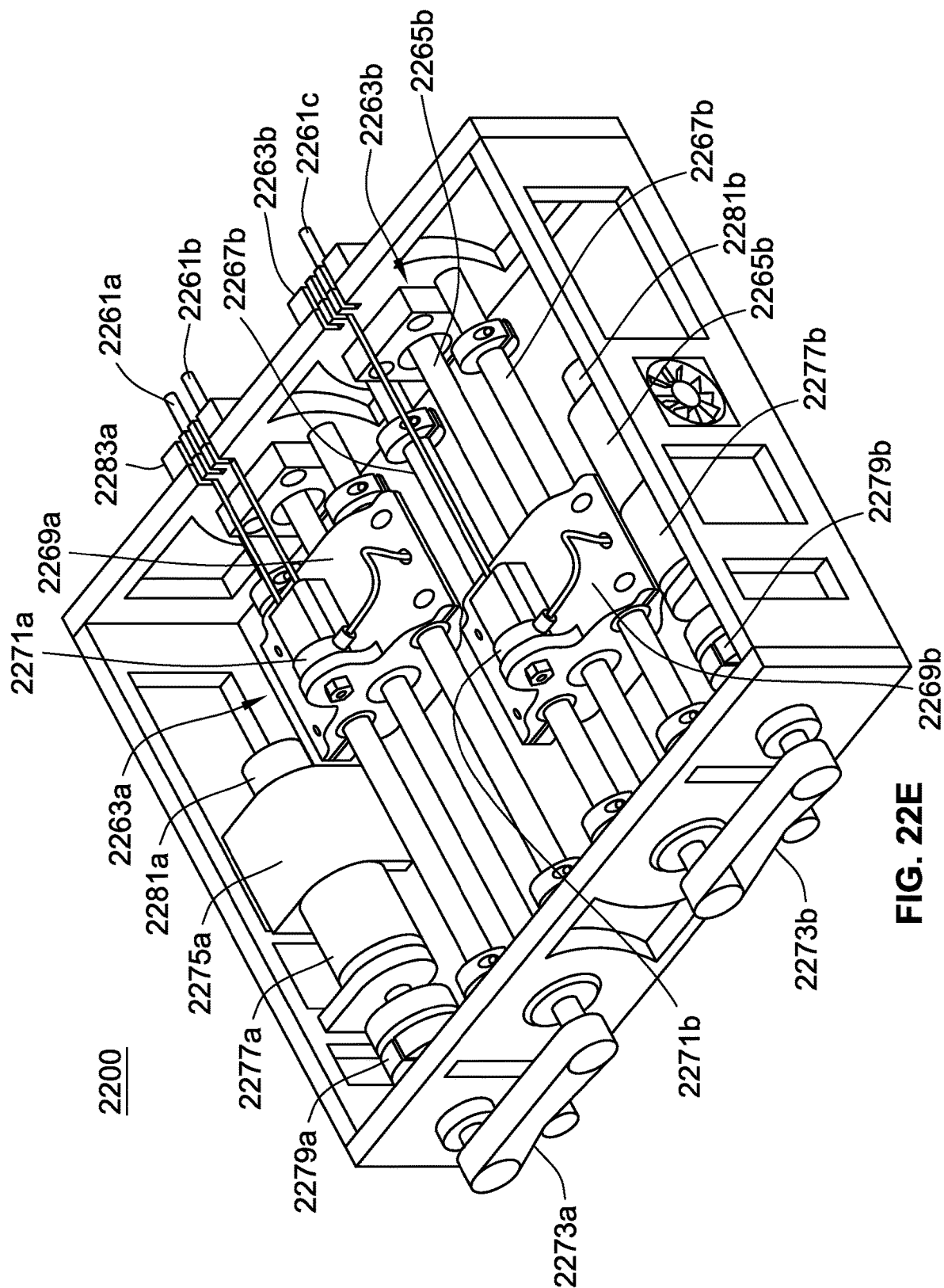

FIG. 22E illustrates a multi joint actuation platform 2260, according to at least some aspects of the present concepts. The multi joint actuation platform 2260 may replace the actuation system described above with respect to FIGS. 22A-22D, such as when the individual is local to a medical provider-in-the-loop. The multi joint actuation platform 2260 can replicate the torques and powers at various body parts of the individual wearing the assistive flexible suit 100 during various movements. The multi joint actuation platform 2260 can be one of multiple multi joint actuation platforms within the offboard control system 200. For example, the multi joint actuation platform 2260 can replicate the torques and powers for the hip joints, the knee joints, and the ankle joints of the individual wearing the assistive flexible suit 100 while walking. The multi joint actuation platform 2260 provides for large ranges of motion and high forces depending on the needs of the individual wearing the assistive flexible suit 100.

As illustrated, the multi joint actuation platform 2260 connects to force transmission elements 2261a through 2261c that connect to the assistive flexible suit 100. By way of example, the force transmission elements 2261a and 2261c may be Bowden cables; however, other force transmission elements may be used that transmit forces mechanically, pneumatically, hydraulically, magnetically, electrically, electro-magnetically, electro-mechanically, etcetera. As illustrated in FIG. 22E, the multi joint actuation platform 2260 is connected to Bowden cables 2261a-2261c.

The Bowden cables 2261a-2261c are connected to drive shafts 2263a and 2263b. Each drift shaft 2263a and 2263b may be formed of ball screws 2265a and 2265b with pairs of guide rails 2267a and 2267b on either side of the ball screws 2265a and 2265b. Below the ball screws 2265a and 2265b may be linear potentiometers (e.g., manufactured by P3 America, Inc.) to measure the displacements of the force transmission elements 2261a through 2261c. Carriages 2269a and 2269b may run on the guide rails 2267a and 2267b and actuate according to the rotation of the ball screws 2265a and 2265b. The carriages 2269a and 2269b may include load cells 2271a and 2271b at the connection points between the carriages 2269a and 2269b and the Bowden cables 2261a and 2261b. The load cells 2271a and 2271b measure the loads applied to the Bowden cables 2261a and 2261b by operation of the multi joint actuation platform 2260. The load cells 2271a and 2271b may be in combination with other load cells positioned throughout the assistive flexible 100 suit to provide an overall load analysis provided by the assistive flexible suit 100.

As an example, the load cells 2271a and 2271b may be a Futek load cell with a measuring range of ±2224 N (2N resolution), for example, and can measure the tension force in the Bowden cables 2261a through 2261c. At the distal ends of the Bowden cables 2261a and 2261b (not shown) may be additional Futek load cells with a measuring range of ±1112 N (1N resolution), for example, to measure the actual force applied to the assistive flexible suit 100 and the individual.

The ball screws 2265a and 2265b connect to timing belts 2273a and 2273b. The timing belts 2273a and 2273b connect to motors 2275a and 2275b. Operation of the motors 2275a and 2275b rotate the timing belts 2273a and 2273b, which drive the ball screws 2265a and 2265b and move the carriages 2269a and 2269b connected to the Bowden cables 2261a and 2261b. Depending on the application of the multi joint actuation platform 2260, the timing belts 2273a and 2273b are connected to the motors 2275a and 2275b through gear boxes 2277a and 2277b and spring disc couplings 2279a and 2279b. The gear boxes 2277a and 2277b and the spring disc couplings 2279a and 2279b allow for adjustments in the ranges of motion and the torques provided by the motors 2275a and 2275b. By way of example, the travel length of the carriages 2269a and 2269b may be up to 270 mm. This range of motion loosens the requirements on the length of the Bowden cables 2261a and 2261b and positions of the anchor elements with respect to the assistive flexible suit 100. The carriages 2269a and 2269b may connect, electronically, to the motors 2275a and 2275b by E-chain connections (not shown).

As illustrated, a single carriage (e.g., 2269b) connects to a single force transmission element (e.g., Bowden cable 2261c). Alternatively, or in addition, within a single multi joint actuation platform 2260, a single carriage (e.g., 2269a) connects to multiple force transmission elements (e.g., Bowden cables 2261a and 2261b). Connection of multiple force transmission elements to a single carriage provides for a single motor to control multiple degrees of freedom of multiple joints of the individual wearing the assistive flexible suit 100 within the same phase of, for example, the individual's gait. Including multiple motors 2275a and 2275b within the same multi joint actuation platform 2260 provides for control of multiple different degrees of freedom with respect to multiple different body parts of the individual. For example, the motor 2275a may control ankle plantar flexion and hip extension using the same carriage 2271a connected to two different Bowden cables 2261 and 2261b, and the motor 2275b may control ankle dorsiflexion.

Alternatively, a single motor within the multi joint actuation platform 2260 may control multiple carriages. For example, the motor 2275a may connect to both carriage 2269a and 2269b by modifying the timing belt 2273a and timing belt 2273b to be a single timing belt that drives both ball screws 2265a and 2265b of both drive shafts 2263a and 2263b. Like the pulley embodiment described above, this modification to the timing belts 2273a and 2273b may allow for out of phase actuation of body parts of the individual if, for example, the carriages 2269a and 2269b are connected to the drive shafts 2263a and 2263b out of phase.

Connected to the motors 2275a and 2275b may be encoders 2281a and 2281b. The encoders 2281a and 2281b determine the position of the carriages 2271a and 2271b. A digital encoder may be used to reduce effects from radio frequency (RF) interference from controllers of the motors 2275a and 2275b. As an exemplary embodiment, the encoders 2281a and 2281b may be a Maxon 4line encoder (500 counts/rev) for measuring the speeds of the motors 2275a and 2275b. In one embodiment, the multi joint actuation platform 2260 can include a data acquisition element that accepts sensor signals and outputs reference voltages to the actuator. Current and voltage sensors built in the multi joint actuation platform 2260 enable the current and voltage sent to the motors 2275a and 2275b to be measured. These sensors allow, for example, measuring the amount of energy consumed by the system, the efficiency of the mechanical transmission, and the actual power delivered to the human body and to the assistive flexible suit 100.

As described above, the multi joint actuation platform 2260 can be within the offboard control system 200. The offboard control system 200 may be a mobile, 4-wheeled cart with 6 (or more) linearly actuated degrees of freedom to assist over ground movement of a person in combination with the assistive flexible suit 100. However, other arrangements of the offboard control system 200 exist without deviating from the spirit and scope of the disclosure, such as suspending the offboard control system 200 from a hanging rail to facilitate over-ground walking in a laboratory. As described above, the offboard control system 200, including one or more multi joint actuation platforms 2260, can assist healthy people, such as by training healthy people how to walk more efficiently (e.g., removing inefficient walking habits, such as removing pigeon-toed walking), and can assist the rehabilitation of people with impairments, such as gait impairments. The offboard control system 200 within the 4-wheeled cart may be pushed by a medical provider (or other person) to follow an individual wearing the assistive flexible suit 100 while assisting the individual walking over ground or on a treadmill.

In one embodiment, the cart housing the overboard control system 200 may include a structure, such as a gantry-type device, that can provide full or partial body weight support for the individual. By way of example, the cart can include a frame with a harness that interfaces to the individual to support the individual's body weight. The cart may include passive and/or motorized wheels to assist with, for example, the individual's movement when the individual cannot, or cannot entirely, support his or her own body weight or the additional weight of the assistive flexible suit 100 and any actuators worn on the assistive flexible suit 100.

The offboard control system 200 may include, in one embodiment, an interface to display real-time gait parameters as measured by the sensors on the assistive flexible suit 100, as well as for controlling the profile and timing of assistance delivered by the assistive flexible suit in real time. The interface allows the offboard control system 200 to be used as a tool in physical therapy, to allow a medical provider to adjust the assistive flexible suit 100 in accordance with the specific needs to improve movement of an individual. The interface allows a medical provider to adjust the assistive flexible suit 100 as the individual progresses throughout interaction with the assistive flexible suit 100, to ensure that the assistive flexible suit 100 provides an amount and timing of assistance throughout the individual's treatment to improve the individual's movement. The interface allows a medical provider to control the forces and timing of dorsiflexion and plantar flexion assistance as provided by the assistive flexible suit 100. By way of example, the interface allows a medical provider to enter inputs for controlling the maximum force to apply on force transmission elements with respect to dorsiflexion and plantar flexion about ankles of an individual. The interface may further allow a technician to enter inputs for controlling the beginning and ending time points for the ramp-up and ramp-down for each force based on a calculated gait cycle. When a new force profile is generated, the interface may present the new force profile superimposed on top of a current or previous force profile to emphasize any differences between the new and previous and/or current profiles. In one embodiment, the new profile can be confirmed through the interface, by the medical provider, before the offboard control system applies the new profile to the suit.

In one embodiment, safety measures can be built into the interface to prevent accidental inputs that exceed preset allowable force or position limits. For example, impedance, force, and position limits can be set and/or modified within the interface.

In one embodiment, the interface may include a commenting pane that allows the researcher to enter comments that are time-synced to the changes in force profile. The comments may include information such as why a particular change was made or what was working successfully.

The interface may present and/or output one or more of parameters with respect to movement of an individual, including stance symmetry (e.g., amount of time single-leg stance on each leg), step length, speed/cadence, knee extension, plantar flexion force, degrees of dorsiflexion, and ground clearance. These outputs may be displayed quantitatively or graphically. Further, medical providers can select the parameters they wish to view in real time.

The offboard control system 200, the assistive flexible suit 100, and/or any subcomponent thereof (e.g., an actuator, sensor, etc.) can include one or more storage devices that can store data measured and collected, including all of the data that is collected by the sensors throughout the assistive flexible suit 100. The ability to save and later present data regarding movement of an individual allows the medical provider-in-the-loop and/or the individual to view data accrued between treatments. Such data collected and saved may include long term trends regarding: walking speed, distance walked per day, level of assistance supplied by the suit, and hours of suit use per day. Further, the storage devices may log the forces and motion profiles experienced by the individual wearing the assistive flexible suit 100 (or data or metrics that are extracted from these (e.g. cadence)). Logging such information allows a medical provider-in-the-loop to monitor the progress and mobility of the individual overtime (e.g., hours, days, weeks, months, years, etc.). In one embodiment, and in compliance with various rules and regulations concerning the sharing of such personal information regarding the individual's medical history, the logged material can be shared on social networks or allow a therapist to remotely monitor the individual's progress.

Based on the offboard system 200 allowing a medical provider to be within the loop in monitoring and modifying movement of an individual wearing the assistive flexible suit 100, the offboard system 200 can be used to treat various conditions, such as neuromuscular conditions, that lead to gait impairments and limited mobility. The offboard control system 200 can also be applied to patients with limited mobility caused by age or non-neurological conditions. Exemplary conditions that can be treated using the offboard system include: hemiparetic stroke gait impairments, which may include any or all of the following gait abnormalities: hip circumduction (hip hike), weakened dorsiflexion (drop foot), trunk extension (lurching), ankle inversion, reduced ankle range of motion, reduced knee flexion, flat footed landing at heel strike, reduced plantar flexion during push-off, reduced time spent in single leg stance on affected side.

By using the offboard control system 200 to control the multi joint actuation platform 2260 and/or one or more actuators worn on the assistive flexible suit 100 (e.g., actuation systems of FIGS. 22A-22D), in combination with the assistive flexible suit 100, a medical provider can work with an individual to obtain the following benefits associated with movement: improved temporal symmetry in hemiparetic gait, improved spatial symmetry in hemiparetic gait, increased ankle range of motion of an affected side during the gait cycle in hemiparetic gait, increased ground clearance during swing phase in patients with weakened dorsiflexion, increased plantar flexion force during push-off in patients with weakened plantar flexion, increased self-selected walking speed in patients with reduced mobility, reduced compensatory walking movements in the non-sagittal plane (such as hip hike), improved walking confidence, increased endurance (e.g., able to walk longer distances), increased self-selected walking speed, and long term promotion of proper gait patterns may result in a reduced need for assistance from the suit, or may eliminate the need for the assistive flexible suit 100 altogether. Sensor data from the exosuit can be used to quantify an individual's performance for any measure, such as one or more of above-described measures.

In one embodiment, the offboard control system 200 may communicate with one or more other functional elements within the assistive flexible suit. One such functional element is a haptic feedback unit. As discussed above, a haptic feedback unit includes one or more sensors that function to provide information to a wearer tactically. Such information may inform the wearer to properly align or tension the assistive flexible suit 100 when donning the assistive flexible suit 100. The information may also include notification of events such as low-battery, irregular variations in gait when fatigued, etc. Accordingly, such information can be provided based on above threshold stimulation to provide feedback and silent notification of events.

Figure 36:
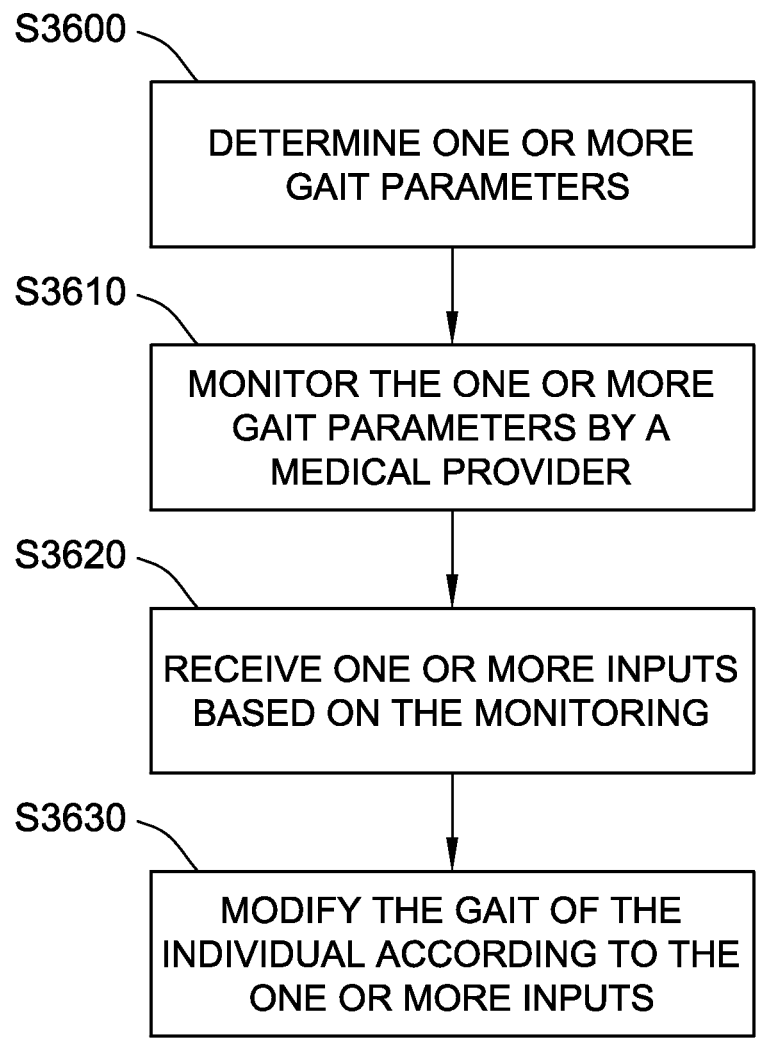
FIG. 36 shows acts in a method according to at least some aspects of the present concepts.

FIG. 36 shows acts in a method according to at least some aspects of the present concepts. The acts of the process shown with respect to FIG. 36 may be practiced in accord with the above disclosure to achieve the following steps. The method of FIG. 36 comprises an act of determining one or more gait parameters of the individual based on one or more sensors connected to the individual through and assistive flexible suit (such as assistive flexible suit 100) (act S3600). The one or more sensors output one or more sensor readings. The sensor readings can be analyzed to determine the gait parameters of the wearer's movement. The one or more gait parameters may relate to a single gait event within a gait cycle of the individual, relate to two gait events within a gait cycle of the individual, or may relate to more than two gait events within a gait cycle of the individual. The gait events may relate to one or more limbs and/or body parts of the individual. In one embodiment, the determining may occur while the individual wearing the assistive flexible suit 100 walks within a controlled environment, such as in an environment of the medical provider across the floor or on a treadmill. Alternately, the determining may occur while the individual wearing the assistive flexible suit 100 walks outside of a controlled environment, such as over ground in an outside environment. Whether inside or outside of a controlled environment, the determining of the one or more gait parameters may occur while the individual and the control unit move forward.

At act S3610, a medical provider monitors the one or more gait parameters through a control unit. The control unit may be the offboard control system 200, which may include a display and/or another presentation device. The offboard control system 200 outputs and/or presents one or more of the gait parameters for the medical provider to view. Based on the output and/or presentation, the medical provider can evaluate the one or more gait parameters, which characterize the individual's movement.

At act S3620, the medical provider inputs, through the control unit (such as the offboard control system 200), one or more inputs based on the medical provider monitoring the one or more gait parameters. The inputs may modify any control parameter of the control unit and/or the assistive flexible suit. Thus, the control parameters may relate to one or more control profiles of one or more actuators (e.g., multi joint actuation platform 2260 and/or actuator systems 2200 and 2220a-2220c) within and/or connected to the control unit and the assistive flexible suit.

At act 53630, the control unit and/or the assistive flexible suit modifies the gait of the individual based on the one or more inputs by the medical provider. The modification can be any change as described above, such as modifying one or more motor control profiles of one or more motors. By way of example, the control unit may control one or more actuators (e.g., multi joint actuation platform 2260 and/or actuator systems 2200 and 2220a-2220c) that are in mechanical communication with the individual through the assistive flexible suit. The modification of the control of the one or more actuators may modify the gait of the individual with respect to a limb of the individual, and the monitored gait parameters may be of the limb. Alternately, the modification of the control of the one or more actuators may modify the gait of the individual with respect to a limb of the individual, and the monitored gait parameters may be of a contralateral limb of the modified limb. Further, as described above, the controlling may be control of two limbs of the individual by a single actuator of the one or more actuators.

Based on the foregoing process described with respect to FIG. 36, a medical provider can monitor and adjust the movement of an individual wearing an assistive flexible suit assisted by a control unit and/or one or more actuators to improve the individual's movement.

Figure 23:
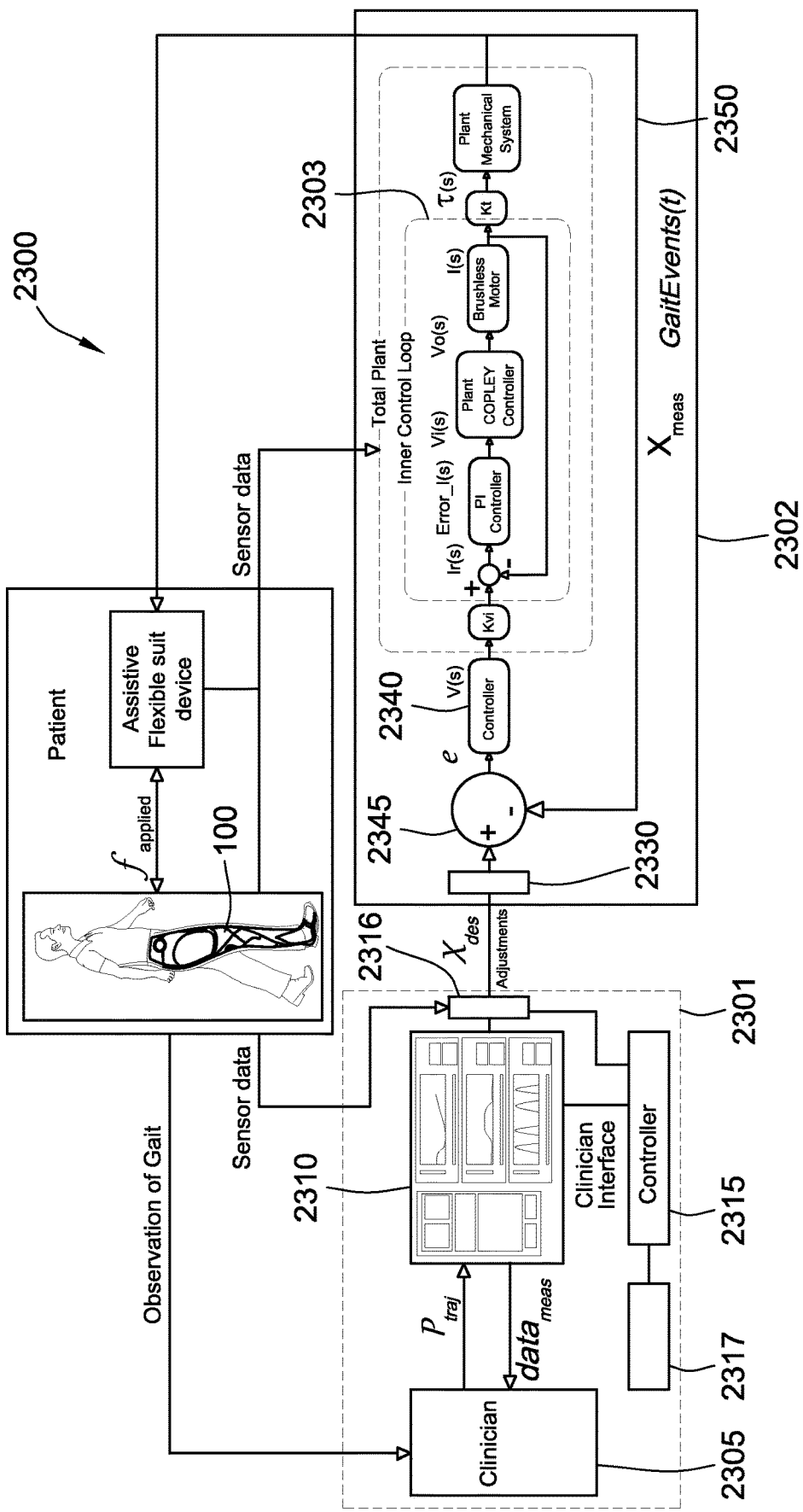
FIG. 23 shows an example of a hybrid control system according to at least some aspects of the present concepts.

FIG. 23 shows an example of a hybrid control system 2300 according to at least some aspects of the present concepts. In general, the hybrid control system 2300 adjusts operational characteristics of an assistive flexible suit 100 actuation system 105 to thereby alter one or more characteristics (e.g., magnitude, timing, duration, rate of change, time rate of change, profile, etc.) of forces output by the actuation system and, correspondingly, the moments or torques delivered by the assistive flexible suit to the wearer. The control strategy disclosed in FIG. 23 works on any gait pattern and is not dependent on the strong regularities of physiological gait. Impaired gait is less regular than physiological gait; every patient has a different gait pattern depending on the malady or condition, advancement of the rehabilitation therapy, and types of compensatory movement developed by the patient. Despite this significant variability, the control strategies disclosed herein work on any gait pattern.

The hybrid control system 2300 of FIG. 23 shows, generally, a first control loop 2301 and a second control loop 2302. In the first control loop 2301, a medical provider (e.g., clinician, doctor, etc.) 2305 makes observations of the patient's gait. These observations may comprise direct visual observations of the patient as the patient walks or ambulates (e.g., on a floor, across a surface, on a treadmill, etc.) and/or observations of patient gait data on a user interface, such as, but not limited to, a controller-based 2315 graphical user interface ("GUI") 2310 of a tablet device, laptop computer, smart phone, smart watch, Google Glass, computer terminal, computer, or the like. The first control loop 2301 controller 2315 is further operatively associated with a communication device 2316 and a physical computer-readable storage device 2317 bearing an instruction set configured, upon execution by the controller, to cause the controller to receive, via the communication device, an output of the assistive flexible suit sensor(s) 120 and/or an output of sensor(s) external to the assistive flexible suit sensor(s) (e.g., area sensors, optical sensors, etc.) to provide information relating to at least one body segment (e.g., foot, cnemis, thigh, etc.) relating to a position of or a movement of the at least one joint (e.g., ankle joint, knee joint, hip joint, etc.). The controller may comprise, by way of example, a central processing unit (CPU) connected to a main memory operatively associated with one or more physical computer-readable storage device 2317. The controller may include any suitable processor(s), such as those made by Intel and AMD. Communication device 2316 is configured to communicate with the second control loop 2302, the assistive flexible suit 100 system, and/or a bus, another computer, processor(s), device(s), service(s), or network.

Although FIG. 23 depicts an embodiment wherein a medical provider 2305 makes observations of the patient's gait, either directly (e.g., visual observation of patient, etc.) or remote (e.g., observation of data profiles, kinematic plots, etc.), the first control loop 2301 may omit the "clinician-in-the-loop" and instead utilize an algorithm or set of algorithms to adapt trajectories based on analysis of the kinematic data from the sensor(s) 120. By way of example, the first control loop 2301 could determine a difference between a current kinematic profile and a desired kinematic profile and provide an immediate correction to an acute condition and/or periodic corrections (e.g., daily, weekly, etc.) in accord with a patient treatment schedule.

The sensor(s) 120 comprise, by way of example and without limitation, one or more sensors comprising one or more foot switches, pressure insoles, inertial measurement units (IMU), accelerometers, gyroscopes, load cells, cable tension force, strain sensors, hyperelastic strain sensors, voltage sensor, actuator voltage sensor, actuator current sensor, physiological sensors (e.g., emg, muscle tone, muscle stiffness, muscle actuation, etc.), etcetera. Exemplary sensors may include, but are not limited to those disclosed in WO 2014/109799 A1, WO 2013/044226 A2, WO 2013/033669 A2, WO 2012/103073 A2, WO 2012/050938 A2, WO 2011/008934 A2; U.S. Pat. No. 8,316,719 B2, and PCT Application No. PCT/US2014/040340, each of which is hereby incorporated herein by reference in its entirety. In accord with at least some aspects of the present concepts, an IMU may comprise a CHRobotics UM7-LT Orientation Sensor, manufactured by CHRobotics of Payson, Utah. In accord with at least some aspects of the present concepts, a gyroscope may comprise an ST Microelectronics LPY503AL manufactured by ST Microelectronics of Geneva, CH. In accord with at least some aspects of the present concepts, a load cell may comprise a Futek LSB200 miniature s beam load cell, manufactured by Futek of Irvine, Calif.

The controller 2315 is configured to process raw sensor information and/or pre-processed sensor information (e.g., one or more higher level variables, such as an averaging of data, are performed by another controller or processor) and display on the GUI 2310 the information relating to the at least one body segment in relation to at least one gait event.

The controller 2315 is further configured to receive an input from the medical provider 2305, via the GUI 2310, comprising one or more modified parameter(s) of an actuation signal. The modified parameter(s) of an actuation signal, labeled as $X_{des}$ in FIG. 23, is output from the first control loop 2301 communication device 2316 to a communication device 2330 of the second control loop 2302. The output of the GUI 2310 is, for each degree of freedom (DOF), a trajectory (e.g., position trajectory, etc.) defined in relation to X number of gait events or gait phases. For example, the modified parameter(s) of an actuation signal ($X_{des}$) may comprise a trajectory defined in relation to a gait cycle (e.g., defined in terms of 0-100% of gait, a trajectory between the gait events of a detected heel strike and detected toe off, a trajectory between the gait events of a mid-stance and a successive mid-stance, etc.).

In at least some aspects, the user interface 2310 advantageously permits any of impedance, force, and position limits to be modified within the interface.

In some aspects, the user interface 2310 includes inputs for the maximum force that the actuation system (e.g., actuator 105) can apply across the joint(s) of the wearer (e.g., maximum forces applied to the dorsiflexion and plantar flexion cables), which can help to ensure that forces exceeding safe levels for a particular patient are not applied. As additional protection, when a new force profile is generated, it is optionally drawn superimposed on top of the current force profile to emphasize any differences between the two profiles. Protection may be further enhanced by requiring the medical provider to actively confirm the acceptability of the new profile before it can be passed onto the second control loop 2302 for application to the assistive flexible suit. Advantageously, the user interface 2310 comprises a commenting pane or record keeping function that permits, or optionally requires, the researcher to enter comments that are time-synced to the changes in force profile to explain why a particular change was made, particular expectations for the change, or to note patient progress on the current profile.

In at least some aspects of the present concepts, the first control loop 2301 need not necessarily require the user interface 2310. Specifically, the present concepts include a situation, such as a period between office visits, where a patient contacts a medical provider (e.g., via phone, email, text, etc.) to note a particular problem or change that may require a minor adjustment until such time as another office visit may be arranged. In such instances, a medical provider could input one or more minor adjustments responsive not to visually observed gait characteristics, as indicated in FIG. 23, but rather to descriptive information provided by the wearer. In such instances, the medical provider could either directly output adjustments from the first control loop 2301 or, alternatively, output an instruction to the second control loop 2302 enabling the wearer to personally make an adjustment within parameters specified by the medical provider.

The second (inner) control loop 2302 is configured to generate position, force, impedance or admittance profiles based on a predetermined timing event (i.e., any event before actuation in the specific gait cycle). By way of example, the predetermined timing event can comprise sensor data from a contralateral leg, such as the transition from a loading response to mid-stance in one leg corresponding to the transition from late stance to swing in the other leg). This approach advantageously adapts assistance to gait within the same step. As described below, the controller can be "trained" by a medical provider (e.g., a clinician) via a medical provider input device (e.g. binary and/or continuous) into which the medical provider inputs adjustments as the wearer of the assistive flexible suit walks or ambulates relative to the medical provider.

The second (inner) control loop 2302 takes the modified parameter(s) of an actuation signal ($X_{des}$)(e.g., trajectory) for the detected events and stretches the modified parameter(s) to temporally match those events. By way of example, the modified parameter(s) of an actuation signal ($X_{des}$) defined by the medical provider 2305 comprise a desired adjustment of a trajectory for plantar flexion assistance wherein the trajectory between heel strike and toe off is set to zero and the trajectory from toe off to the next heel strike is set to be 50%. However, the second control loop 2302 is detecting, via sensor(s) 120, heel strikes and toe offs in the time domain and determining that the timing between these events is X seconds (or milliseconds), where X is any number. The second control loop 2302 then takes the trajectory received from the first (outer) control loop 2301 and stretches it in the known time domain and then proceeds to the next event. Stated differently, while the modified parameter(s) of an actuation signal from the first control loop 2301 is defined in terms of gait (e.g., gait percentage, gait phase, gait events, etc.), generation of that trajectory in the assistive flexible suit 100 actuator(s) 105 requires a position or force profile in the time domain (e.g., seconds, ms, etc.). Accordingly, a transformation is performed to convert the modified parameter(s) of an actuation signal (e.g., x-axis is gait percent) into the time domain (e.g., x-axis is time) based on a determined timing of successive gait events (e.g., heel strike) by their respective sensor-based time stamps. Following integration of the modified parameter(s) of an actuation signal into the time domain prior to output to comparator (summing point) 2345, the second control loop 2302 outputs to the actuator(s) 105 a corresponding position or force trajectory. In at least some aspects of the present concepts, the second control loop 2302 comprises a processing device running MATLAB Simulink (manufactured by MathWorks of Natick, Mass.) and a NI DAQ board (National Instruments Data Acquisition Board manufactured by National Instruments of Austin, Tex.).

Returning to the first control loop 2301, the medical provider 2305 determines what type, amount and profile of assistance is desired from the assistive flexible suit 100 for the patient based, at least in part, on the medical provider's observations of the patient's gait. These observations may comprise direct visual observations of the patient as the patient walks or ambulates (e.g., on a floor, across a surface, on a treadmill, etc.) and/or observations of patient gait data on a user interface, such as, but not limited to, a graphical user interface ("GUI") of a tablet device, laptop computer, smart phone, smart watch, Google Glass, computer terminal, computer, or the like. In the latter case, the patient need not be physically present at a location of the medical provider 2305. Instead, the assistive flexible suit 100 sensor(s) 120 and communication device (e.g., wireless device, wireless sensors, wi-fi device, cellular device, etc.) transmit the gait information (e.g., gait events, etc.) to the first control loop 2301 as raw data or processed data (e.g., averaged, integrated, etc.). The medical provider 2305 performs the same analysis as before and, via input to the GUI 2310 or other user interface (e.g., keyboard, keypad, etc.), outputs (e.g., wirelessly via a communication device 2316) the modified parameter(s) of an actuation signal to the assistive flexible suit 100 second control loop 2302.

FIG. 23 shows, by way of example, one potential second control loop 2302 embodiment in accord with at least some aspects of the present concepts. The specific architecture of this second control loop (low level control) 2302 is not critical to the inventive concepts and the second control loop may comprise, for example, a cable position control, a cable force control, an impedance/admittance control, etc. The important characteristic of the second control loop 2302 is simply that it is configured to detect one or more gait events and generate trajectories (e.g., force signal, velocity signal, etc.) that are adapted responsive to the output of the first control loop 2301. As mentioned above, in at least some aspects of the present concepts, one or more processors (located locally and/or remotely to the assistive flexible suit), in accord with one or more instruction sets borne by physical memory devices (located locally and/or remotely to the assistive flexible suit), are configured to monitor a wearer's gait in an unassisted condition (e.g., via one or more sensors disposed on the assistive flexible suit or externally thereto) and then modify one or more aspects of a force trajectory output by the at least one actuator to thereby modify the assistive torque developed across the at least one axis of the at least one joint during movement of the at least one joint, the wearer's modified gait being used as a further input to the one or more processors and associated one or more instruction sets for further evaluation of the wearer's gait and further iterative modification of one or more aspects of a force trajectory output by the at least one actuator. Thus, the system (without a clinician-in-the-loop in the present example) uses one or more sensors to see how a patient walks with no assistance from the assistive flexible suit, learns what assistance is needed by the patient, determines a force or combination of forces to apply at one or more points during the gait cycle, monitors patient kinematics responsive to the applied force(s), and continues to iteratively refine the applied force(s) until a desired result is achieved. A significant feature of the assistive flexible suit is that patients can walk normally (e.g. with their normal pathological gait) and their normal pathological gait can be accurately monitored with sensors because the suit is so lightweight and flexible that it doesn't alter the patient's normal gait—a feat not able to be duplicated by conventional rigid exoskeletons.

Although FIG. 23 depicts an embodiment wherein a medical provider 2305 makes observations of the patient's gait, either directly (e.g., visual observation of patient, etc.) or remote (e.g., observation of data profiles, kinematic plots, etc.), the first control loop 2301 may omit the "clinician-in-the-loop" and instead utilize an algorithm or set of algorithms to adapt trajectories based on analysis of the kinematic data from the sensor(s) 120. By way of example, the first control loop 2301 could determine a difference between a current kinematic profile and a desired kinematic profile and provide an immediate correction to an acute condition and/or periodic corrections (e.g., daily, weekly, etc.) in accord with a patient treatment schedule.

While the aspects of the assistive flexible suit disclosed herein provide acute benefits to gait while worn, the assistive benefits are not limited to such benefits. Indeed, use of the assistive flexible suit in combination with adjuvant therapies, such as partial body weight support and functional electrical stimulation, can have a substantial impact after stroke by altering trajectories often set during the critical first weeks after stroke, potentially reducing the need for assistive devices (e.g., cane or walker), ankle-foot orthoses, and gait training that encourages and reinforces compensatory walking patterns over the restoration of normal mechanics. Moreover, the assistive flexible suit is desirably integrated into all phases of rehabilitation, not only early stages.

Outpatient rehabilitation is often limited both by duration and environmental context. The integration of assistive flexible suits into rehabilitation (e.g., post-stroke gait rehabilitation, etc.) has the potential to overcome the duration and environmental limitations by bridging the gap between the clinic and the patient's home environment in a manner that maximizes rehabilitation efforts and transforms normal day-to-day activities into meaningful opportunities for gait training. As one example of the application of the present concepts to a patient's normal day-to-day activities, in a paradigm in which a patient is prescribed a certain amount of outpatient physical therapy (e.g., 3 days a week), a medical provider (e.g., a physical therapist) can discuss with the patient the patient's needs on that day and remotely interface with the assistive flexible suit via a user interface (e.g., a wireless tablet interface, etc.) to customize an assistance profile that meets the patient's needs on that day (see, e.g., FIG. 23). The medical provider and patient can then capitalize on the immediate increase in capacity provided by the assistive flexible suit and carry out a more intensive gait retraining program than was previously possible, ultimately maximizing the repetition and intensity principles of experience-dependent neuroplasticity. The medical provider could also utilize the real-time data collected by the assistive flexible suit's sensors to evaluate within-session and across-session progress.

Although using the assistive flexible suit in-clinic provides the medical provider with a unique and innovative tool to assist with patient mobility and training, the present concepts significantly permit a medical provider to discharge a patient home with the assistive flexible suit programmed to execute an individualized, progressive in-the-community rehabilitation program (e.g., 3-5 days a week of 1 hour of assistive flexible suit assisted walking). Concurrently, spatiotemporal and step activity data can be continuously recorded for review by the medical provider and, optionally, the patient. This review, for example, could be enabled to occur remotely in real-time or at some later point in time (e.g., during a later point in time during the rehabilitation but offset from real-time, post-rehabilitation, etc.), or when the patient returns to a clinical setting for treatment. This in-the-community rehabilitation data serves to provide the patient and medical provider with specific knowledge of performance and results that may be critical in promoting inter-session carryover of gains made during treatment. Furthermore, patients could upload their data to a social network (e.g. www.patientslikeme.com) and demonstrate their progress to a support community, providing additional positive reinforcement. Advantageously, such an assistive flexible suit based neurorehabilitation program works synergistically with a patient's daily community engagements (e.g., a walk to a local store), thus maximizing the rehabilitation potential of day-to-day activities.

It is believed that a rehabilitation model that shifts the emphasis of targeted gait rehabilitation from a number of sessions per week (e.g., 3-5 sessions) in a clinical-environment to the day-to-day community activities of the patient, will yield significant improvements in patient rehabilitation. Improvements in clinic-measured walking speed (ie, walking capacity) following a clinic-based locomotor program may not translate into increased community walking activity due to the inability to train clinic-based walking speed in a context meaningful to community walking. For example, a subject who can walk faster in the calmness of the clinic may be limited by deficits in their balance self-efficacy at the thought of crossing a busy street or when attempting to walk faster on an uneven, noisy sidewalk crowded by pedestrians. Moreover, particularly when a medical provider such as a therapist is available to monitor the assistive flexible suit sensor data in real-time and fine-tune the assistance provided as needed to match the patient's changing needs, patients will likely feel more empowered to engage in community-based activities.

Figure 24:
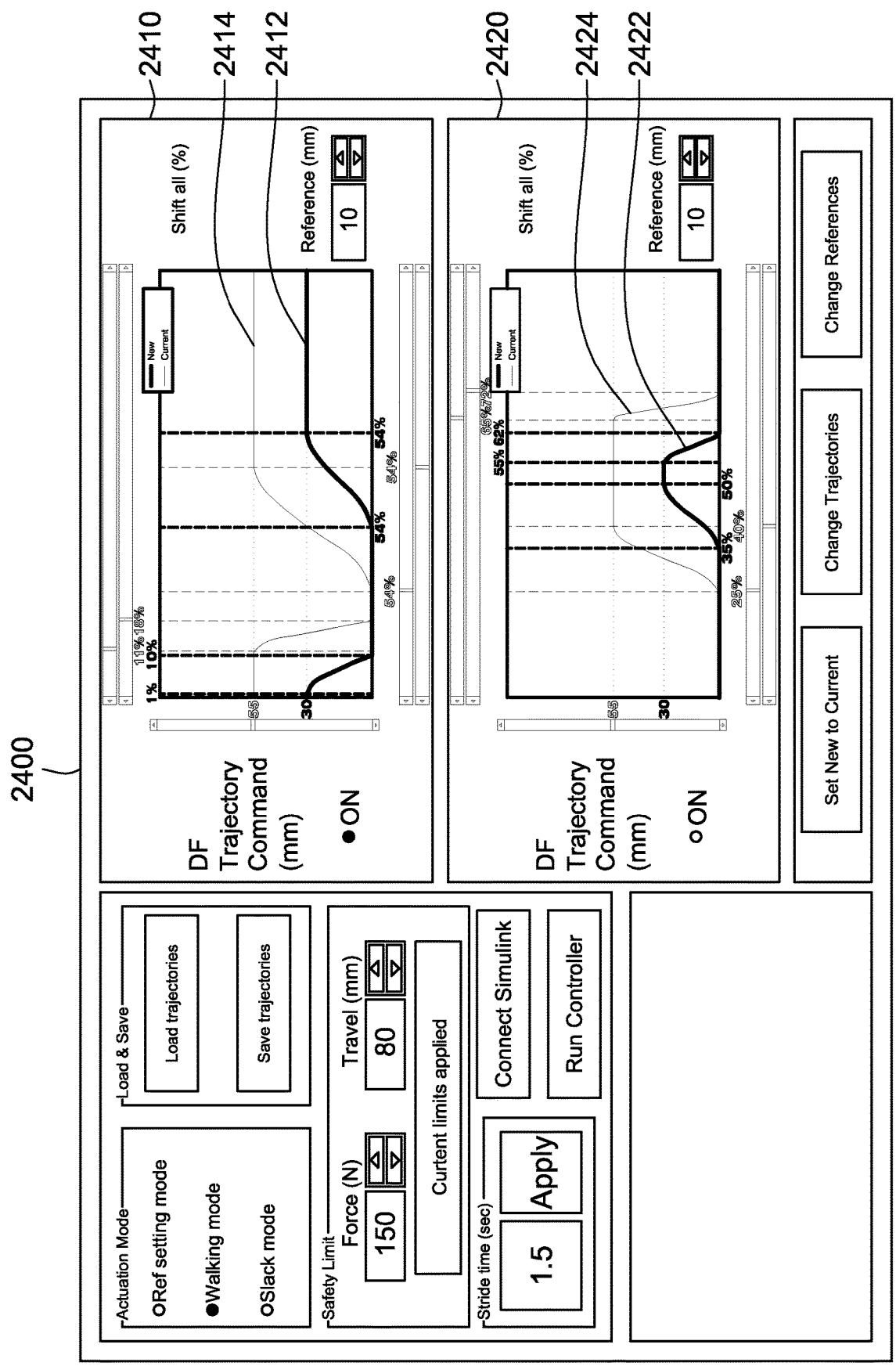
FIG. 24 shows an example of a clinician interface according to at least some aspects of the present concepts.

FIG. 24 shows an example of a first control loop 2301 GUI 2310 according to at least some aspects of the present concepts. This example concerns an embodiment of the assistive flexible suit 100 having two actively controlled degrees of freedom, shown in the GUI screen shot 2400 as a dorsiflexion plot 2410 (DF Trajectory Command) and an ankle plantar flexion plot 2420 (PF Trajectory Command). It can be seen that these plots 2410, 2420 allow control of very finely commanded trajectories. In this example, the actuation signals (e.g., trajectories) are defined by a medical provider 2305 from a heel strike (0% of the plots) to the next heel strike (100%).

In the dorsiflexion plot 2410, the current trajectory 2412 shows that the position (DF Trajectory Command)(mm) is decreasing from a level of about 30 mm travel down to a zero or near zero level (i.e., slack) over a gait phase from 0% gait to about 11% gait, whereat is remains at or near zero until about 40% gait, at which point it rises and plateaus again at about a 30 mm travel at about 62% gait, where it stays for the remainder of the gait cycle. In the "new" trajectory 2414 commanded by the modified parameters of an actuation signal input into the GUI 2400 is decreasing from a new level of about 55 mm down to a zero or near zero level (i.e., slack) over a gait phase from 0% gait to about 18% gait, whereat is remains at or near zero until about 25% gait, at which point it rises and plateaus again, at 55 mm, at about 54% gait, where it stays for the remainder of the gait cycle.

In the plantar flexion plot 2420, the current trajectory 2422 shows that the position (PF Trajectory Command) (mm) is zero or near zero (i.e., slack) over a gait phase from 0% gait to about 35% gait, where it increases until about 50% gait, at which point it plateaus at 25 mm and remains until about 55% gait, whereat it decreases back down to zero or near zero (i.e., slack) over a gait phase from about 55% gait to about 62% gait and remains at zero or near zero for the remainder of the gait cycle.

Figure 25:
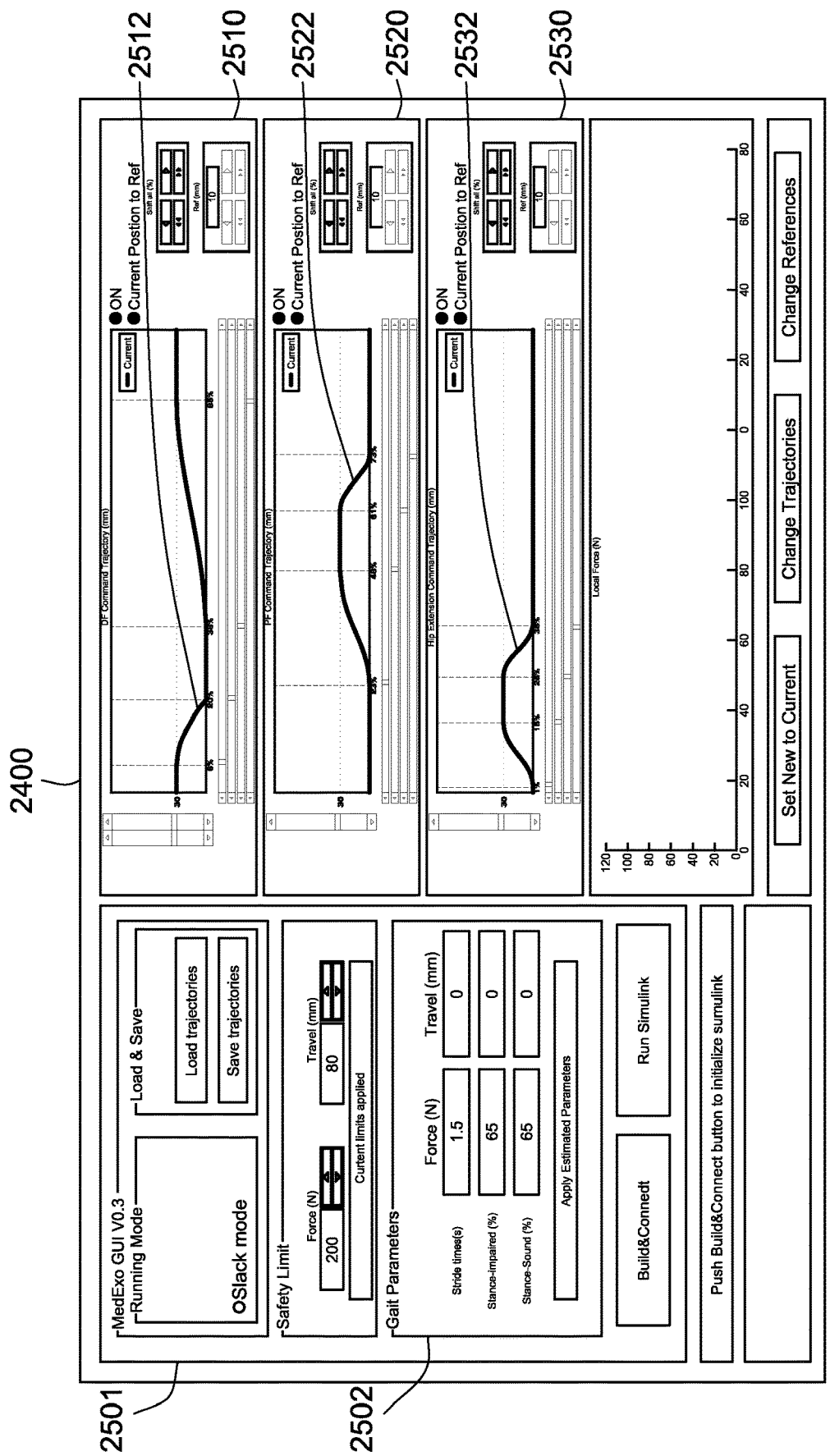
FIG. 25 shows another example of a clinician interface according to at least some aspects of the present concepts.

FIG. 25 shows another example of a first control loop 2301 GUI 2310 according to at least some aspects of the present concepts. FIG. 25 shows, in particular, an embodiment of the assistive flexible suit 100 having three actively controlled degrees of freedom, shown in the GUI screen shot 2500 as a dorsiflexion plot 2510 (DF Command Trajectory) (mm), an ankle plantar flexion plot 2520 (PF Command Trajectory)(mm) and a hip extension plot 2530 (Hip Extension Command Trajectory)(mm). As compared to the example of FIG. 24, this example of a GUI 2500 allows a finer level of control over the trajectories. In particular, as is see in the dorsiflexion plot 2510, the current DF Command Trajectory 2512 decreases in a curvilinear manner between about 6% gait and about 20% gait and increases in a curvilinear manner between about 36% gait and about 85% gait, rather than a more linear progression. The GUI 2500 of FIG. 25 provides very relevant data to the medical provider in window 2501 such as, but not limited to, stride time, % stance period on the impaired leg, and % stance on the sound leg, shown in window 2502. Additional data provided to the medical provider 2305 may include, by way of example, any spatial temporal gait variable such as gait symmetry, swing duration or cadence.

Figure 26:
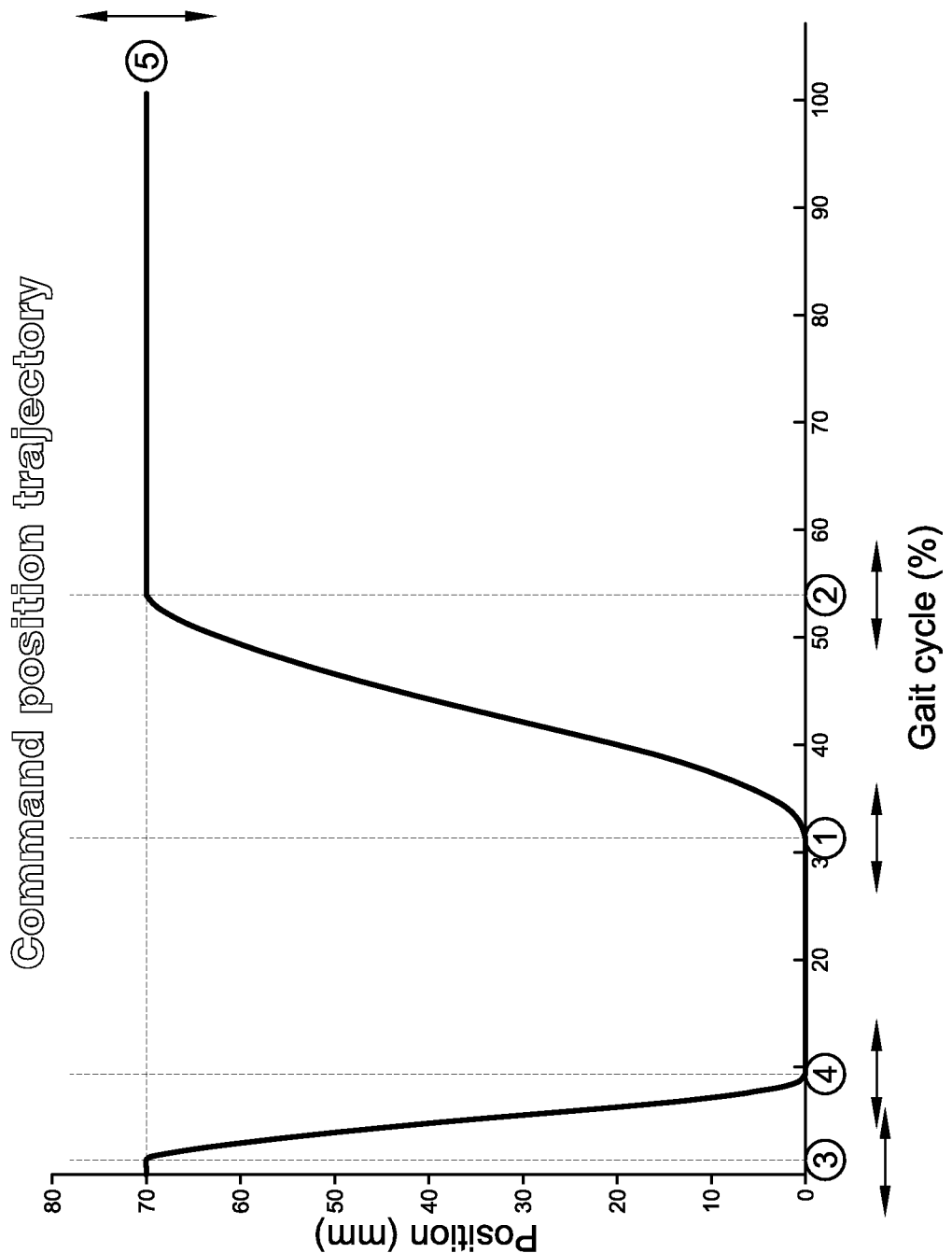
FIG. 26 shows an example of a trajectory control according to at least some aspects of the present concepts.

FIG. 26 shows an example of a trajectory control according to at least some aspects of the present concepts. Further to FIGS. 24-25, FIG. 26 shows an example of degree of control that can be given to the actuation of each degree of freedom of the assistive flexible suit 100. For simplicity, the example depicted relates to position control of one assistive flexible suit 100 actuator 105. Of course, the assistive flexible suit 100 actuator 105 could alternatively be controlled in another manner, such as via force, impedance, admittance, or other joint-level variable(s). In the example of FIG. 26, five parameters (labeled in numbered circles 1-5) are tunable either directly by the medical provider 2305, or with the help of an operator. These five parameters determine the position of the actuator cable (e.g., Bowden cable) at different moments of the gait cycle, referred from a 0% (heel strike) to 100% (following heel strike) of the impaired side gait. The five parameters are, from left to right, (3) the gait % at which the cable begins to release (eccentric), (4) the gait % at which a slack position is reached, (1) the gait % at which the cable begins to shorten (concentric), (2) the gait % at which maximum dorsiflexion is reached, and (5) setting of the maximum dorsiflexion position.

Figure 27:
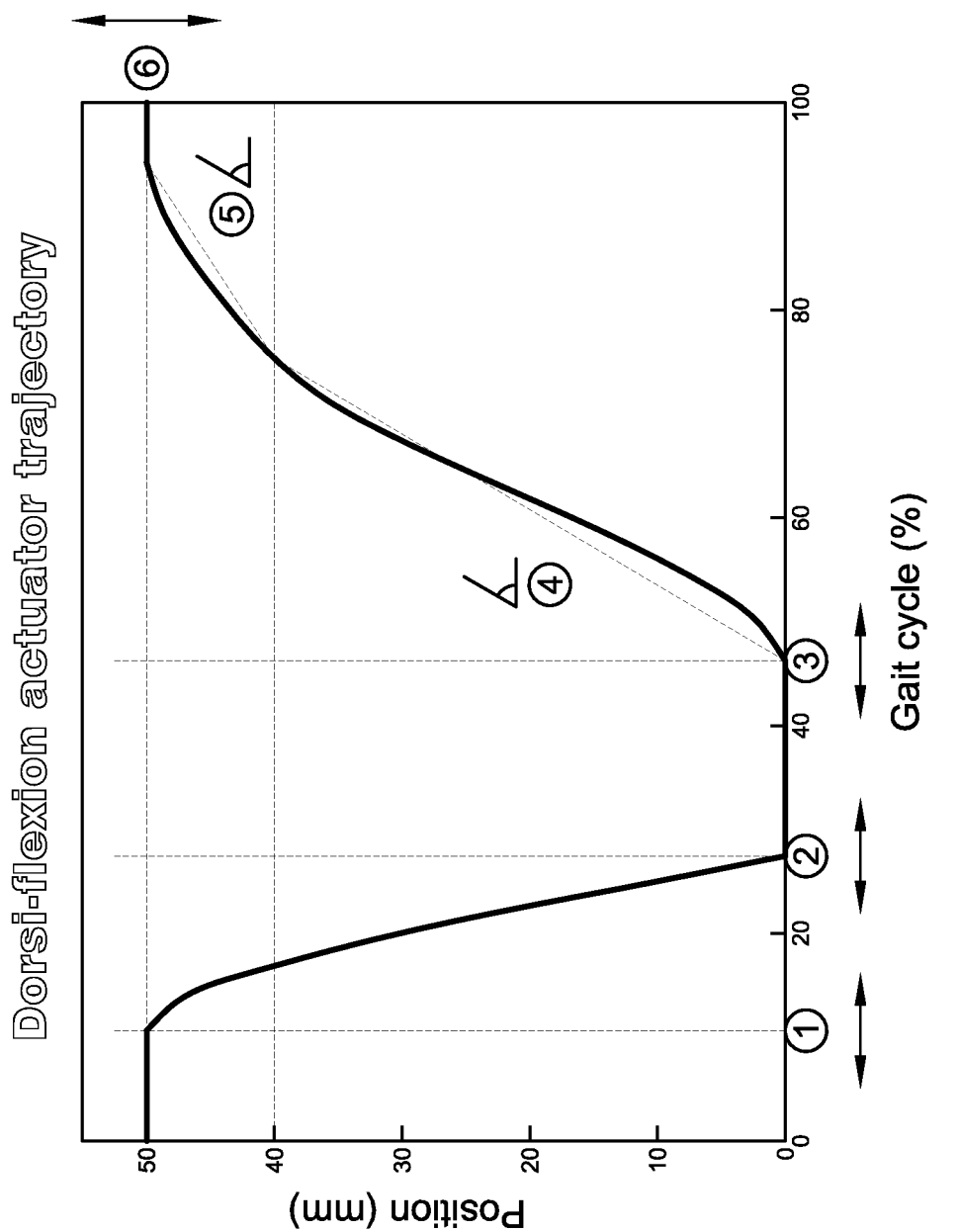
FIG. 27 shows another example of a trajectory control according to at least some aspects of the present concepts.

FIG. 27 shows another example of a trajectory control according to at least some aspects of the present concepts. Similar to FIG. 26, FIG. 27 shows an example of degree of control that can be given to the actuation of each degree of freedom of the assistive flexible suit 100. However, rather than the fairly linear trajectory shown in FIG. 26, FIG. 27 shows a more complex trajectory control with more highly-tunable section. In particular, the trajectories can be seen to be curvilinear, such as the trajectory between about 50-100% gait cycle. In accord with the present concepts, the trajectories can be any combination of linear or curvilinear (characterized by a curved line, which may have one or more than one inflection points) segments, without limitation.

In relation to the discussion above, the automated control part of the system architecture performed in the second control loop 2302 comprises two steps (1) detecting one or more gait events based on measurement from the affected leg, sound leg, a combination of the affected and sound legs and/or data from other body part(s) (e.g., events detected on the legs may include heel strike of the affected side, heel strike of the sound side, toe off on the affected/sound side, heel off affected/sound side, or foot-flat section of gait) and (2) adapting a trajectory (x-axis is % gait from 0%-100% or % phase of gait) defined in the medical provider 2305 interface (e.g., GUI 2310) to a trajectory defined in terms of time (seconds), that can be generated by the actuator. As previously noted, to generate a command to the actuators, the actuation profile is advantageously defined as a function of time so the trajectory input by the medical provider 2305 in relation to % gait must be converted to a trajectory with a x-axis in seconds. In at least some aspects of the present concepts, where one event is detected (e.g., affected leg heel strike), an average of the last N steps duration (heel strike time minus previous heel strike time) is updated. N may advantageously comprise a small number (e.g., 2-5), but can be any integer (e.g., N can be one, in which case the previous step duration is used as predictor of the step duration). Then, a profile is generated by "stretching" the trajectory expressed in % gait uniformly so that 0% corresponds to the current time, and 100% corresponds to the current time plus the average duration of the last N steps.

In at least some aspects of the present concepts, where two gait events are detected, the second control loop 2302 automated control architecture (1) detects two gait events (e.g., heel strike and toe off on a sound leg, heel strike of assisted leg and heel strike of contralateral leg, two events on a sound leg, heel strike and toe off on a contralateral leg, two events on a contralateral leg, etc.) and (2) assistance is defined relative to these two gait events and adapted based on the trajectory defined in the first control loop.

In accord with the present concepts, the gait events can be detected using sensors from either leg (ipsi or contralateral leg) or both legs. As to the assistance defined relative to the two gait events, a first part of the trajectory is defined after the first gait event is detected and a second part of the trajectory is defined after the second event is detected. This allows the commanded actuation profile to be more synchronized with the gait of the wearer of the assistive flexible suit 100. This is particularly important on a patient, where the predictability of the gait is very low. By way of example, different gait events for the same patient may have differing durations therebetween (e.g., a duration between a first and a second heel strike may be different than the second heel strike and a third heel strike).

Figure 28:
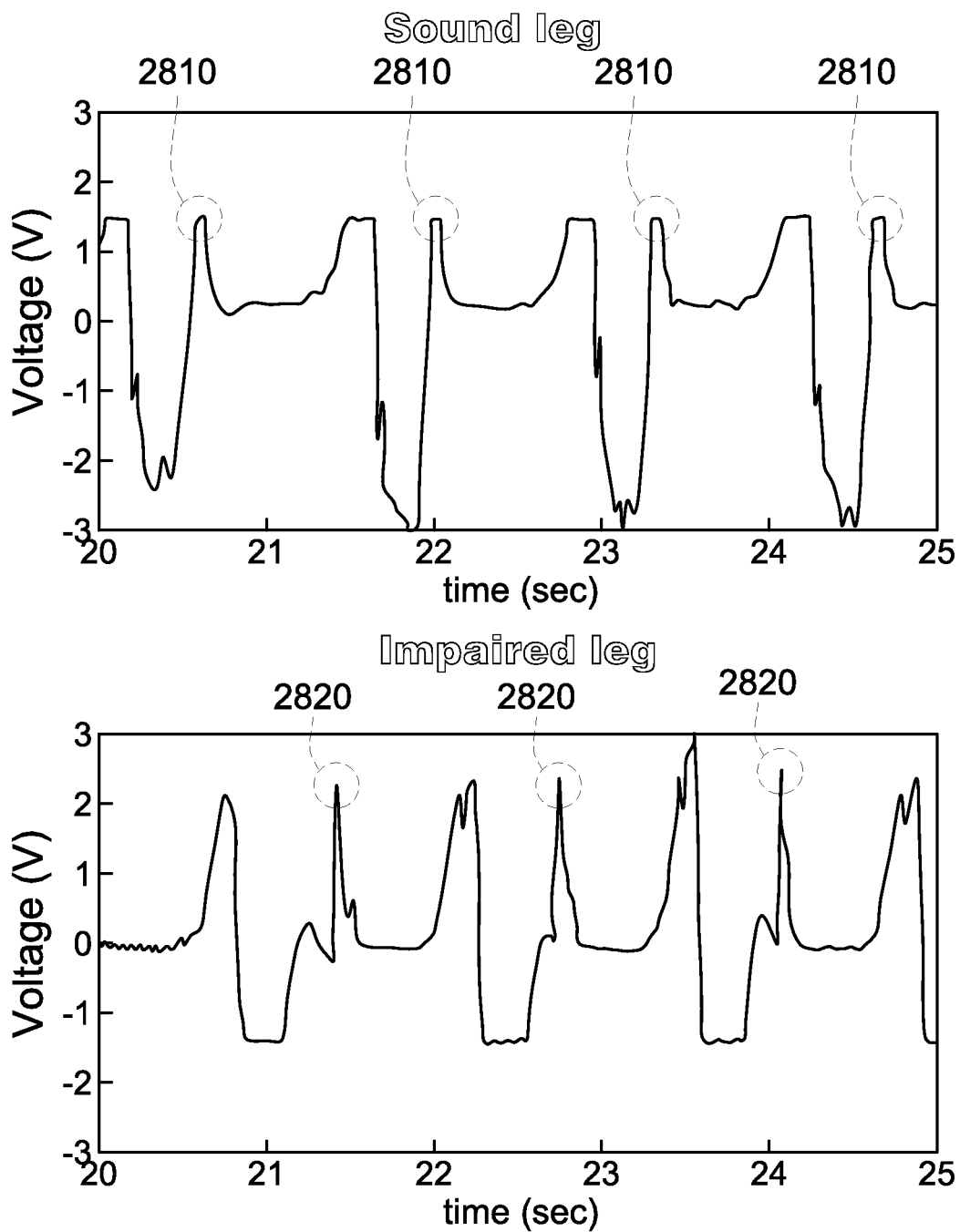
FIG. 28 shows an example of event detection using a gyroscope according to at least some aspects of the present concepts.

FIG. 28 shows an example of event detection using gyroscopes according to at least some aspects of the present concepts. A gyroscope (by itself or as part of an inertial measurement unit (IMU)) mounted on the assistive flexible suit 100, or externally thereto (e.g., on a shoe) can provide valuable information to detect gait events during walking. Of particular challenge in designing the present system were enabling sufficient robustness to work reliably and adaptively when applied to signals coming from the affected or sound leg, on different patients with different gait manifestations leading to different gait characteristics or patterns (e.g., different foot velocities), and to keep working after actuation is provided, which changes the foot speed pattern. FIG. 28 depicts signals from the sound leg (top) and impaired leg (bottom) of a stroke patient, wherein the impairment particularly involves the foot kinematics. The heel strikes 2810 of the sound leg (top) are seen to be very different from the heel strikes 2820 of the impaired leg. Further, the heel strikes 2820 exhibit step-to-step variance. Aspects of the control strategy for the assistive flexible suit 100 that utilize one or more gyroscopes advantageously permit collection of and exploitation of certain observed characteristics (regularities) of the experimental data such as, but not limited to, a strong downward trend (corresponding to the foot swing phase) always occurring before heel strike, a heel strike corresponds to a positive local peak in the signal subsequent to a negative dip, and a positive local peak that is not preceded by a negative dip is not a heel strike.

FIGS. 29A-29B show examples of adaptive thresholds according to at least some aspects of the present concepts wherein the assistive flexible suit 100 system comprises gyroscopes as part of a gait event detection subsystem. FIGS. 29A-29B show, relative to underlying sound leg gait pattern 2905 (raw gyro data) and impaired leg gait pattern 2915 (raw gyro data), a positive threshold 2910 and a negative threshold 2920. The positive threshold 2910 corresponds to X*average of the last N detected positive peaks (X<1, e.g., 0.5, etc.). This positive threshold 2910 is updated every time a positive peak is confirmed. The negative threshold 2920 corresponds to Y*average of the last N detected negative peaks (Y<1, e.g., 0.5, etc.). The negative threshold 2920 is updated every time a negative peak is detected. FIGS. 29A-29B also show heel strike confirmation stamps 2925 and search windows 2330. These graphs show how the positive and negative thresholds 2910, 2920 are adapted for each and every step. The thresholds are initialized at a predetermined number (e.g., 1V) and the patient or wearer utilizing the assistive flexible suit 100 is instructed to walk for a few steps with the assistive flexible suit in a passive state and the positive and negative thresholds 2910, 2920 converge to their natural value. After this initialization, "the algorithm can be used" with the assistive flexible suit in an active mode.

FIGS. 30A-30B show an example of heel strike detection according to at least some aspects of the present concepts wherein a gyroscope is utilized on a stroke patient with a sound leg (top gait pattern) and an impaired leg (bottom gait pattern). In the present example, the sensor data is gyro data, but the sensor data could be obtained from or derived from one or more other sensors, without limitation, in accord with other aspects of the present concepts. In accord the at least some aspects, a moving average is kept with the last Z milliseconds of the data signal. It at least some aspects of the present concepts, Z is set to a value between 20-50 ms, but Z could alternatively be set to another lesser or greater value in accord with other aspects of the present concepts. This moving average is updated at each heel strike confirmation time stamp 3025 (see also, e.g., reference numeral 2925 of FIGS. 29A-29B). When the moving average falls below the negative threshold 3020, a peak search 3040 is enabled and initiated. When the moving average rises above the positive threshold 3010, a search for the maximum value is started, keeping track of the time and magnitude of the maximum value 3050. When the data signal goes below the maximum value 3050 for a predetermined time, the peak is confirmed at time stamp 3075. In at least some aspects, this predetermined time may be between about 5-10 ms, but the predetermined time could be a time less than, or greater than, that exemplary range. The heel strike detection system then outputs the time of the detected maximum (peak) 3050 and the delay between the time of the actual peak and the time the peak was confirmed 3075. The positive and negative thresholds 3010, 3020 are then respectively updated with the positive and negative peaks.

In relation to FIGS. 30A-30B, and in accord with at least some aspects of the present concepts, when an average of differentiation of the moving window is below a predetermined negative value, which can be a fixed value or an adaptive value, and a current gyro signal is below a negative threshold (search window trigger threshold), a peak search is enabled. In such aspects, when the moving average goes above a positive threshold a search for the maximum is started and conducted by keeping track of the time and magnitudes to permit determination of the maximum value therefrom. When the gyro signal falls below 80% of the difference between the maximum value and the minimum value while the search window is open, the peak is confirmed. The controller executing the heel strike algorithm then outputs to the control system the time of the detected maximum peak and the delay in time from the time at which the peak was detected and confirmed. The thresholds are updated with the positive and negative peaks.

Figure 31A:
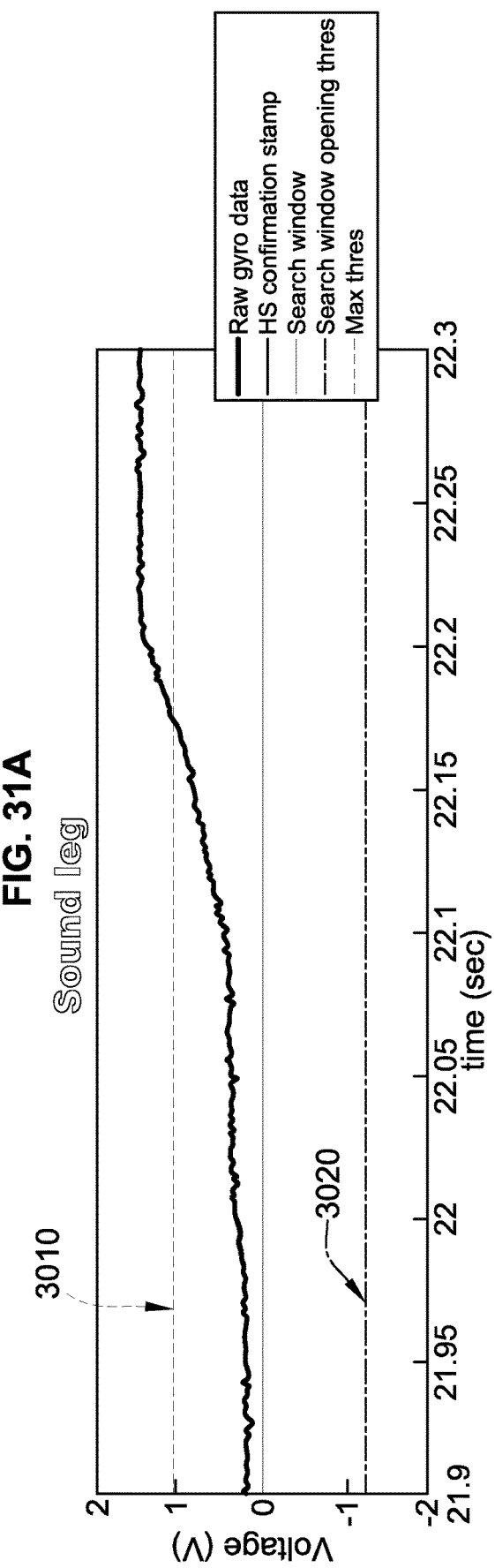
FIGS. 31A-31B show another example of detection of heel strike according to at least some aspects of the present concepts.
Figure 31B:
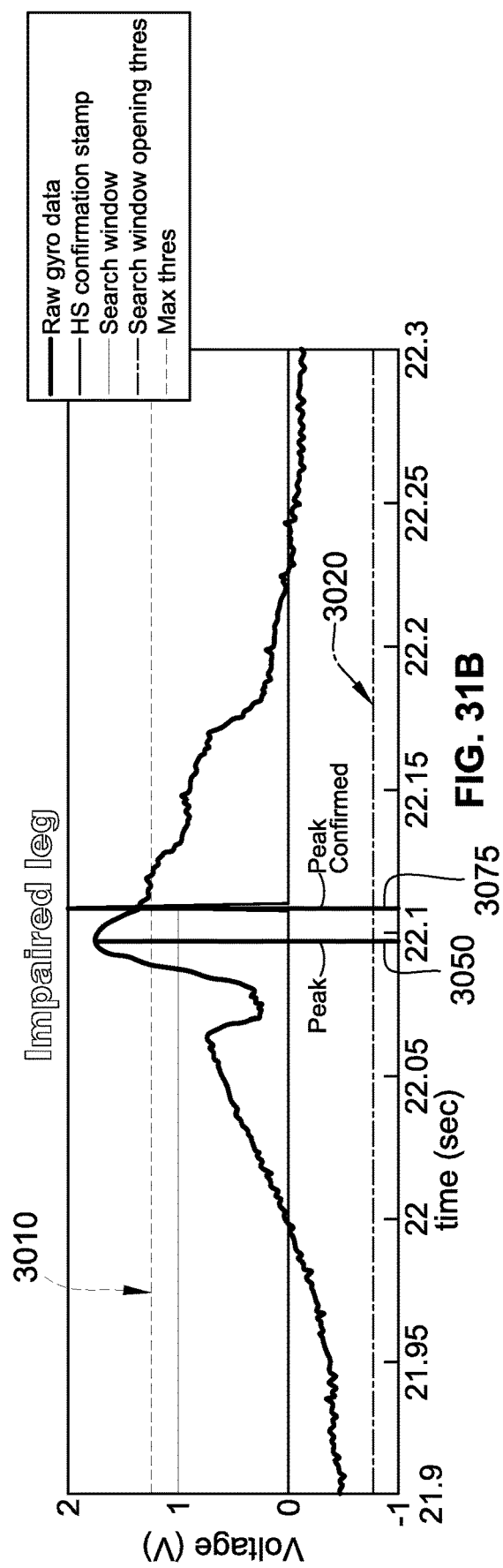
Figure 32:
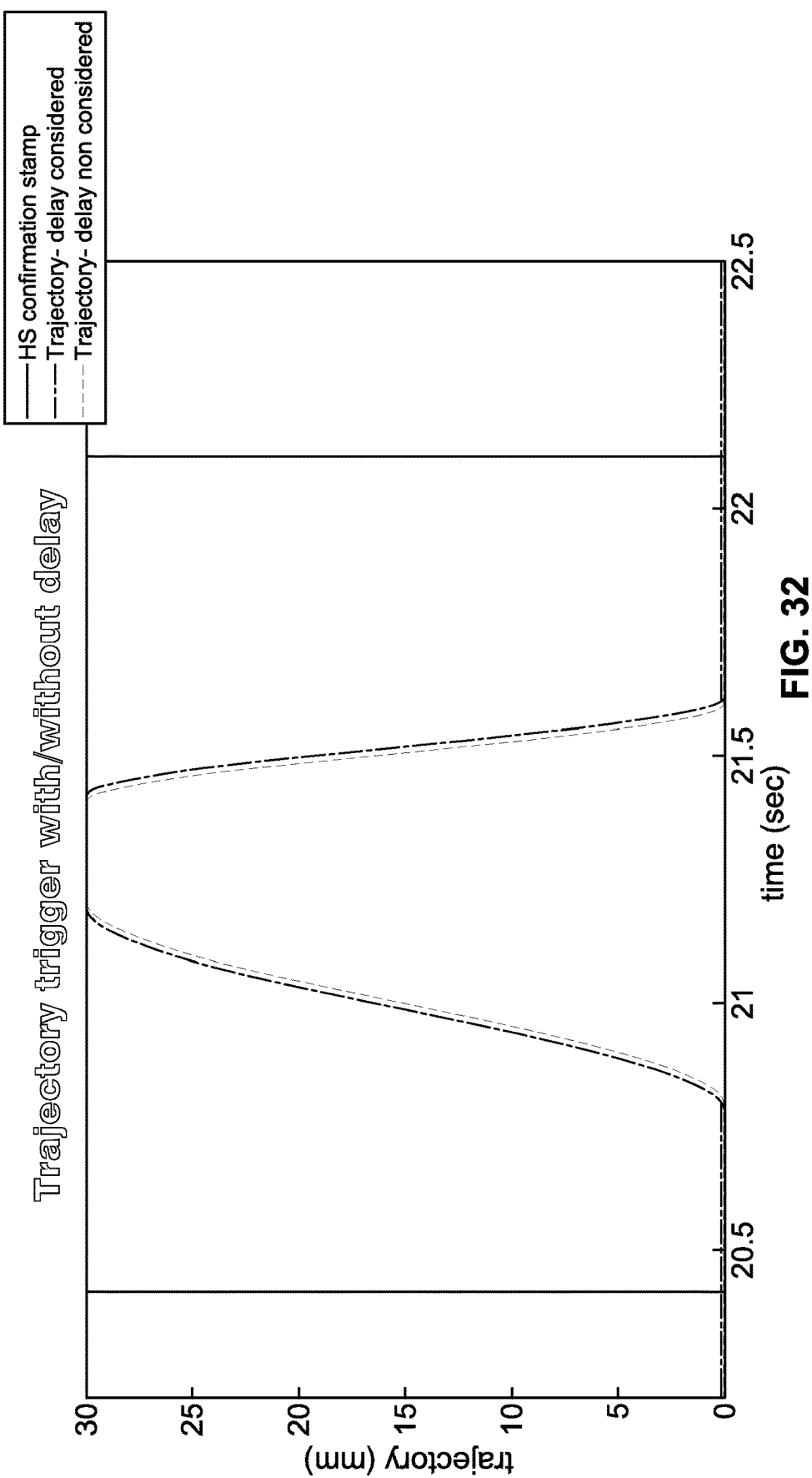
FIG. 32 shows an example of delay compensation for detected heel strike according to at least some aspects of the present concepts.

FIGS. 31A-31B show enlarged portions of the gait patterns in FIGS. 30A-30B to more clearly illustrate details of the positive and negative thresholds 3010, 3020 and aspects of the heel strike detection system, particularly focusing on the time frame between 20.5 seconds and 22.5 seconds. In this time frame, in this example, the heel strike detection system outputs also the delay between the time 3075 at which the peak was confirmed and the time 3050 of the actual peak. This enables the heel strike detection system to automatically adjust the trajectory generation to take this delay into account, as is shown in FIG. 32, which shows an example of delay compensation for detected heel strike according to at least some aspects of the present concepts. Specifically, FIG. 32 shows the effect of compensating for the delay between the real heel strike (the time 3050 of the maximum) and the confirmation of the peak at time 3075 when generating the trajectory or profile (in this case, a plantar flexion trajectory).

FIGS. 33A-33B show gait patterns for initiation and termination of walking (non-continuous walking with repeated gait initiation and termination) of a stroke patient during overground walking, including gait pattern analysis according to at least some aspects of the present concepts. It can be seen that the adaptive threshold method utilizing the positive threshold 3010 and negative threshold 3020, described above, ensures reliable detection of all peaks in all conditions, on both legs, even if the starting values were identical at the beginning (adaptive effect). Accordingly, this method and system can detect every single heel strike during the gait, including the first and last, with no special modification being required to detect initiation of walking or termination of walking.

Figures 34A, 34B:
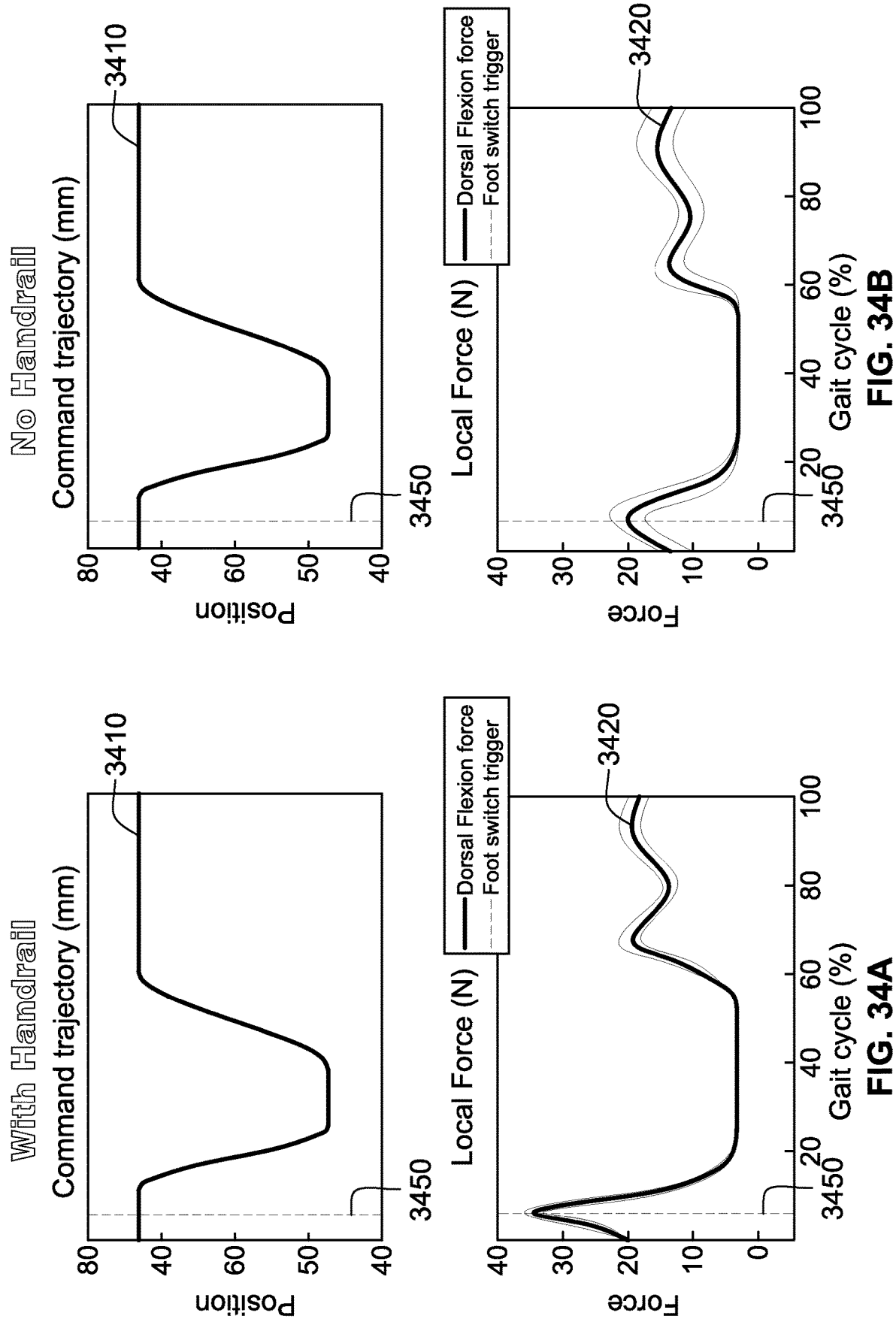
FIGS. 34A-34B show examples of commanded trajectories and local forces for dorsi flexor forces with handrail and without handrail according to at least some aspects of the present concepts.

FIGS. 34A-34B show examples of commanded trajectories 3410 for a position control actuator (mm) and local forces (N), particularly dorsi flexor forces 3420, relative to heel strike 3450, for situations with handrail and without handrail, according to at least some aspects of the present concepts.

Figure 35A:
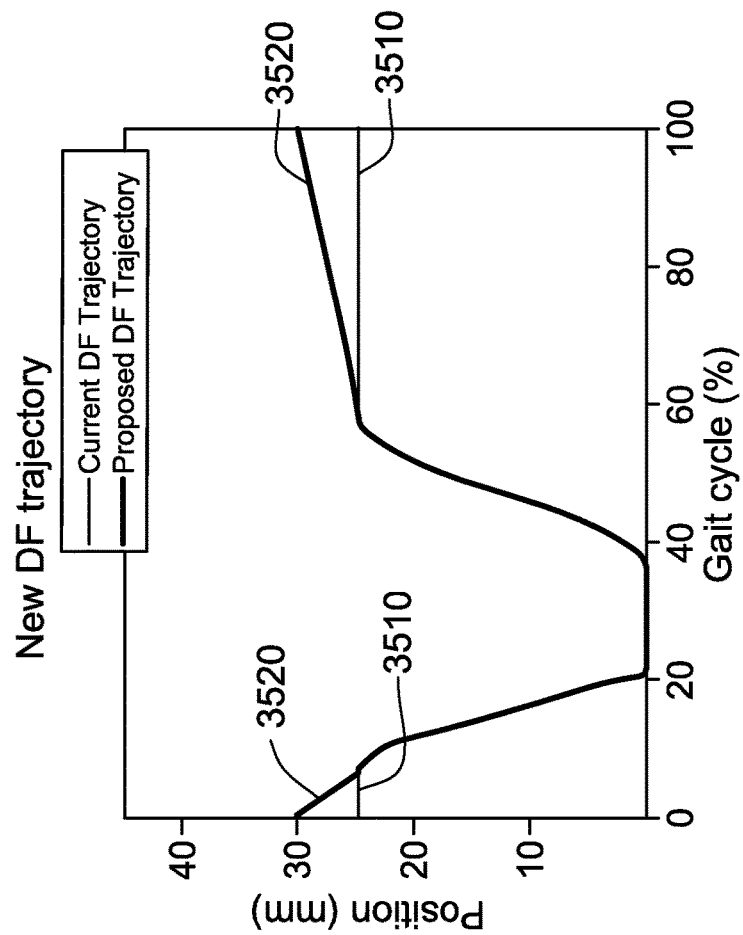
FIGS. 35A-35B show controller concepts according to at least some aspects of the present concepts.
Figure 35B:
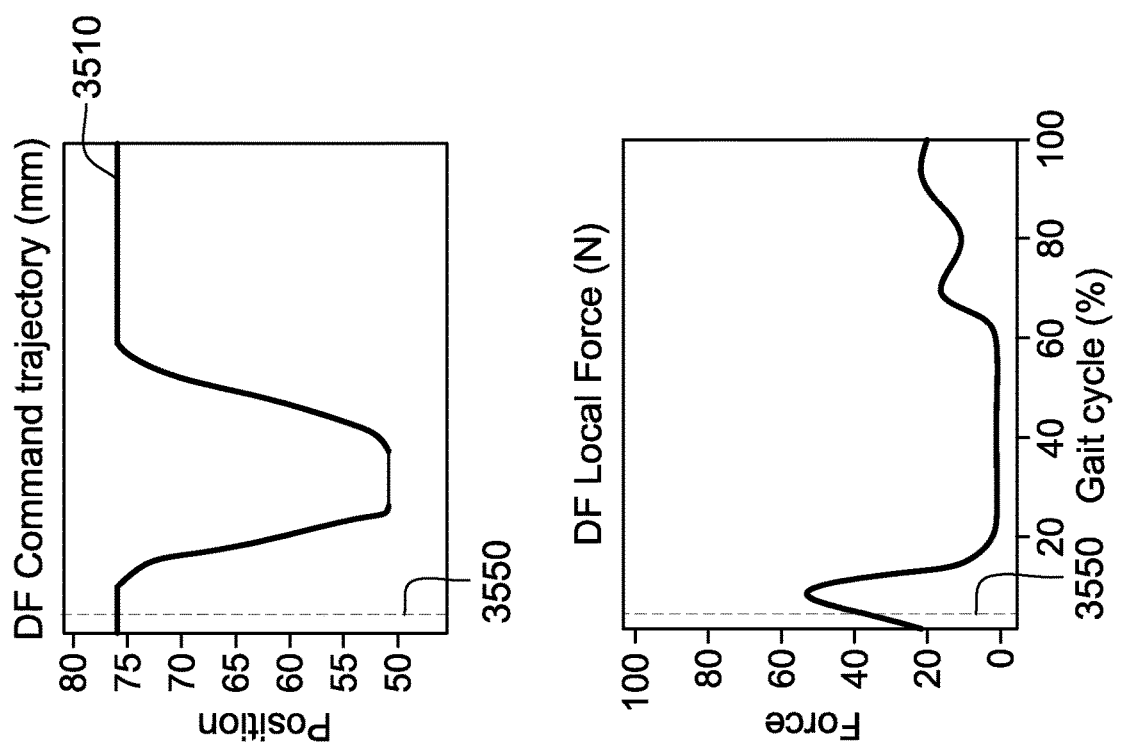

FIGS. 35A-35B show controller concepts according to at least some aspects of the present concepts wherein a dorsiflexion (DF) command trajectory (mm) is shown at the top of FIG. 35A and a dorsiflexion local force (N) is shown at the bottom of FIG. 35A, in relation to an indication of heel strike 3550. FIG. 35B shows the current DF command trajectory 3510 of FIG. 35A as it is to be modified by a proposed DF command trajectory 3520 in subsequent steps.

Figure 37:
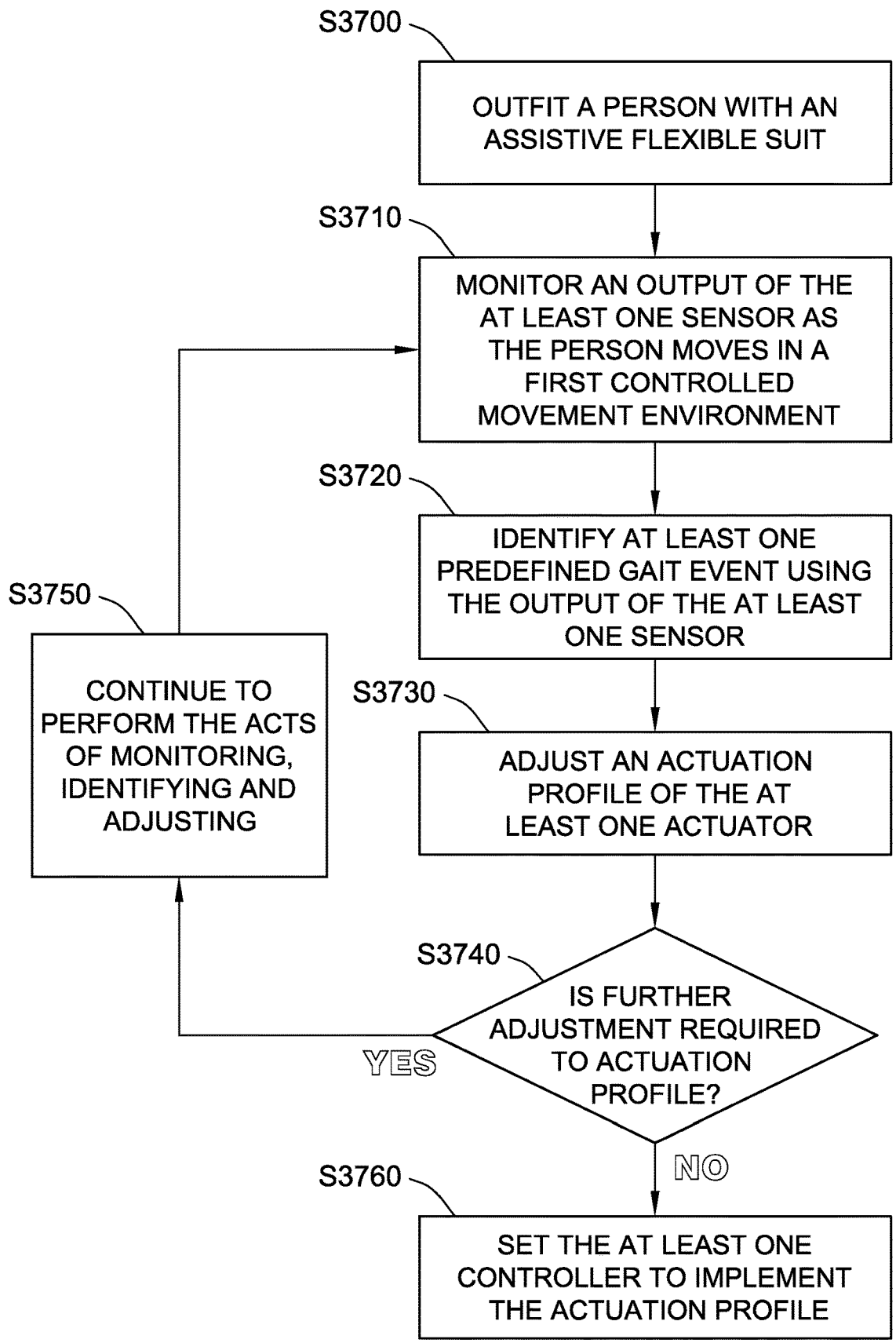
FIG. 37 shows acts in another method according to at least some aspects of the present concepts.

FIG. 37 shows acts in a method according to at least some aspects of the present concepts. The steps of the process shown with respect to FIG. 37 may be practiced in accord with the above disclosure to achieve the following steps. The method of FIG. 37 comprises an act of outfitting a person with an assistive flexible suit 100 (act S3700), such as is described herein. As described above, the assistive flexible suit is unilateral or bilateral in that it modifies movement of an individual with respect to one side of the individual about the sagittal plane, or both sides of the individual about the sagittal plane. However, although the flexible assistive suit may be described as unilateral, a unilateral assistive flexible suit may at least include one or more sensors on the side not assistive by the flexible assistive suit. In one embodiment, the assistive flexible suit includes a resilient element attached to one or more of the plurality of attachment points to permit modification of one or more of plantar flexion, dorsiflexion, supination, pronation, inversion, eversion, adduction, or abduction via reactive forces generated by the resilient element.

By way of example, the assistive flexible suit (such as assistive flexible suit 100) may include at least a first anchor element configured for positioning at or near a first body part and a second anchor element configured for positioning at or near a second body part. The assistive flexible suit may further include a plurality of connection elements extending between the first anchor element and the second anchor element, and at least one of the plurality of connection elements spanning at least one joint disposed between the first anchor element and the second anchor element. The assistive flexible suit also includes at least one sensor, at least one actuator, at least one force transmission element connecting an output of the at least one actuator to the second body part, and at least one controller configured to actuate the at least one actuator responsive to one or more predefined events occurring during movement to produce an actuation profile generating a moment about the at least one joint during movement of the at least one joint. In one embodiment, the at least one sensor is a plurality of sensors, with at least a first sensor disposed on a first leg and at least a second sensor disposed on a second leg.

The at least one assistive flexible suit actuator is configured to output a first force profile to impart a first torque profile across a first joint during the gait cycle output a second force profile to impart a second torque profile across a second joint during the gait cycle. Further, the assistive flexible suit includes a plurality of force transmission elements connecting an output of the at least one actuator to a plurality of attachment points at or about the second body part. More specifically, the plurality of force transmission elements may connect an output of the at least one actuator to a plurality of attachment points selected to permit modification of one or more of plantar flexion, dorsiflexion, supination, pronation, inversion, eversion, adduction, or abduction. More specifically, a force transmission element of the plurality of force transmission elements may connect to an output of the at least one actuator to a first attachment point to permit modification of plantar flexion about the ankle, and a force transmission element of the plurality of force transmission elements may connect an output of the at least one actuator to a second attachment point to permit modification of dorsiflexion about the ankle. Alternatively, or in addition, a force transmission element of the plurality of force transmission elements may connect an output of the at least one actuator to a first attachment point to permit modification of supination about the ankle, and a force transmission element of the plurality of force transmission elements connects an output of the at least one actuator to a second attachment point to permit modification of pronation about the ankle. Alternatively, or in addition, a force transmission element of the plurality of force transmission elements may connect an output of the at least one actuator to a first attachment point to permit modification of inversion about the ankle, and wherein a second force transmission element of the plurality of force transmission elements may connect an output of the at least one actuator to a second attachment point to permit modification of eversion about the ankle. At least some of the plurality of force transmission elements may be modular and selectively incorporated into or removed from the assistive flexible suit to provide selective connection between an output of the at least one actuator to one or more attachment points to selectively modify one or more of plantar flexion, dorsiflexion, supination, pronation, inversion, eversion, adduction, or abduction.

The method further comprises an act S3710 of monitoring an output of the at least one sensor as the wearer moves in a first controlled movement environment (act S3710), which may comprise, by way of example, a treadmill, a floor, or other surface which enables a wearer of the assistive flexible suit 100 to produce a reference gait pattern that is not unduly influenced by irregularities in the environment navigated. In other aspects, following performance of the acts shown in FIG. 37, the person wearing the assistive flexible suit may also be monitored in a second controlled movement environment (e.g., a floor, an instrumented floor, a substrate, level ground, an inclined surface, a declined surface, stairs, etc.) and refinements to one or more settings of the assistive flexible suit 100 actuation system performed, as described herein. In at least some aspects, the act of monitoring is performed by a medical provider in the loop via a suitable user interface.

At act 53720, at least one predefined gait event is identified using the output of the at least one sensor. In at least some aspects, the identified at least one predefined gait event comprises at least one of a heel strike, toe off, heel off, foot flat, foot landing, a start of controlled dorsiflexion, a start of powered plantar flexion, a height of wearer's center of mass relative to the ground, an initiation of a muscle eccentric contraction, or an initiation of a muscle concentric contraction. In one aspect of the present concepts, the at least one predefined gait event comprises two or more gait events. In yet other aspects, the predetermined gait events comprise both of a first gait event relating to an assisted leg and a second gait event relating to a contralateral leg.

At act S3730 in FIG. 37, an actuation profile of the at least one actuator is adjusted. In some aspects, the act of adjusting of the actuation profile includes adjusting one or more of a timing of actuation of an actuator, a ramp up force profile delivered by the actuator, a ramp down force profile delivered by the actuator, a maximum amplitude of force delivered by actuator, or a duration of force delivered by the actuator. Likewise, the act of adjusting of the actuation profile includes adjusting one or more of a timing, a ramp up force profile delivered, a ramp down force profile delivered, a maximum amplitude of force delivered, or a duration of force delivered by a plurality of actuators. As used herein, the terms "ramp up" and "ramp down" are generally used to refer, respectively, to an increase in value from a first value to a second value and a decrease in value from a first value to a second value with no limitation in the path between the first value and the second value. Thus, the ramp up or ramp down could be linear and/or curvilinear and/or a plurality segments that are individually linear and/or curvilinear, without limitation, and such increase(s) or decrease(s) can have any rate(s) of increase and/or decrease, inclusive of plateaus between the first value and the second value wherein there is no increase or decrease. In at least some aspects of the present concepts, the "ramp up" or "ramp down" may comprise a substantially linear, gradual increase or decrease in force, respectively, but the present concepts are not limited thereto. In some aspects, the adjusting of the actuation profile includes modification of dorsiflexion and/or plantar flexion. Any of the above described modifications may include, for example, an act of providing an assistive moment to one or more joints or providing a resistive moment to one or more joints.

In at least some aspects of the present concepts, sensor data is output from one or more sensors 120 of the assistive flexible suit 100 to a remote computer, controller or server (e.g., controller 2315 in FIG. 23) using an embedded (e.g., attached to assistive flexible suit) or external (e.g., personal cellular phone) wireless communication device operatively associated with the assistive flexible suit 100. In at least some other aspects of the present concepts, sensor data is output from one or more sensors 120 of the assistive flexible suit 100 to a local computer, controller or server (e.g., controller 2315 in FIG. 23) using a wireless or a hardwired connection therebetween. In an example of in-the-community rehabilitation, the sensor data provides, by way of example, performance metrics on kinematics (ROM), walking speed, walking distance, and assistive force profiles, enabling a medical provider to monitor the sensor data in real-time and to provide real-time inputs to the assistive flexible suit to actively facilitate the patient's rehabilitation.

Likewise, an updated actuation profile instruction sent from the medical provider (e.g., output from the first control loop 2301 of FIG. 23), in some aspects of the present concepts, is received by a wireless communication device (e.g., communication device 2330 of the second control loop 2302 of FIG. 23, a communication device integrated into a personal device such as a watch or a tablet, etc.) and implemented by an assistive flexible suit controller. The updated actuation profile instruction set may comprise a small adjustment (e.g., less than about a 25%, less than about a 20%, less than about a 10%, less than about a 5%, less than about a 3%, etc.) in one or more characteristics of an actuation profile. The present concepts certainly include larger changes in magnitude to any characteristic of actuation, without limitation, and the above description of smaller adjustments are intended merely to illustrate some possible ranges of adjustment, not limitations on the extent of potential adjustments.

These adjustments are input, in at least some aspects of the present concepts, a medical provider "in the loop" via a GUI interface and the medical provider determines what type, amount and profile of assistance provides a desired improvement in gait. However, the present concepts expressly include utilization of the wearer "in the loop," in lieu of, or complementary to, the medical provider. In such aspects, the wearer is enabled to input manual, direct adjustments to the second control loop 2302 through a suitable user interface (e.g., cell phone application, suit-based controls, etc.). Particularly following progression of a wearer's therapy or rehabilitation, such patient may be empowered by the medical provider and/or control system to input small changes at-will, or from time-to-time (e.g., on a schedule), such changes being expected to be smaller incremental adjustments than those noted above made directly by the medical provider. For example, a wearer may be permitted to make an adjustment of only up to about 1% or 2% of a characteristic of actuation profile, optionally within a predetermined time period (e.g., 1% change permitted per minute, 1% change permitted in a 10 minute interval, etc.). As previously noted, actuation profile characteristics include, but are not limited to, a timing of actuation of an actuator (e.g., a start time and/or a stop time), a ramp up force profile delivered by the actuator (e.g., an amplitude and/or a rate of increase), a ramp down force profile delivered by the actuator (e.g., a rate of decrease), a maximum amplitude of force delivered by actuator, or a duration of force delivered by the actuator. In such instances, the wearer is optionally empowered to make a small adjustment to see what "feels" better or more natural at a given time, in a given environment. In this regard, the assistive flexible suit 100 may comprise a plurality of modes that are set by a medical provider (e.g., walking at a first pace, walking at a second pace faster than the first pace, walking on an incline, walking on a decline, walking on a surface requiring a first degree of foot-ground clearance, walking on a surface requiring a first degree of foot-ground clearance greater than the first degree of foot-ground clearance, and/or a manual mode that permits the wearer to make small adjustments, etc.) and/or set by a wearer.

At act S3740, it is determined whether further adjustment to the actuation profile is required, such as by the medical provider "in the loop". If "yes," the process proceeds to act S3750. If "no," the process proceeds to act S3760, where the at least one controller is set to implement the actuation profile.

At act S3750, the above acts of monitoring, identifying, and adjusting (S3710-S3740) continue to be performed until an actuation profile of actuator(s) generates a beneficial moment about the joint(s) of interest to promote an improvement in gait, at which point the determination in act S3740 is "no" and the method proceeds then to act S3760. In one embodiment, the above steps are iteratively performed to yield a second actuation profile promoting an improvement in a second gait different from the gait, with the gait including a first walking pattern (e.g., a first mode of operation) and a second walking pattern (e.g., a second mode of operation).

Although FIG. 37 depicts a single iteration of adjustment of the assistive flexible suit 100, such as would occur in an office visit to a medical provider, it is to be understood that the acts of FIG. 37, and optionally other acts disclosed herein, would be performed periodically to adjust the actuation profile of the actuator(s) to provide continuing rehabilitative or therapeutic benefit to the wearer.

As should be apparent from the preceding discussion, the various aspects of the assistive flexible suit disclosed herein are not limited to clinical use, but are rather particularly suited for extension to the home and community with an individualized rehabilitation program designed to increase the patient's mobility and movement (e.g., walking, navigation of stairs, etc.). The assistive flexible suit provides both an active orthotic effect (e.g., applying restorative forces in parallel with the impaired musculature) and a rehabilitative effect (e.g., using sensors to measure key parameters of walking—spatiotemporal variables and step activity —) to facilitate implementation of patient-specific walking activity programs that target both walking strategy and quantity.

In any of the above aspects, the improvement in gait may include, by way of example and without limitation, an improved left-right symmetry, improved temporal symmetry in hemiparetic gait, improved spatial symmetry in hemiparetic gait, increased ankle range of motion of an affected side during the gait cycle in hemiparetic gait, increased ground clearance during swing phase, increased plantar flexion force during push-off, increased self-selected walking speed, and/or reduced compensatory movements in the non-sagittal plane. By way of example, measurements of the suit-wearer interaction forces and kinematics of the healthy and paretic legs to determine the gait asymmetry for each step, the controller is able to focus on restoring bi-lateral symmetry between both legs by providing different levels of assistance for each limb. For the paretic leg, it will provide active assistance or cues to either replace missing function in the case of complete muscle weakness (e.g. dorsiflexion assistance for foot drop) or restore joint power in the case of weak muscles (e.g. plantar flexion assistance for push off). For hemiparetic stroke patients, the healthy leg often has to work significantly harder and so the controller will also augment the healthy leg if necessary, thus helping to delay the onset of fatigue for the patient.

As to a location of the sensor(s) 120, in at least some aspects, one or more sensors are disposed on one of the wearer's body parts (e.g., an impaired leg), and the beneficial moment about the at least one joint is provided to that body part. In other aspects, one or more sensors are disposed on one of the wearer's body parts (e.g., a sound leg, an arm, the torso, the head, etc.), and the beneficial moment about the at least one joint is provided to another body part (e.g., an impaired leg). In one aspect, the beneficial moment applied about one or more joints is provided to at least a first body part (e.g., an impaired leg) responsive to an output of one or more sensors on that first body part or on another body part. In another aspect, the beneficial moment applied about one or more joints is provided to at least a first body part (e.g., an impaired leg) responsive to an output of a combination of sensors on different body parts (e.g., on both legs). Thus, when a joint to be assisted is a joint on the first leg, the beneficial moment about the joint may be triggered responsive to an output from one or more sensors on the second leg. Alternately, a beneficial moment to be applied about a joint of the first leg may be triggered responsive to an output from a combination of sensors on the first leg and the second leg. By way of example, one or more sensors are disposed on a first leg and one or more sensors are disposed on a second leg, with the beneficial moment being applied about at least one joint (e.g., ankle, knee, hip) of one of the legs (e.g., the first leg or the second leg) to provide an improvement in gait responsive to an output of the sensors on both legs. As previously noted, the sensor data senses and outputs data indicative of (e.g., direct or indirect measurement) of a condition correlated to one or more predetermined gait events (e.g., a heel strike sensor directly measures a heel strike event, etc.) such as a heel strike, toe off, heel off, foot flat, foot flat, foot landing, a start of controlled dorsiflexion, a start of powered plantar flexion, a height of wearer's center of mass relative to the ground, an initiation of a muscle eccentric contraction, or an initiation of a muscle concentric contraction.

In at least some aspects, a method for configuring an assistive flexible suit 100 comprises the act of outfitting a person with an assistive flexible suit comprising at least a first anchor element configured for positioning at or near a first body part, a second anchor element configured for positioning at or near a second body part, a plurality of connection elements extending between the first anchor element and the second anchor element, wherein at least one of the plurality of connection elements spans at least one joint disposed between the first anchor element and the second anchor element. By way of example and without limitation, the first body part comprises a thigh and the second body part comprises the cnemis, with the at least one joint being the knee therebetween. By way of further example, the first body part comprises the cnemis and the second body part comprises a foot, with the at least one joint being the ankle therebetween. As previously noted, the assistive flexible suit 100 comprises one or more sensors, one or more actuators, and one or more force transmission elements connecting an output of the actuator(s) to the second body part, together with one or more controllers configured, responsive to the sensor(s), to actuate the actuator(s) attachment(s) at predetermined times during movement of the joint(s) to generate a beneficial moment about the joint(s).

The above method for configuring an assistive flexible suit 100 further includes the act of connecting a force transmission element to a corresponding actuator of an offboard actuation system 200 to provide an output of the offboard actuator to the second body part. In this capacity, the offboard actuator actuates the force transmission element in lieu of the native assistive flexible suit actuator. So configured, the method includes the acts of monitoring an output of the sensor(s) as the person moves in a first controlled movement environment and identifying at least one predetermined gait event using the output of the sensor (s). The method further includes the acts of controlling an actuation of the offboard actuator(s), using an offboard controller, responsive to the output of the sensor(s) and adjusting an actuation profile of the offboard actuator(s). The acts of monitoring, identifying, controlling and adjusting continue to be performed until an actuation profile yields a desired beneficial moment(s) about the joint(s) (e.g., such as a moment promoting, or in fact providing, an improvement in gait). The adjusting of the actuation profile may comprise, for example, adjusting any one of, or combination of, a timing of actuation of actuator(s), a ramp up force profile delivered by the actuator(s), a ramp down force profile delivered by the actuator(s), a maximum amplitude of force delivered by the actuator(s), or a duration of force delivered by the actuator(s). In particular examples, the adjusting of the actuation profile comprises adjusting of the actuation profile to modify dorsiflexion or plantar flexion.

Following use of the offboard actuation system 200 (e.g., as part of the first control loop 2301 of FIG. 23) to collect the data necessary to properly adjust the assistive flexible suit actuation profile parameters, the method includes the acts of connecting the assistive flexible suit actuator(s) to the force transmission element(s) and setting the assistive flexible suit controller to implement the actuation profile via the actuator(s) to provide the desired beneficial moment(s) about the joint(s).

In accord with yet other aspects of the present concepts, a method for dynamically adjusting control outputs of an assistive flexible suit 100 (e.g., a unilateral assistive flexible suit configured to impart one or more actuation profiles across one or more joints of only one leg or a bilateral assistive flexible suit configured to impart one or more actuation profiles across one or more joints of two legs) to enhance mobility of a person exhibiting an off-normal gait pattern includes the acts of setting at least one assistive flexible suit actuator to output a first actuation profile across a first joint over a first range of movement during a gait cycle. Following such setting of the first actuation profile, the method includes the act of monitoring an output of at least a first sensor on a first body part and an output of at least a second sensor on a second body part during the gait cycle, the second body part being out of phase with the first body part over at least a portion of the gait cycle. Each of the first sensor and second sensor are configured to provide, respectively, first and second information relating to a gait pattern to at least one controller, such as a first control loop 2301 controller 2315 and/or assistive flexible suit 100 (second control loop) controller, which is then advantageously, but not necessarily, displayed on a display device, such as a first control loop GUI 2310. A variance in the gait pattern is then determined relative to a reference gait pattern using the first and second information. This determination may be performed by the medical provider (e.g., viewing an output of the GUI 2310) or by one or more controllers (e.g., via the first control loop 2301 controller 2315, assistive flexible suit 100 controller, or another controller). Responsive to such determination, the method further includes the act of determining a second actuation profile across the first joint during the gait cycle to decrease the variance in, or increase the symmetry in, the gait pattern from the reference gait pattern, such act of determination also being performed by the medical provider or by one or more controllers. The method further includes the act of setting the at least one assistive flexible suit actuator to output the second actuation profile across the first joint during successive gait cycles. In at least some aspects, the variance in, or symmetry in, the gait pattern comprises a symmetry in movement across at least one of a sagittal plane or a coronal plane.

In accord with at least some aspects of the above method, the first body part is a first leg and the second body part is a second leg and, more particularly, wherein the first leg is impaired and the second leg is sound.

The above method may further comprise an assistive flexible suit comprising one or more actuators configured to act on multiple joints, such as one or more actuators configured to output a first force profile or first torque profile across a first joint during the gait cycle and to output a second force profile or second torque profile across a second joint during the gait cycle, such forces or torques being applied over a predetermined range of movement, or ranges of movement, during a gait cycle.

In view of the above, the assistive flexible suit 100 system is, in various aspects, configured to provide wearers the ability to move more readily and easily. For example, the assistive flexible suit 100 system can provide improved foot clearance (dorsiflexion assistance) and more powerful push off (plantar flexion assistance), resulting in enhanced forward propulsion. In addition, the assistive flexible suit 100 system promotes more time spent on the paretic leg, a more stable and symmetric gait pattern, improved kinematics and a faster self-selected walking speed. It is further believed that the augmented propulsion from the ankle will enable patients to gradually be able to drop compensatory motions such as hip hiking, circumduction and knee bending.

FIG. 38 shows, via a sensor signal 3800 (a gyro signal in the present example), a representation of detection of full ground contact and toe-off for a patient's sound leg (top) and impaired leg (bottom) according to at least some aspects of the present concepts. In the present example, the sensor data 3800 is gyro data, but the sensor data could be obtained from or derived from one or more other sensors, without limitation, in accord with other aspects of the present concepts. The detection of full ground contact is accomplished by determining the period when the foot makes full contact 3820 with the ground following the heel strike (HS) confirmation stamp 3830. This period of full contact 3820 is the most reliable in terms of sensor signal 3800 (e.g., gyro signal) consistency because the foot cannot move regardless of patient's spasticity as the ground is acting as a physical constraint on the foot, preventing movement of the foot and preventing significant changes in the sensor signal. In at least some aspects of the present concepts, a complete foot contact 3820 is established when both an 1) average of the moving window and a 2) standard deviation of the moving window are below certain thresholds and the signal stays there for a predetermined period of time. This predetermined period of time, in at least some aspects of the present concepts, is set to be about 150 ms. In other aspects of the present concepts, the predetermined period of time could be less than, or greater than, this exemplary amount. Moreover, the predetermined period of time may be selected by a medical provider consistent with patient-specific gait observations. Following lapse of the predetermined period of time (e.g., 150 ms) while the aforementioned two conditions continue to be satisfied, to make sure that plateau is maintained, the gait phase of complete foot contact 3820 is confirmed. Complete foot contact 3820 is determined to terminate when the sensor data 3800 deviates from satisfying the aforementioned two conditions.

As to toe off detection, toe off occurs when the foot is completely separated from the ground. Therefore, the toe off is taken to be the first peak 3840 after the full foot contact period 3820 is determined to be complete. This toe off peak 3840 has been determined to be reliable, as foot motion is physically constrained by the ground right before the toe off peak 3840, and becomes free after toe off. In accord with at least some aspects of the present concepts, an toe off search window 3810 is opened at least substantially subsequent to an end of full foot contact 3820 and closed at least substantially subsequent to confirmation of toe off by the toe-off (TO) confirmation stamp 3840.

Figure 39:
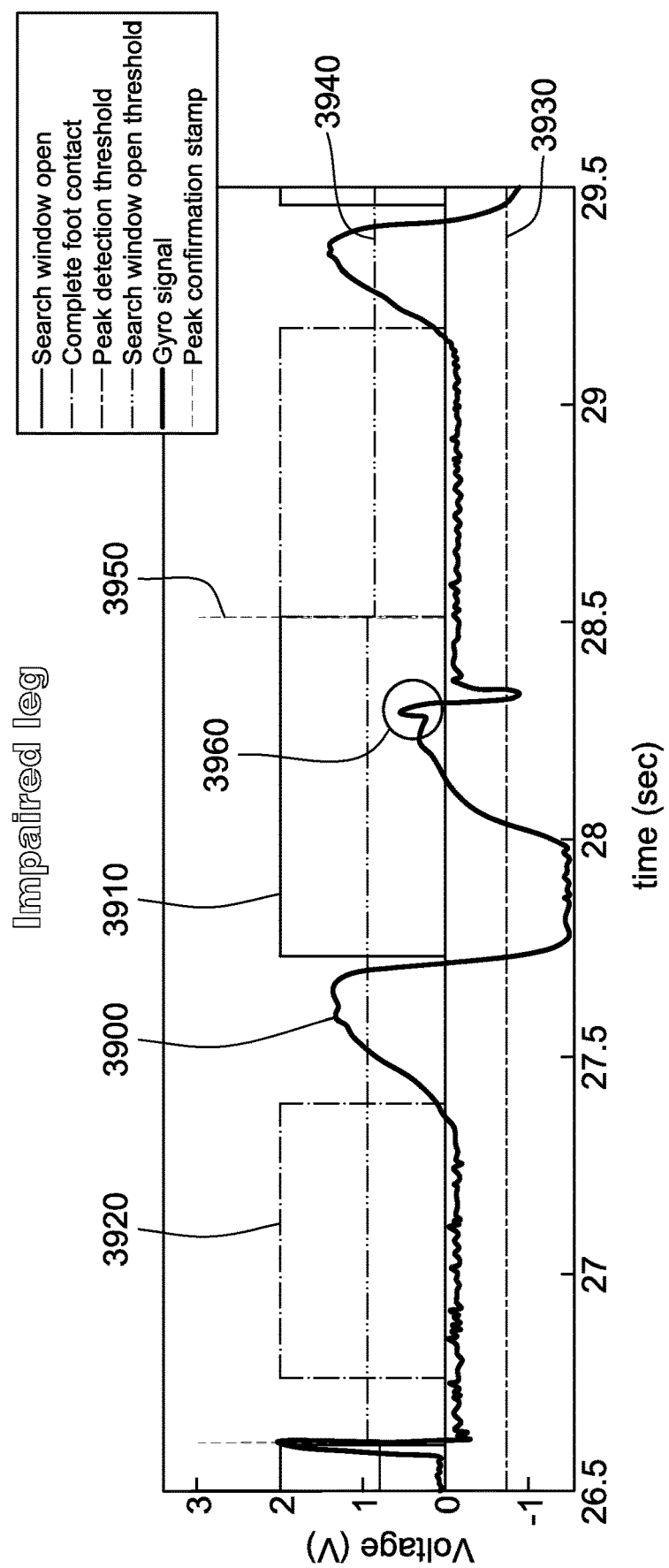
FIG. 39 shows a representation of a detection algorithm, according to at least some aspects of the present concepts, wherein a heel strike peak is not noticeable.

FIG. 39 shows a representation of a detection algorithm, according to at least some aspects of the present concepts, for an exceptional case wherein a heel strike peak 3960 is not noticeable. As is shown by the depicted sensor data (e.g., a gyro) for a patient's impaired leg, the gyro signal peak corresponding to a heel strike peak 3960 may not be significant and may not exceed a predetermined peak detection threshold 3930. This may occur, for example, when a patient tries to land their foot safely on the ground in a manner that minimizes ground reaction force (GRF). In accord with at least some aspects of the present concepts, even when this happens and the minimized heel strike peak 3960 is not detected, the control system advantageously imposes a heel strike confirmation stamp 3950 to permit consecutive gait segmentation. As was described above in relation to FIG. 38, complete foot contact 3920 is a reliable gait event that starts to present in early stance. Therefore, in accord with at least some aspects of the present concepts, the heel strike algorithm imposes a heel strike confirmation stamp 3950 when complete foot contact 3920 is detected before a heel strike peak is detected.

Figure 40:
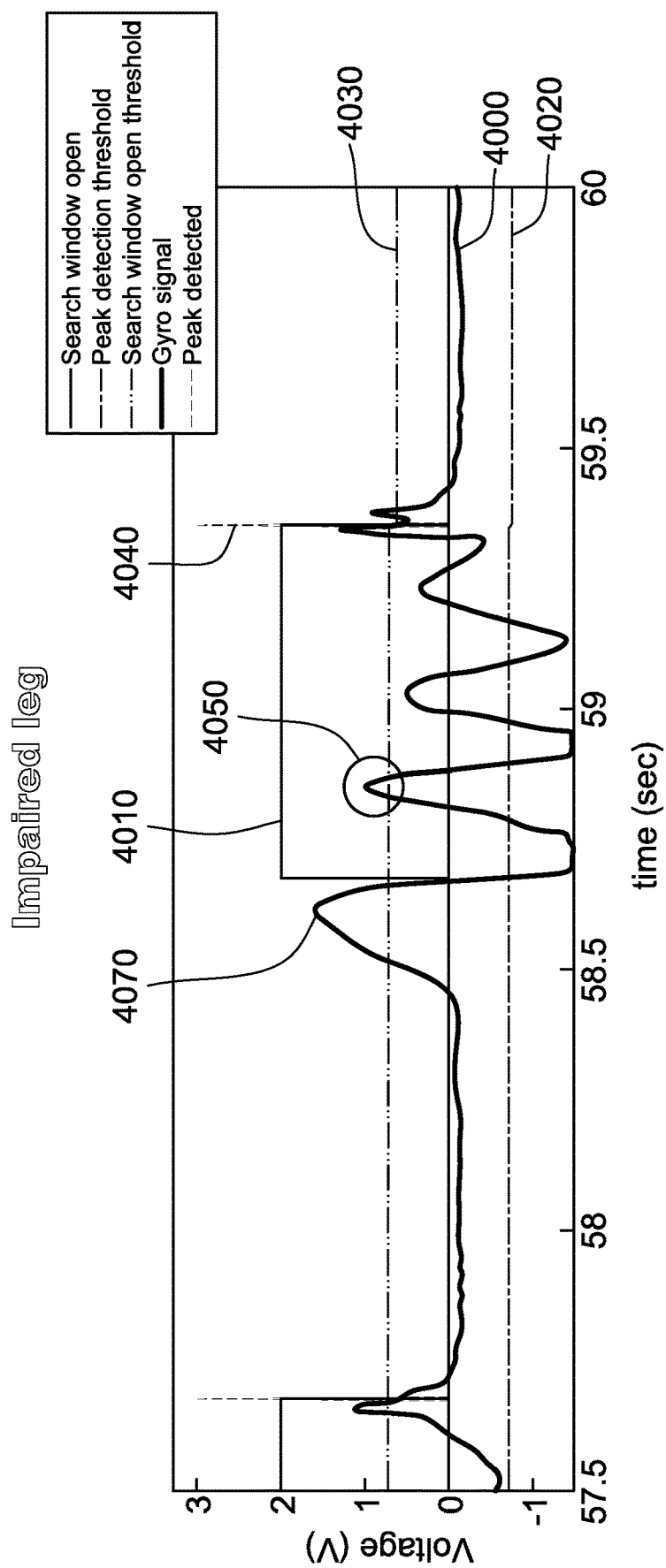
FIG. 40 shows a representation of a detection algorithm, according to at least some aspects of the present concepts, wherein a gyro signal during swing phase is oscillatory.

FIG. 40 shows a representation of a detection algorithm, according to at least some aspects of the present concepts, wherein a sensor signal (e.g., gyro signal, etc.) during a swing phase is oscillatory. In the present example, the sensor data 4000 is gyro data, but the sensor data could be obtained from or derived from one or more other sensors, without limitation, in accord with other aspects of the present concepts. FIG. 40 represents a case wherein a patient "quivers" an impaired side foot during the swing phase due to a motor control deficit. The quivering or foot tremors may produce multiple peaks in the data signal (e.g., gyro signal) 4000 during the swing phase, as is shown in FIG. 40. Multiple peaks are especially prominent when the patient's foot quivers in the sagittal plane. In order not to identify these multiple peaks as the peak corresponding to heel strike (i.e., heel strike peak 4040), which would otherwise cause an inappropriate actuation trigger, the heel strike algorithm measures the search window open 4010 duration, updates the duration, and instructs the controller(s) not to search for the heel strike during an initial portion of the gait. In at least one aspect of the present concepts, the heel strike algorithm instructs the controller(s) not to search for the heel strike during an initial 70% of search window 4010 duration after the search window is opened. In at least some aspects, the heel strike algorithm utilizes a running average of search window duration, or other prior kinematic data for the patient (e.g., patient historic data for similar gait events, patient historic data from the same limb segment, patient historic data from another limb segment, etc.) to instruct the controller(s) to more narrowly focus the heel strike detection during a subset of the gait, optionally with reference to another limb segment. By way of example, and without limitation, this prior kinematic data may comprise, but is not limited to, a time-based limitation (e.g., after an initial 50% of search window 4010 duration, etc.) and/or a sensor signal characteristic pattern (e.g., after the search window is opened and after a predetermined minimum number of origin (0 V) crossings, following which the heel strike peak detection is implemented. In view of the above, the search window open 4010 signal is based on the most reliable cue (toe off peak 4070 shown between about 58.5-58.6 seconds in FIG. 40), and ignores the least reliable data with an adaptive threshold. As shown in FIG. 40, the sensor data 4000 reliability is the worst right after toe off 4070 as the foot can move freely while ankle acceleration generated with push-off remains. This period, during which the data is shown in FIG. 40 to be unreliable, is thus ignored via an adaptive window duration threshold that advantageously performs heel strike detection only during a period for which the data is expected to prove reliable.

Figure 41:
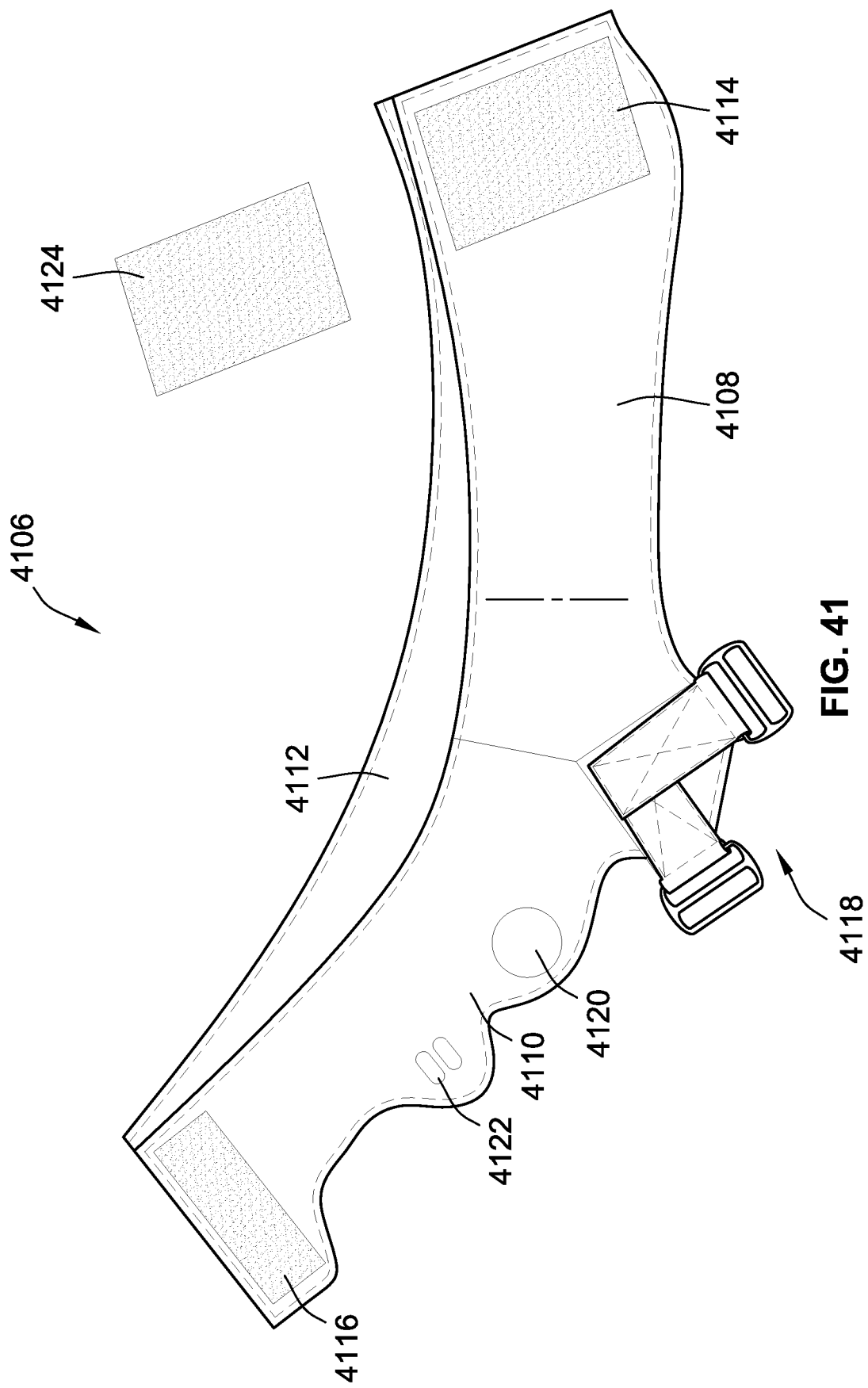
FIG. 41 is a front perspective-view illustration of an optional "unilateral" waist belt module for an assistive flexible suit in accord with aspects of the present disclosure.

Turning next to FIG. 41, there is shown a perspective-view illustration of a "unilateral" waist belt 4106 that is configured as a suspension anchor (or "anchor element") for an assistive flexible suit, such as flexible suit 300 of FIGS. 3A and 3B. Waist belt 4106 is designed to couple (e.g., wrap around and attach circumferentially via an expandable inner diameter) to the pelvis of the wearer. Similar to the waist belt architecture presented in FIG. 3D at 306, the waist belt 4106 of FIG. 41, when properly situated and attached, extends over one or both superolateral iliac crests of the pelvic girdle, which operate as load-bearing support members or anchor points for supporting reaction forces. By allowing the waist belt 4106 to tightly conform to the wearer's body, the natural features of the body help to maintain the belt 4106 in position during operation of the assistive suit.

In accord with the illustrated embodiment, the waist belt 4106 is configured to extend continuously around the pelvis of the wearer, situated at least partially above one or both iliac crests. By way of non-limiting example, waist belt 4106 comprises a first inextensible or substantially inextensible panel 4108 that originates proximate a first (e.g., right) ilium, crosses over the front of the wearer's pelvic region, wraps around and at least partially above the crest of the second (e.g., left) ilium, and terminates at the rear of the second ilium (e.g., adjacent user's the lower lumbar region). A second inextensible or substantially inextensible panel 4110 originates over the first (e.g., right) ilium, wraps around and at least partially under the crest of the first ilium, and terminates at the rear of the first ilium (e.g., adjacent the lower lumbar region). A stretchable (e.g., elastic fabric) waistband 4112 conforms the waist belt 4106 to the user's pelvis, provides comfort during use, and can help to make up any height difference between the two sides of the waist belt 4106 to avoid confusion during donning e.g., so that the resulting overall waistband is level.

First and second hook-and-loop fastening panels 4114 and 4116, respectively, provide attachment points for adjustably securing the waist belt 4106 in place. The first fastening panel 1414 (i.e., attachment point) is off center and shifted toward the sound leg to be opposite the main direction of pull during operation of the assistive suit. An optional removable hook-and-loop fastening panel 1424 can be provided to allow the waist belt 4106 to be reversible but ensure the "teeth" of the hook-and-loop fastening panels face away from the wearer, which improves comfort and helps to prevent chafing. The waist belt 4106 is also provided with plantar-flexion attachment loops 4118 for connecting the belt 4106 to a plantarflexion module (e.g., foot module 312 of FIGS. 3A and 3B or other disclosed foot attachment element). Hip joint interface 4120 is configured as a connection point for passive lateral hip support modules. Back attachment interface 4122 is configured as a connection point for hip extension modules. The unilateral waist belt 4106 of FIG. 41 is designed to resist migration under unilateral pulling. While generally intended for unilateral use, the waist belt 4106 can be reversible (e.g., worn inside out) to allow for either left-side or right-side impairment assistance. When worn, the waist belt 4106 is configured to be "pre-tilted" in a direction that the belt 4106 tends to migrate—i.e., the force path occurs higher on the sound side and lower on the impaired side of the wearer.

As used herein, the terms clinician and medical provider are intended broadly to refer to any provider of health care services, such as preventive, curative, promotional or rehabilitative health care services and may comprise, but is not limited to, any health professional such as physicians, physician assistants, nurses (including advanced practice registered nurses), therapists, chiropractors, clinical officers, physical therapists, occupational therapists, or medical prosthetic technicians (collectively referred to as "medical provider" for brevity). Moreover, the medical provider need not necessarily be local to the wearer of the assistive flexible suit 100 when adjustments are made and, in accord with at least some aspects of the present concepts, and without consideration of particular licensing requirements for the practice of telemedicine by medical providers, the present concepts expressly include the adjustment of the assistive flexible suit 100 by a medical provider that is located remotely from the wearer (e.g., in another part of the same state, in another state, or even in another country, etc.). In such aspects, the act of monitoring an output a one or more sensor(s) as the wearer moves in a first controlled movement environment may comprise remotely monitoring information transmitted by the sensor(s), over a communication pathway (e.g., Internet, LAN, WAN, cellular transmission, etc.), to the medical provider's user interface (e.g., processing device and display). The medical provider then analyzes the sensor data, determines an appropriate adjustment, and outputs the adjustments to an assistive flexible suit 100 control system. The sensor(s) may comprise, for example, sensors external to the assistive flexible suit 100. By way of example, an external camera (e.g., a camera integrated with a wearer's home computer or a wearer's cellular phone, a camera in a telemedicine suite, etc.) may be used to provide visual cues of the wearer's gait to the medical provider (e.g., as the wearer walks toward the camera, away from the camera, and/or at another angle relative to the camera within the camera's field of view, etc.) to supplement raw data or processed data from the assistive flexible suit 100 sensor(s) 120.

By way of example, after patient rehabilitation is completed in a clinical setting, the patient then wears or takes the assistive flexible suit home and uses it in accord with a rehabilitation schedule (e.g., a predetermined number of hours per day or per week) and/or at a self-selected frequency and/or duration (e.g. in excess of a minimum rehabilitation schedule) to maintain a higher level of function.

It should be understood that any and all combinations and permutations of the features, functions and concepts discussed in detail herein are contemplated as being part of the inventive subject matter (provided such concepts are not explicitly disclaimed or mutually inconsistent). For example, although differing in appearance, the individual systems and devices and functional componentry depicted and discussed herein can each take on any of the various forms, optional configurations, and functional alternatives described above and below with respect to the other disclosed embodiments, unless explicitly disclaimed or otherwise logically prohibited. Also, the technology described herein may be embodied as various methods, of which numerous examples have been provided. The acts performed as part of any method may be ordered in any suitable way. Accordingly, embodiments may be constructed in which acts are performed in an order different than illustrated, even though shown as sequential acts in illustrative embodiments, in which some acts are performed simultaneously, in which some acts are omitted, and/or in which some acts are adopted from other illustrated embodiments.

Each of these embodiments and obvious variations thereof is contemplated as falling within the spirit and scope of the claimed invention, at least some aspects of which are set forth in the following claims. Moreover, the present concepts expressly include any and all combinations and subcombinations of the preceding elements and aspects. By way of example, an "off-the-shelf" assistive flexible suit 100 may be designed and optimized to address a particular disorder (e.g., Parkinson's disease, stroke, etc.) to address the specific gait issues associated therewith (e.g., impaired regulation of stride length, reduced gait speed, altered cadence, stride time variability, etc.), with a medical provider in-the-loop to provide patient-specific adjustments, as needed, to calibrate the sensor(s) and tune the controller output (e.g., trajectories, etc.). Alternatively, a modular assistive flexible suit 100 may be assembled from a variety of modules to address a patient's specific needs and gait issues, with a medical provider in-the-loop to provide patient-specific adjustments.

What is claimed:

1. A method for promoting an improvement in a gait of a person, the method comprising:
    outfitting the person having an impaired gait with an assistive flexible suit, the assistive flexible suit including one or more flexible connections disposed between one or more anchor straps, being configured to span one or more joints of a leg of the person, and having at least one actuator configured to apply a tensile force to the one or more anchor straps using the one or more flexible connections for the assistive flexible suit to generate a moment about at least one of the one or more joints and at least one sensor configured to measure the gait of the person in real-time;
    monitoring with at least one processor an output of the at least one sensor as the person moves to identify with the at least one processor at least one gait event occurring during successive strides of the person;
    generating, with the at least one processor and based at least in part on a timing of the at least one gait event, a reference trajectory;
    generating, with the at least one processor and based at least in part on the reference trajectory, an actuation profile for promoting the improvement in the gait of the person;
    updating the reference trajectory, with the at least one processor and based on continued monitoring of the output of the at least one sensor, wherein the output of the at least one sensor includes kinematic sensor data; and
    adjusting the actuation profile, with the at least one processor and based on the updated reference trajectory, until the assistive flexible suit generates the moment about the at least one of the one or more joints that results in the improvement in the gait of the person.

2. The method of claim 1,
    wherein the adjusting of the actuation profile comprises adjusting one or more of a timing of actuation of the at least one actuator, a ramp up force profile delivered by the at least one actuator, a ramp down force profile delivered by the at least one actuator, a maximum amplitude of force delivered by the at least one actuator, or a duration of force delivered by the at least one actuator.

3. The method of claim 1,
    wherein the at least one gait event identified comprises at least one of a heel strike, a toe off, a heel off, a foot flat, a foot landing, a start of controlled dorsiflexion, a start of powered plantarflexion, a height of the person's center of mass relative to ground, an initiation of a muscle eccentric contraction, and an initiation of a muscle concentric contraction.

4. The method of claim 1,
    wherein the improvement in the gait comprises at least one of improved forward propulsion, enhanced forward hip swing, increased stability, an improved left-right symmetry, improved temporal symmetry in hemiparetic gait, improved spatial symmetry in hemiparetic gait, increased joint range of motion of an affected side in hemiparetic gait, increased ground clearance during swing phase, increased plantar flexion force during push-off, increased self-selected walking speed, or reduced compensatory movements.

5. The method of claim 1,
    wherein at least the steps of monitoring and adjusting are performed by a medical provider via a user interface.

6. The method of claim 1,
    wherein at least the steps of monitoring and adjusting are performed by the person outfitted with the assistive flexible suit via a user interface.

7. The method of claim 1,
    wherein at least the step of monitoring is performed by a detection algorithm operating on the at least one processor.

8. The method of claim 1,
    wherein at least the step of adjusting is automatically performed by a control algorithm on the at least one processor.

9. The method of claim 1,
    wherein the step of monitoring is performed as the person moves with the assistive flexible suit in a transparent state.

10. The method of claim 1,
    wherein the step of monitoring includes:
        monitoring an output of at least a first sensor of the at least one sensor adapted to be located on an impaired leg during a gait cycle to provide first information relating to a gait pattern; and
    wherein the step of adjusting includes:
        determining a variance between the gait pattern of the impaired leg and a reference gait pattern, and
        adjusting the actuation profile to decrease the variance between the gait pattern of the impaired leg and the reference gait pattern.

11. The method of claim 1,
    wherein the step of monitoring includes:
        monitoring an output of at least a first sensor of the at least one sensor adapted to be located on an impaired leg during a gait cycle, the first sensor being configured to provide first information relating to a gait pattern of the impaired leg to an assistive flexible suit processor, and
        monitoring an output of at least a second sensor of the at least one sensor adapted to be located on a sound leg during the gait cycle, the second sensor being configured to provide second information relating to a gait pattern of the sound leg to the assistive flexible suit processor; and wherein the step of adjusting includes:
  determining a variance between the gait pattern of the impaired leg and the gait pattern of the sound leg, using the first information and the second information, and
  determining a second actuation profile, acting across the one or more joints, configured to decrease the variance between the gait pattern of the impaired leg and the gait pattern of the sound leg.

12. The method of claim 1, wherein at least the step of monitoring is performed as the person moves in a first controlled environment.

13. The method of claim 12, wherein subsequent to the steps of monitoring, generating, and adjusting, the method further comprising:
  monitoring the output of the at least one sensor as the person moves in a second controlled environment to identify the at least one gait event occurring during the successive strides of the person;
  generating, based at least in part on the timing of the at least one gait event, a second actuation profile for promoting a second improvement in the gait of the person; and
  adjusting the second actuation profile, based on continued monitoring of the output of the at least one sensor, until the assistive flexible suit generates the moment about the at least one of the one or more joints that results in the second improvement in the gait of the person.

14. The method of claim 13, wherein movement in the first controlled environment comprises walking on a treadmill, and movement in the second controlled environment comprises walking on a floor or an instrumented floor.

15. The method of claim 1, wherein at least the step of monitoring is performed as the person moves outside of a controlled environment.

16. The method of claim 1, wherein the at least one actuator is configured to apply the tensile force to a first portion of the person's body and a second portion of the person's body, wherein the at least one of the one or more joints is disposed between the first and second portions of the person's body.

17. The method of claim 1, wherein the moment assists movement of the at least one of the one or more joints.

18. The method of claim 1, wherein the moment resists movement of the at least one of the one or more joints.

19. The method of claim 1, wherein generating the actuation profile comprises transforming the reference trajectory into a time domain based at least partly on one or more measured gait events.

20. The method of claim 1, wherein monitoring the output of the at least one sensor as the person moves to identify the at least one gait event occurring during the successive strides of the person comprises updating an average timing of the at least one gait event occurring during a predetermined number of immediately previous strides.

21. The method of claim 1, further comprising determining a mode of movement based at least in part on the output of the at least one sensor, and wherein updating the reference trajectory includes updating the reference trajectory based at least in part on the determined mode of movement.

22. The method of claim 1, wherein updating the reference trajectory includes updating a position profile and/or a force profile as a function of gait cycle percentage.

23. A system for promoting an improvement in a gait of a person, the system comprising:
  an assistive flexible suit including one or more flexible connections disposed between one or more anchor straps, the assistive flexible suit configured to span one or more joints of a leg of a person having an impaired gait, and having at least one actuator configured to apply a tensile force to the one or more anchor straps using the one or more flexible connections for the assistive flexible suit to generate a moment about at least one of the one or more joints;
  at least one sensor configured to measure the gait of the person in real-time;
  at least one user interface configured for displaying an output of the at least one sensor as the person moves, and for receiving user input, wherein the output of the at least one sensor includes kinematic sensor data; and
  at least one processor configured to:
    generate a reference trajectory based at least in part on the user input received by the at least one user interface;
    actuate the at least one actuator according to an actuation profile based at least in part on the reference trajectory;
    update the reference trajectory based at least in part on the user input received by the at least one user interface, wherein the user input is based at least in part on the kinematic sensor data; and
    adjust the actuation profile based on the updated reference trajectory.

24. The system of claim 23, wherein adjusting the actuation profile comprises adjusting one or more of: a timing of actuation of the at least one actuator, a ramp up force profile delivered by the at least one actuator, a ramp down force profile delivered by the at least one actuator, a maximum amplitude of force delivered by the at least one actuator, and a duration of force delivered by the at least one actuator.

25. The system of claim 23, wherein the output of the at least one sensor contains information suitable for identifying at least one gait event occurring during successive strides of the person, and
wherein the at least one gait event comprises at least one of a heel strike, a toe off, a heel off, a foot flat, a foot landing, a start of controlled dorsiflexion, a start of powered plantarflexion, a height of the person's center of mass relative to ground, an initiation of a muscle eccentric contraction, and an initiation of a muscle concentric contraction.

26. The system of claim 23, wherein the improvement in the gait comprises at least one of improved forward propulsion, enhanced forward hip swing, increased stability, an improved left-right symmetry, improved temporal symmetry in hemiparetic gait, improved spatial symmetry in hemiparetic gait, increased joint range of motion of an affected side during the gait cycle in hemiparetic gait, increased ground clearance during swing phase, increased plantar flexion force during push-off, increased self-selected walking speed, and reduced compensatory movements.

27. The system of claim 23, wherein the user input includes information regarding the actuation profile for actuating the at least one actuator.

28. The system of claim 23, wherein the user input includes information regarding a timing of at least one gait event occurring during successive strides of the person, and wherein the at least one processor is configured to generate, based at least in part on the timing of the at least one gait event, the actuation profile for promoting the improvement in the gait of the person.

29. The system of claim 28, wherein the user input also includes information regarding one or more adjustments to the actuation profile for promoting the improvement in the gait of the person.

30. The system of claim 28, wherein the at least one processor is further configured for adjusting, based on continued output of the at least one sensor, the actuation profile until the actuation profile promotes the improvement in the gait of the person.

31. The system of claim 23, wherein the at least one processor is configured to monitor the output of the at least one sensor as the person moves to identify at least one gait event occurring during successive strides of the person, and
wherein the user input includes information regarding the actuation profile for actuating the at least one actuator and one or more adjustments to the actuation profile for promoting the improvement in the gait of the person.

32. The system of claim 31, wherein the at least one processor is configured to detect the at least one gait event as the person moves with the assistive flexible suit in a transparent state.

33. The system of claim 23, wherein the at least one sensor comprises at least a first sensor adapted to be located on an impaired leg of the person when worn, the first sensor configured to measure a gait pattern of the impaired leg,
wherein the at least one user interface is configured for displaying the gait pattern of the impaired leg and a reference gait pattern, and
wherein one or more adjustments to the actuation profile are configured to decrease a variance between the gait pattern of the impaired leg and the reference gait pattern.

34. The system of claim 23, wherein the at least one sensor comprises at least a first sensor adapted to be located on an impaired leg of the person when worn, the first sensor configured to measure a gait pattern of the impaired leg and at least a second sensor adapted to be located on a sound leg of the person when worn, the second sensor configured to measure a gait pattern of the sound leg, and
wherein one or more adjustments to the actuation profile are configured to decrease a variance between the gait pattern of the impaired leg and the gait pattern of the sound leg.

35. The system of claim 23, wherein the user input includes information regarding one or more adjustments to the actuation profile for promoting the improvement in the gait of the person.

36. The system of claim 23, further comprising a plurality of anchors configured for positioning on a body of the person and wherein the one or more flexible connections includes at least one flexible connection operatively coupling at least two of the plurality of anchors.

37. The system of claim 23, wherein the at least one actuator is disposed on the assistive flexible suit.

38. The system of claim 23, wherein the at least one processor is further configured to determine a mode of movement based at least in part on the output of the at least one sensor, and wherein updating the reference trajectory includes updating the reference trajectory based at least in part on the determined mode of movement.

39. The system of claim 23, wherein the at least one processor configured to update the reference trajectory includes the at least one processor configured to update a position profile and/or a force profile as a function of gait cycle percentage.

* * * * *